United States Patent
Xie et al.

(10) Patent No.: US 12,391,692 B2
(45) Date of Patent: *Aug. 19, 2025

(54) SPIRO RING-CONTAINING QUINAZOLINE COMPOUND

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Gang Cao, Shanghai (CN); Lihui Qian, Shanghai (CN)

(73) Assignee: WIGEN BOIMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 574 days.

This patent is subject to a terminal disclaimer.

(21) Appl. No.: 17/799,060

(22) PCT Filed: Mar. 23, 2021

(86) PCT No.: PCT/CN2021/082251
§ 371 (c)(1),
(2) Date: Aug. 11, 2022

(87) PCT Pub. No.: WO2021/190467
PCT Pub. Date: Sep. 30, 2021

(65) Prior Publication Data
US 2023/0128824 A1 Apr. 27, 2023

(30) Foreign Application Priority Data
Mar. 25, 2020 (CN) .................. 202010222766.X

(51) Int. Cl.
| | | |
|---|---|---|
| C07D 239/72 | (2006.01) |
| A61K 31/517 | (2006.01) |
| A61P 35/00 | (2006.01) |
| C07D 471/10 | (2006.01) |
| C07D 519/00 | (2006.01) |

(52) U.S. Cl.
CPC .......... *C07D 471/10* (2013.01); *A61P 35/00* (2018.01); *C07D 519/00* (2013.01); *C07B 2200/07* (2013.01); *C07B 2200/13* (2013.01)

(58) Field of Classification Search
CPC ...... C07D 239/72; A61K 31/517; A61P 35/00
USPC ................. 544/284, 283; 514/266.2
See application file for complete search history.

(56) References Cited

U.S. PATENT DOCUMENTS

2019/0292182 A1* 9/2019 Kuramoto .............. A61P 35/00

FOREIGN PATENT DOCUMENTS

| CN | 108779097 A | 11/2018 |
| CN | 110267957 A | 9/2019 |
| CN | 112110918 A | 12/2020 |
| CN | 113754659 A | 12/2021 |
| JP | 2018513853 A | 5/2018 |
| JP | 2023508482 A | 3/2023 |
| WO | 2018143315 A1 | 8/2018 |
| WO | 2020028706 A1 | 2/2020 |
| WO | 2020113071 A1 | 6/2020 |
| WO | 2020177629 A1 | 9/2020 |

OTHER PUBLICATIONS

European Search Report and Written Opinion from EP 21776359 (date of completion of the search: Feb. 20, 2024).

* cited by examiner

*Primary Examiner* — Charanjit Aulakh
(74) *Attorney, Agent, or Firm* — SZDC Law PC

(57) ABSTRACT

The present invention relates to a compound of general formula (1) and a preparation method therefor, and use of the compound of formula (1) and isomers, crystalline forms and pharmaceutically acceptable salts thereof as an irreversible inhibitor for a K-Ras G12C mutant protein in preparing a medicament for resisting Ras-related diseases such as tumors.

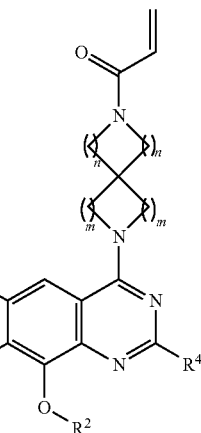

(1)

7 Claims, No Drawings

SPIRO RING-CONTAINING QUINAZOLINE COMPOUND

The present application is the National Stage Application of PCT/CN2021/082251, filed on Mar. 23, 2021, which claims priority to Chinese Patent Application No. CN202010222766X filed on Mar. 25, 2020, which is incorporated herein by reference in its entirety.

TECHNICAL FIELD

The present invention belongs to the field of medicinal chemistry, and particularly to a spiro ring-containing quinazoline compound, a preparation method therefor, and use of the compound as a K-Ras G12C inhibitor in preparing antitumor medicaments.

BACKGROUND

Ras protein family members are important signal transduction molecules in cells, and play an important role in the growth and development. Extensive analysis and study of in vitro tumor cells, animal models and human tumor samples indicate that the over-activation of Ras family proteins is an early event in the development of human tumors and is one of the important causes of the development and progression of many types of cancer. Targeting Ras proteins and inhibiting the Ras protein activity are therefore important means of treating related tumors. An Ras protein exists in two forms. It is in an unactivated resting state when bound to GDP, and when a cell receives signals such as growth factor stimulation, it is bound to GTP and thus activated. Activated Ras proteins recruit a variety of signal-transducing adaptor proteins to promote phosphorylation of downstream signaling molecules such as ERK and S6, thereby activating the Ras signal transduction pathway and regulating the growth, survival, migration and differentiation of cells. Ras proteins can hydrolyze GTP back to GDP due to their GTPase activity. Besides, the GTPase-activating proteins (GAPs) in cells interact with Ras, greatly improving the GTPase activity of Ras and thereby preventing Ras proteins from being overly activated.

Mutations in the K-Ras, H-Ras and N-Ras proteins of the Ras protein family are one of the common genetic mutations in a variety of tumors, and are a major factor leading to over-activation of Ras proteins in tumors. Compared to the wild-type Ras proteins, Ras proteins with these mutations have unregulated activity; they are stably bound to GTP and constantly activated, thereby promoting the growth, migration and differentiation of tumor cells. Among these mutations, those in K-Ras proteins are the most common ones, accounting for 85% of all Ras mutations, while those in N-Ras (12%) and H-Ras (3%) are relatively rare. K-Ras mutations are very common in many types of cancer, including pancreatic cancer (95%), colorectal cancer (45%), lung cancer (25%), etc., while relatively rare (<2%) in breast cancer, ovarian cancer and brain cancer. K-Ras mutations mainly occur at position G12, and G12C mutation is the most common one. For example, in non-small cell lung cancer (NSCLC), about 50% of K-Ras mutations are K-Ras G12C, and G12V and G12D are the second most common mutations. Genomic studies show that K-Ras mutations in non-small cell lung cancer generally do not coexist with EGFR, ALK, ROS1, RET and BRAF mutations, but coexist with STK11, KEAP1, TP53 and other mutations, suggesting that K-Ras mutations may be involved in malignant transformation, proliferation and invasion of cells synergistically with STK11, KEAP1, TP53 and other mutations. In addition to tumors, abnormal activation of Ras proteins is also involved in non-tumor diseases including diabetes, neurodegenerative diseases, etc. Hence, Ras protein-targeting small-molecule compounds can benefit a large number of cancer patients with specific genetic mutations and non-cancer patients with over-activation of the Ras pathway.

Since the discovery of Ras mutations in tumors that happened forty years ago, although we have gained deeper insight into the pathogenesis involving the Ras pathway, no clinically effective therapeutic approach targeting Ras proteins has yet come onto the market for a large number of patients with Ras protein mutations and over-activation of the Ras pathway. Therefore, the development of a high-activity small-molecule inhibitor targeted at Ras proteins, particularly the K-Ras G12C protein with high frequency of mutation, is of great clinical significance.

K-Ras G12C muteins, as a leading therapeutic target, have not been extensively researched at present, and only a few compounds, such as AMG510 of Amgen and MRTX849 of Mirati, have been under clinical research. In 2018, a K-Ras G12C mutation-targeting covalent inhibitor ARS-1620 was reported in Cell (Cell, 2018, 172: 578-589). A class of spiro compounds with K-Ras G12C activity and anti-tumor activity in mice are reported in patent WO2018/143315, and a general formula A, and a representative compound B (Example 35 in the patent) thereof are shown as the structures below (refer to the patent for the definitions of the symbols in the formula):

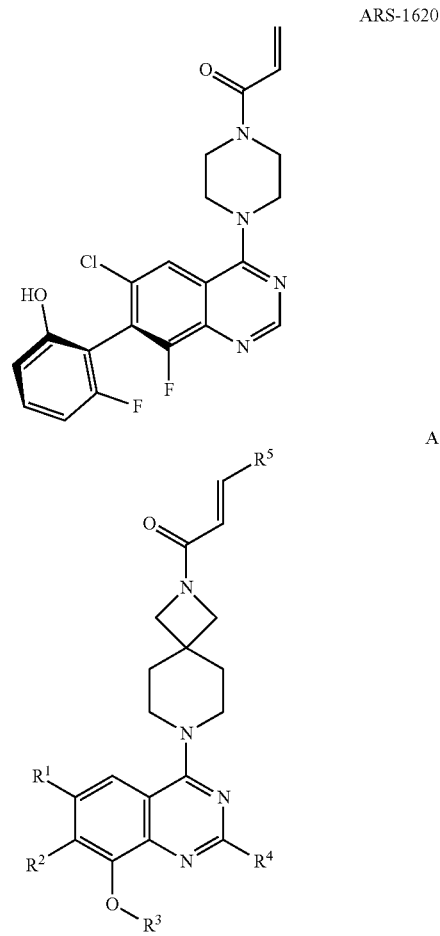

-continued

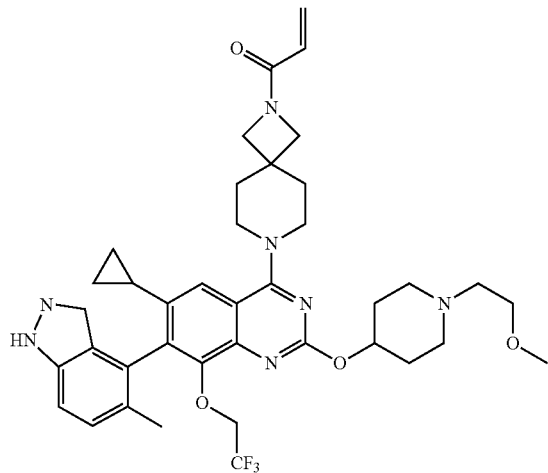

Currently, there is an urgent need to study and discover compounds with good K-Ras G12C activity and superior pharmacokinetic properties.

SUMMARY

The present invention aims to provide a compound of general formula (1) or isomers, crystalline forms, pharmaceutically acceptable salts, hydrates or solvates thereof:

(1)

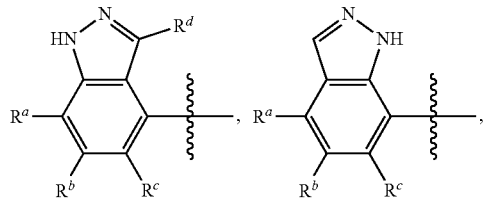

wherein in the general formula (1):

m is an integer of 1 or 2;

n is an integer of 1 or 2;

$R^1$ is H, halogen, C1-C3 alkyl, C2-C4 alkenyl, C2-C4 alkynyl or C3-C6 cycloalkyl;

$R^2$ is C1-C3 alkyl or halogenated C1-C3 alkyl;

$R^3$ is

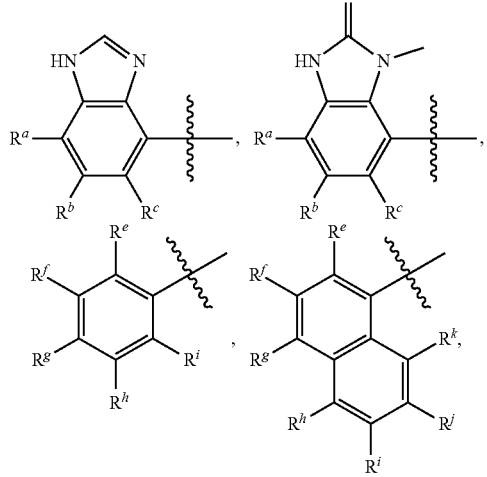

wherein $R^a$ is H or F, $R^b$ is H, F, Cl or Me, $R^c$ is H, F, Cl or Me, $R^d$ is F, Cl, $NH_2$, Me or cyclopropyl, and $R^e$, $R^f$, $R^g$, $R^h$, $R^i$, and $R^k$ are independently H, F, Cl, OH, OMe, $NH_2$, $CF_3$, C1-C3 alkyl or C3-C6 cycloalkyl;

$R^4$ is

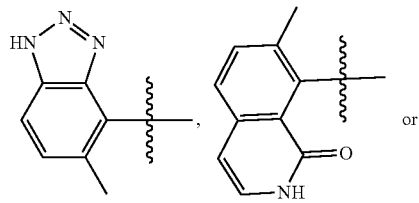

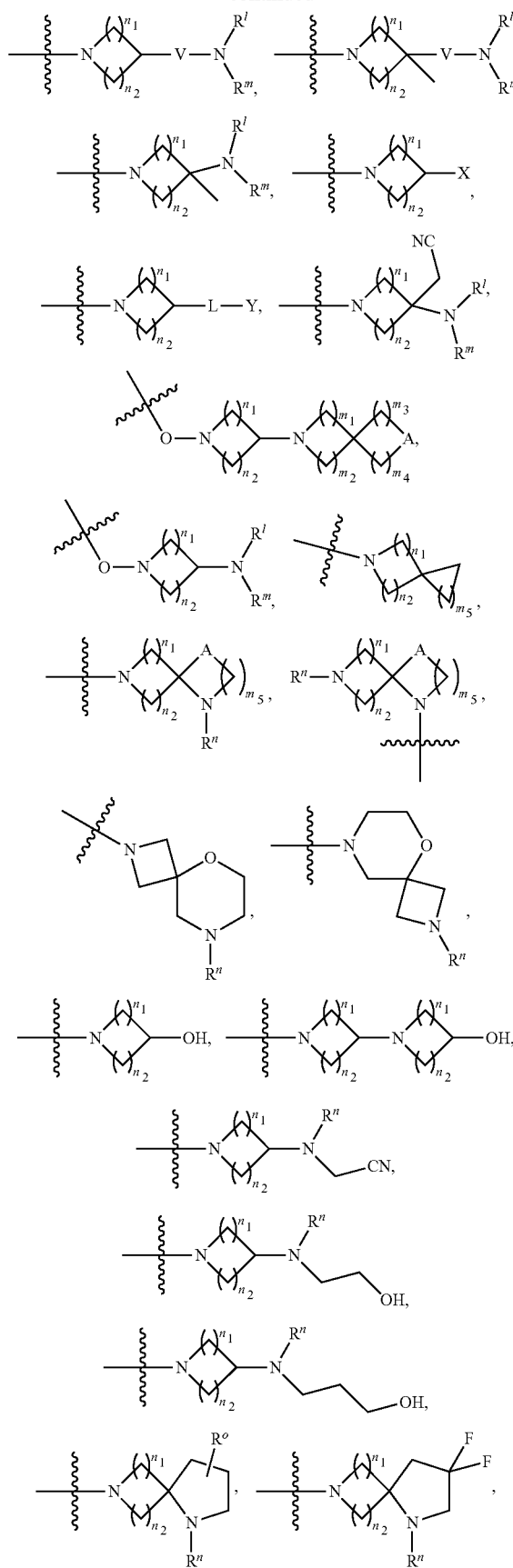
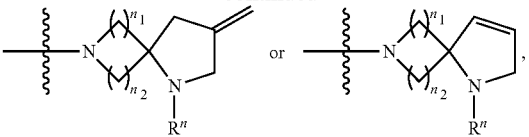
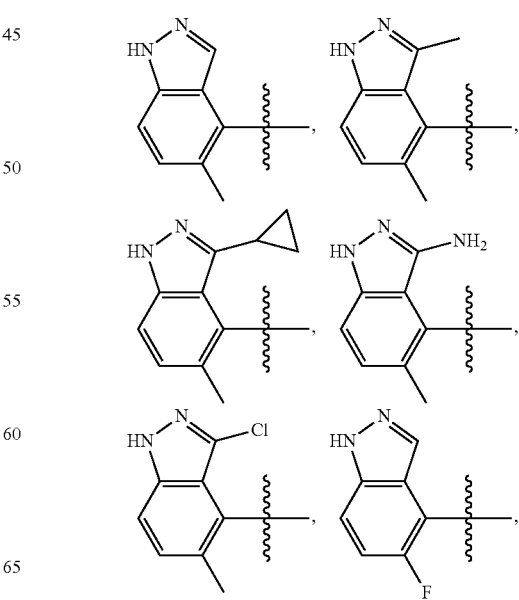

wherein $n_1$ and $n_2$ are independently integers of 1 or 2, $m_1$, $m_2$, $m_3$ and $m_4$ are independently integers of 0, 1, 2, 3 or 4, and $m_5$ is an integer of 1, 2 or 3; A is —CH$_2$—, —O—, —S—, —SO—, —SO$_2$— or —N(C1-C3 alkyl)-, V is —CH$_2$—, —SO$_2$— or —CO—, and L is —O—, —S—, —SO$_2$—, —SO— or —CO—; X is a 5- to 7-membered heteroaryl or a partially saturated 5- to 7-membered heterocycloalkyl; Y is C3-C6 cycloalkyl, heterocycloalkyl, (C3-C6) cycloalkyl-(C1-C3) alkyl- or heterocycloalkyl-(C1-C3) alkyl-; $R^l$ and $R^m$ are independently C1-C3 alkyl, halogenated C1-C3 alkyl, hydroxyl-substituted C1-C3 alkyl, cyano-substituted C1-C3 alkyl, C3-C6 cycloalkyl, (C1-C3) alkoxy-(C2-C3) alkyl-, (halogenated C1-C3) alkoxy-(C2-C3) alkyl-, (C3-C6) cycloalkyl-(C1-C3) alkyl-; or $R^l$ and $R^m$, together with a N atom, form 3- to 8-membered heterocycloalkyl, wherein the 3- to 8-membered heterocycloalkyl can be substituted with 1-3 substituents selected from OH, halogen, cyano, C1-C3 alkyl, C3-C6 cycloalkyl, heterocycloalkyl, (C1-C3) alkoxy and (halogenated C1-C3) alkoxy; $R^n$ is C1-C3 alkyl, C2-C4 alkenyl, C2-C4 alkynyl, C3-C6 cycloalkyl, heterocycloalkyl, halogenated C1-C3 alkyl, hydroxyl-substituted C1-C3 alkyl, cyano-substituted C1-C3 alkyl, (C1-C3) alkoxy-(C2-C3) alkyl-, (halogenated C1-C3) alkoxy-(C2-C3) alkyl-, (C3-C6) cycloalkyl-(C1-C3) alkyl- or heterocycloalkyl-(C1-C3) alkyl-; and $R^o$ is OH, halogen, cyano, C1-C3 alkyl, C1-C3 alkoxy or C3-C6 cycloalkyl.

In another preferred embodiment, wherein in the general formula (1), 10 is H, F, Cl, Me, Et, isopropyl, vinyl, ethynyl or cyclopropyl.

In another preferred embodiment, wherein in the general formula (1), $R^2$ is CH$_3$, CH$_3$CH$_2$, CF$_3$CH$_2$, CHF$_2$CH$_2$ or CF$_3$(CH$_3$)CH.

In another preferred embodiment, wherein in the general formula (1), $R^3$ is

7
-continued
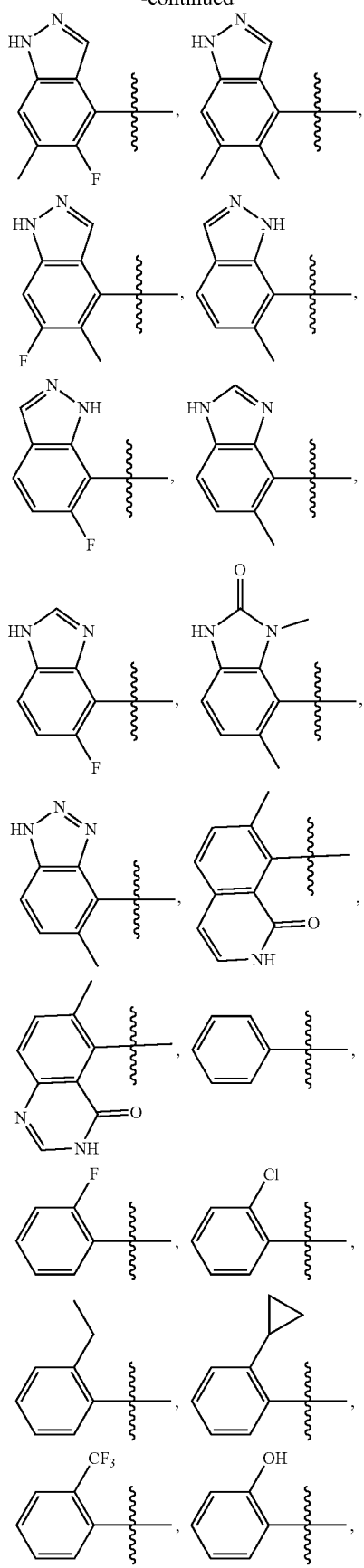
8
-continued
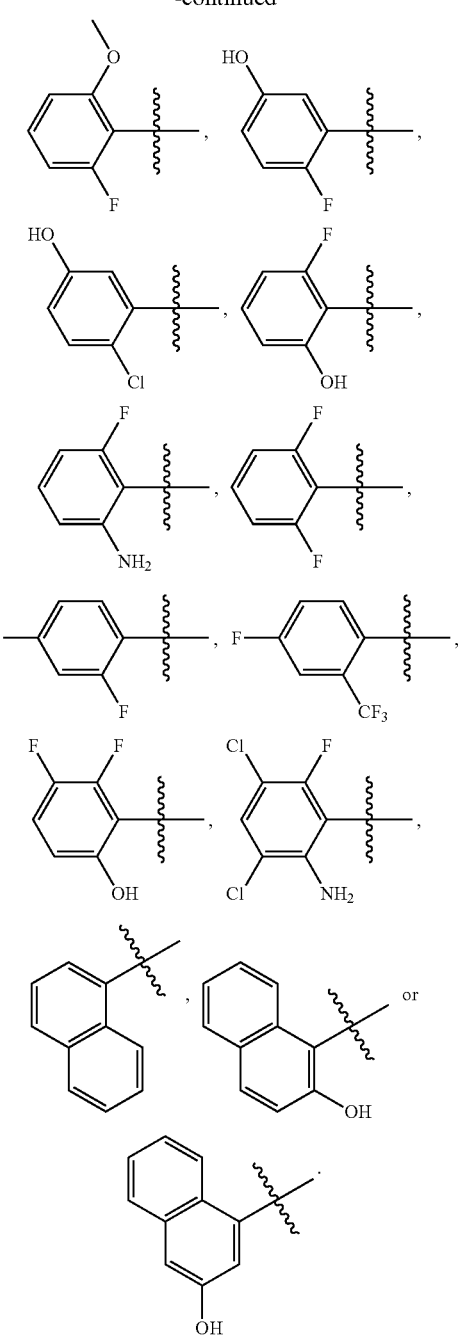
In another preferred embodiment, wherein in the general formula (1), $R^4$ is
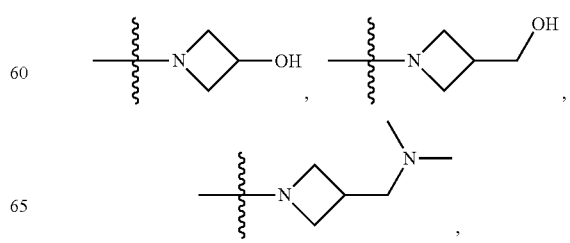

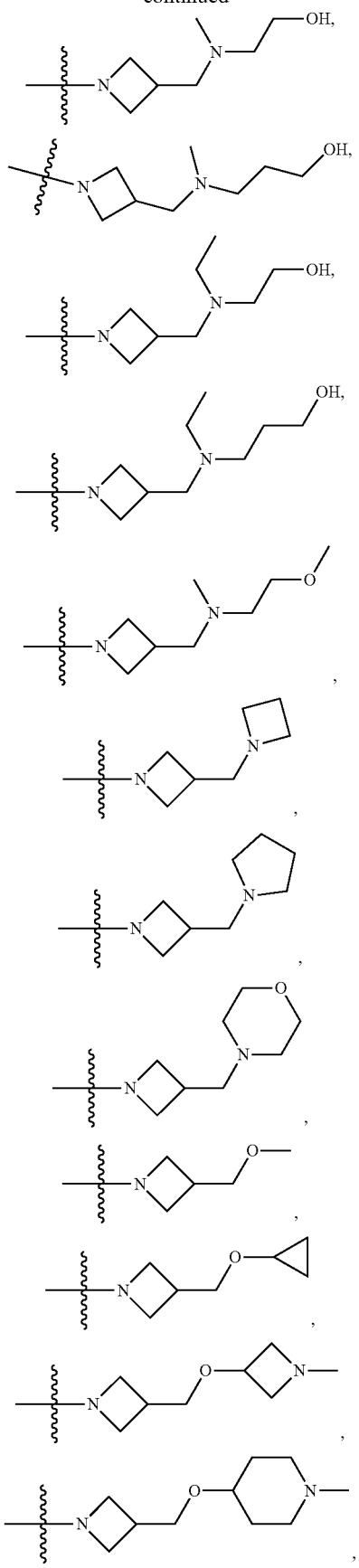
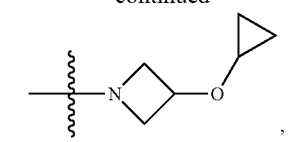
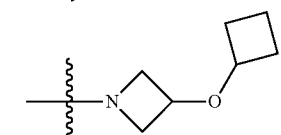
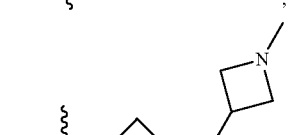
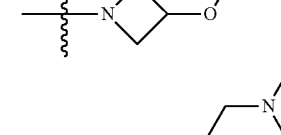
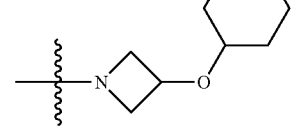
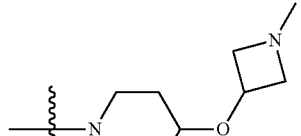
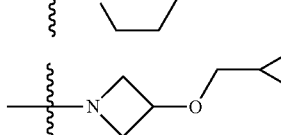
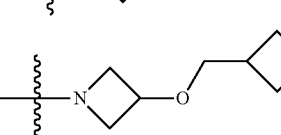
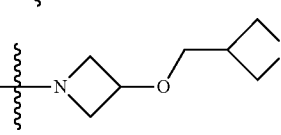
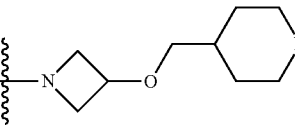
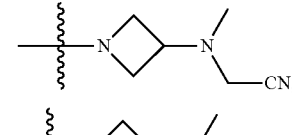
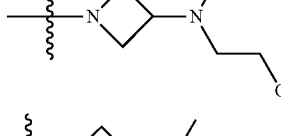
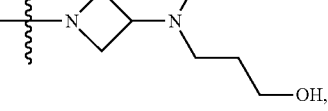

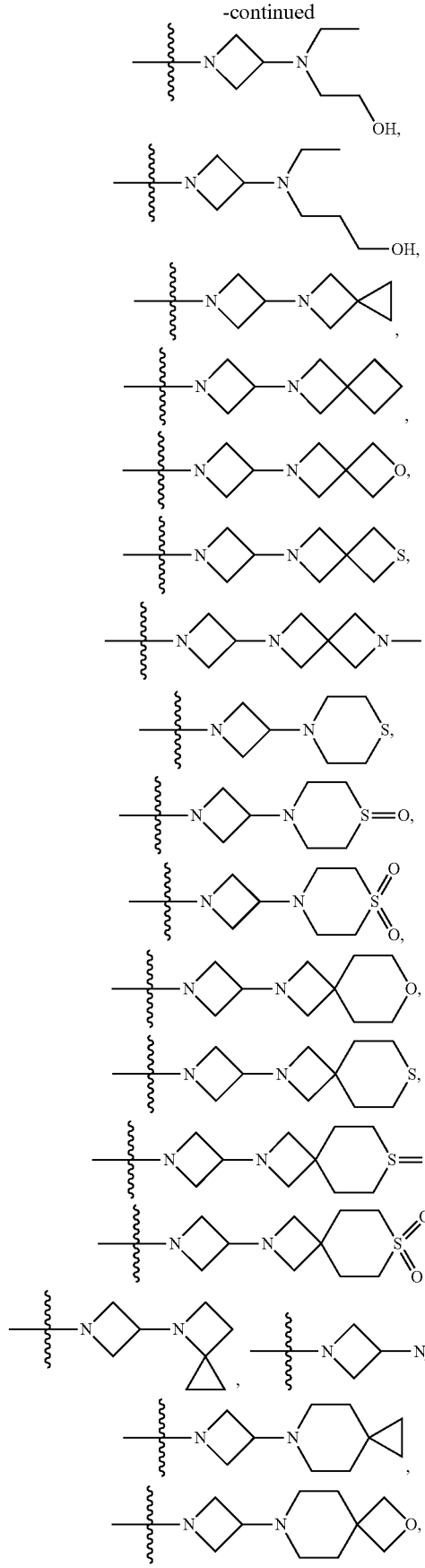
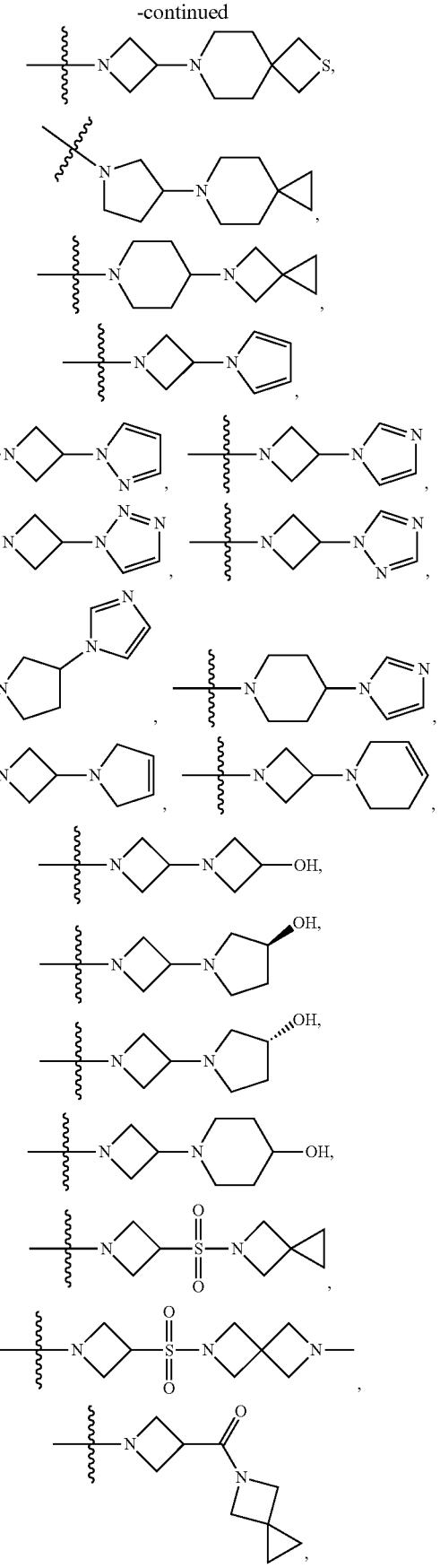

-continued

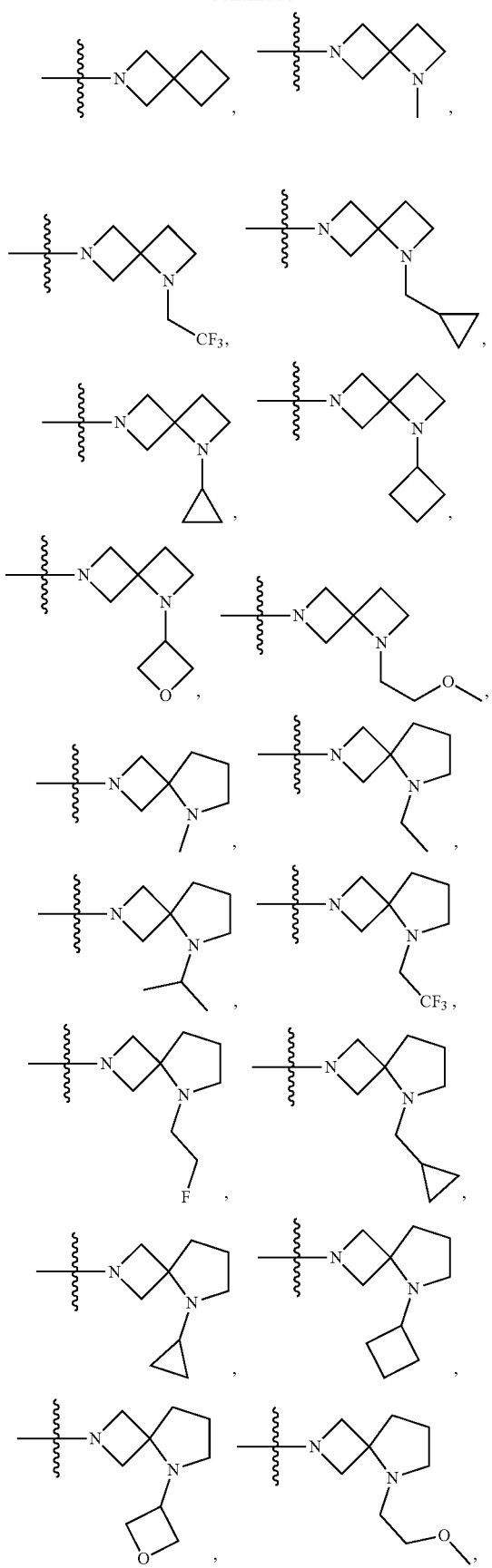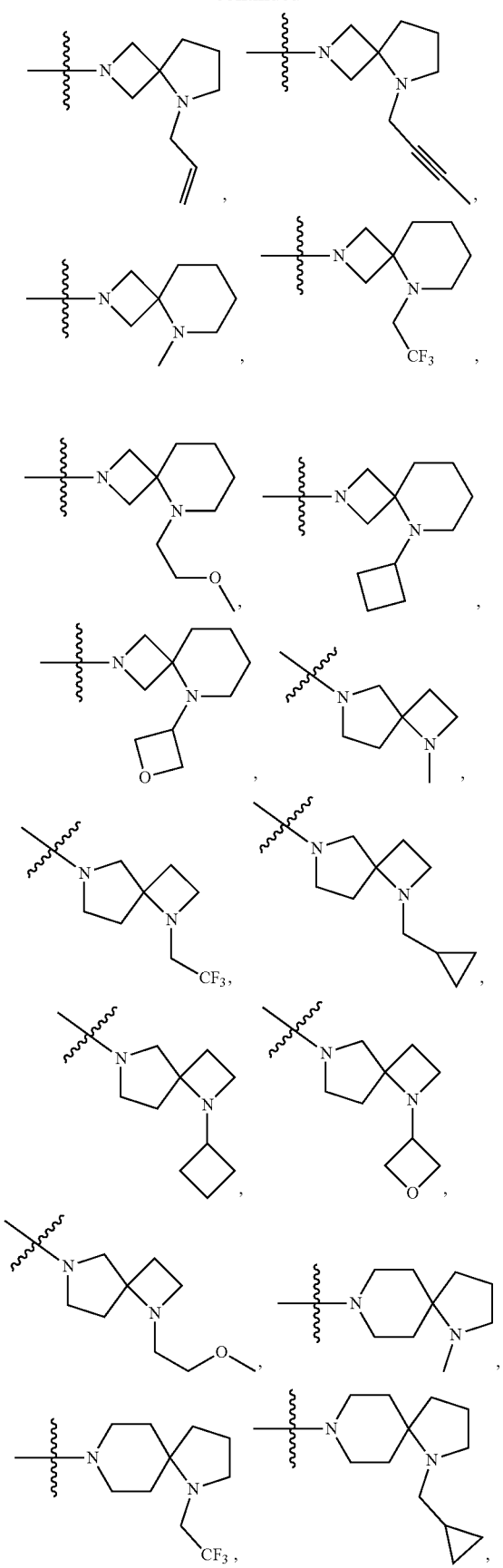

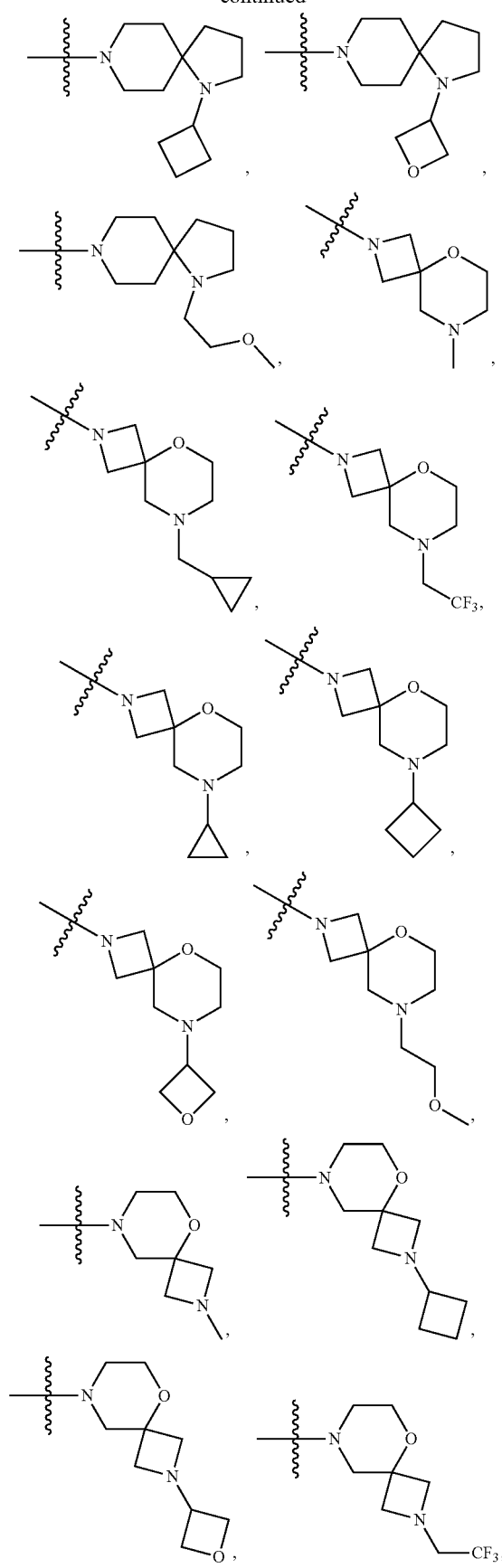
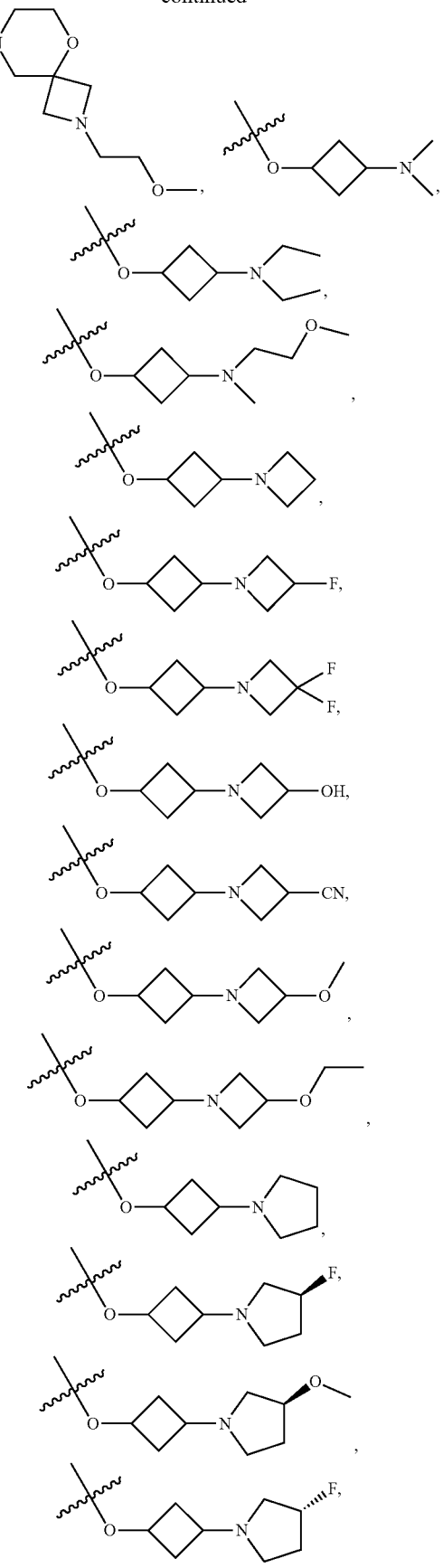

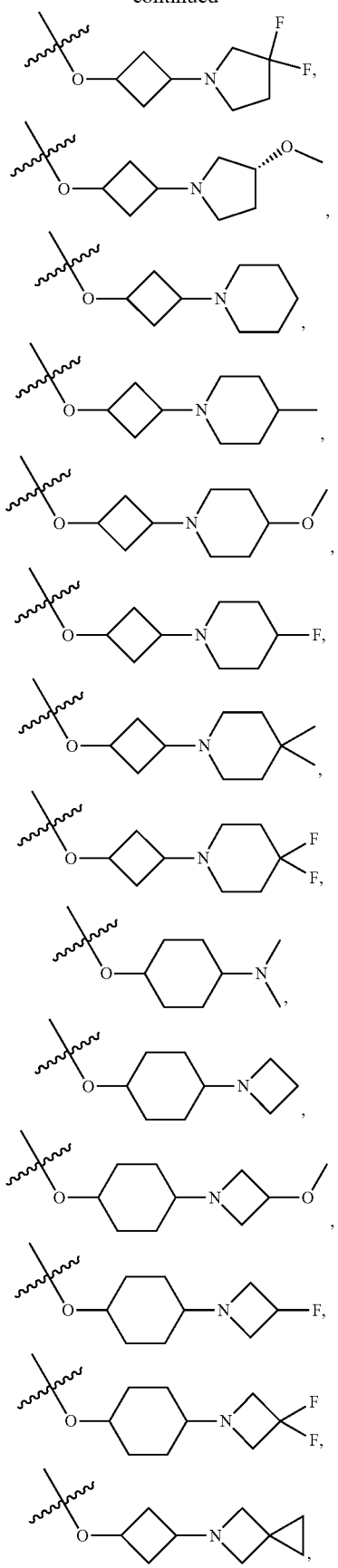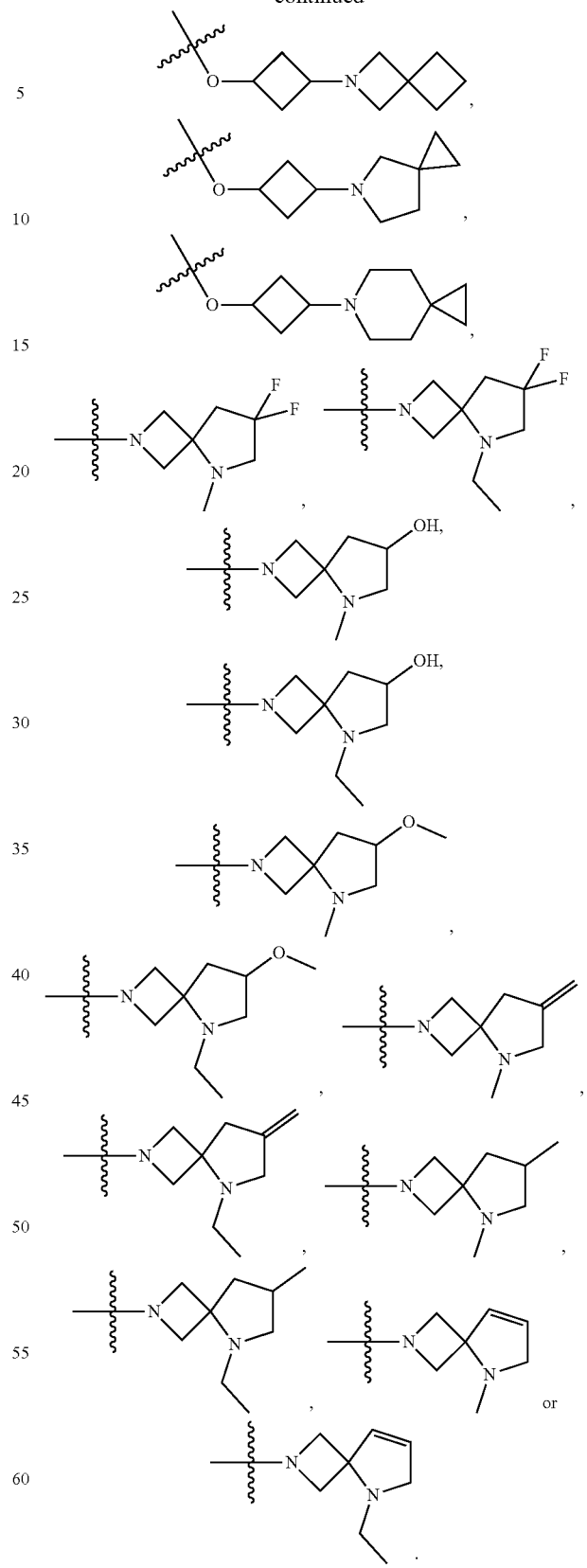
In various embodiments, representative compounds of the present invention have one of the following structures:

21
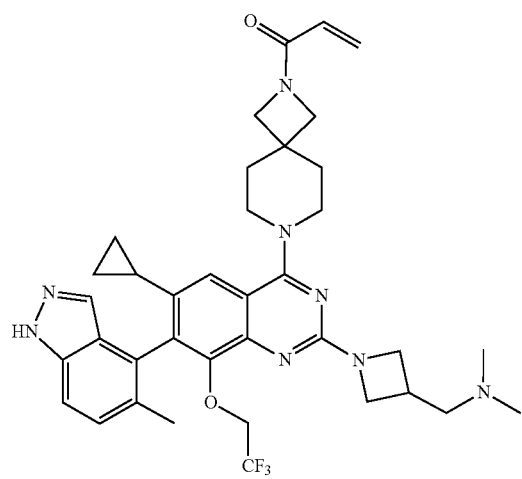
1
22
-continued
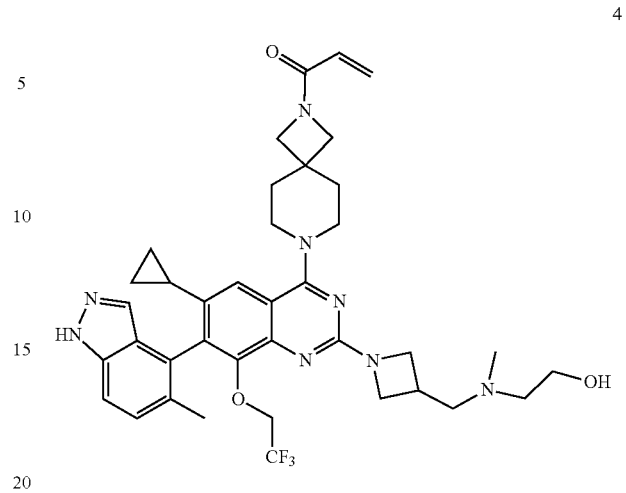
4
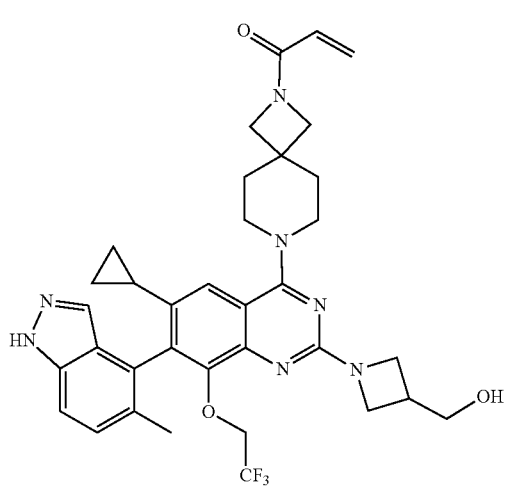
2
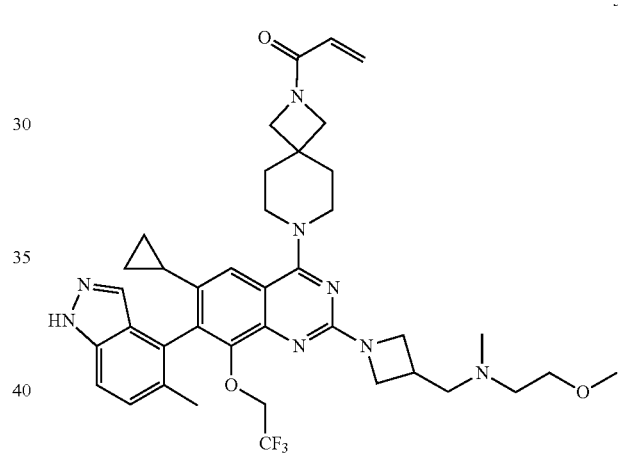
5
3
6

7
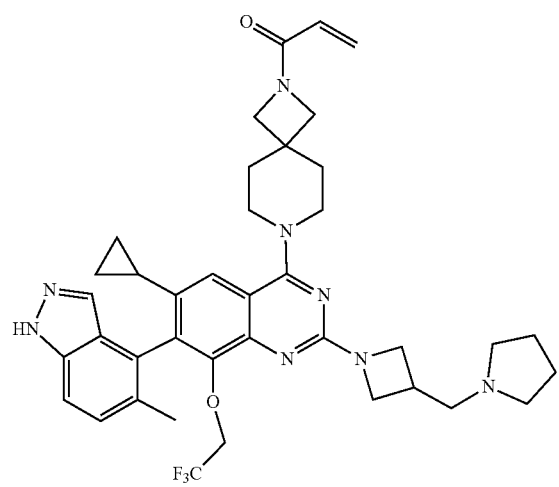
8
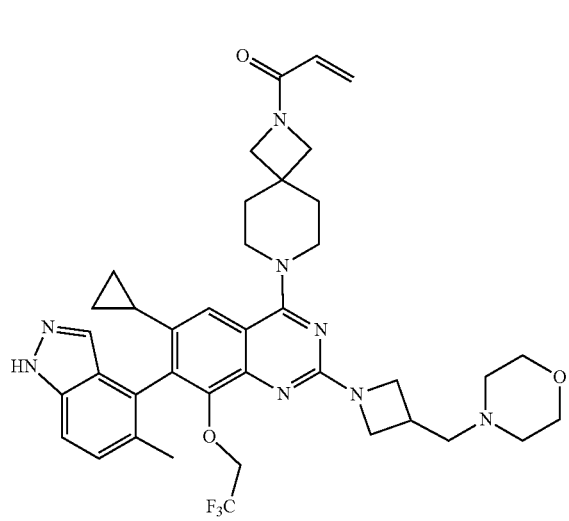
9
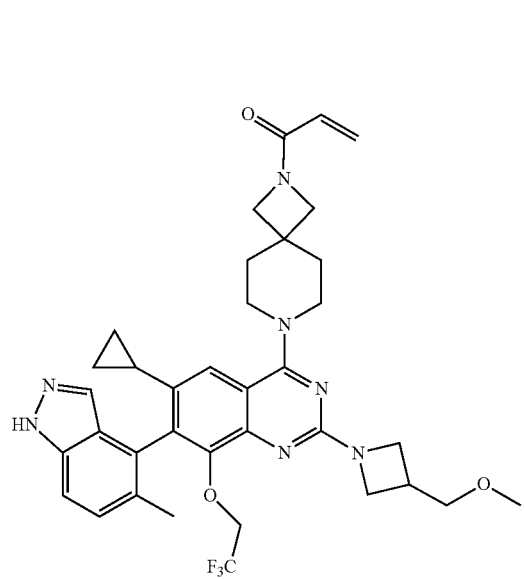
10
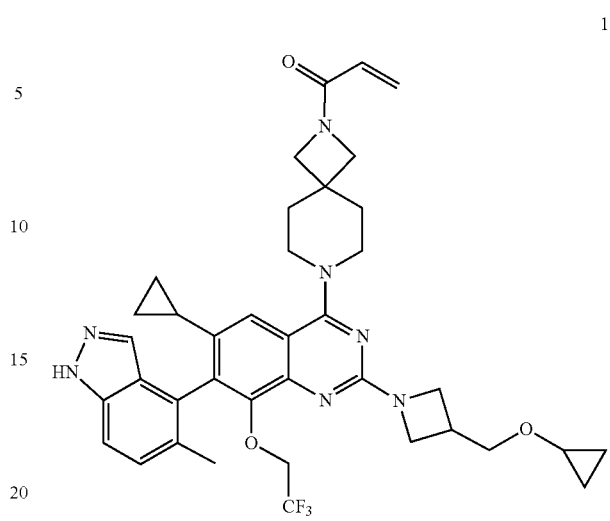
11
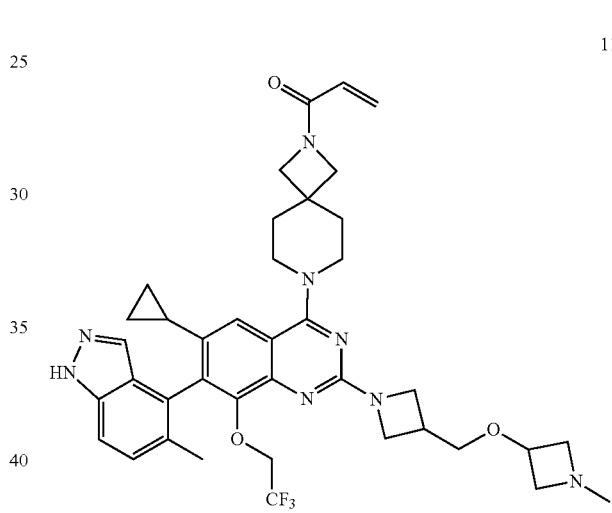
12
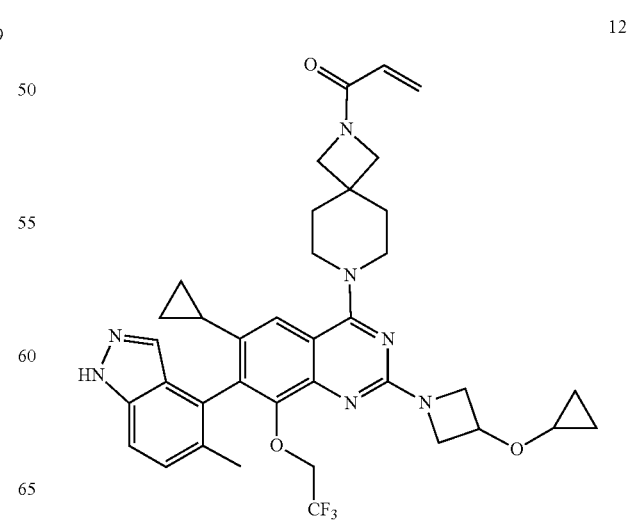

-continued
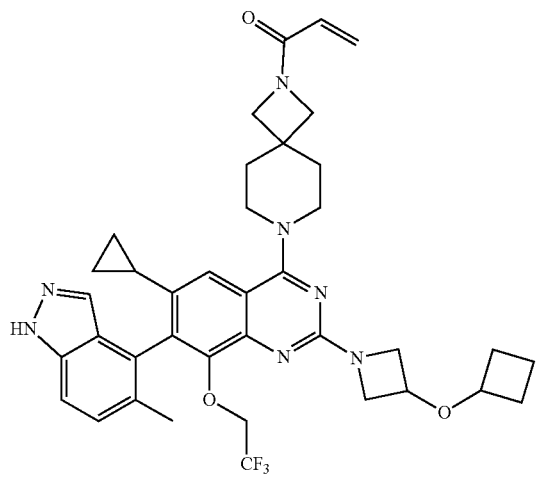
13
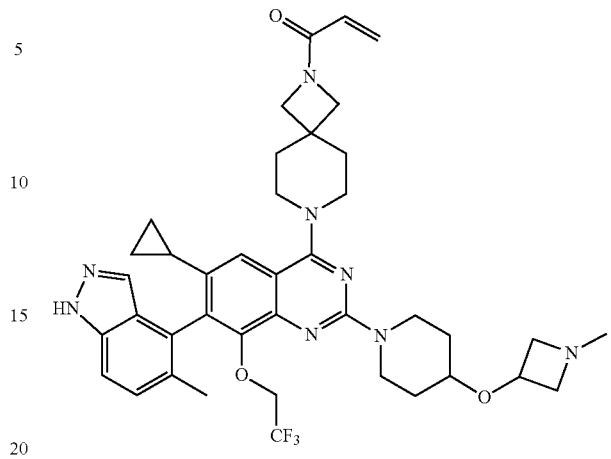
16
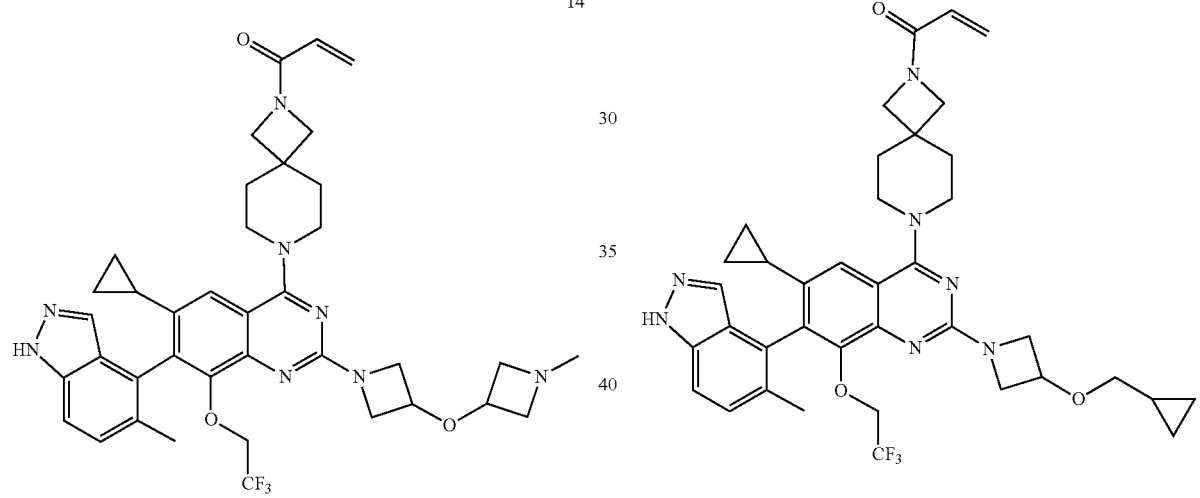
14
17
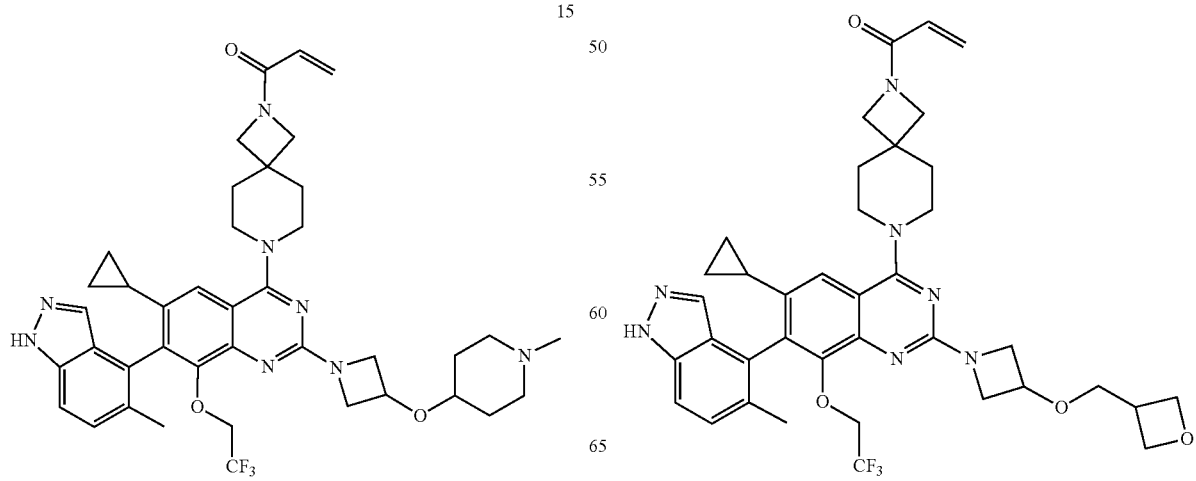
15
18

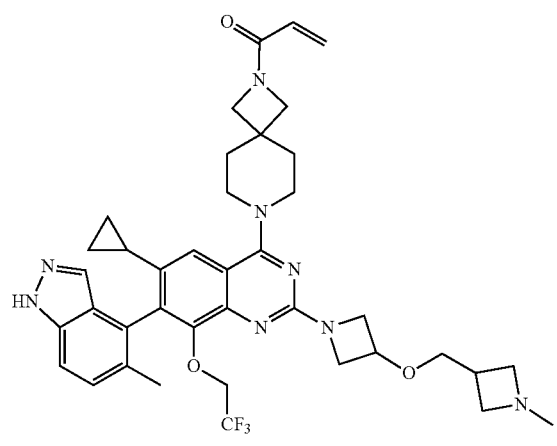
19
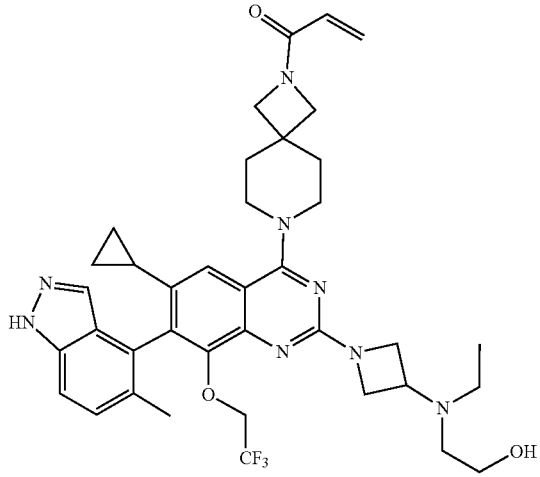
22
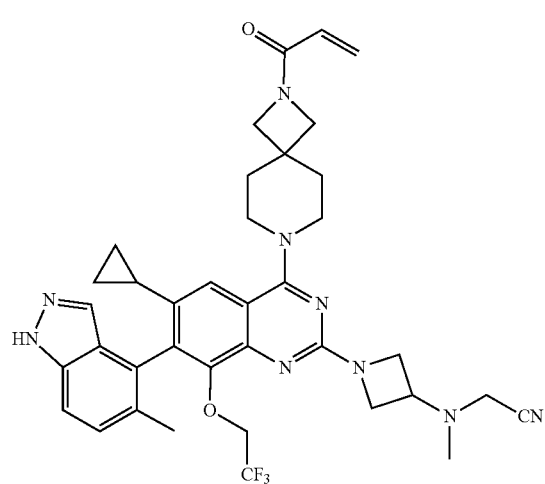
20
21
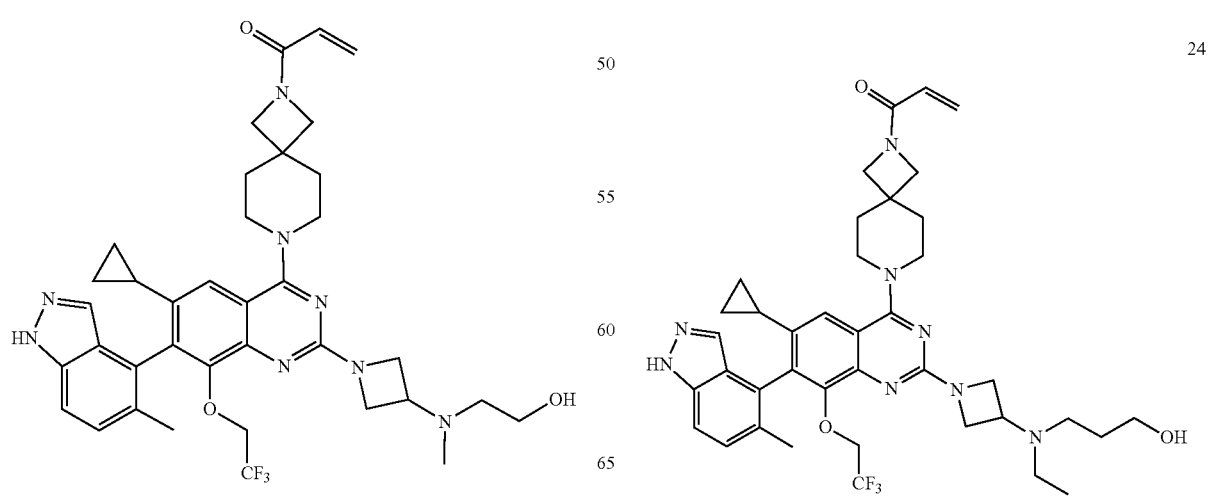
23
24

25
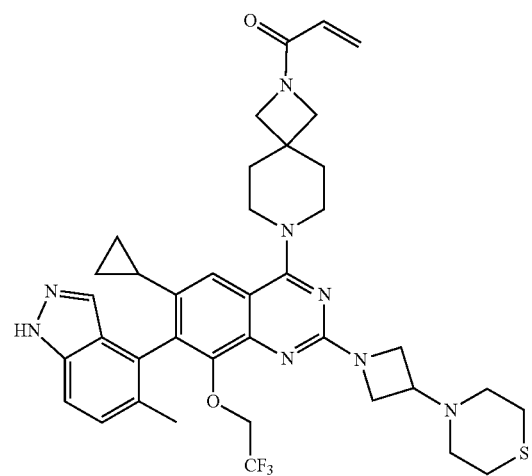
26
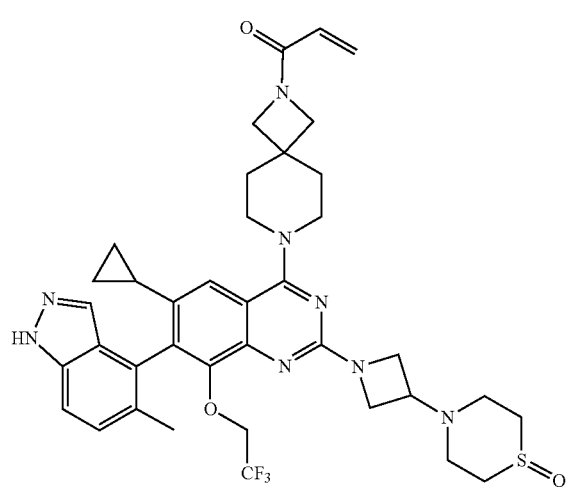
27
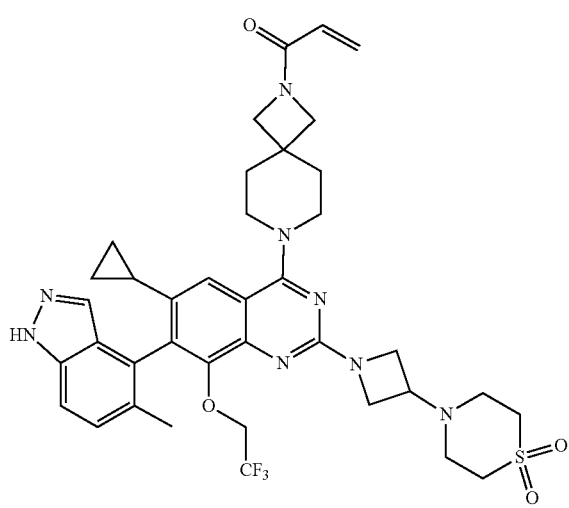
28
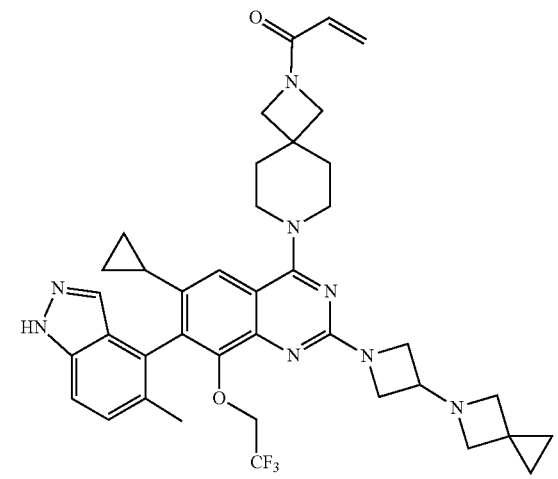
29
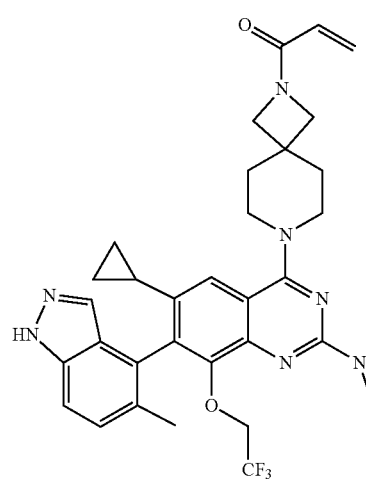
30

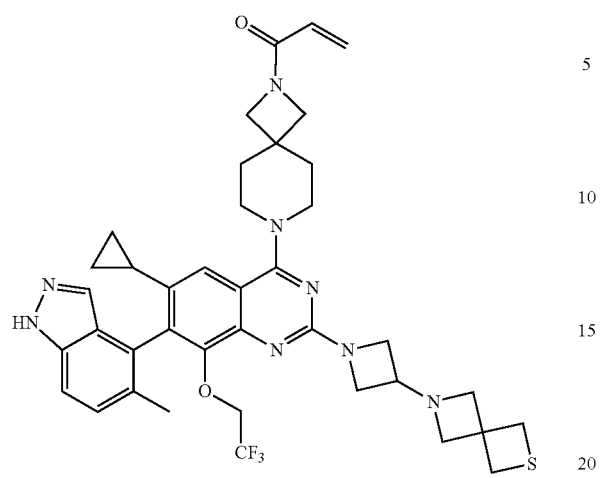
31
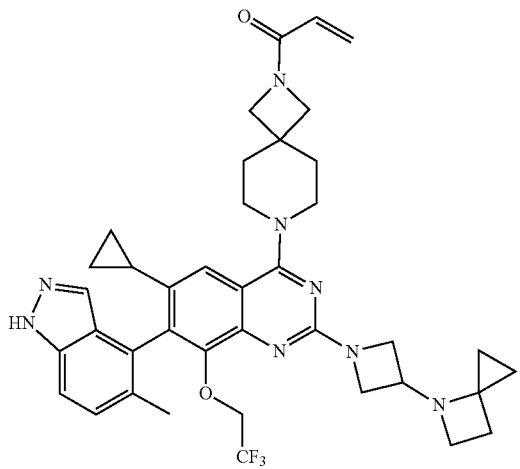
34
32
35
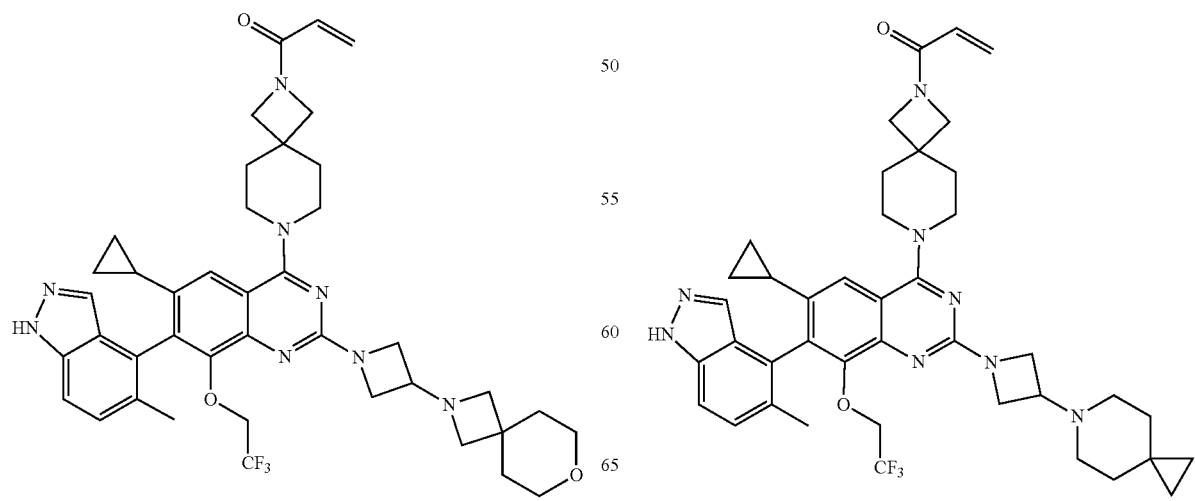
33
36

37
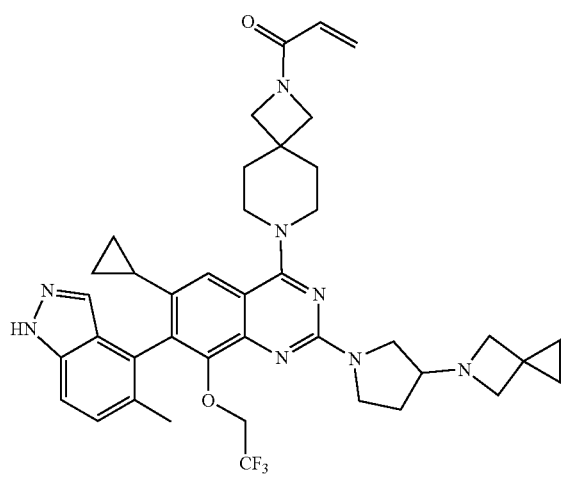
38
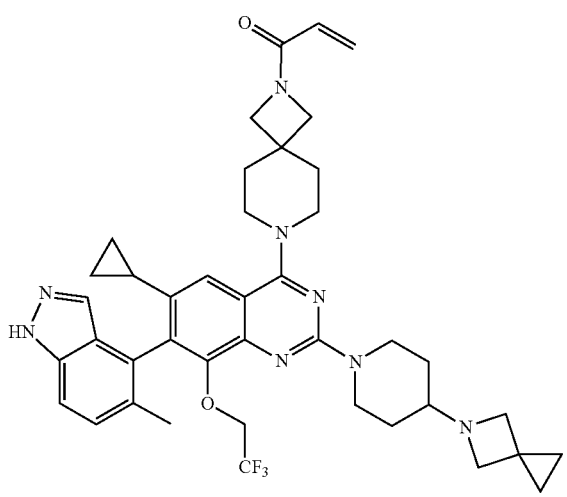
39
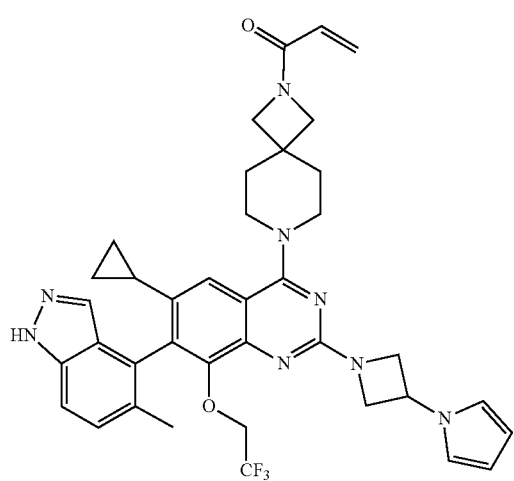
40
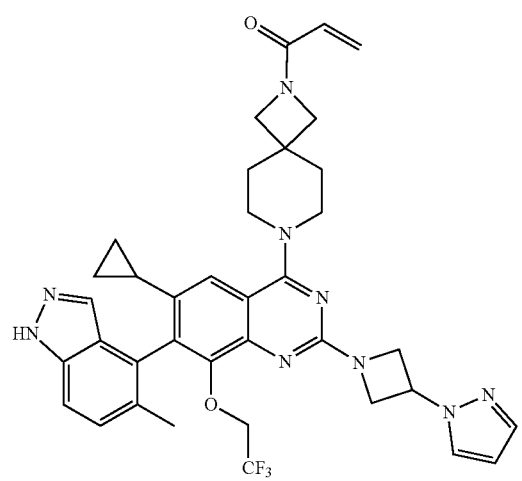
41
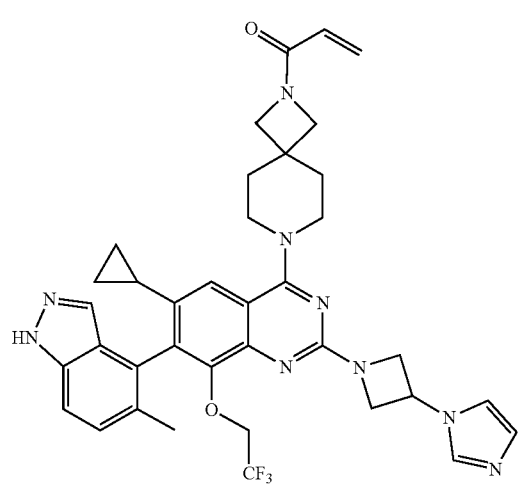
42
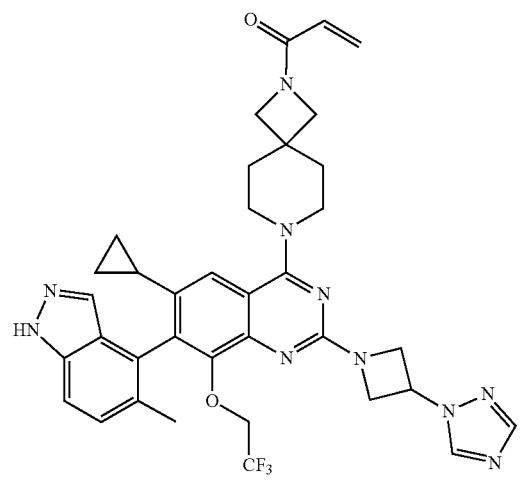

43
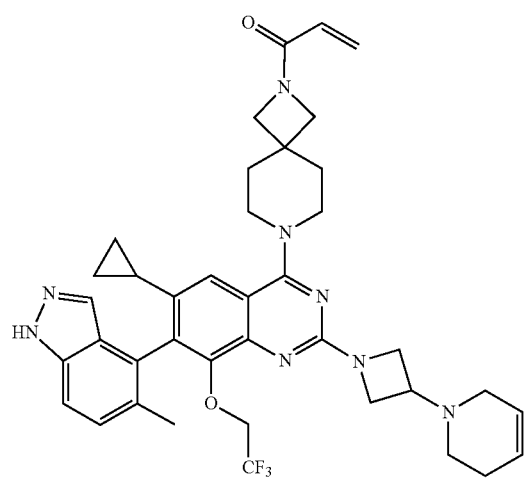
44
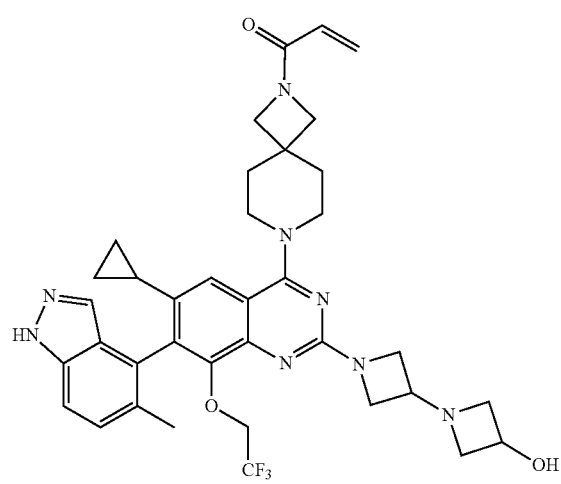
45
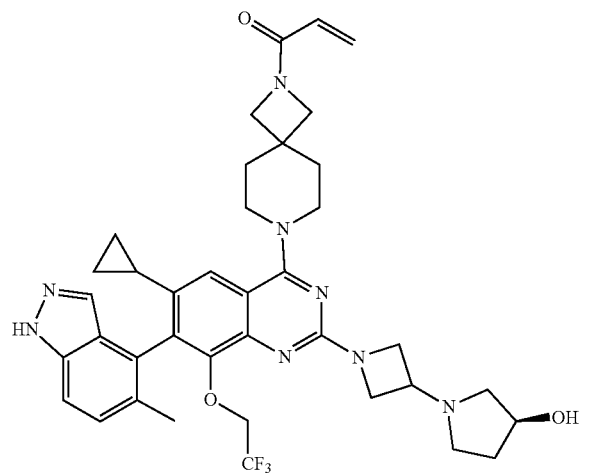
46
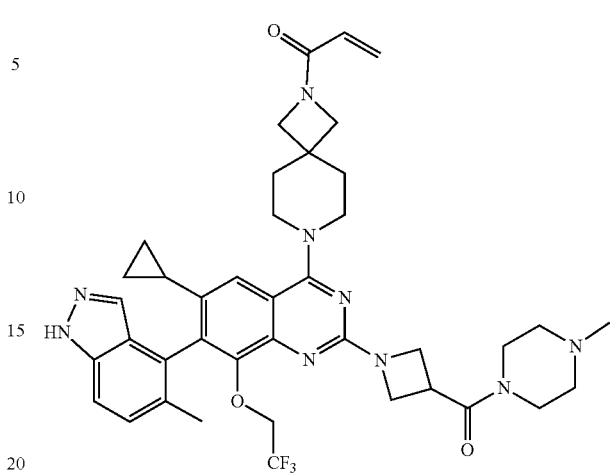
47
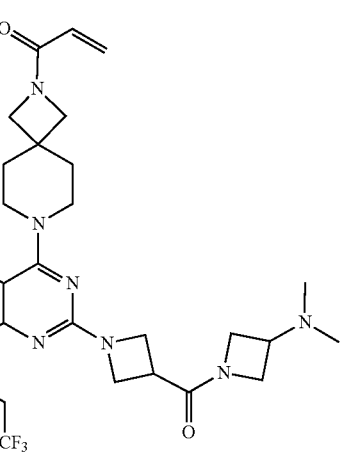
48
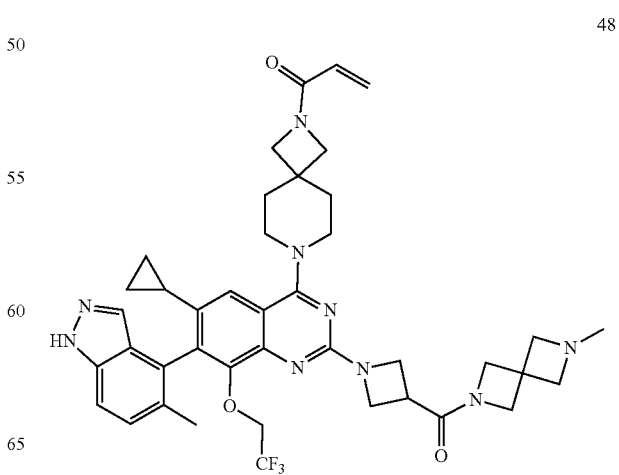

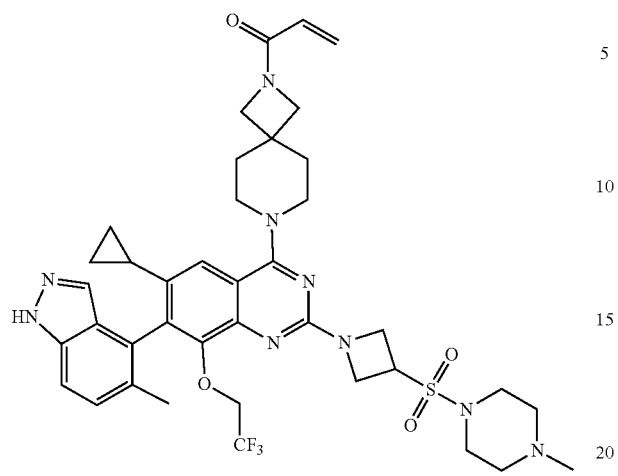
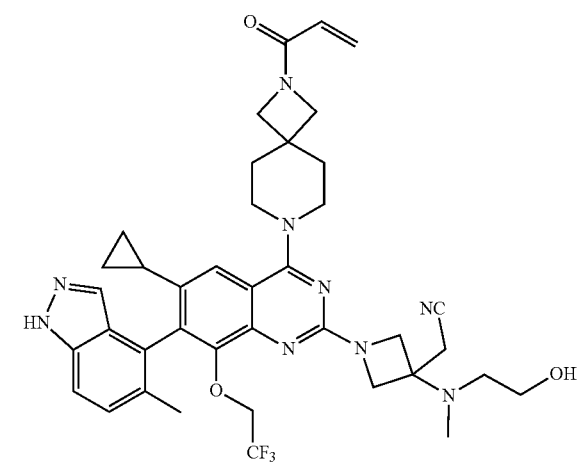

55
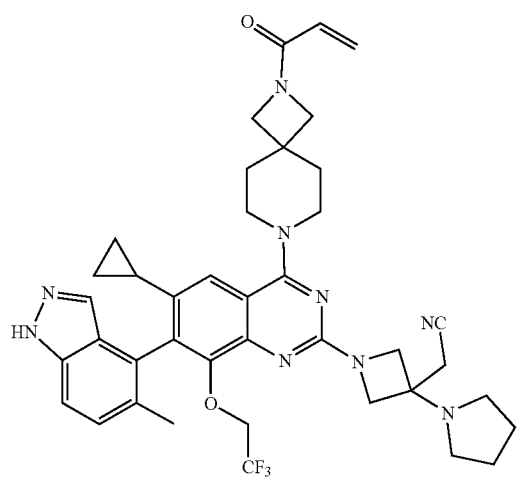
56
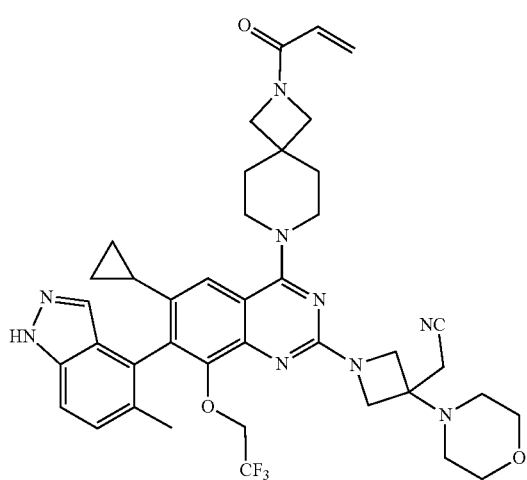
57
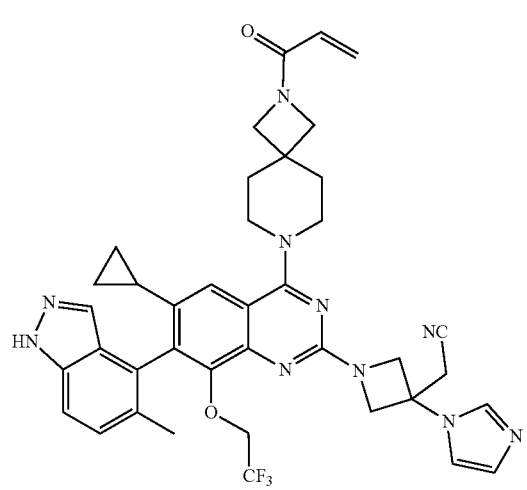
58
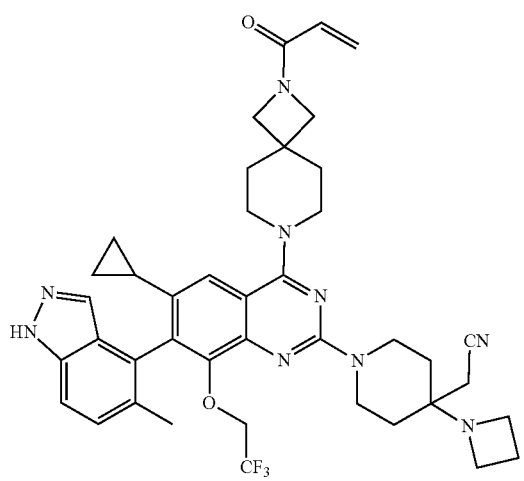
59
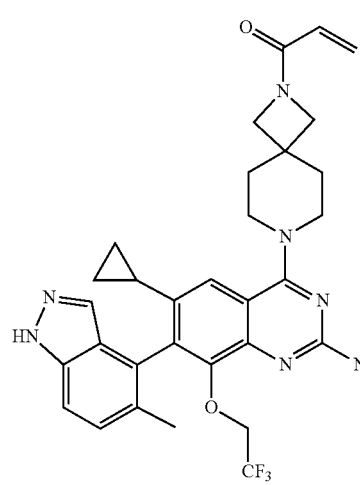
60
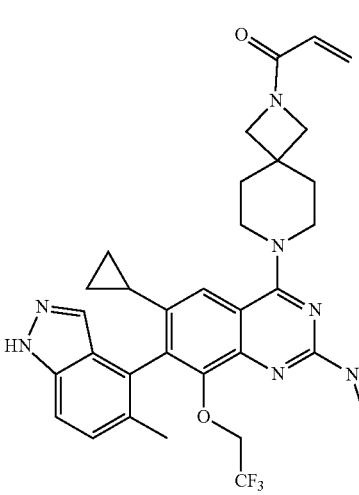

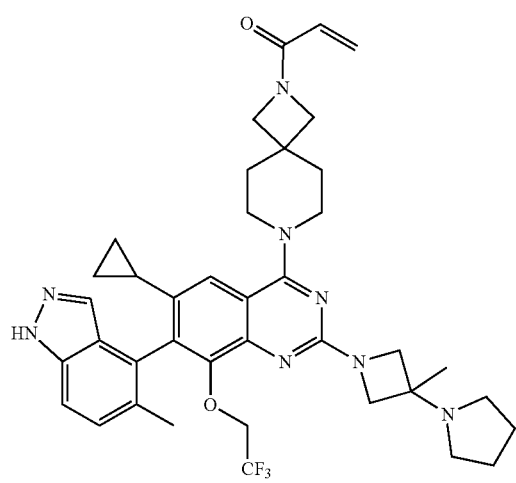
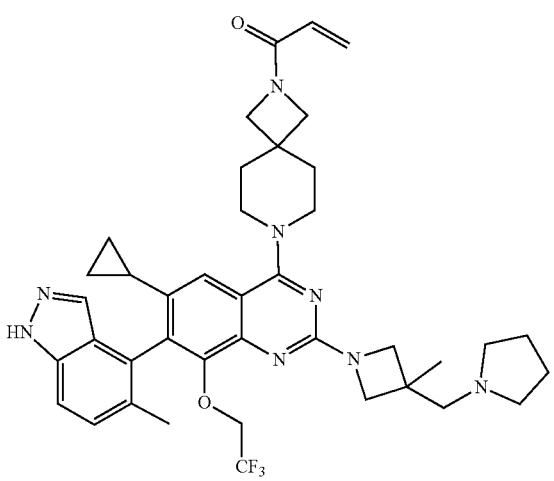

67
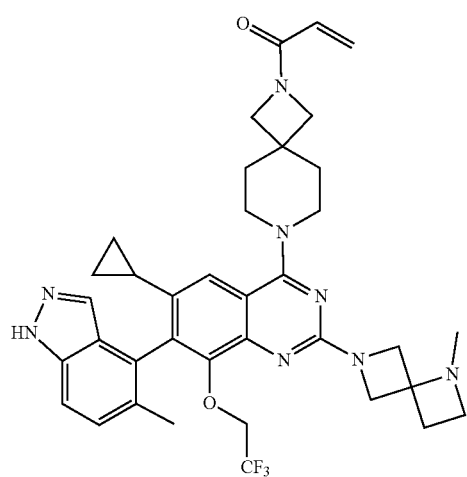
70
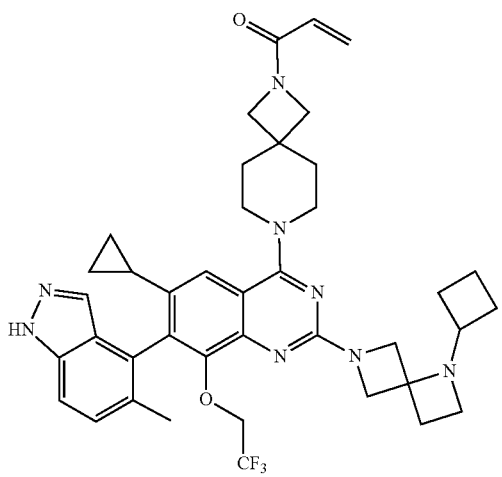
68
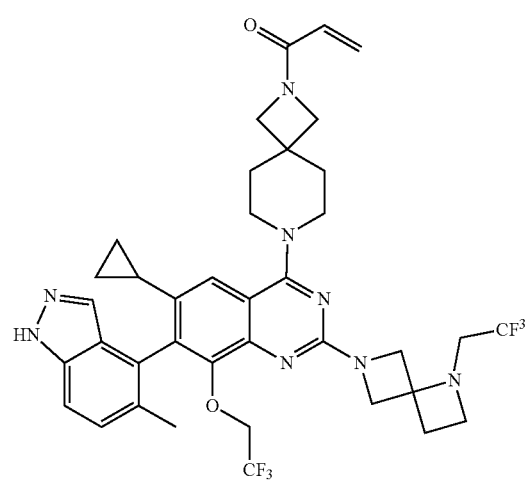
71
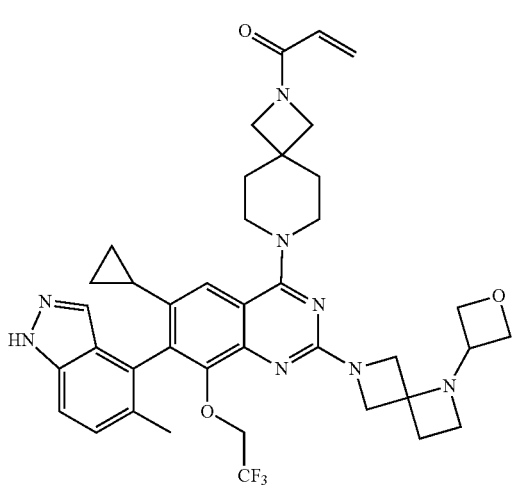
69
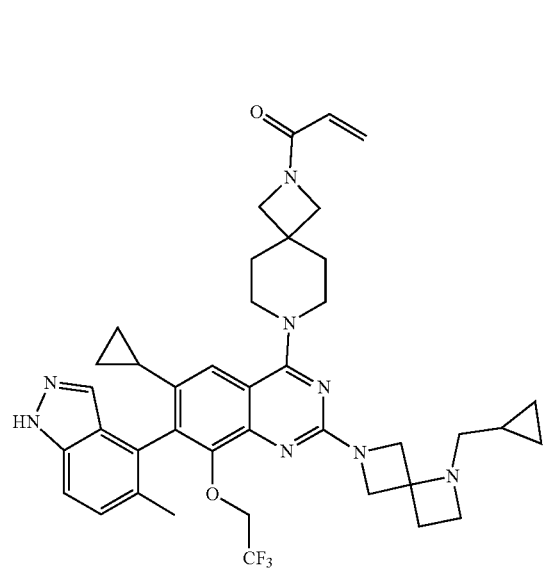
72
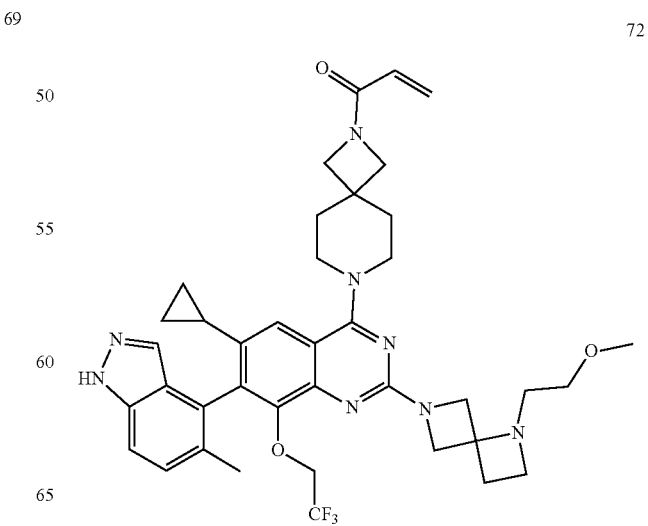

73
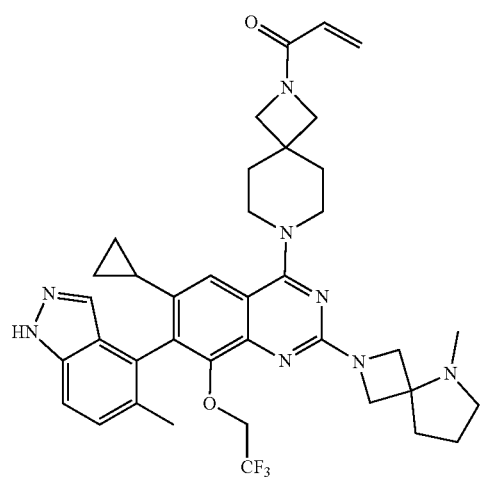
74
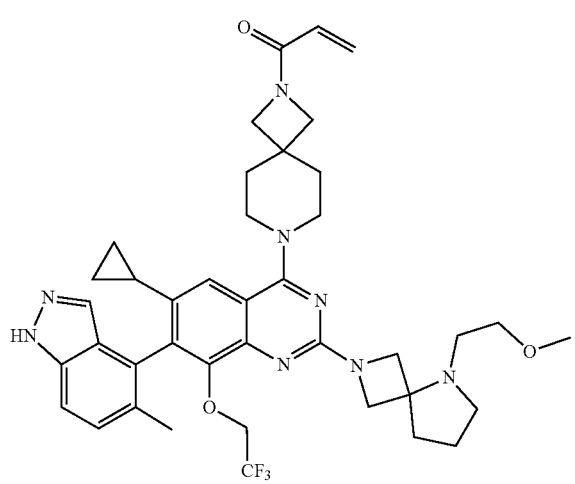
75
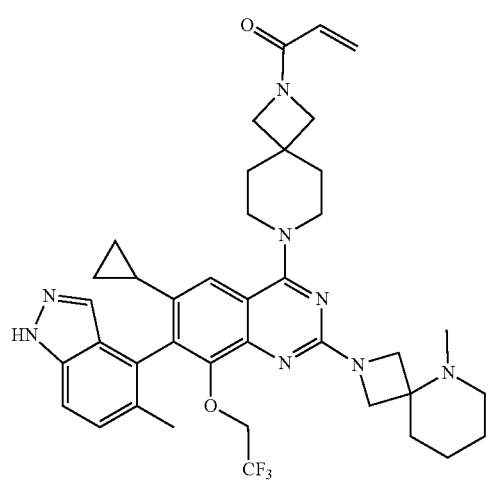
76
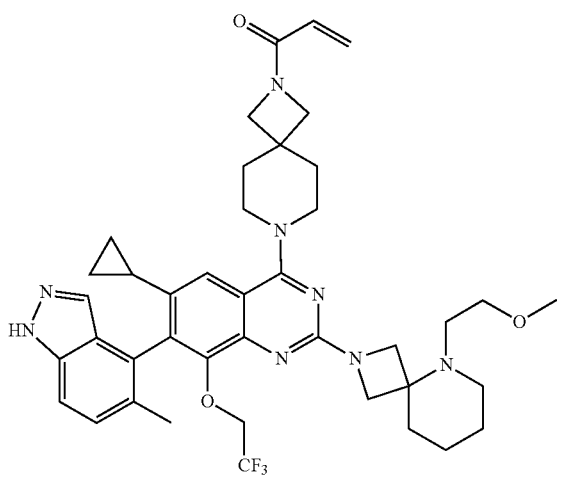
77
78

47
-continued
79
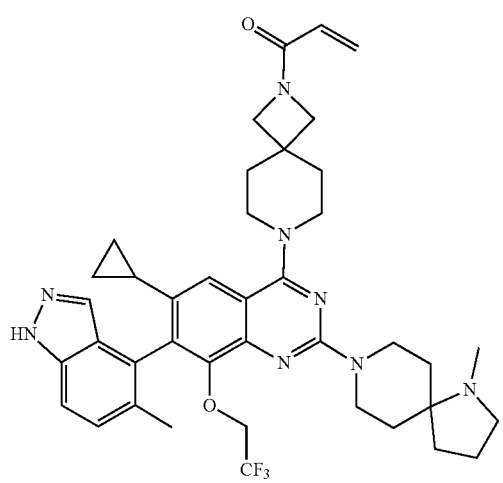
80
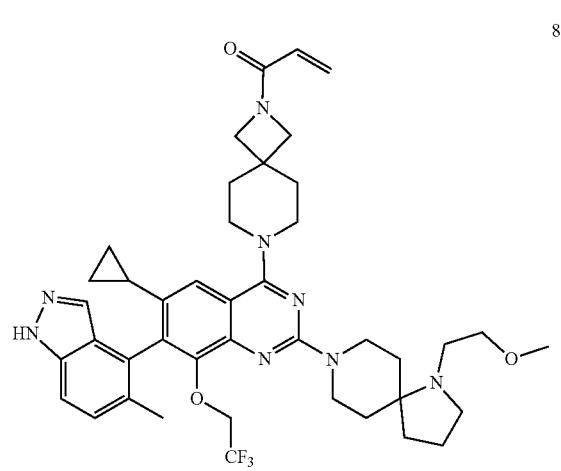
81
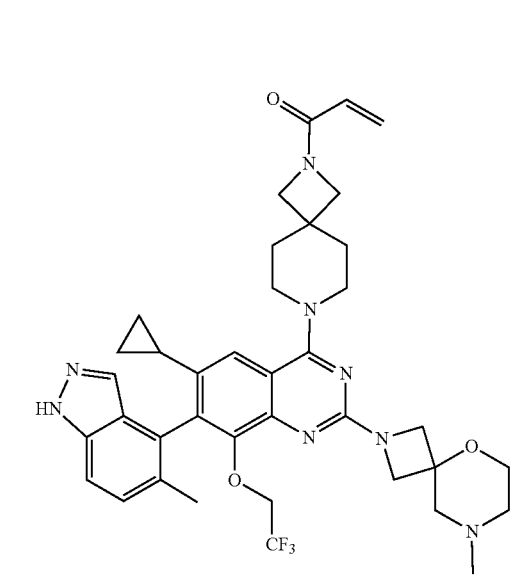
48
-continued
82
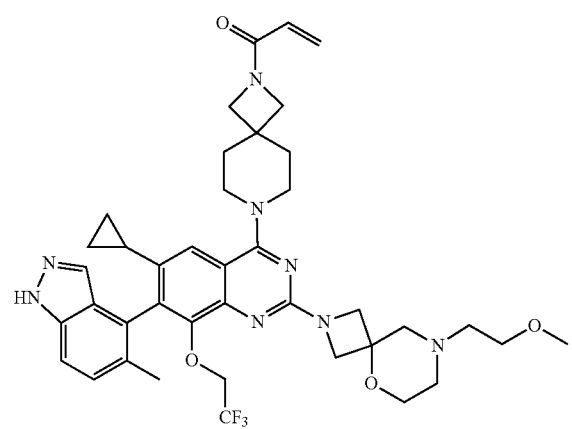
83
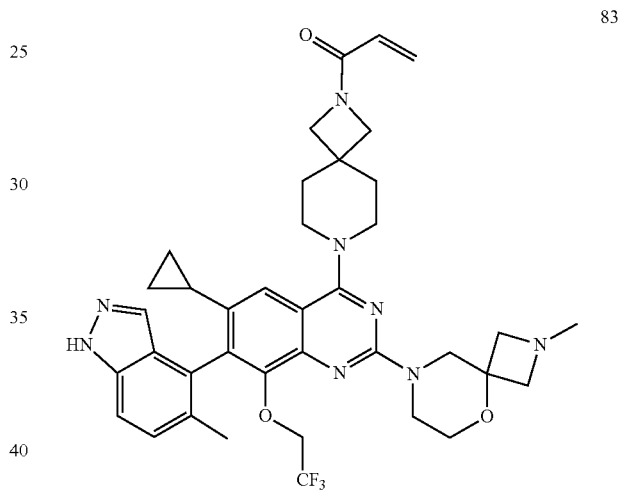
84
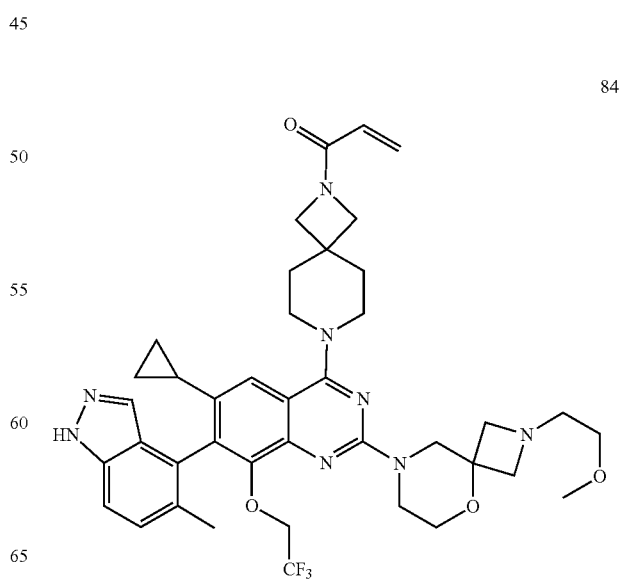

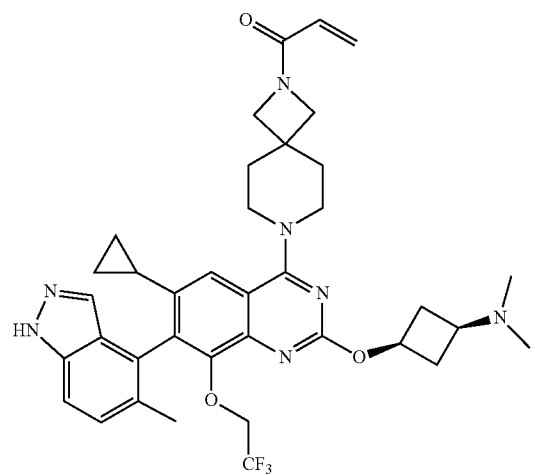
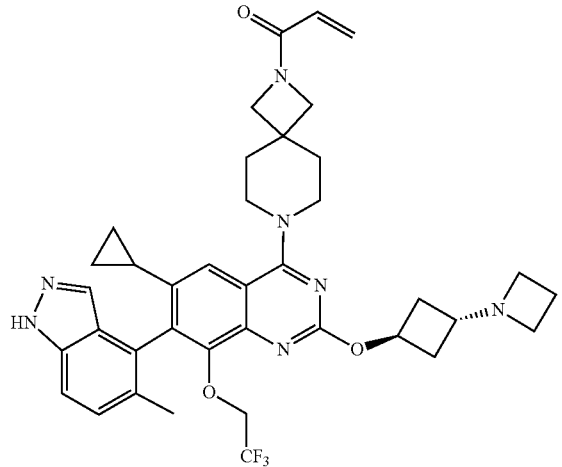

-continued
91
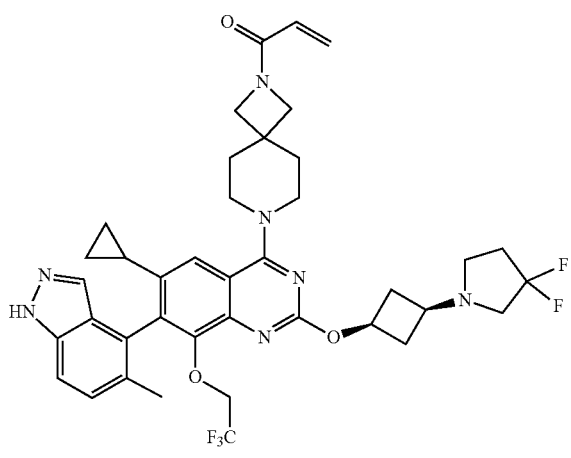
92
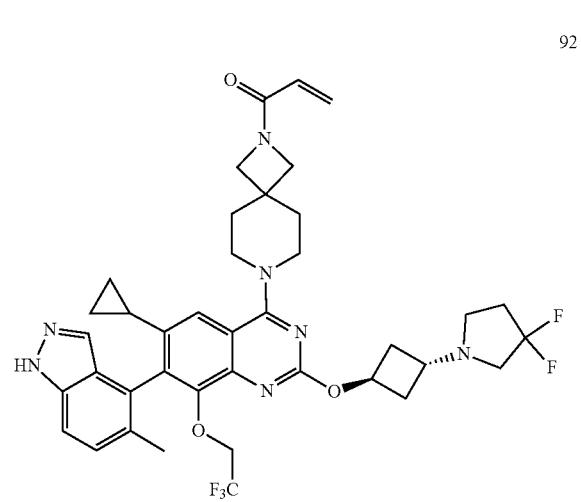
93
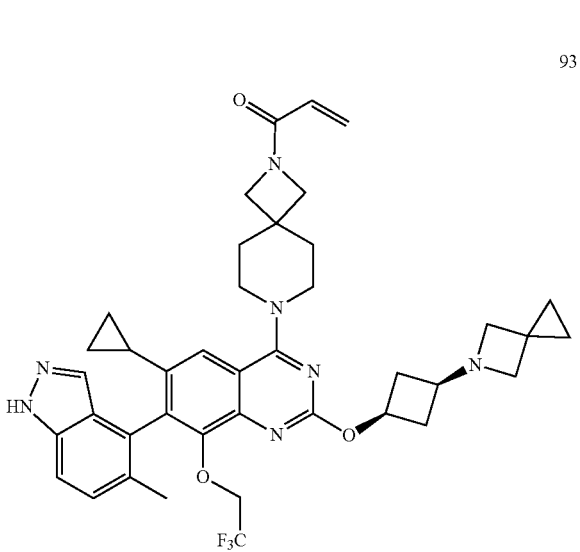
-continued
94
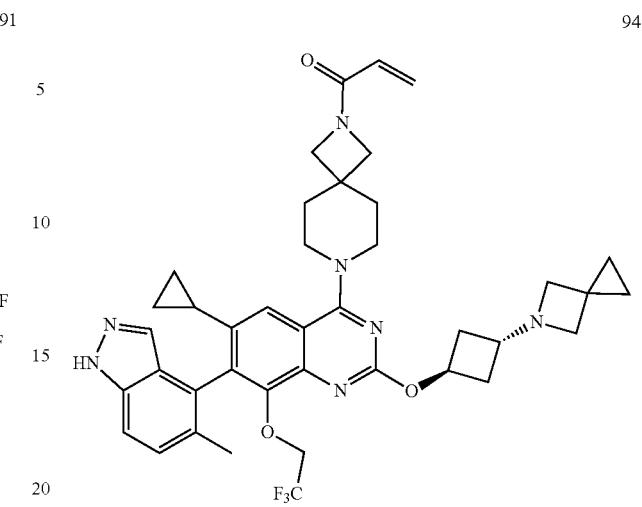
95
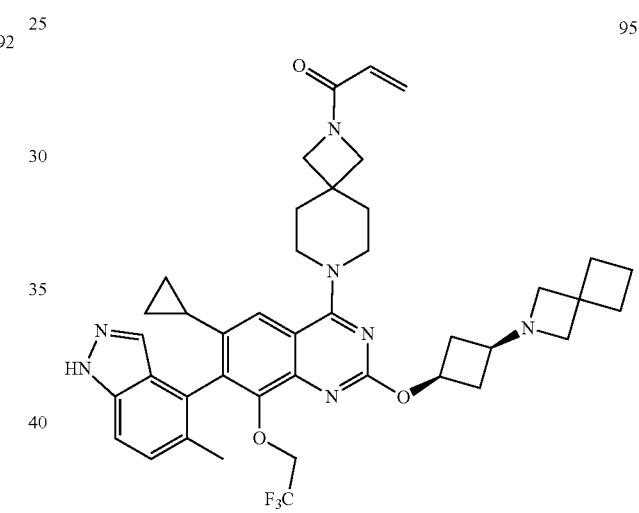
96
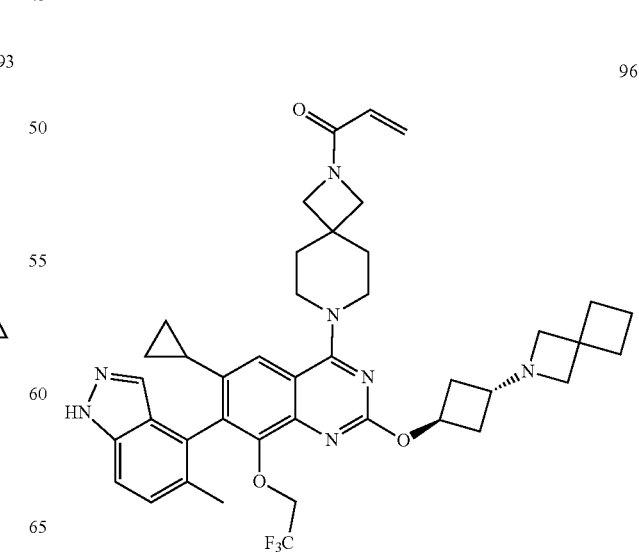

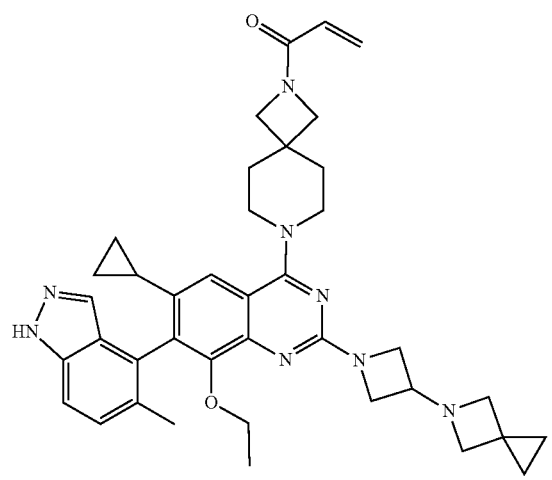
97
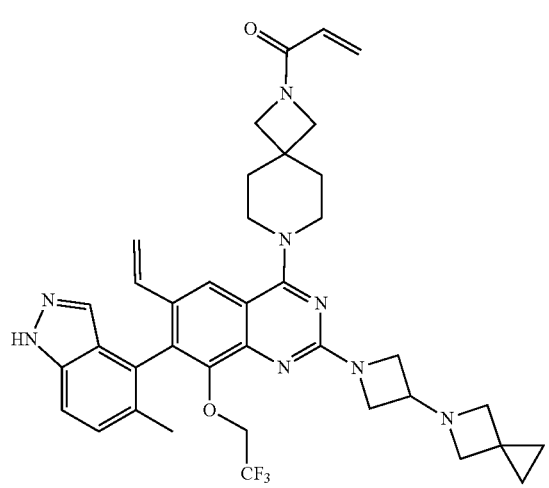
100
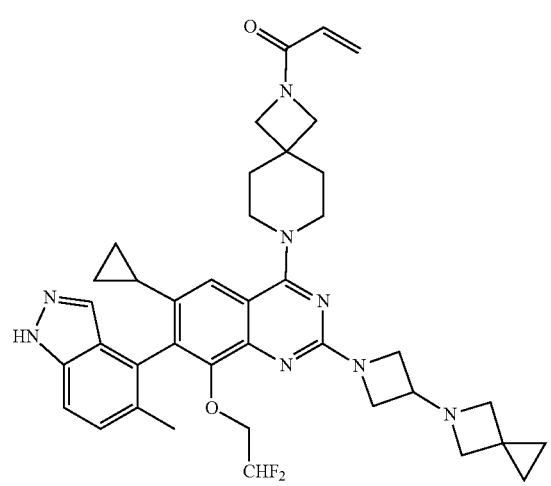
98
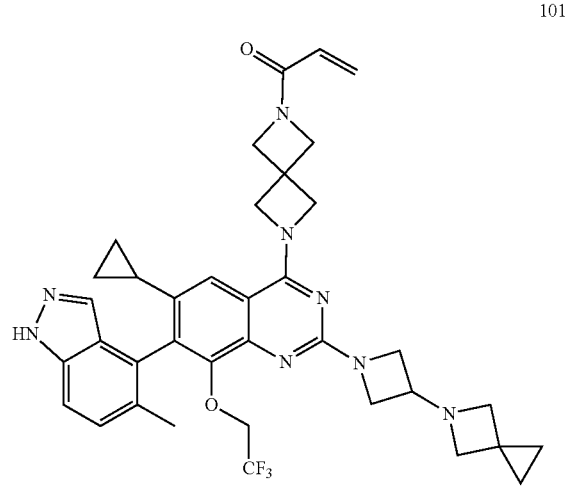
101
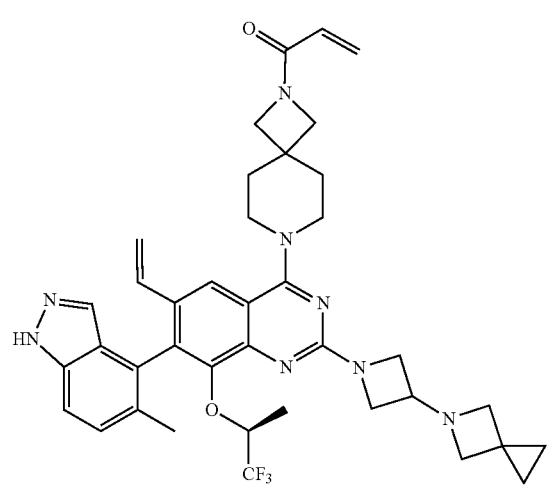
99
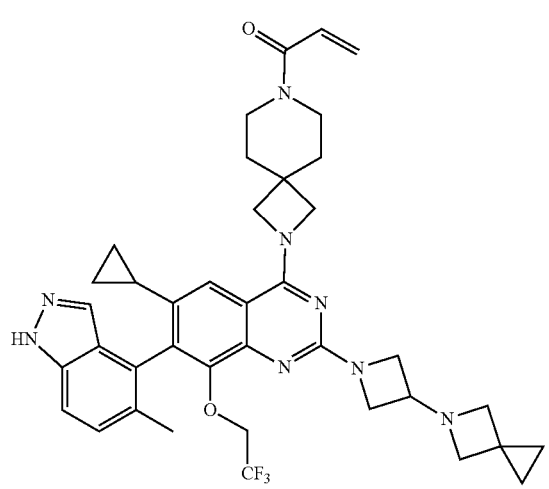
102

103
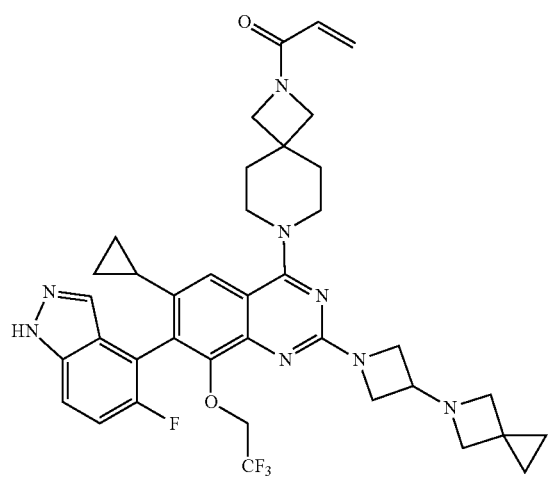
106
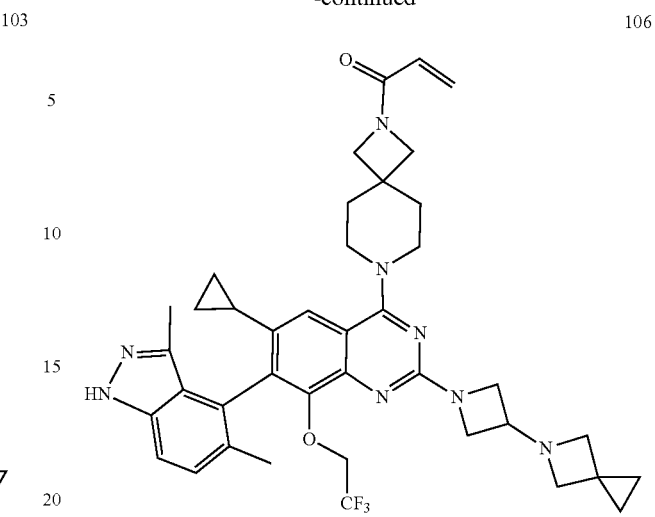
104
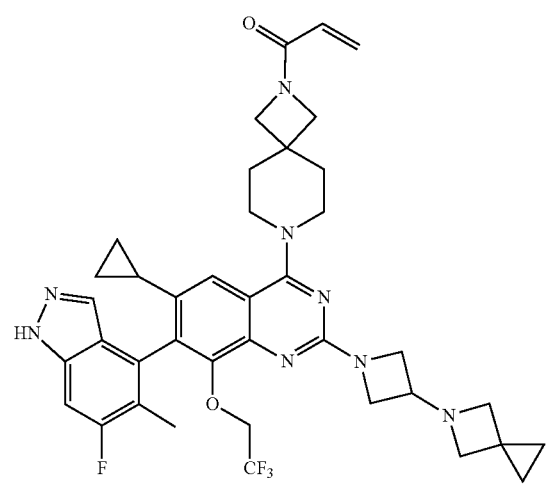
107
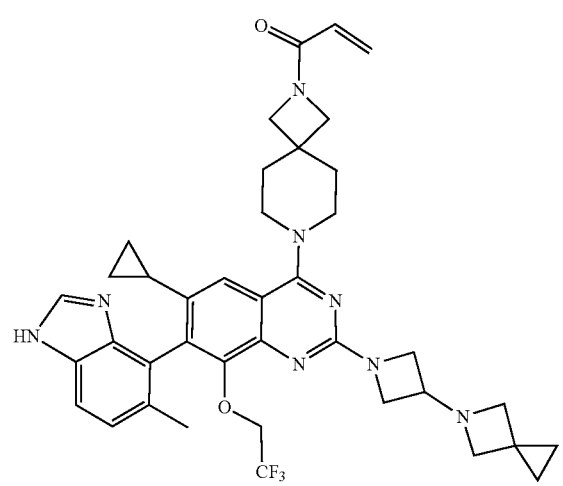
105
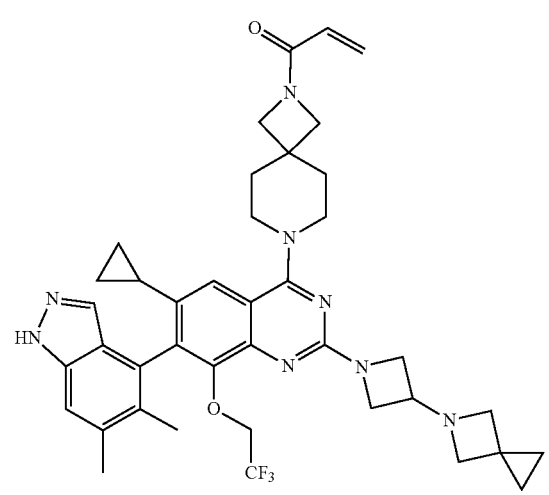
108
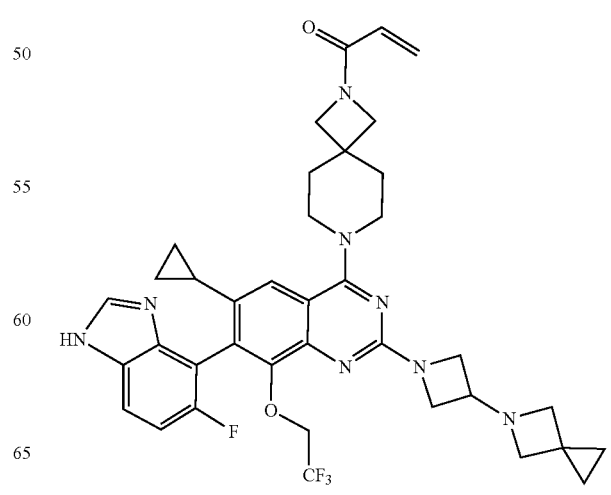

109 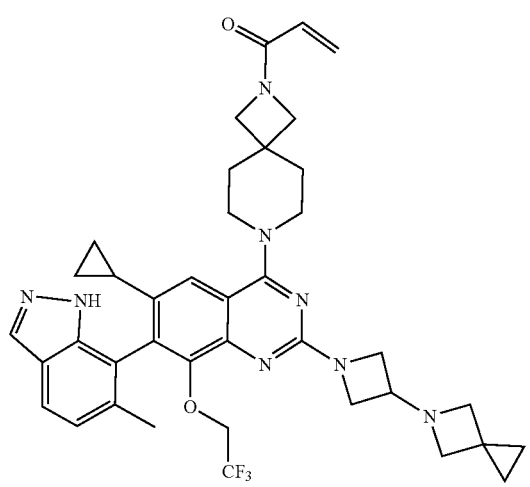
110 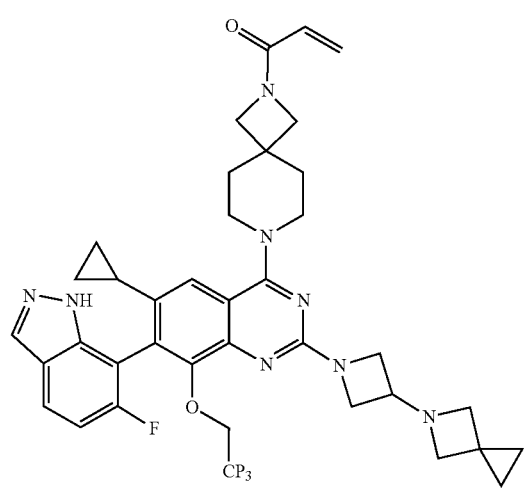
111 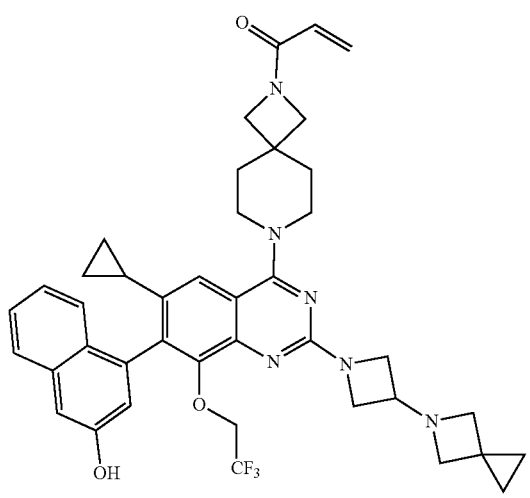
112 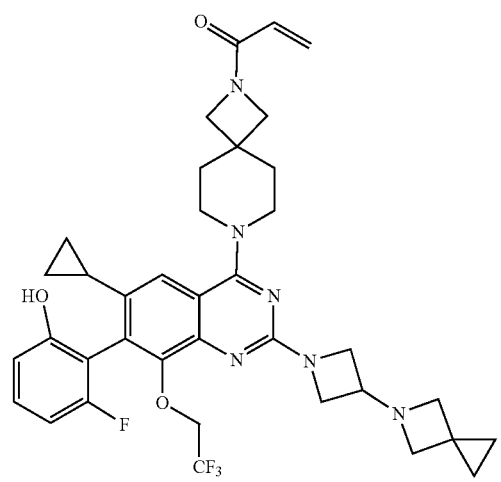
113 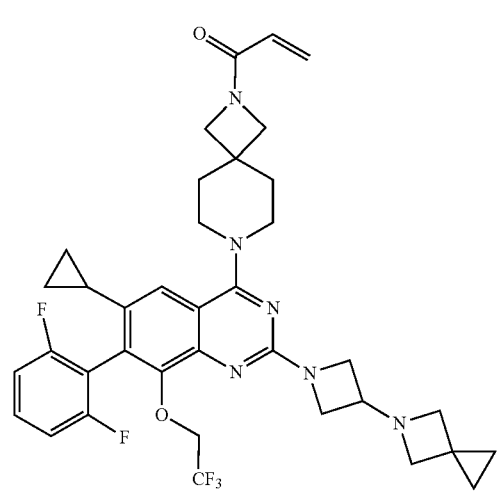
114 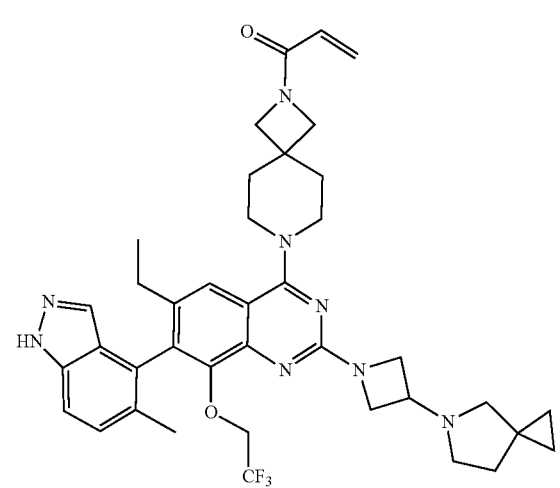

115 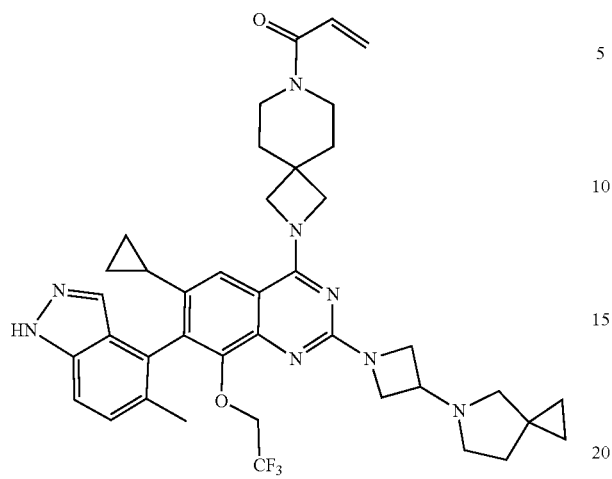
116 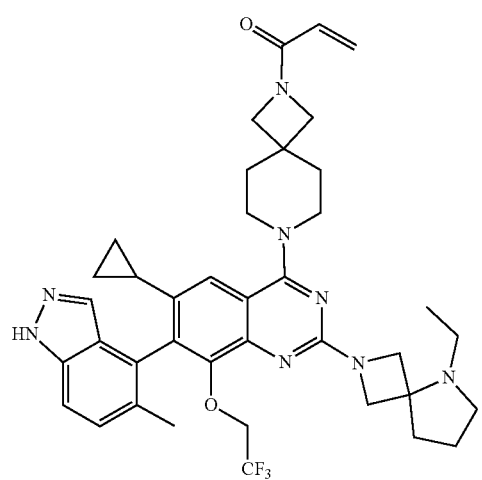
117 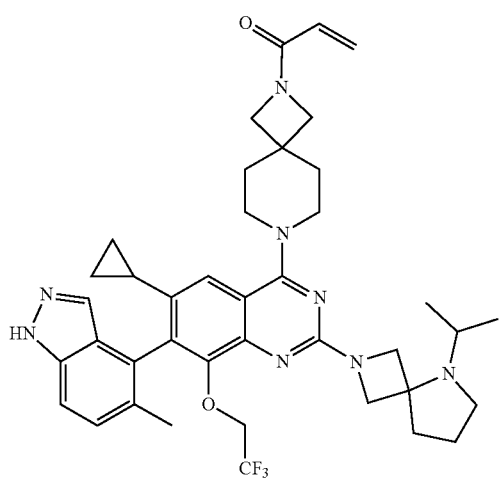
118 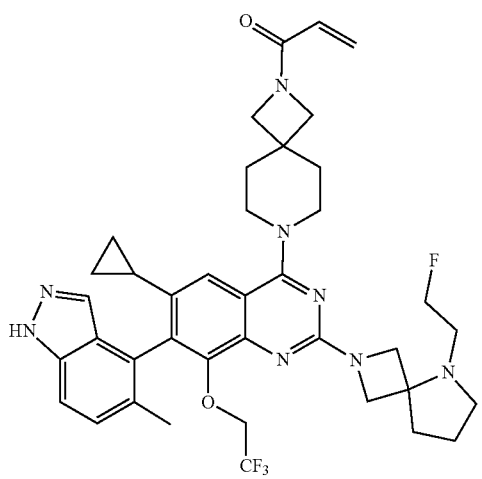
119 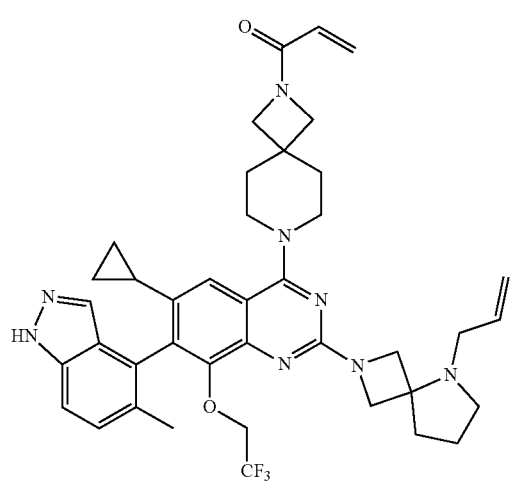
120 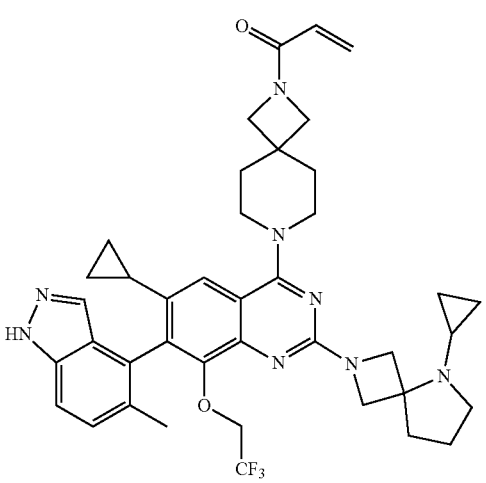

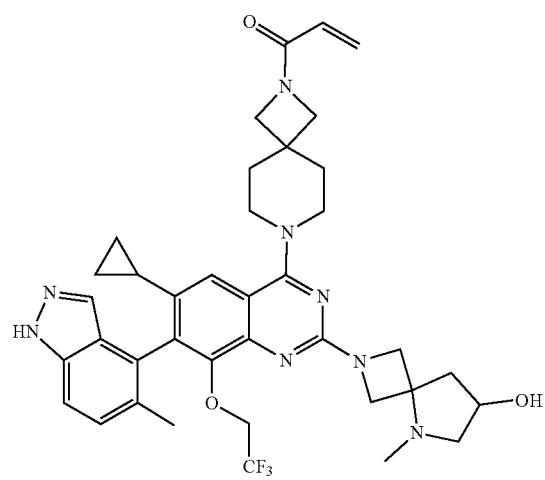
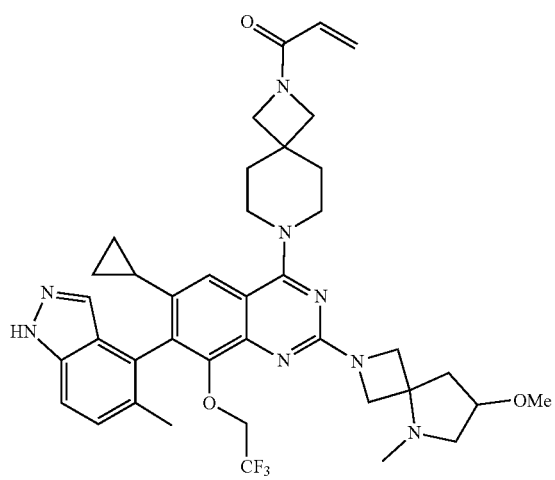

127
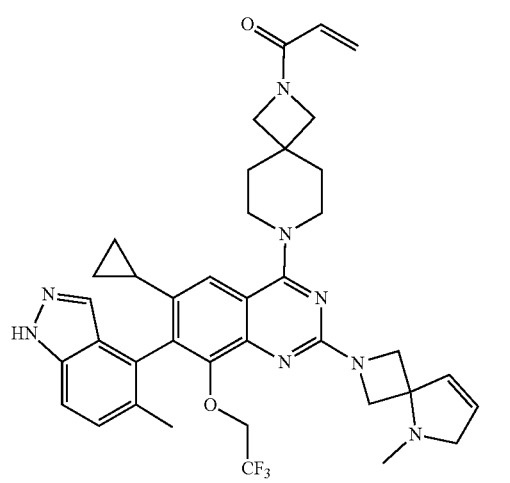
128
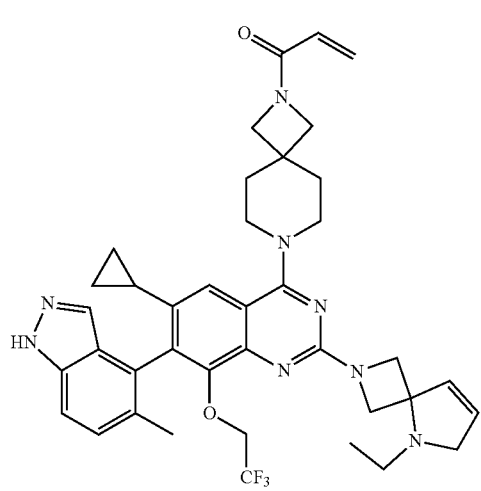
129
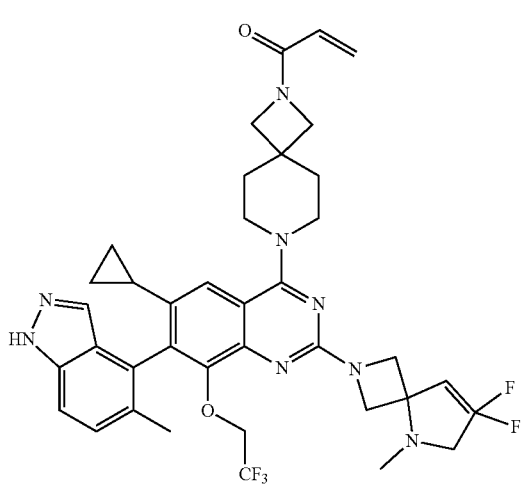
130
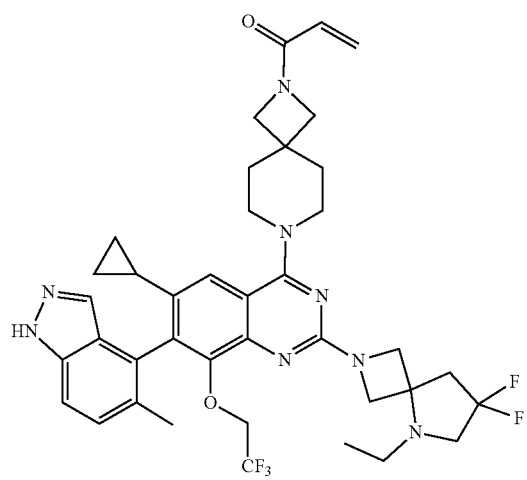
131
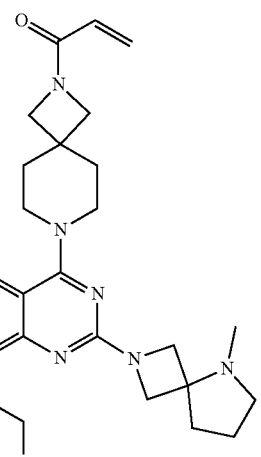
or
132
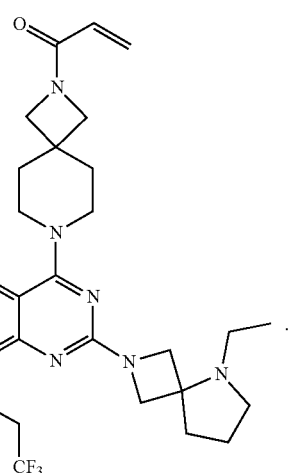
Another object of the present invention is to provide a pharmaceutical composition comprising a pharmaceutically acceptable excipient or carrier, and the compound of general formula (1) or the isomers, crystalline forms, pharmaceutically acceptable salts, hydrates or solvates thereof of the present invention as active ingredients.

The present invention also provides use of the compound of general formula (1) or isomers, crystalline forms, pharmaceutically acceptable salts, hydrates or solvates thereof, or the pharmaceutical composition described above, in preparing a medicament for treating, regulating and/or preventing a disease related to a K-Ras G12C mutant protein.

Still another object of the present invention is to provide a method for treating a disease mediated by a K-Ras G12C mutation, which comprises administering to a subject the above compound of general formula (1) or the isomers, crystalline forms, pharmaceutically acceptable salts, hydrates or solvates thereof of the present invention, or the above pharmaceutical composition of the present invention. The disease mediated by a K-Ras G12C mutation may be hematological cancer and a solid tumor.

Through synthesis and careful studies on various novel compounds with K-RAS G12C inhibitory effects, the inventors found that the compound of general formula (1) has strong inhibitory activity against K-RAS G12C when $R^4$ is a non-aromatic heterocyclic ring or a spiro ring. In addition, the compound also shows strong in vivo antitumor activity in the evaluation of antitumor activity in mice.

It should be understood that both the above general description and the following detailed description of the present invention are exemplary and explanatory, and are intended to provide further explanation of the present invention claimed.

Synthesis of the Compounds

Methods for preparing the compounds of general formulas (1) of the present invention are hereafter described in detail, but these specific methods do not limit the present invention in any way.

The compounds of general formulas (1) described above may be synthesized using standard synthetic techniques or well-known techniques in combination with the methods described herein. In addition, solvents, temperatures and other reaction conditions mentioned herein may vary. Starting materials for the synthesis of the compounds may be obtained synthetically or commercially. The compounds described herein and other related compounds having different substituents may be synthesized using well-known techniques and starting materials, including the methods found in March, ADVANCED ORGANIC CHEMISTRY, 4th Ed., (Wiley 1992); Carey and Sundberg, ADVANCED ORGANIC CHEMISTRY, 4th Ed., Vols. A and B (Plenum 2000, 2001), and Green and Wuts, PROTECTIVE GROUPS IN ORGANIC SYNTHESIS, 3rd Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention also provides a method for preparing the compounds of general formulas (1), which are prepared using general reaction scheme 1 below:

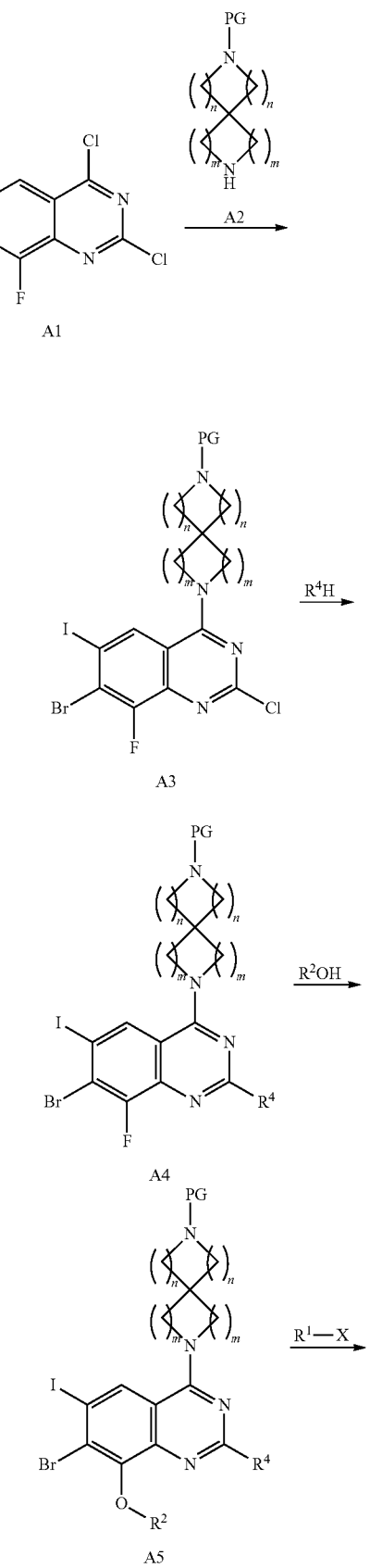

General reaction scheme 1

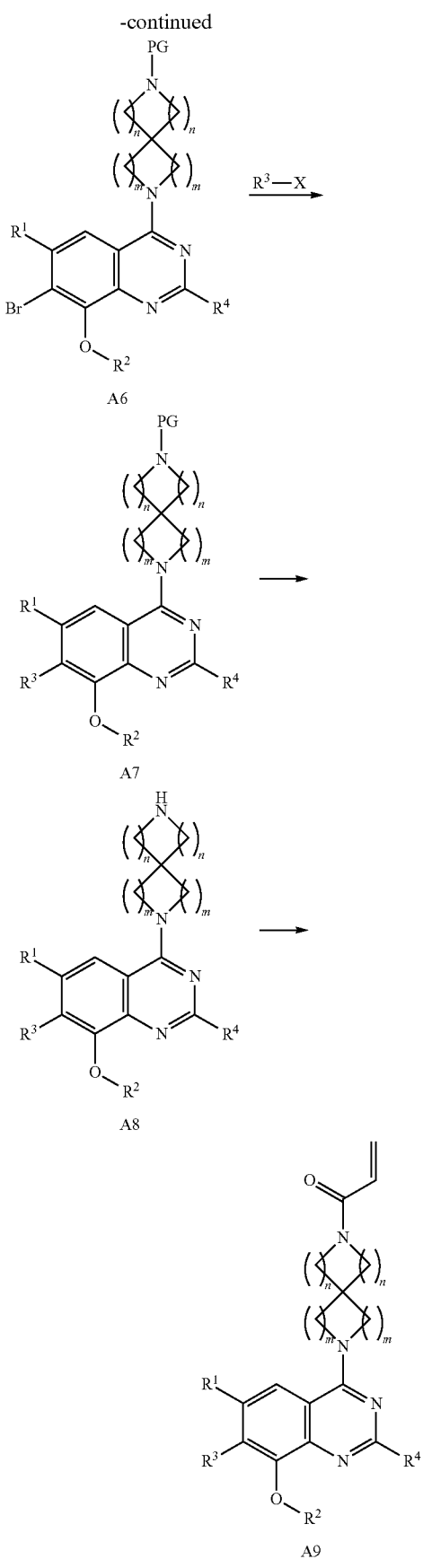

In an embodiment of the compound of general formula (1), the preparation may be performed according to general reaction scheme 1, wherein m, n, $R^1$, $R^2$, $R^3$ and $R^4$ are defined as above, PG represents a protecting group, and X represents boric acid, a borate or a trifluoroborate. As shown in general reaction scheme 1, compound A1 (synthesized according to WO2018/143315) is reacted with compound A2 under basic conditions to give compound A3, compound A3 is reacted with $R^4$H under basic conditions to give compound A4, compound A4 is reacted with $R^2$OH under basic conditions to give compound A5; compound A5 and $R^1$—X are subjected to a coupling reaction to give compound A6, and compound A6 and $R^3$—X are subjected to another coupling reaction to give compound A7; the protecting group is removed from compound A7 to give compound A8, and compound A8 is reacted with acryloyl chloride or acrylic anhydride to give the target compound A9.

Further Forms of Compounds

"Pharmaceutically acceptable" herein refers to a substance, such as a carrier or diluent, which will not cause a compound to lose its biological activity or properties. It is relatively non-toxic; for example, when an individual is given a substance, it will not cause unwanted biological effects or interact with any component contained therein in a deleterious manner.

The term "pharmaceutically acceptable salt" refers to a form of a compound that does not cause significant irritation to the organism for drug administration or eliminate the biological activity and properties of the compound. In certain specific aspects, pharmaceutically acceptable salts are obtained by reacting the compounds of general formulas (1) with acids, e.g. inorganic acids such as hydrochloric acid, hydrobromic acid, hydrofluoric acid, sulfuric acid, phosphoric acid and nitric acid, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid and p-toluenesulfonic acid, and acidic amino acids such as aspartic acid and glutamic acid.

It should be understood that references to pharmaceutically acceptable salts include solvent addition forms or crystal forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. The solvates of the compounds of general formulas (1) are conveniently prepared or formed according to the methods described herein. For example, the hydrates of the compounds of general formulas (1) are conveniently prepared by recrystallization from a mixed solvent of water/organic solvent, wherein the organic solvent used includes, but is not limited to, tetrahydrofuran, acetone, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific examples, the compounds of general formulas (1) are prepared into different forms, including but not limited to amorphous, pulverized and nanoparticle forms. In addition, the compound of general formula (1) includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compounds of general formulas (1) have axial chiralities and/or chiral centers and thus occur in the form of a racemate, racemic mixture, single enantiomer, diastereomeric compound and single diastereomer. Each of these axial chiralities will independently produce two optical isomers, and all possible optical isomers, diastereomeric mixtures and pure or partially pure compounds are included within the scope of the present invention. The present invention is meant to include all such isomeric forms of these compounds.

The compound of the present invention may contain an unnatural proportion of atomic isotopes at one or more of the atoms that constitute the compound. For example, the compound may be labeled with radioactive isotopes, such as tritium ($^3$H), iodine-125 ($^{125}$I) and C-14 ($^{14}$C). For another example, a hydrogen atom of the compound may be replaced by deuterium to form a deuterated compound, and the bond formed by deuterium and carbon is firmer than that formed by a common hydrogen atom and carbon. Compared with an undeuterated drug, the deuterated drug generally has the advantages of reducing toxic and side effects, increasing drug stability, enhancing efficacy, prolonging in vivo half-life period of the drug and the like. All isotopic variations of the compound of the present invention, whether radioactive or not, are encompassed within the scope of the present invention.

Terminology

Unless otherwise stated, the terms used in the present application, including those in the specification and claims, are defined as follows. It must be noted that in the specification and the appended claims, the singular forms "a" and "an" include plural meanings unless the context clearly indicates otherwise. Unless otherwise stated, conventional methods of mass spectrometry, nuclear magnetic resonance spectroscopy, HPLC, protein chemistry, biochemistry, recombinant DNA technology and pharmacology are used. In the present application, "or" or "and" is used to mean "and/or" unless otherwise stated.

Unless otherwise specified, "alkyl" refers to a saturated aliphatic hydrocarbon group, including linear and branched groups containing 1 to 6 carbon atoms. Lower alkyl containing 1 to 4 carbon atoms, such as methyl, ethyl, propyl, 2-propyl, n-butyl, isobutyl or tert-butyl, is preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH$, $^iPr$, $^nPr$, $^iBu$, $^nBu$ and $^tBu$.

Unless otherwise specified, "alkenyl" refers to an unsaturated aliphatic hydrocarbon group containing carbon-carbon double bonds, including linear and branched groups containing 1 to 6 carbon atoms. Lower alkenyl containing 1 to 4 carbon atoms, such as vinyl, 1-propenyl, 1-butenyl or 2-methylpropenyl, is preferred.

Unless otherwise specified, "alkynyl" refers to an unsaturated aliphatic hydrocarbon group containing carbon-carbon triple bonds, including linear and branched groups containing 1 to 6 carbon atoms. Lower alkenyl containing 1 to 4 carbon atoms, such as ethynyl, 1-propynyl or 1-butynyl, is preferred.

Unless otherwise specified, "cycloalkyl" refers to a 3- to 6-membered all-carbon monocyclic aliphatic hydrocarbon group, wherein one or more of the rings may contain one or more double bonds, but none of them has a fully conjugated π-electron system. For example, cyclopropyl, cyclobutyl, cyclopentyl, cyclohexane, and cyclohexadiene.

Unless otherwise specified, "alkoxy" refers to an alkyl group that bonds to the rest of the molecule through an ether oxygen atom. Representative alkoxy groups are ones having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^iPrO$, $^nPrO$, $^iBuO$, $^nBuO$ and $^tBuO$.

Unless otherwise specified, "heteroaryl" refers to an aromatic group containing one or more heteroatoms (O, S or N) and it is monocyclic or polycyclic; for example, a monocyclic heteroaryl ring fuses with one or more carbocyclic aromatic groups or other monocyclic heterocyclyl groups. Examples of heteroaryl include, but are not limited to, pyridyl, pyridazinyl, imidazolyl, pyrimidinyl, pyrazolyl, triazolyl, pyrazinyl, quinolinyl, isoquinolinyl, tetrazolyl, furyl, thienyl, isoxazolyl, thiazolyl, oxazolyl, isothiazolyl, pyrrolyl, indolyl, benzimidazolyl, benzofuryl, benzothiazolyl, benzothienyl, benzoxazolyl, benzopyridyl, and pyrrolopyrimidinyl.

Unless otherwise specified, "heterocycloalkyl" refers to a saturated or partially unsaturated ring system group containing one or more heteroatoms (O, S or N), wherein the nitrogen and sulfur atoms are optionally oxidized, and the nitrogen atom is optionally quaternized as a ring atom. Unless otherwise stated, the "heterocycloalkyl" ring system may be a monocyclic, bicyclic, spiro or polycyclic ring system. "Heterocycloalkyl" may link to the rest of the molecule through one or more ring carbons or heteroatoms. Examples of "heterocycloalkyl" include, but are not limited to, pyrrolidine, piperidine, N-methylpiperidine, tetrahydroimidazole, pyrazolidine, butyrolactam, valerolactam, imidazolidinone, hydantoin, dioxolane, phthalimide, pyrimidine-2,4(1H,3H)-dione, 1,4-dioxane, morpholine, thiomorpholine, thiomorpholine-S-oxide, thiomorpholine-S, S-oxide, piperazine, pyran, pyridone, 3-pyrroline, thiopyran, pyrone, tetrahydrofuran, tetrahydrothiophene, quinuclidine, 2-azaspiro[3.3]heptane, etc. Unless otherwise specified, "halogen" (or halo) refers to fluorine, chlorine, bromine, or iodine. The term "halo" (or "halogenated") before a group name indicates that the group is partially or fully halogenated, that is, substituted in any combination by F, Cl, Br or I, preferably by F or Cl.

Specific Pharmaceutical and Medical Terminology

The term "acceptable", as used herein, means that a formula component or an active ingredient does not unduly adversely affect a general therapeutic target's health.

The terms "treatment," "treatment course," or "therapy", as used herein, include alleviating, inhibiting, or ameliorating a symptom or condition of a disease; inhibiting the development of complications; ameliorating or preventing underlying metabolic syndrome; inhibiting the development of the disease or symptom, e.g., controlling the progression of the disease or condition; alleviating the disease or symptom; causing the disease or symptom to subside; alleviating a complication caused by the disease or symptom, or preventing or treating a sign caused by the disease or symptom. As used herein, a compound or pharmaceutical composition, when administered, can ameliorate a disease, symptom, or condition, particularly meaning ameliorating the severity, delaying the onset, slowing the progression, or reducing the duration of the disease. Fixed or temporary administration, or continuous or intermittent administration, may be attributed to or associated with the administration.

The "active ingredient" refers to compounds of general formulas (1) through (3), and pharmaceutically acceptable inorganic or organic salts of the compounds of general formulas (1) through (3). The compounds of the present invention may contain one or more asymmetric centers (axial chirality) and thus occur in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), is capable of inducing a desired pharmacological and/or physiological response by local and/or systemic action.

The term "administered, administering or administration" refers herein to the direct administration of the compound or composition, or the administration of a prodrug, derivative, analog or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range±10%, 5%, 1%, or 0.5%. Alternatively, the term "about" indicates that the actual value falls within the acceptable standard error of a mean, as considered by those skilled in the art. All ranges, quantities, values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be construed as the significant digits indicated or the numerical value obtained using conventional rounding rules.

Unless otherwise defined in the specification, the scientific and technical terms used herein have the same meaning as commonly understood by those skilled in the art. Furthermore, the singular nouns used in the specification encompass their plural forms, unless contradicted by context; the plural nouns used also encompass their singular forms.

Therapeutic Use

The present invention provides a method for using the compound or pharmaceutical composition of the present invention to treat diseases, including but not limited to conditions involving G12C K-Ras, G12C H-Ras and/or G12C N-Ras mutations (e.g., cancer).

In some embodiments, a method for treating cancer is provided, the method comprising administering to an individual in need thereof an effective amount of a pharmaceutical composition of any of the aforementioned compounds of structural general formulas (1) through (3) protected. In some embodiments, the cancer is mediated by K-Ras, H-Ras and/or G12C N-Ras mutations. In other embodiments, the cancer is lung cancer, pancreatic cancer, colon cancer, MYH-associated polyposis, or colorectal cancer.

Route of Administration

The compound and the pharmaceutically acceptable salt thereof of the present invention can be prepared into various preparations which include the compound or the pharmaceutically acceptable salt thereof disclosed herein in a safe and effective amount range and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound of the present invention and with each other, without significantly diminishing the pharmaceutical efficacy of the compound. Examples of pharmaceutically acceptable excipients or carriers are cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water, etc. When the compound of the present invention is administered, it may be administered orally, rectally, parenterally (intravenously, intramuscularly or subcutaneously) or topically.

Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may also include buffers.

Solid dosage forms such as tablets, dragees, capsules, pills and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, groundnut oil, corn germ oil, olive oil, castor oil and sesame oil, or mixtures of these substances.

Besides such inert diluents, the composition may also include adjuvants, such as wetting agents, emulsifiers, suspending agents, sweeteners, flavoring agents, and perfuming agents. Suspensions, in addition to the active compound, may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound of the present invention include ointments, pulvises, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds.

When the pharmaceutical composition is used, a safe and effective amount of the compound of the present invention is administered to a mammal (such as a human) to be treated, wherein the administration dose is a pharmaceutically effective administration dose. For a human weighing 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise expressly stated, the features disclosed are merely general examples of equivalent or similar features.

DETAILED DESCRIPTION

Various specific aspects, features and advantages of the compounds, methods and pharmaceutical compositions described above are set forth in detail in the following description, which makes the present invention clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, 1H-NMR spectra were recorded with a Vian Mercury 400 nuclear magnetic resonance spectrometer, and chemical shifts are expressed in δ (ppm); silica gel for separation was 200-300 mesh silica gel if not specified, and the ratio of the eluents was volume ratio.

In the present invention, the following abbreviations are used: MeCN represents acetonitrile; DCM represents dichloromethane; DIPEA represents diisopropylethylamine; dioxane represents 1,4-dioxane; DMF represents dimethylformamide; h represents hour; $K_3PO_4$ represents potassium phosphate; min represents minute; MS represents mass spectroscopy; NaH represents sodium hydride; NMR represents nuclear magnetic resonance; $Pd_2(dba)_3$ represents tris(dibenzylideneacetone)dipalladium; $Pd(dppf)Cl_2$ represents [1,1'-bis(diphenylphosphino)ferrocene]palladium dichloride; TFA ($CF_3COOH$) represents trifluoroacetic acid; TLC represents thin layer chromatography; THF represents tetrahydrofuran; and Xantphos represents 4,5-bis(diphenylphosphane)-9,9-dimethylxanthene.

Example 1 Synthesis of 1-(7-(6-cyclopropyl-2-(3-((dimethylamino)methyl)azetidin-1-yl)-7-(5-methyl-1H-indazol-4-yl)-8-(2,2,2-trifluoroethoxy)quinazolin-4-yl)-2,7-diazaspiro[3.5]non-2-yl)prop-2-en-1-one (Compound 1)

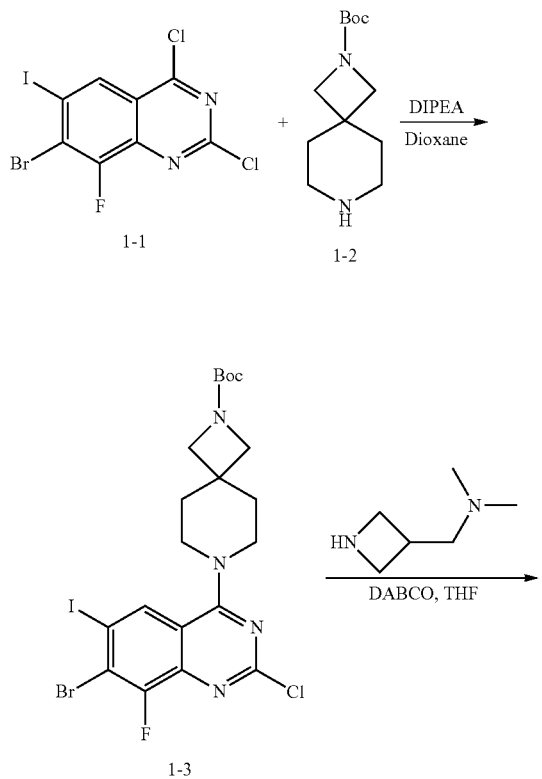

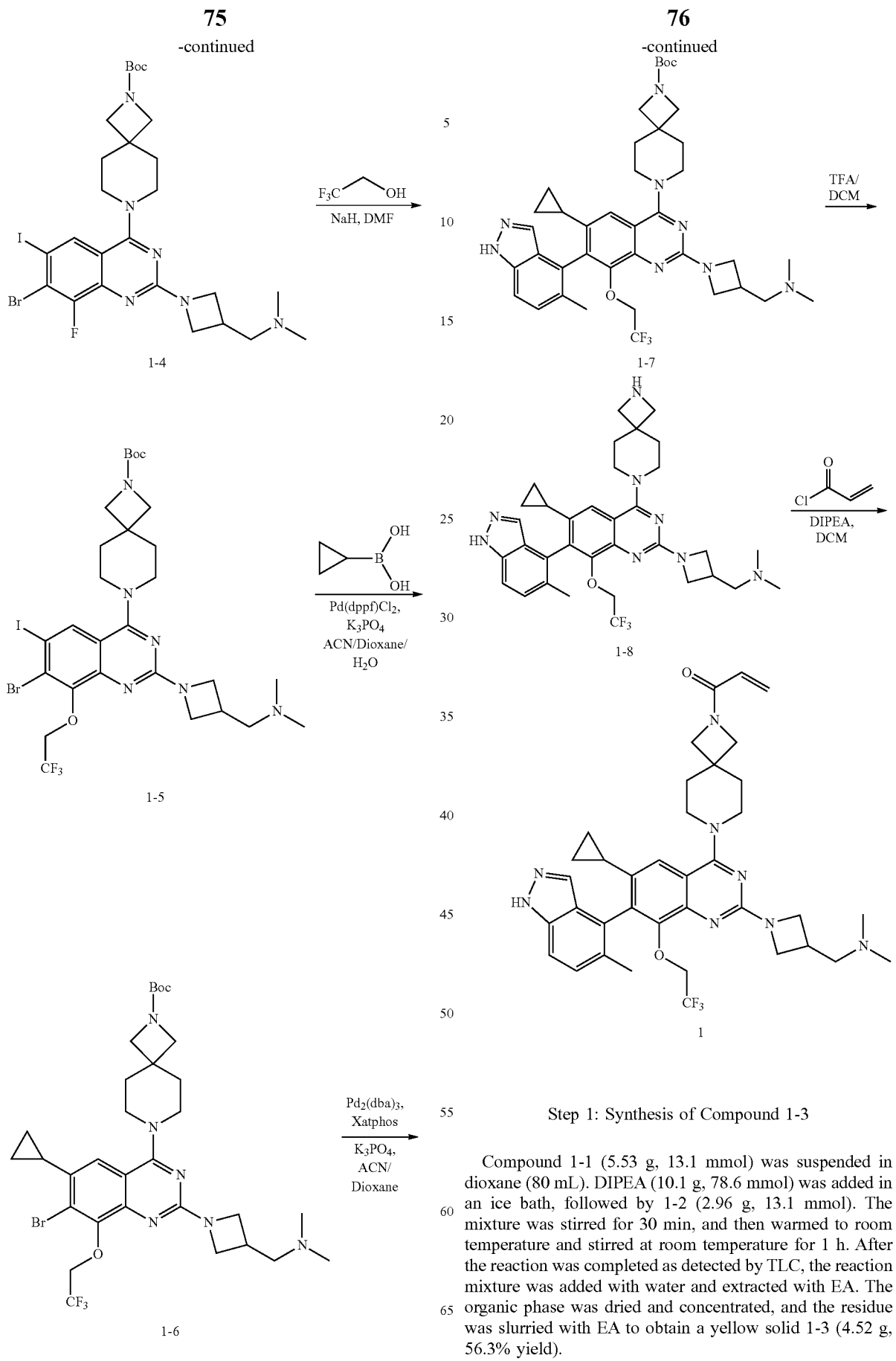

Step 1: Synthesis of Compound 1-3

Compound 1-1 (5.53 g, 13.1 mmol) was suspended in dioxane (80 mL). DIPEA (10.1 g, 78.6 mmol) was added in an ice bath, followed by 1-2 (2.96 g, 13.1 mmol). The mixture was stirred for 30 min, and then warmed to room temperature and stirred at room temperature for 1 h. After the reaction was completed as detected by TLC, the reaction mixture was added with water and extracted with EA. The organic phase was dried and concentrated, and the residue was slurried with EA to obtain a yellow solid 1-3 (4.52 g, 56.3% yield).

$^1$H NMR (400 MHz, DMSO-d$_6$) δ: 8.26 (d, J=1.5 Hz, 1H), 3.79 (s, 4H), 3.65 (s, 4H), 1.86 (t, J=5.3 Hz, 4H), 1.39 (s, 9H); MS(ESI): MS (ESI): 611.2 [M+1]$^+$.

Step 2: Synthesis of Compound 1-4

Compound 1-3 (4.28 g, 7.0 mmol) was dissolved in a mixed solution of DMF (40 mL) and THF (40 mL). 1-(azetidin-3-yl)-N,N-dimethylmethylamine (1.60 g, 14.0 mmol) and DABCO (155 mg, 1.4 mmol) were added. The mixture was stirred at room temperature overnight. After the reaction was completed, the reaction mixture was added with water and extracted with EA. The organic phase was dried and concentrated, and the residue was purified by column chromatography to obtain compound 1-4 (3.62 g, 75.1% yield). MS(ESI): 689.2 [M+1]$^+$.

Step 3: Synthesis of Compound 1-5

Trifluoroethanol (0.75 g, 7.5 mmol) was dissolved in anhydrous DMF (10 mL). NaH (60%, 0.60 g, 15.0 mmol) was added in an ice bath. The mixture was stirred at room temperature for 5 min to obtain sodium trifluoroethoxide. Compound 1-4 (3.45 g, 5.0 mmol) was dissolved in anhydrous THF (40 mL). The solution of sodium trifluoroethoxide in DMF prepared above was added. The mixture was stirred at room temperature overnight. After the reaction was completed, the reaction mixture was added with water and extracted with EA. The organic phase was dried and concentrated, and the residue was purified by column chromatography to obtain compound 1-5 (3.54 g, 92.1% yield). MS (ESI): 769.2 [M+1]$^+$.

Step 4: Synthesis of Compound 1-6

To a single-necked flask were added compound 1-5 (3.08 g, 4.0 mmol), cyclopropylboronic acid (0.43 g, 5.0 mmol), Pd(dppf)Cl$_2$ (0.59 g, 0.8 mmol) and K$_3$PO$_4$ (0.85 g, 4.0 mmol), followed sequentially by MeCN (40 mL), dioxane (40 mL) and H$_2$O (16.5 mL). The mixture was stirred under nitrogen atmosphere at 100° C. for 5 h. After the reaction was completed, the reaction mixture was purified by column chromatography to obtain compound 1-6 (1.78 g, 65.2% yield). MS (ESI): 683.3 [M+1]$^+$.

Step 5: Synthesis of Compound 1-7

To a single-necked flask were added compound 1-6 (1.37 g, 2.0 mmol), 5-methyl-1H-indazole-4-boronic acid (0.53 g, 3.0 mmol), Pd$_2$(dba)$_3$ (0.27 g, 0.3 mmol), Xatphos (0.35 g, 0.6 mmol) and K$_3$PO$_4$ (0.85 g, 4.0 mmol), followed by dioxane (30 mL) and H$_2$O (3 mL). The mixture was stirred under nitrogen at 120° C. overnight. After the reaction was completed, the mixture was purified by column chromatography to obtain compound 1-7 (557 mg, 26.4% yield). MS (ESI): 735.4 [M+1]$^+$.

Step 6: Synthesis of Compound 1-8

Compound 1-7 (515 mg, 0.7 mmol) was dissolved in DCM (10 mL). TFA (3 mL) was added. The mixture was stirred at room temperature for 2 h. After the reaction was completed, the reaction mixture was concentrated, basified with saturated sodium carbonate, and extracted with EA. The organic phase was dried and concentrated to obtain compound 1-8 (445 mg, 100% yield). MS(ESI): 635.4 [M+1]$^+$.

Step 7: Synthesis of Compound 1

Compound 1-8 (318 mg, 0.4 mmol) was dissolved in dry DCM (15 mL). DIPEA (65 mg, 0.5 mmol) was added in an ice salt bath, followed by slowly addition of acryloyl chloride (43 mg, 0.48 mmol). The mixture was reacted in an ice bath for 2 h. The reaction mixture was washed with saturated brine. The organic phase was dried and concentrated, and the residue was purified by column chromatography to obtain compound 1 (181 mg, yield 65.8%).

$^1$H NMR (400 MHz, DMSO-d$_6$) δ 12.93 (s, 1H), 7.43-7.45 (m, 2H), 7.31 (d, J=8.4 Hz, 1H), 7.10 (s, 1H), 6.34 (dd, J=16.9, 10.3 Hz, 1H), 6.09-6.14 (m, 1H), 5.67-5.70 (m, 1H), 4.80-4.90 (m, 1H), 4.49-4.59 (m, 1H), 4.02-4.10 (m, 4H), 3.83-3.87 (m, 2H), 3.74 (s, 2H), 3.57 (s, 4H), 2.10-2.15 (m, 12H), 1.92-2.02 (m, 4H), 1.26-1.29 (m, 1H), 0.48-0.61 (m, 4H), MS (ESI): 689.4 [M+1]$^+$

By the separation and purification on a chiral column, two axially chiral isomer of the compound 1 may be obtained:

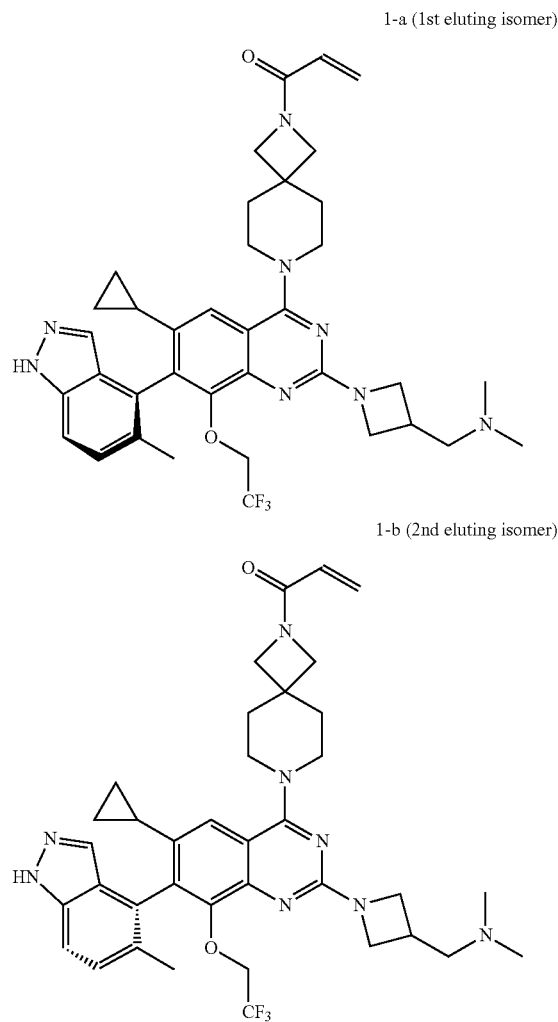

Example 2-132. Synthesis of Compound 2-132

The target compound 2-132 was obtained using different starting materials according to a synthesis method similar to that in Example 1.

TABLE 1
| | Compound structure | [M + H]⁺ |
|---|---|---|
| 2 | 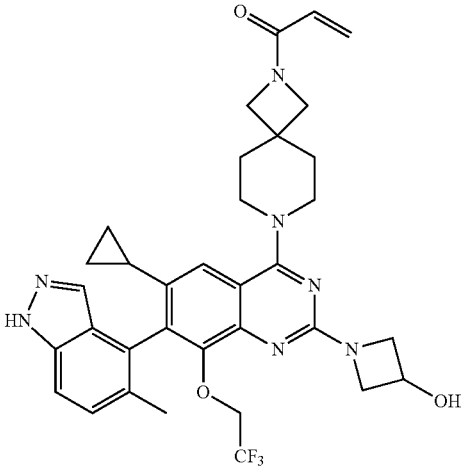 [SMILES: C=CC(=O)N1CC2(CCN(c3nc(N4CC(O)C4)nc4c(OCC(F)(F)F)c(-c5c(C)ccc6[nH]ncc56)c(C5CC5)cc34)CC2)C1] | 648.3 |
| 3 | 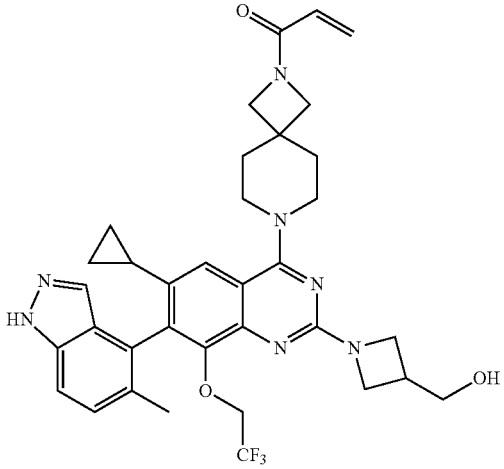 [SMILES: C=CC(=O)N1CC2(CCN(c3nc(N4CC(CO)C4)nc4c(OCC(F)(F)F)c(-c5c(C)ccc6[nH]ncc56)c(C5CC5)cc34)CC2)C1] | 662.3 |
| 4 | 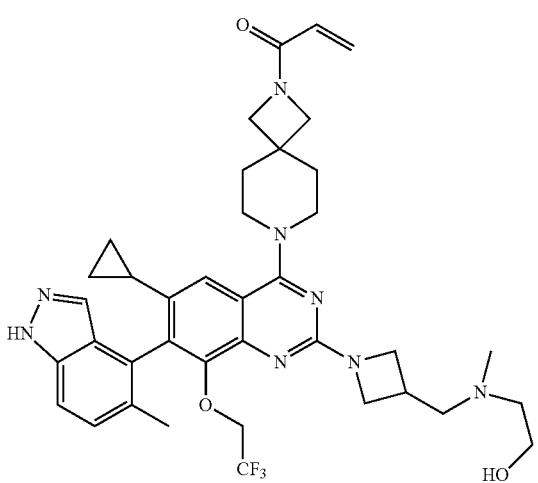 [SMILES: C=CC(=O)N1CC2(CCN(c3nc(N4CC(CN(C)CCO)C4)nc4c(OCC(F)(F)F)c(-c5c(C)ccc6[nH]ncc56)c(C5CC5)cc34)CC2)C1] | 719.4 |

TABLE 1-continued

| | Compound structure | [M + H]+ |
|---|---|---|
| 5 | 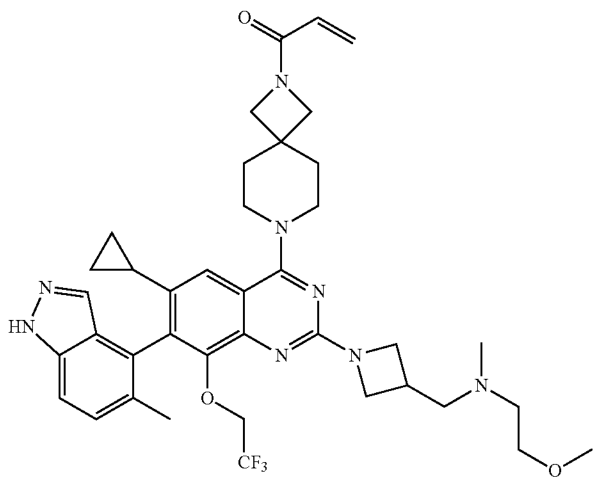 [SMILES: C=CC(=O)N1CC2(CCN(c3nc(N4CC(CN(C)CCOC)C4)nc4c(OCC(F)(F)F)c(-c5c(C)ccc6[nH]ncc56)c(C5CC5)cc34)CC2)C1] | 733.4 |
| 6 | 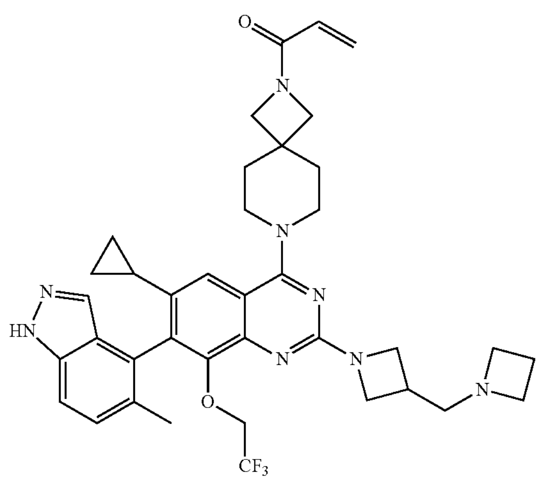 | 701.4 |
| 7 | 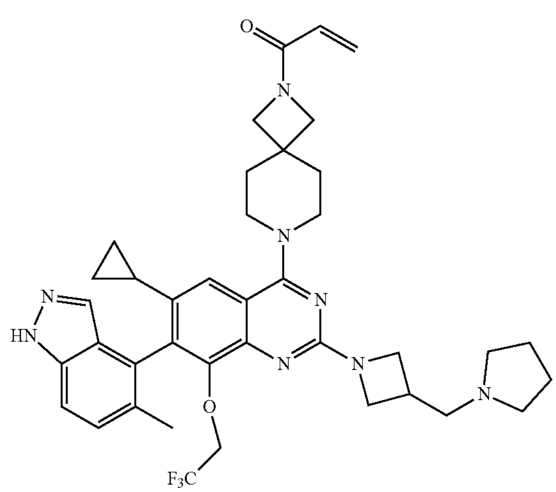 [SMILES: C=CC(=O)N1CC2(CCN(c3nc(N4CC(CN5CCCC5)C4)nc4c(OCC(F)(F)F)c(-c5c(C)ccc6[nH]ncc56)c(C5CC5)cc34)CC2)C1] | 715.4 |

TABLE 1-continued
| | Compound structure | [M + H]+ |
|---|---|---|
| 8 | 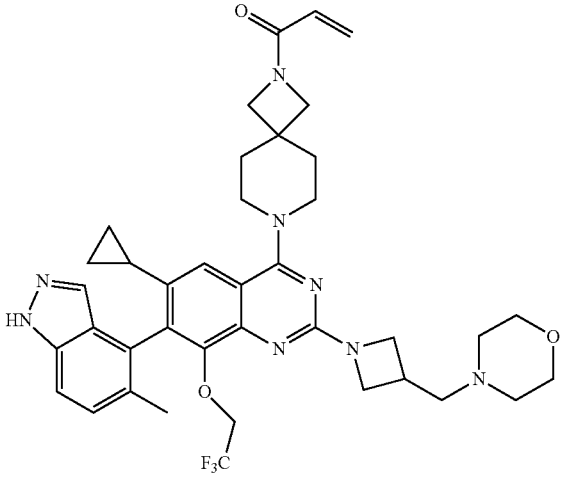 [SMILES: C=CC(=O)N1CC2(CCN(c3nc(N4CC(CN5CCOCC5)C4)nc4c(OCC(F)(F)F)c(-c5c(C)ccc6[nH]ncc56)c(C5CC5)cc34)CC2)C1] | 731.4 |
| 9 | 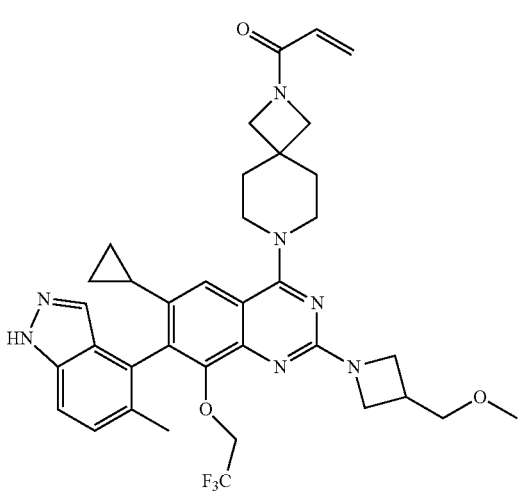 [SMILES: C=CC(=O)N1CC2(CCN(c3nc(N4CC(COC)C4)nc4c(OCC(F)(F)F)c(-c5c(C)ccc6[nH]ncc56)c(C5CC5)cc34)CC2)C1] | 676.3 |
| 10 | 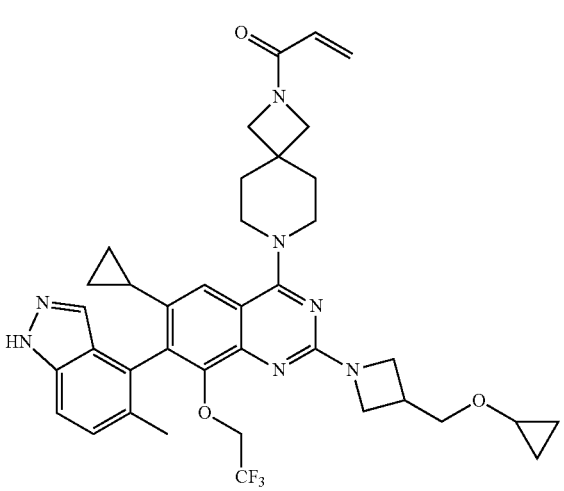 [SMILES: C=CC(=O)N1CC2(CCN(c3nc(N4CC(COC5CC5)C4)nc4c(OCC(F)(F)F)c(-c5c(C)ccc6[nH]ncc56)c(C5CC5)cc34)CC2)C1] | 702.3 |

TABLE 1-continued

| | Compound structure | [M + H]+ |
|---|---|---|
| 11 | 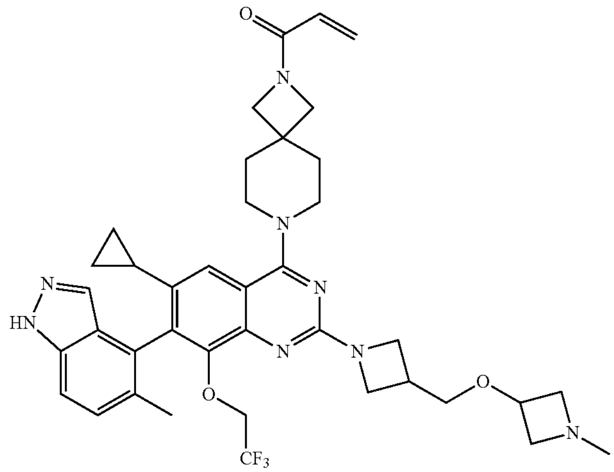 [SMILES: C=CC(=O)N1CC2(CCN(c3nc(N4CC(COC5CN(C)C5)C4)nc4c(OCC(F)(F)F)c(-c5c(C)ccc6[nH]ncc56)c(C5CC5)cc34)CC2)C1] | 731.4 |
| 12 | 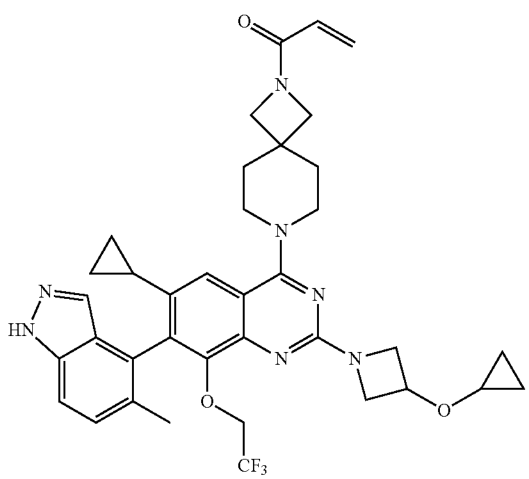 [SMILES: C=CC(=O)N1CC2(CCN(c3nc(N4CC(OC5CC5)C4)nc4c(OCC(F)(F)F)c(-c5c(C)ccc6[nH]ncc56)c(C5CC5)cc34)CC2)C1] | 688.3 |
| 13 | 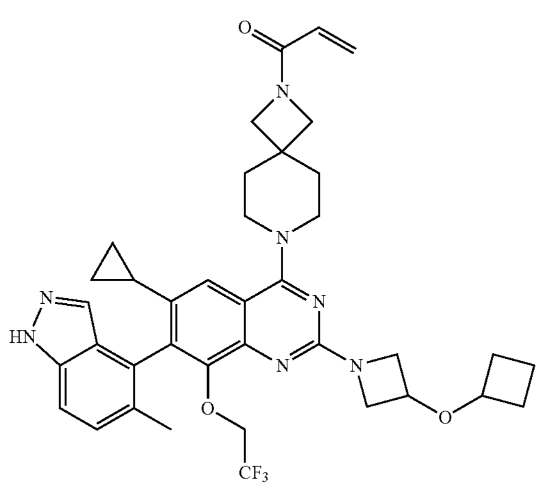 [SMILES: C=CC(=O)N1CC2(CCN(c3nc(N4CC(OC5CCC5)C4)nc4c(OCC(F)(F)F)c(-c5c(C)ccc6[nH]ncc56)c(C5CC5)cc34)CC2)C1] | 702.3 |

TABLE 1-continued
| | Compound structure | [M + H]+ |
|---|---|---|
| 14 | 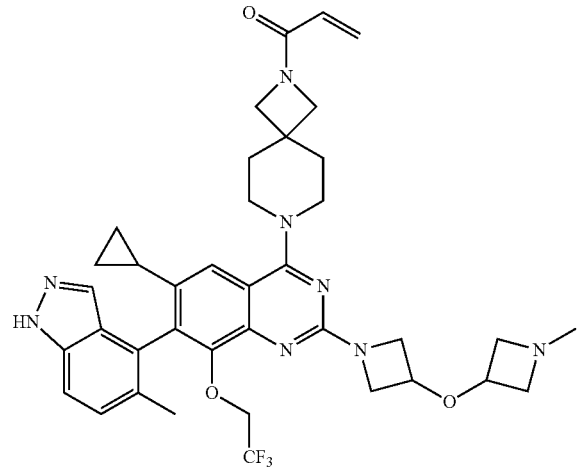 [SMILES: C=CC(=O)N1CC2(CCN(c3nc(N4CC(OC5CN(C)C5)C4)nc4c(OCC(F)(F)F)c(-c5c(C)ccc6[nH]ncc56)c(C5CC5)cc34)CC2)C1] | 717.4 |
| 15 | 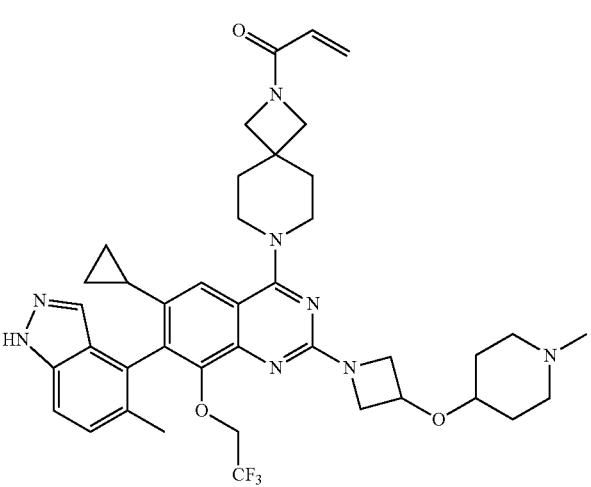 [SMILES: C=CC(=O)N1CC2(CCN(c3nc(N4CC(OC5CCN(C)CC5)C4)nc4c(OCC(F)(F)F)c(-c5c(C)ccc6[nH]ncc56)c(C5CC5)cc34)CC2)C1] | 745.4 |
| 16 | 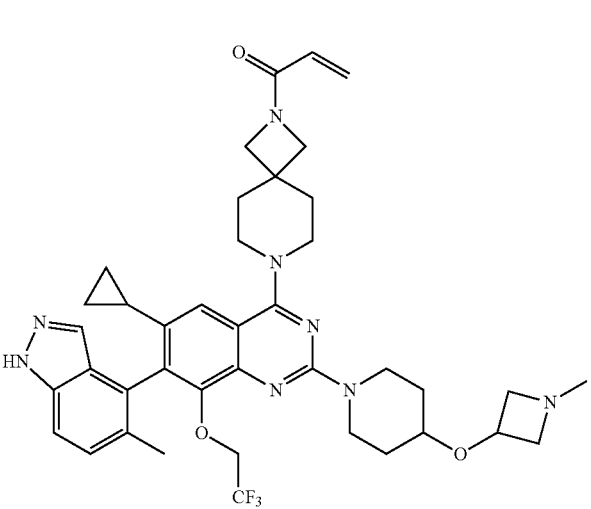 [SMILES: C=CC(=O)N1CC2(CCN(c3nc(N4CCC(OC5CN(C)C5)CC4)nc4c(OCC(F)(F)F)c(-c5c(C)ccc6[nH]ncc56)c(C5CC5)cc34)CC2)C1] | 745.4 |

TABLE 1-continued
| | Compound structure | [M + H]+ |
|---|---|---|
| 17 | 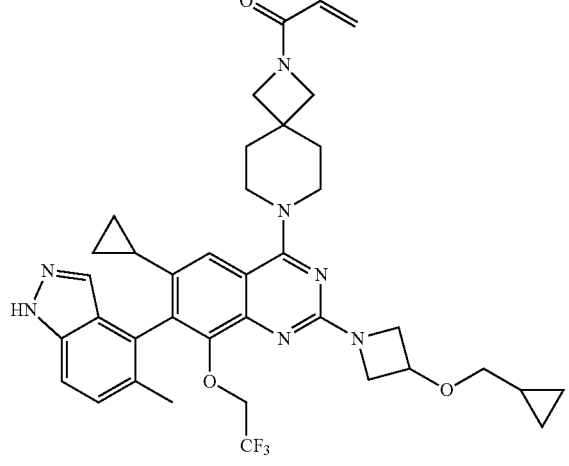 | 702.3 |
| 18 | 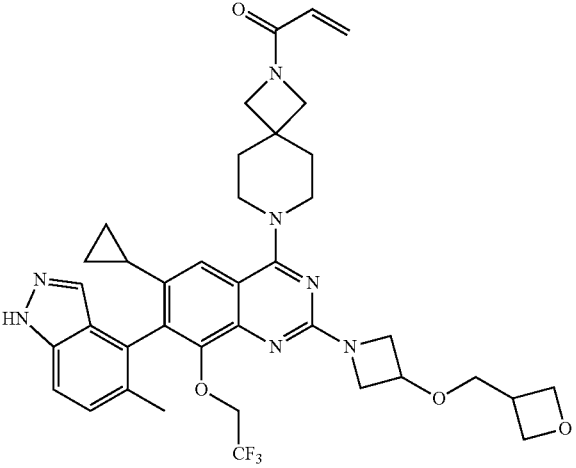 [SMILES: C=CC(=O)N1CC2(CCN(c3nc(N4CC(OCC5COC5)C4)nc4c(OCC(F)(F)F)c(-c5c(C)ccc6[nH]ncc56)c(C5CC5)cc34)CC2)C1] | 718.3 |
| 19 | 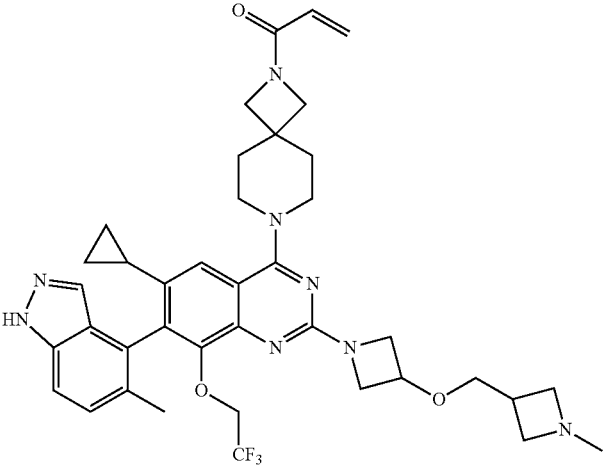 | 731.4 |

TABLE 1-continued
| Compound structure | [M + H]⁺ |
|---|---|
| 20 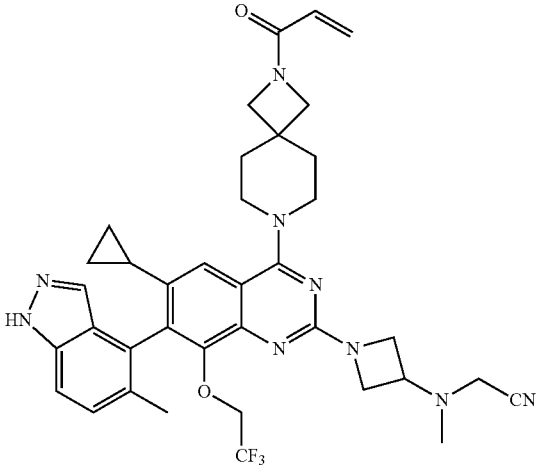 [SMILES: C=CC(=O)N1CC2(CCN(c3nc(N4CC(N(C)CC#N)C4)nc4c(OCC(F)(F)F)c(-c5c(C)ccc6[nH]ncc56)c(C5CC5)cc34)CC2)C1] | 700.3 |
| 21 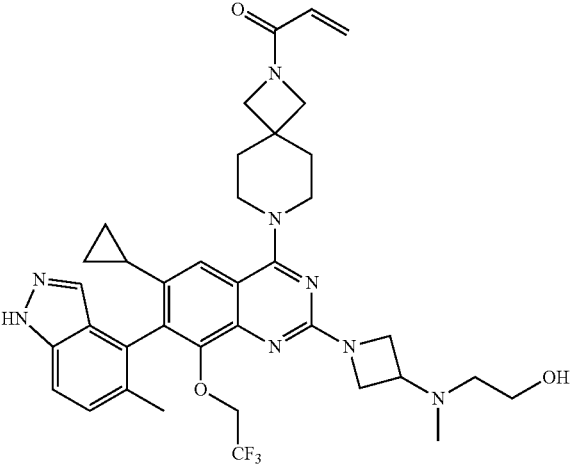 [SMILES: C=CC(=O)N1CC2(CCN(c3nc(N4CC(N(C)CCO)C4)nc4c(OCC(F)(F)F)c(-c5c(C)ccc6[nH]ncc56)c(C5CC5)cc34)CC2)C1] | 705.3 |
| 22 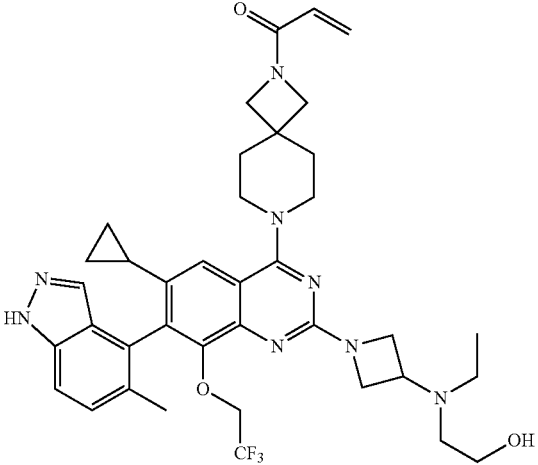 [SMILES: C=CC(=O)N1CC2(CCN(c3nc(N4CC(N(CC)CCO)C4)nc4c(OCC(F)(F)F)c(-c5c(C)ccc6[nH]ncc56)c(C5CC5)cc34)CC2)C1] | 719.4 |

TABLE 1-continued
| | Compound structure | [M + H]+ |
|---|---|---|
| 23 | 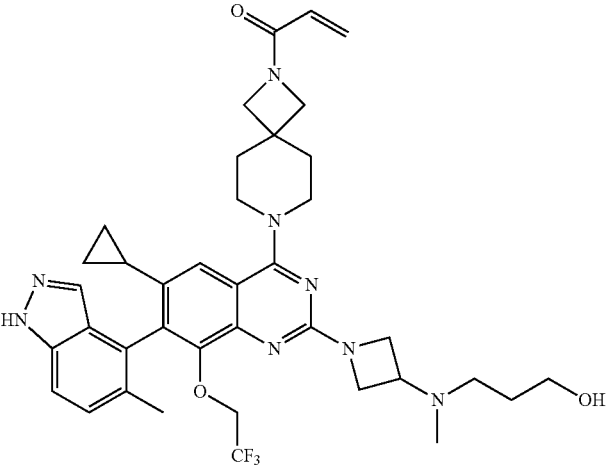 [SMILES: C=CC(=O)N1CC2(CCN(c3nc(N4CC(N(C)CCCO)C4)nc4c(OCC(F)(F)F)c(-c5c(C)ccc6[nH]ncc56)c(C5CC5)cc34)CC2)C1] | 719.4 |
| 24 | 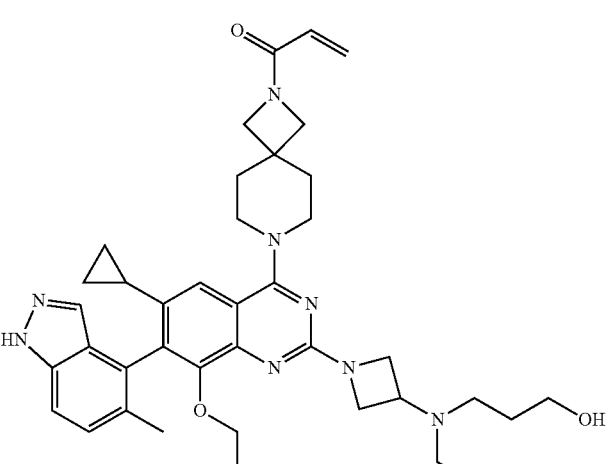 | 733.4 |
| 25 | 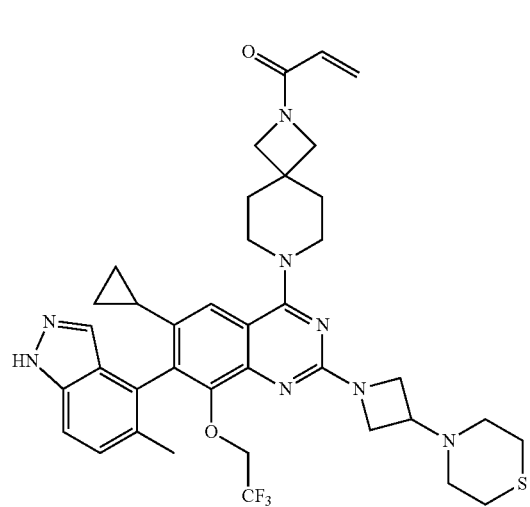 [SMILES: C=CC(=O)N1CC2(CCN(c3nc(N4CC(N5CCSCC5)C4)nc4c(OCC(F)(F)F)c(-c5c(C)ccc6[nH]ncc56)c(C5CC5)cc34)CC2)C1] | 733.3 |

TABLE 1-continued
| | Compound structure | [M + H]+ |
|---|---|---|
| 26 | 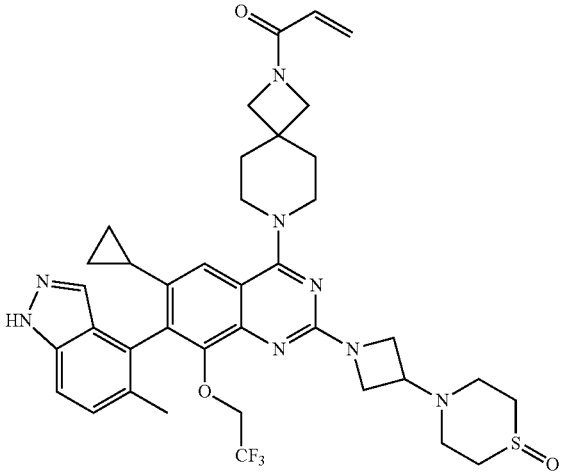 [SMILES: C=CC(=O)N1CC2(CCN(c3nc(N4CC(N5CCS(=O)CC5)C4)nc4c(OCC(F)(F)F)c(-c5c(C)ccc6[nH]ncc56)c(C5CC5)cc34)CC2)C1] | 749.3 |
| 27 | 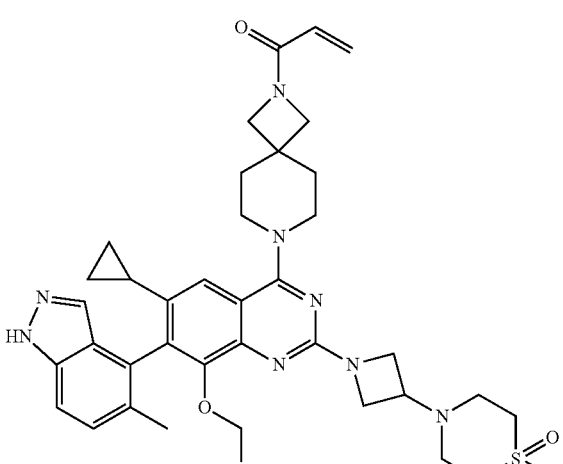 | 765.3 |
| 28 | 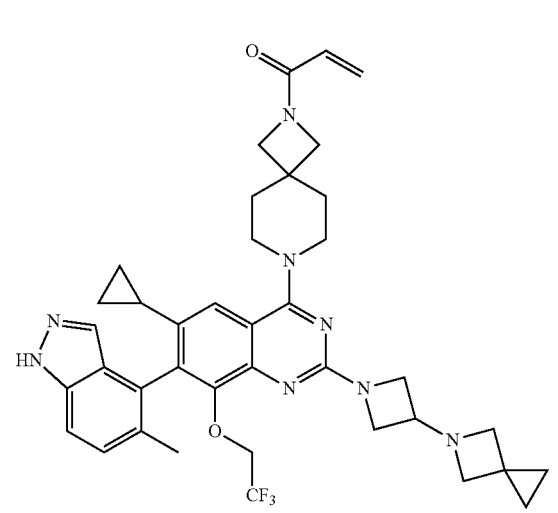 | 713.4 |

TABLE 1-continued

| | Compound structure | [M + H]+ |
|---|---|---|
| 29 | 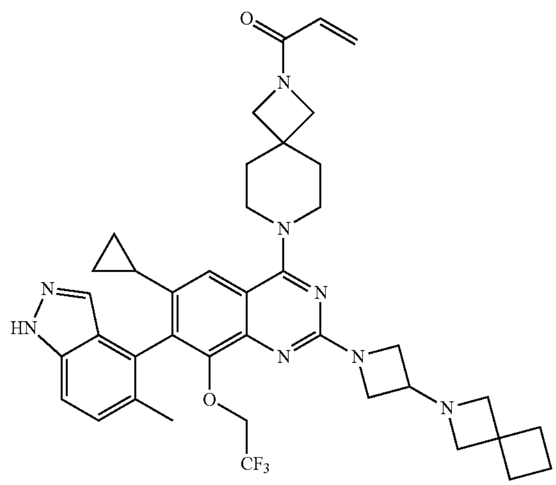 [SMILES: C=CC(=O)N1CC2(CCN(c3nc(N4CC(N5CC6(CCC6)C5)C4)nc4c(OCC(F)(F)F)c(-c5c(C)ccc6[nH]ncc56)c(C5CC5)cc34)CC2)C1] | 727.4 |
| 30 | 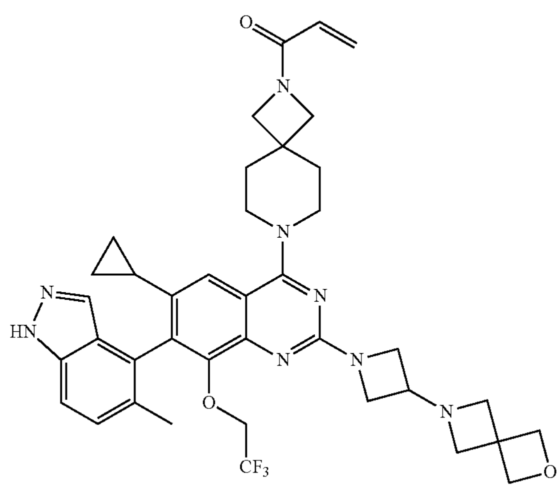 | 729.3 |
| 31 | 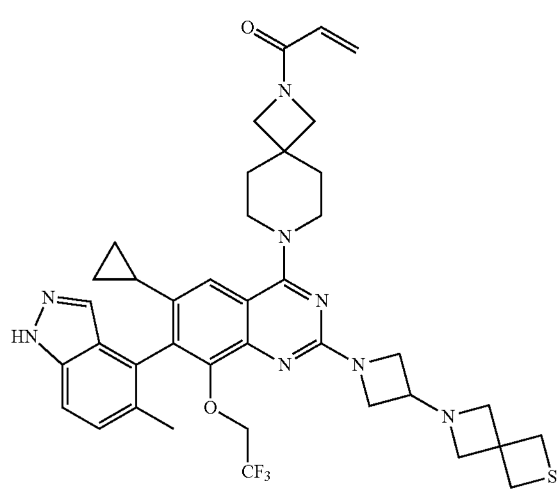 [SMILES: C=CC(=O)N1CC2(CCN(c3nc(N4CC(N5CC6(COC6)C5)C4)nc4c(OCC(F)(F)F)c(-c5c(C)ccc6[nH]ncc56)c(C5CC5)cc34)CC2)C1] | 745.3 |

TABLE 1-continued

| Compound structure | [M + H]+ |
|---|---|
| 32 | 742.4 |
| 33 | 757.4 |
| 34 | 713.4 |

TABLE 1-continued
| | Compound structure | [M + H]+ |
|---|---|---|
| 35 | 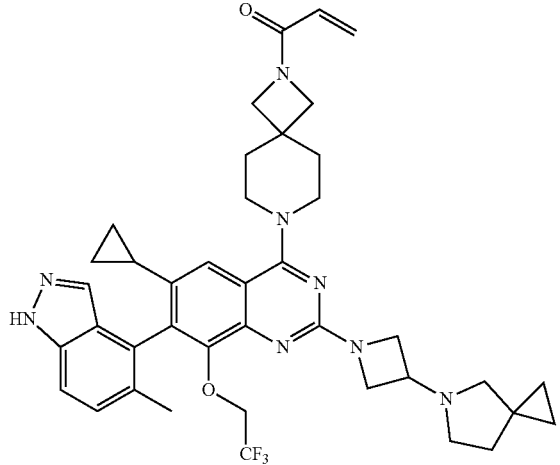 [SMILES: C=CC(=O)N1CC2(CCN(c3nc(N4CC(N5CCC6(CC6)C5)C4)nc4c(OCC(F)(F)F)c(-c5c(C)ccc6[nH]ncc56)c(C5CC5)cc34)CC2)C1] | 727.4 |
| 36 | 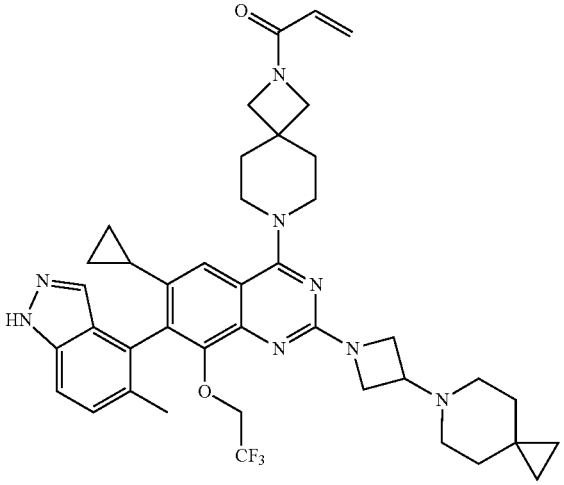 [SMILES: C=CC(=O)N1CC2(CCN(c3nc(N4CC(N5CCC6(CC5)CC6)C4)nc4c(OCC(F)(F)F)c(-c5c(C)ccc6[nH]ncc56)c(C5CC5)cc34)CC2)C1] | 741.4 |
| 37 | 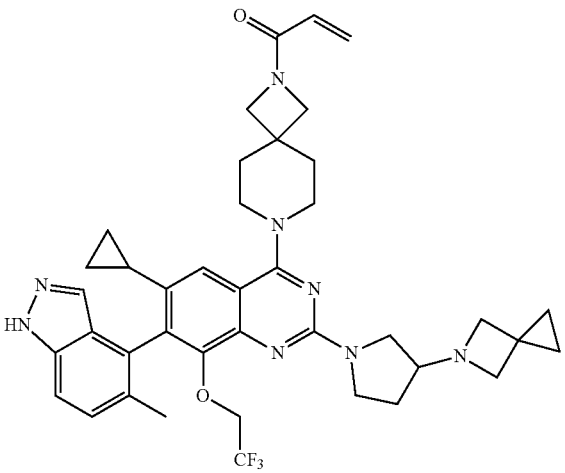 [SMILES: C=CC(=O)N1CC2(CCN(c3nc(N4CCC(N5CC6(CC6)C5)C4)nc4c(OCC(F)(F)F)c(-c5c(C)ccc6[nH]ncc56)c(C5CC5)cc34)CC2)C1] | 727.4 |

TABLE 1-continued

| | Compound structure | [M + H]+ |
|---|---|---|
| 38 | 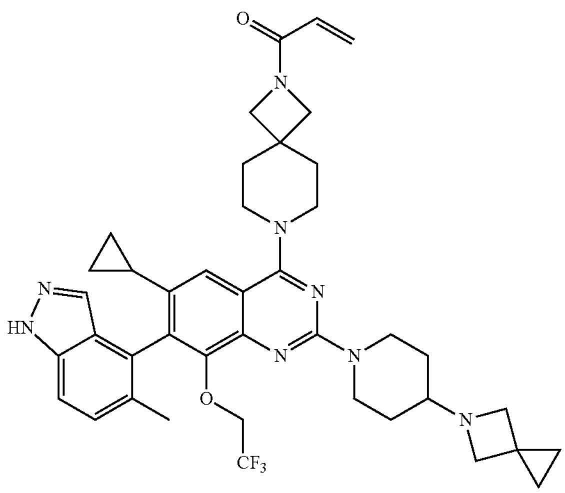 [SMILES: C=CC(=O)N1CC2(CCN(c3nc(N4CCC(N5CC6(CC6)C5)CC4)nc4c(OCC(F)(F)F)c(-c5c(C)ccc6[nH]ncc56)c(C5CC5)cc34)CC2)C1] | 741.4 |
| 39 | 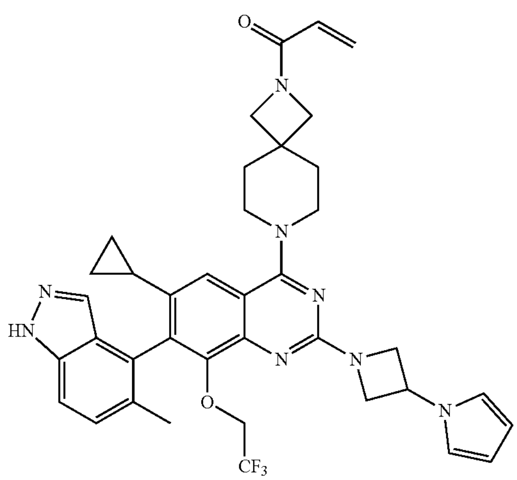 [SMILES: C=CC(=O)N1CC2(CCN(c3nc(N4CC(n5cccc5)C4)nc4c(OCC(F)(F)F)c(-c5c(C)ccc6[nH]ncc56)c(C5CC5)cc34)CC2)C1] | 697.3 |
| 40 | 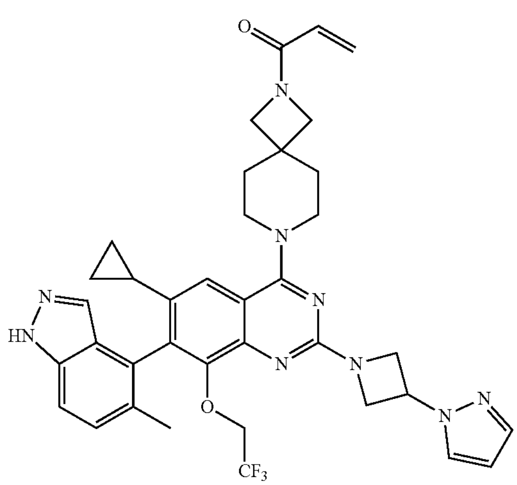 | 698.3 |

TABLE 1-continued

| | Compound structure | [M + H]+ |
|---|---|---|
| 41 | 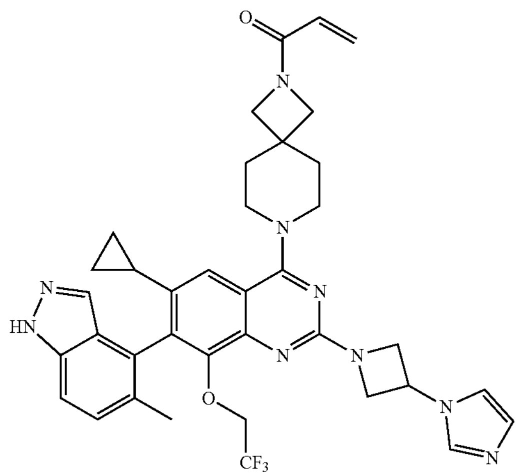 [SMILES: C=CC(=O)N1CC2(CCN(c3nc(N4CC(n5ccnc5)C4)nc4c(OCC(F)(F)F)c(-c5c(C)ccc6[nH]ncc56)c(C5CC5)cc34)CC2)C1] | 698.3 |
| 42 | 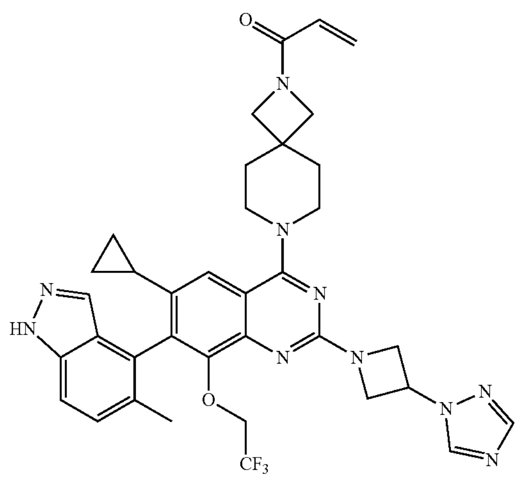 [SMILES: C=CC(=O)N1CC2(CCN(c3nc(N4CC(n5cncn5)C4)nc4c(OCC(F)(F)F)c(-c5c(C)ccc6[nH]ncc56)c(C5CC5)cc34)CC2)C1] | 699.3 |
| 43 | 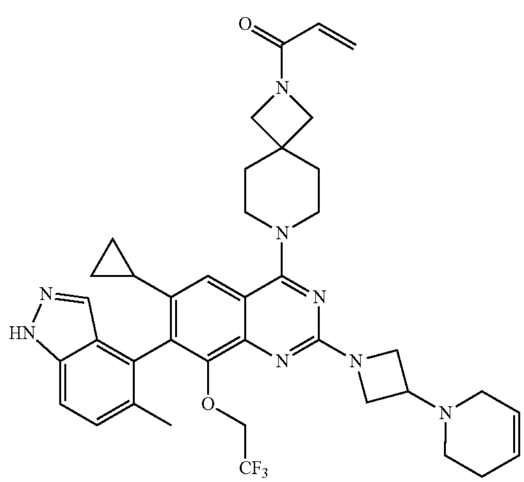 [SMILES: C=CC(=O)N1CC2(CCN(c3nc(N4CC(N5CC=CCC5)C4)nc4c(OCC(F)(F)F)c(-c5c(C)ccc6[nH]ncc56)c(C5CC5)cc34)CC2)C1] | 713.4 |

TABLE 1-continued

| | Compound structure | [M + H]+ |
|---|---|---|
| 44 | 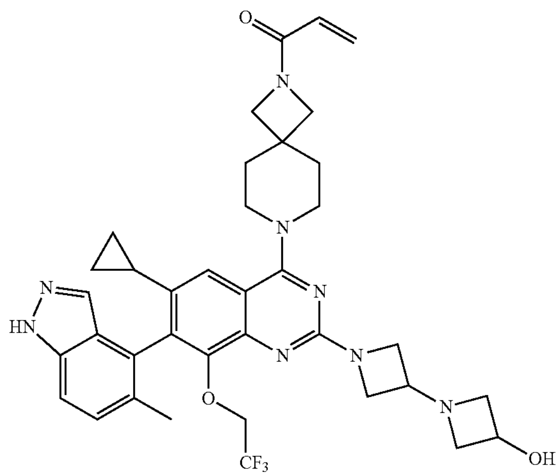 [SMILES: C=CC(=O)N1CC2(CCN(c3nc(N4CC(N5CC(O)C5)C4)nc4c(OCC(F)(F)F)c(-c5c(C)ccc6[nH]ncc56)c(C5CC5)cc34)CC2)C1] | 703.3 |
| 45 | 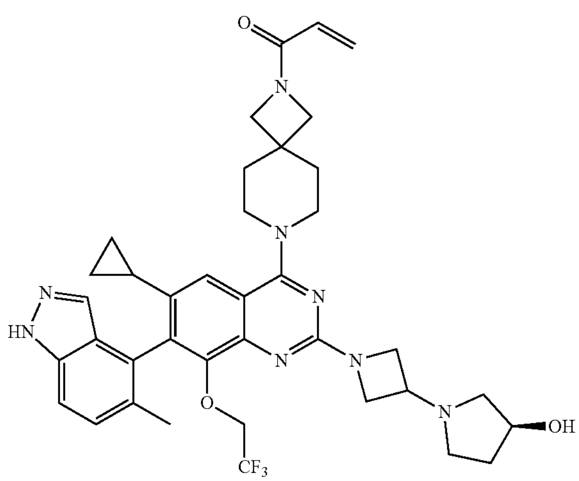 [SMILES: C=CC(=O)N1CC2(CCN(c3nc(N4CC(N5CC[C@H](O)C5)C4)nc4c(OCC(F)(F)F)c(-c5c(C)ccc6[nH]ncc56)c(C5CC5)cc34)CC2)C1] | 717.4 |
| 46 | 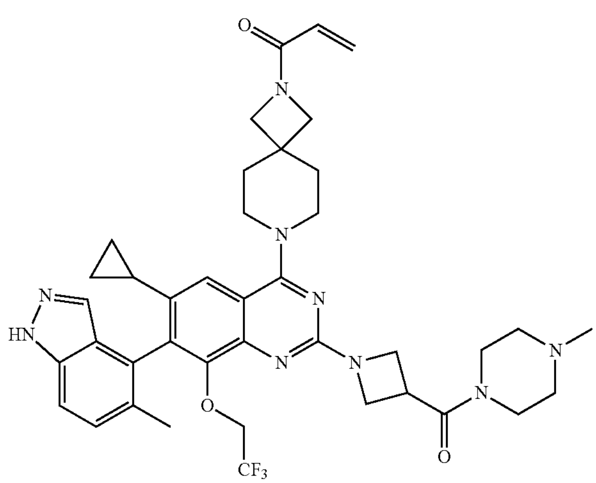 [SMILES: C=CC(=O)N1CC2(CCN(c3nc(N4CC(C(=O)N5CCN(C)CC5)C4)nc4c(OCC(F)(F)F)c(-c5c(C)ccc6[nH]ncc56)c(C5CC5)cc34)CC2)C1] | 758.4 |

TABLE 1-continued

| Compound structure | [M + H]⁺ |
|---|---|
| 47 | 758.4 |
| 48 | 770.4 |
| 49 | 794.3 |

TABLE 1-continued

| Compound structure | [M + H]+ |
|---|---|
| 50 | 794.3 |
| 51 | 714.3 |
| 52 | 744.4 |

TABLE 1-continued

| | Compound structure | [M + H]+ |
|---|---|---|
| 53 | 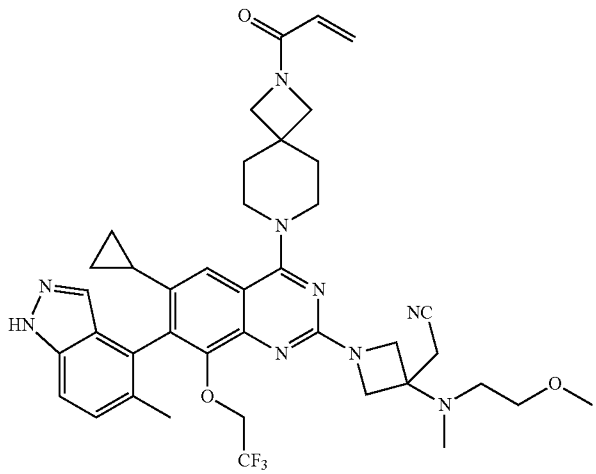 [SMILES: C=CC(=O)N1CC2(CCN(c3nc(N4CC(CC#N)(N(C)CCOC)C4)nc4c(OCC(F)(F)F)c(-c5c(C)ccc6[nH]ncc56)c(C5CC5)cc34)CC2)C1] | 758.4 |
| 54 | 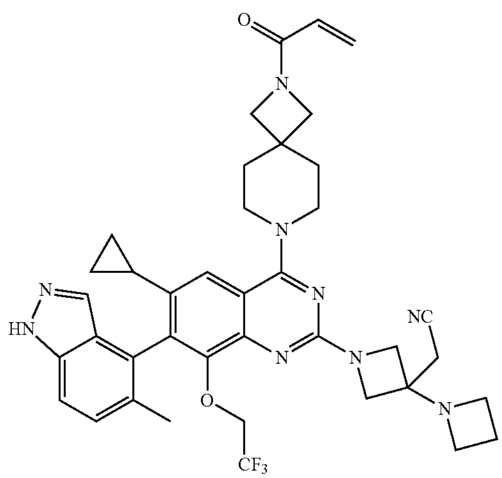 [SMILES: C=CC(=O)N1CC2(CCN(c3nc(N4CC(CC#N)(N5CCC5)C4)nc4c(OCC(F)(F)F)c(-c5c(C)ccc6[nH]ncc56)c(C5CC5)cc34)CC2)C1] | 726.3 |
| 55 | 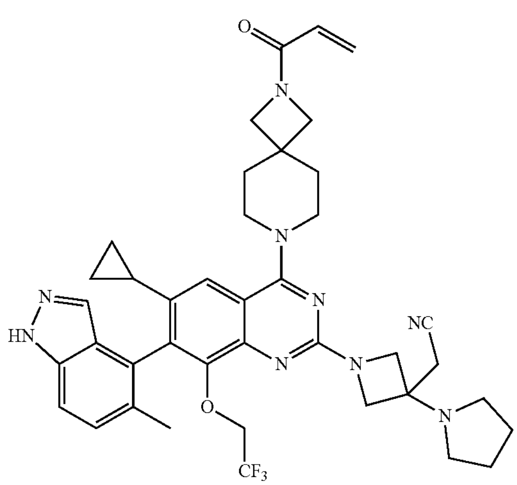 [SMILES: C=CC(=O)N1CC2(CCN(c3nc(N4CC(CC#N)(N5CCCC5)C4)nc4c(OCC(F)(F)F)c(-c5c(C)ccc6[nH]ncc56)c(C5CC5)cc34)CC2)C1] | 740.4 |

TABLE 1-continued

| | Compound structure | [M + H]+ |
|---|---|---|
| 56 | 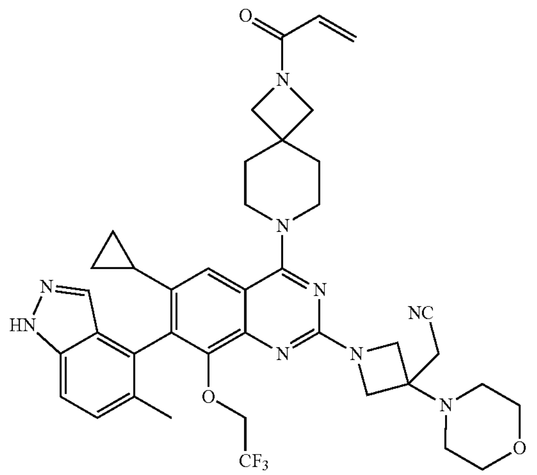 [SMILES: C=CC(=O)N1CC2(CCN(c3nc(N4CC(CC#N)(N5CCOCC5)C4)nc4c(OCC(F)(F)F)c(-c5c(C)ccc6[nH]ncc56)c(C5CC5)cc34)CC2)C1] | 756.4 |
| 57 | 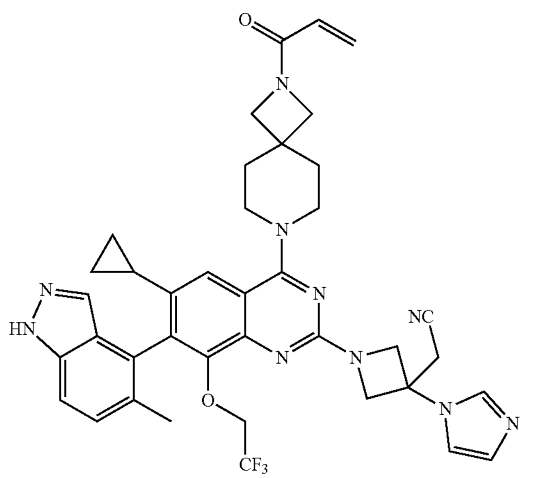 [SMILES: C=CC(=O)N1CC2(CCN(c3nc(N4CC(CC#N)(n5ccnc5)C4)nc4c(OCC(F)(F)F)c(-c5c(C)ccc6[nH]ncc56)c(C5CC5)cc34)CC2)C1] | 737.3 |
| 58 | 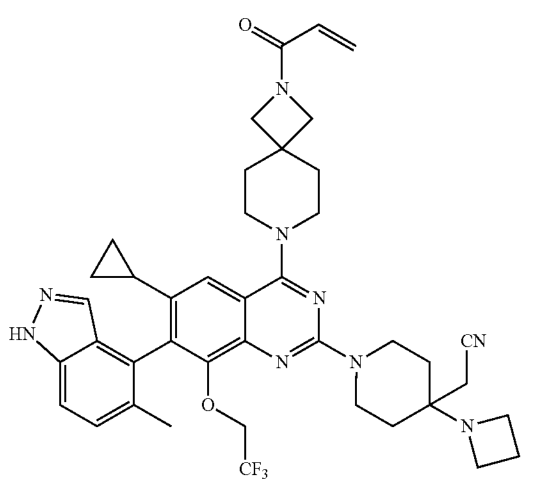 [SMILES: C=CC(=O)N1CC2(CCN(c3nc(N4CCC(CC#N)(N5CCC5)CC4)nc4c(OCC(F)(F)F)c(-c5c(C)ccc6[nH]ncc56)c(C5CC5)cc34)CC2)C1] | 754.4 |

TABLE 1-continued
| | Compound structure | [M + H]+ |
|---|---|---|
| 59 | 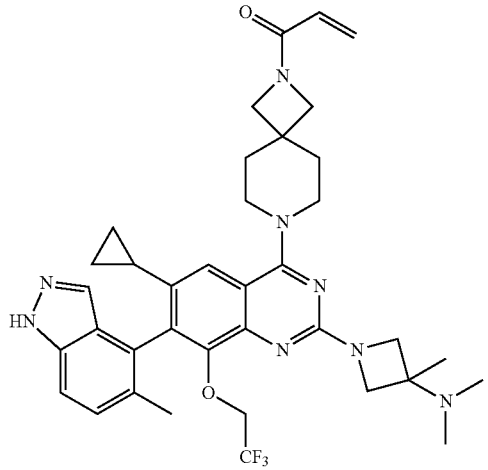 [SMILES: C=CC(=O)N1CC2(CCN(c3nc(N4CC(C)(N(C)C)C4)nc4c(OCC(F)(F)F)c(-c5c(C)ccc6[nH]ncc56)c(C5CC5)cc34)CC2)C1] | 689.4 |
| 60 | 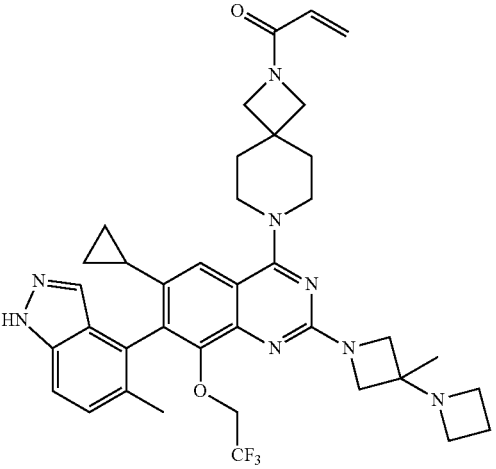 [SMILES: C=CC(=O)N1CC2(CCN(c3nc(N4CC(C)(N5CCC5)C4)nc4c(OCC(F)(F)F)c(-c5c(C)ccc6[nH]ncc56)c(C5CC5)cc34)CC2)C1] | 701.4 |
| 61 | 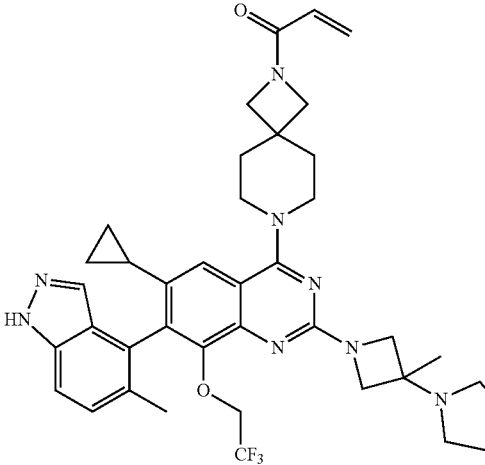 | 715.4 |

TABLE 1-continued

| | Compound structure | [M + H]⁺ |
|---|---|---|
| 62 | 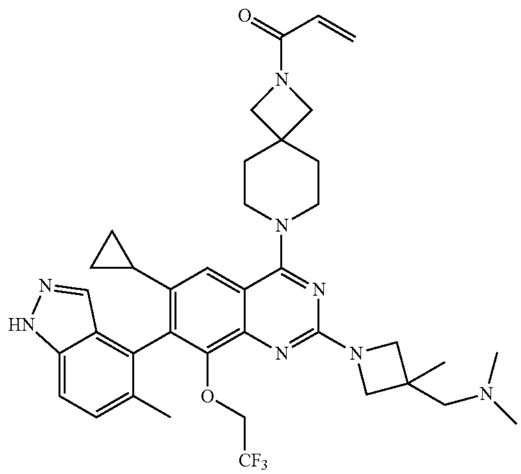 [SMILES: C=CC(=O)N1CC2(CCN(c3nc(N4CC(C)(CN(C)C)C4)nc4c(OCC(F)(F)F)c(-c5c(C)ccc6[nH]ncc56)c(C5CC5)cc34)CC2)C1] | 703.4 |
| 63 | 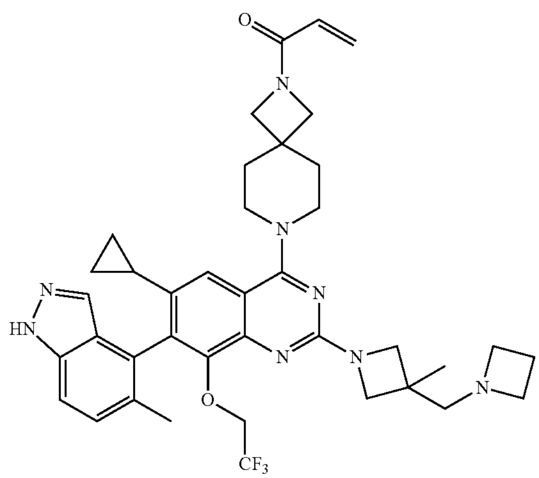 [SMILES: C=CC(=O)N1CC2(CCN(c3nc(N4CC(C)(CN5CCC5)C4)nc4c(OCC(F)(F)F)c(-c5c(C)ccc6[nH]ncc56)c(C5CC5)cc34)CC2)C1] | 715.4 |
| 64 | 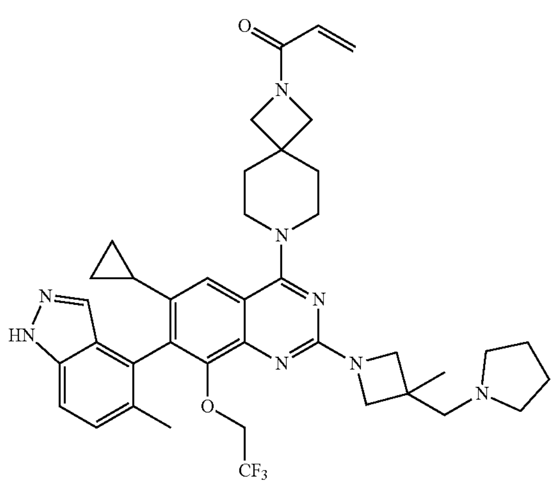 [SMILES: C=CC(=O)N1CC2(CCN(c3nc(N4CC(C)(CN5CCCC5)C4)nc4c(OCC(F)(F)F)c(-c5c(C)ccc6[nH]ncc56)c(C5CC5)cc34)CC2)C1] | 729.4 |

TABLE 1-continued
| | Compound structure | [M + H]⁺ |
|---|---|---|
| 65 | 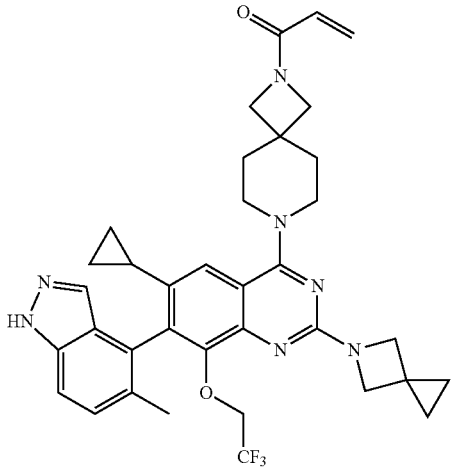 [SMILES: C=CC(=O)N1CC2(CCN(c3nc(N4CC5(CC5)C4)nc4c(OCC(F)(F)F)c(-c5c(C)ccc6[nH]ncc56)c(C5CC5)cc34)CC2)C1] | 658.3 |
| 66 | 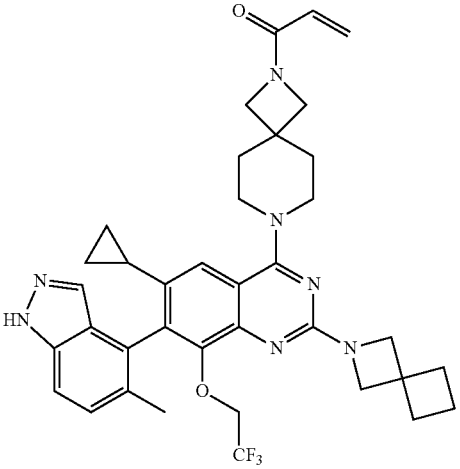 [SMILES: C=CC(=O)N1CC2(CCN(c3nc(N4CC5(CCC5)C4)nc4c(OCC(F)(F)F)c(-c5c(C)ccc6[nH]ncc56)c(C5CC5)cc34)CC2)C1] | 672.3 |
| 67 | 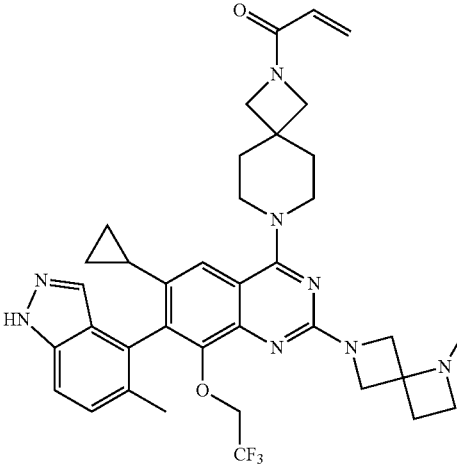 | 687.3 |

TABLE 1-continued
| Compound structure | [M + H]+ |
|---|---|
| 68 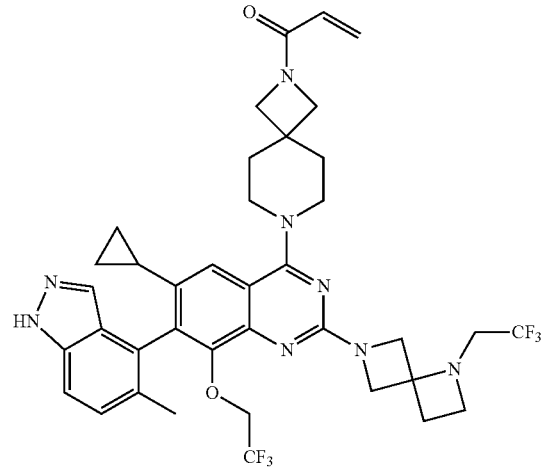 [SMILES: C=CC(=O)N1CC2(CCN(c3nc(N4CC5(CCN5CC(F)(F)F)C4)nc4c(OCC(F)(F)F)c(-c5c(C)ccc6[nH]ncc56)c(C5CC5)cc34)CC2)C1] | 755.3 |
| 69 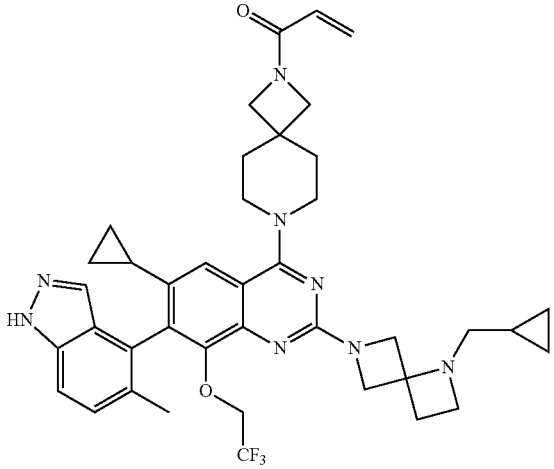 [SMILES: C=CC(=O)N1CC2(CCN(c3nc(N4CC5(CCN5CC5CC5)C4)nc4c(OCC(F)(F)F)c(-c5c(C)ccc6[nH]ncc56)c(C5CC5)cc34)CC2)C1] | 727.4 |
| 70 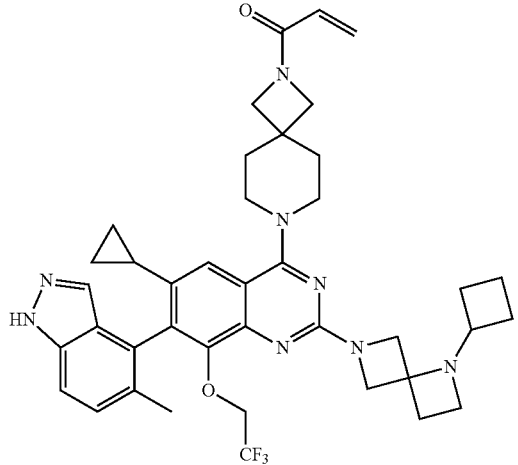 [SMILES: C=CC(=O)N1CC2(CCN(c3nc(N4CC5(CCN5C5CCC5)C4)nc4c(OCC(F)(F)F)c(-c5c(C)ccc6[nH]ncc56)c(C5CC5)cc34)CC2)C1] | 727.4 |

TABLE 1-continued
| Compound structure | [M + H]+ |
|---|---|
| 71 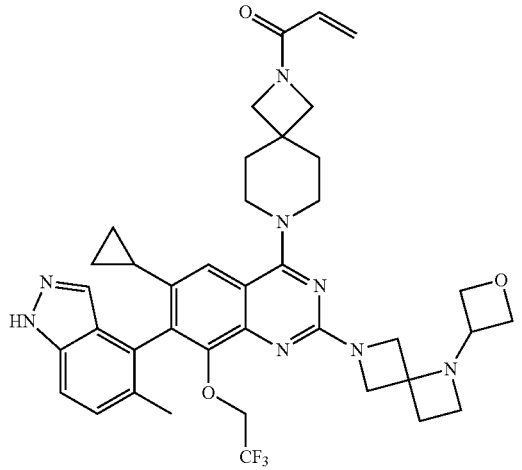 | 729.3 |
| 72 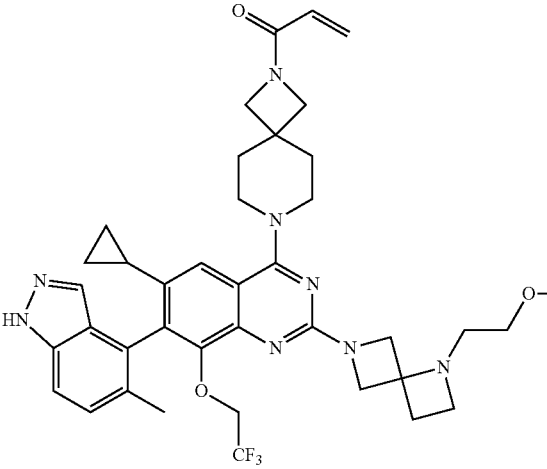 | 731.4 |
| 73 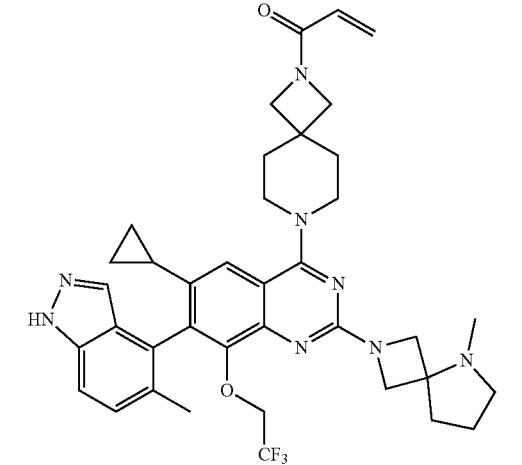 [SMILES: C=CC(=O)N1CC2(CCN(c3nc(N4CC5(CCCN5C)C4)nc4c(OCC(F)(F)F)c(-c5c(C)ccc6[nH]ncc56)c(C5CC5)cc34)CC2)C1] | 701.4 |

TABLE 1-continued

| | Compound structure | [M + H]⁺ |
|---|---|---|
| 74 | 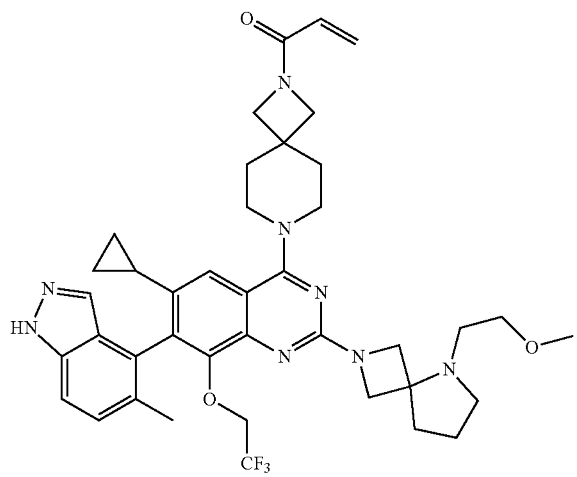 [SMILES: C=CC(=O)N1CC2(CCN(c3nc(N4CC5(CCCN5CCOC)C4)nc4c(OCC(F)(F)F)c(-c5c(C)ccc6[nH]ncc56)c(C5CC5)cc34)CC2)C1] | 745.4 |
| 75 | 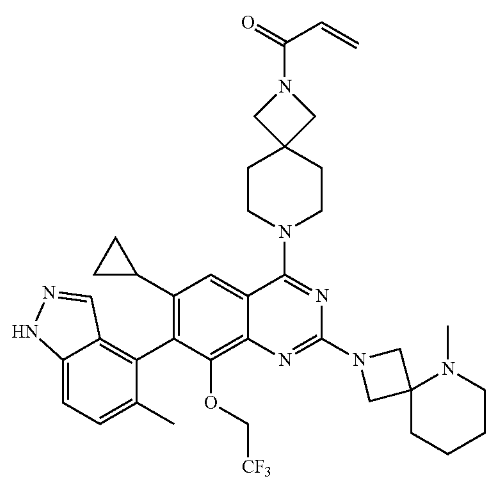 [SMILES: C=CC(=O)N1CC2(CCN(c3nc(N4CC5(CCCCN5C)C4)nc4c(OCC(F)(F)F)c(-c5c(C)ccc6[nH]ncc56)c(C5CC5)cc34)CC2)C1] | 715.4 |
| 76 | 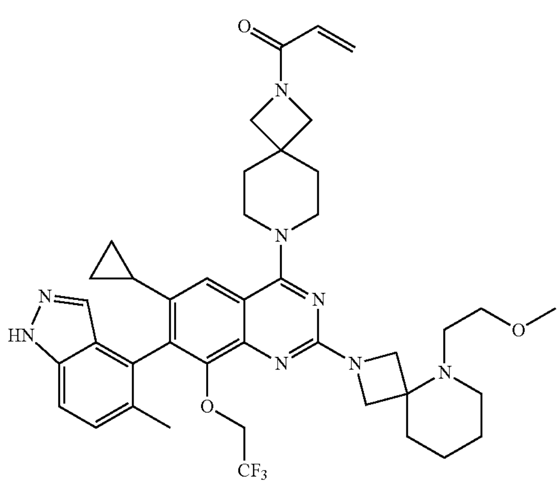 [SMILES: C=CC(=O)N1CC2(CCN(c3nc(N4CC5(CCCCN5CCOC)C4)nc4c(OCC(F)(F)F)c(-c5c(C)ccc6[nH]ncc56)c(C5CC5)cc34)CC2)C1] | 759.4 |

TABLE 1-continued

| | Compound structure | [M + H]+ |
|---|---|---|
| 77 | 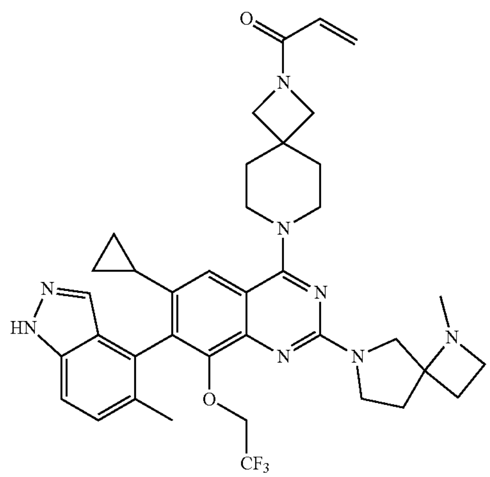 [SMILES: C=CC(=O)N1CC2(CCN(c3nc(N4CCC5(CCN5C)C4)nc4c(OCC(F)(F)F)c(-c5c(C)ccc6[nH]ncc56)c(C5CC5)cc34)CC2)C1] | 701.4 |
| 78 | 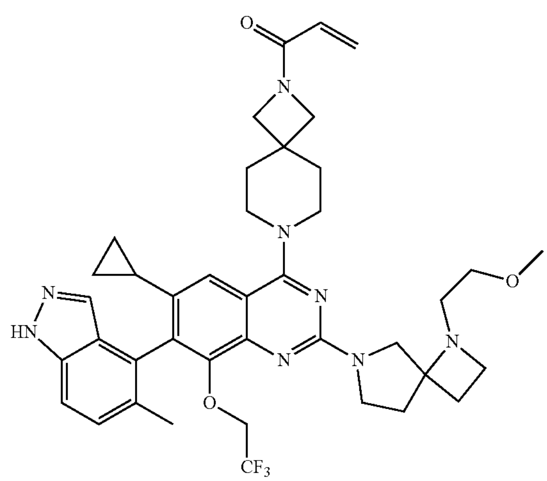 [SMILES: C=CC(=O)N1CC2(CCN(c3nc(N4CCC5(CCN5CCOC)C4)nc4c(OCC(F)(F)F)c(-c5c(C)ccc6[nH]ncc56)c(C5CC5)cc34)CC2)C1] | 745.4 |
| 79 | 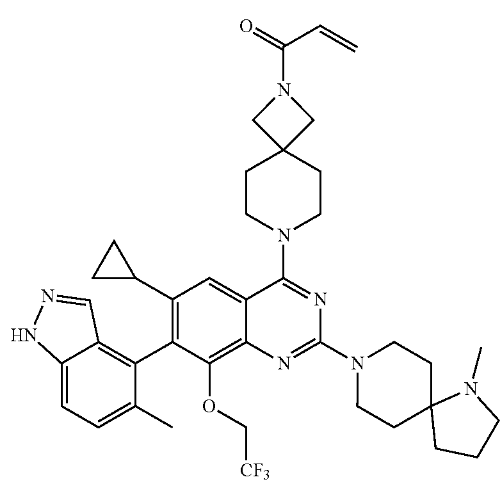 [SMILES: C=CC(=O)N1CC2(CCN(c3nc(N4CCC5(CCCN5C)CC4)nc4c(OCC(F)(F)F)c(-c5c(C)ccc6[nH]ncc56)c(C5CC5)cc34)CC2)C1] | 729.4 |

TABLE 1-continued
| | Compound structure | [M + H]+ |
|---|---|---|
| 80 | 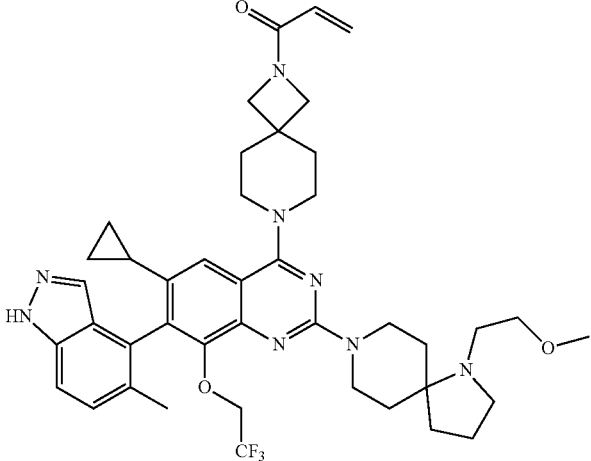 [SMILES: C=CC(=O)N1CC2(CCN(c3nc(N4CCC5(CCCN5CCOC)CC4)nc4c(OCC(F)(F)F)c(-c5c(C)ccc6[nH]ncc56)c(C5CC5)cc34)CC2)C1] | 773.4 |
| 81 | 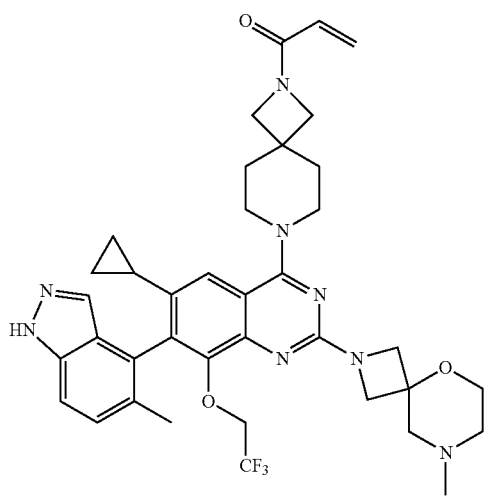 [SMILES: C=CC(=O)N1CC2(CCN(c3nc(N4CC5(CN(C)CCO5)C4)nc4c(OCC(F)(F)F)c(-c5c(C)ccc6[nH]ncc56)c(C5CC5)cc34)CC2)C1] | 717.3 |
| 82 | 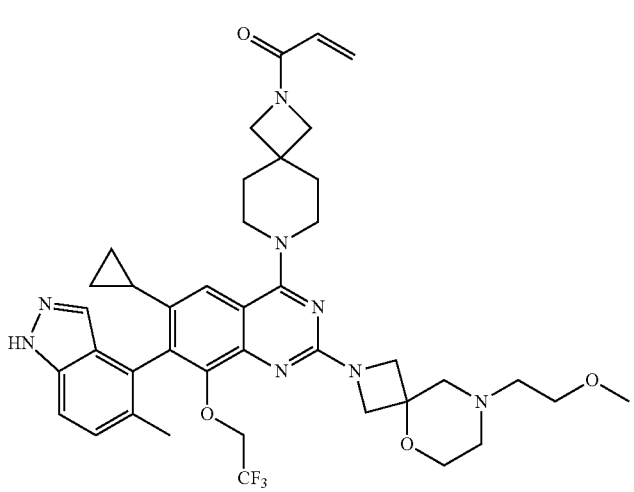 [SMILES: C=CC(=O)N1CC2(CCN(c3nc(N4CC5(CN(CCOC)CCO5)C4)nc4c(OCC(F)(F)F)c(-c5c(C)ccc6[nH]ncc56)c(C5CC5)cc34)CC2)C1] | 761.4 |

TABLE 1-continued
| | Compound structure | [M + H]+ |
|---|---|---|
| 83 | 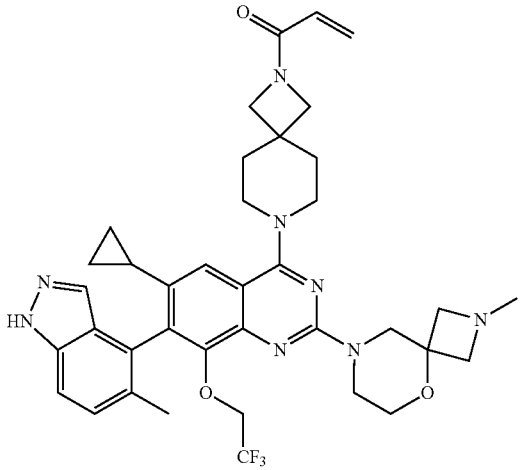 [SMILES: C=CC(=O)N1CC2(CCN(c3nc(N4CCOC5(CN(C)C5)C4)nc4c(OCC(F)(F)F)c(-c5c(C)ccc6[nH]ncc56)c(C5CC5)cc34)CC2)C1] | 717.3 |
| 84 | 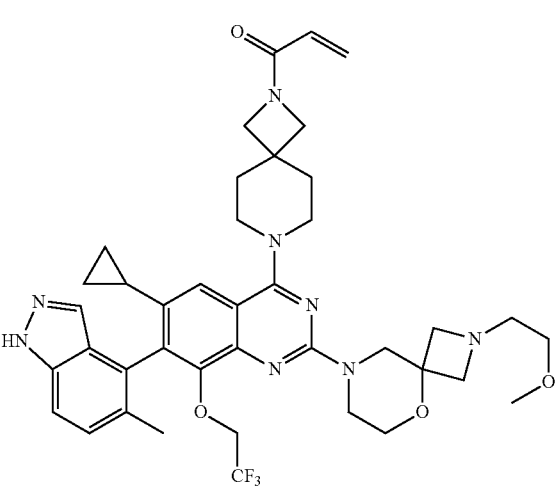 [SMILES: C=CC(=O)N1CC2(CCN(c3nc(N4CCOC5(CN(CCOC)C5)C4)nc4c(OCC(F)(F)F)c(-c5c(C)ccc6[nH]ncc56)c(C5CC5)cc34)CC2)C1] | 761.4 |
| 85 | 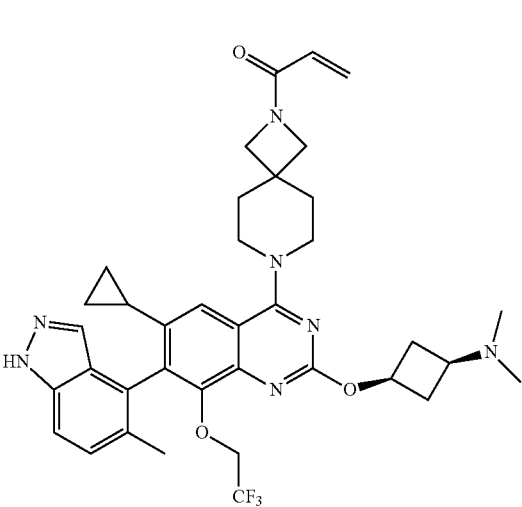 [SMILES: C=CC(=O)N1CC2(CCN(c3nc(O[C@H]4C[C@@H](N(C)C)C4)nc4c(OCC(F)(F)F)c(-c5c(C)ccc6[nH]ncc56)c(C5CC5)cc34)CC2)C1] | 690.3 |

TABLE 1-continued
| Compound structure | [M + H]+ |
|---|---|
| 86 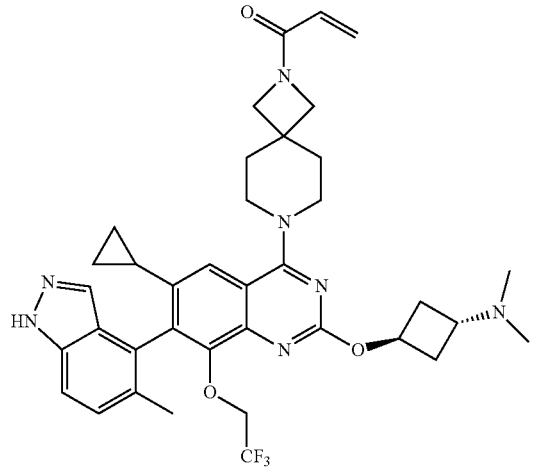 [SMILES: C=CC(=O)N1CC2(CCN(c3nc(O[C@H]4C[C@H](N(C)C)C4)nc4c(OCC(F)(F)F)c(-c5c(C)ccc6[nH]ncc56)c(C5CC5)cc34)CC2)C1] | 690.3 |
| 87 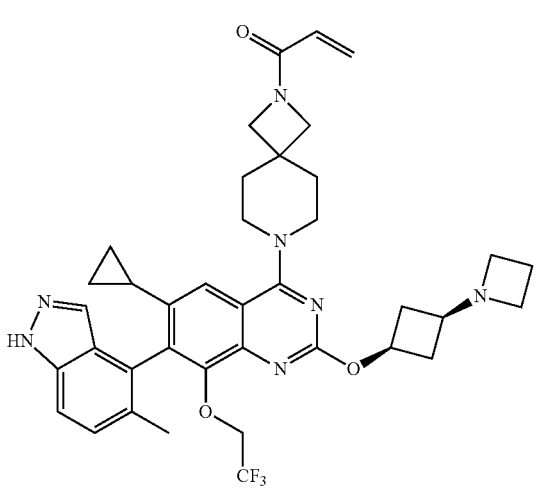 [SMILES: C=CC(=O)N1CC2(CCN(c3nc(O[C@H]4C[C@@H](N5CCC5)C4)nc4c(OCC(F)(F)F)c(-c5c(C)ccc6[nH]ncc56)c(C5CC5)cc34)CC2)C1] | 702.3 |
| 88 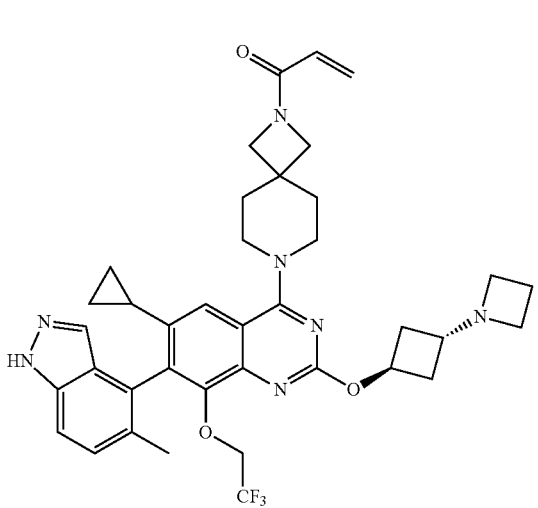 [SMILES: C=CC(=O)N1CC2(CCN(c3nc(O[C@H]4C[C@H](N5CCC5)C4)nc4c(OCC(F)(F)F)c(-c5c(C)ccc6[nH]ncc56)c(C5CC5)cc34)CC2)C1] | 702.3 |

TABLE 1-continued
| | Compound structure | [M + H]+ |
|---|---|---|
| 89 | 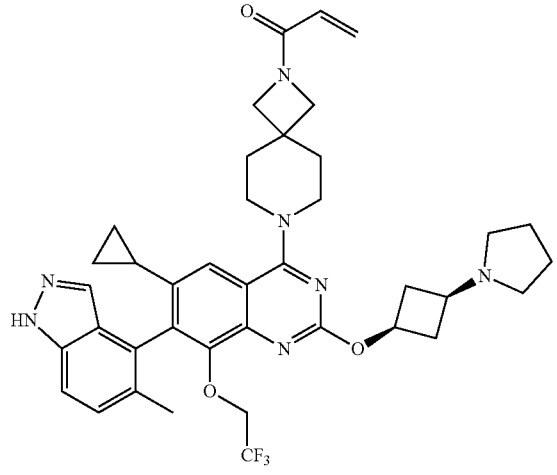 [SMILES: C=CC(=O)N1CC2(CCN(c3nc(O[C@H]4C[C@@H](N5CCCC5)C4)nc4c(OCC(F)(F)F)c(-c5c(C)ccc6[nH]ncc56)c(C5CC5)cc34)CC2)C1] | 716.4 |
| 90 | 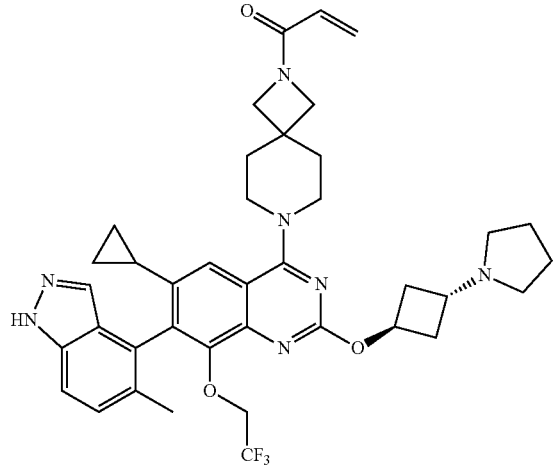 [SMILES: C=CC(=O)N1CC2(CCN(c3nc(O[C@H]4C[C@H](N5CCCC5)C4)nc4c(OCC(F)(F)F)c(-c5c(C)ccc6[nH]ncc56)c(C5CC5)cc34)CC2)C1] | 716.4 |
| 91 | 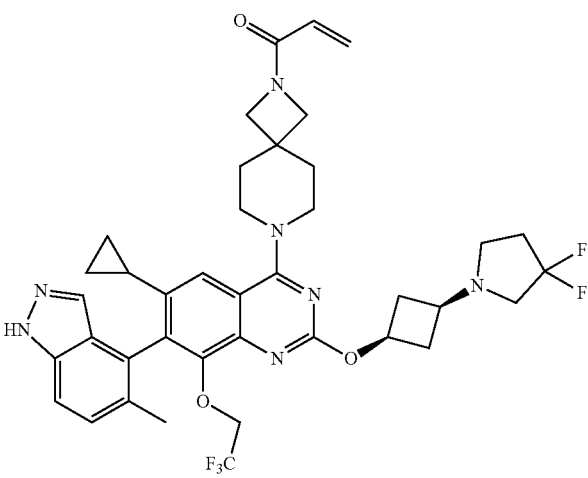 [SMILES: C=CC(=O)N1CC2(CCN(c3nc(O[C@H]4C[C@@H](N5CCC(F)(F)C5)C4)nc4c(OCC(F)(F)F)c(-c5c(C)ccc6[nH]ncc56)c(C5CC5)cc34)CC2)C1] | 752.3 |

TABLE 1-continued
| | Compound structure | [M + H]+ |
|---|---|---|
| 92 | 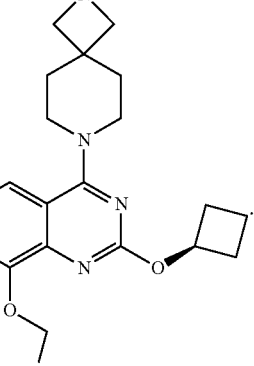 | 752.3 |
| 93 | 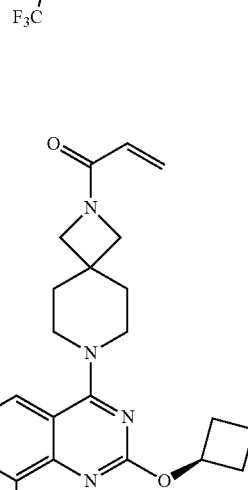 | 728.4 |
| 94 | 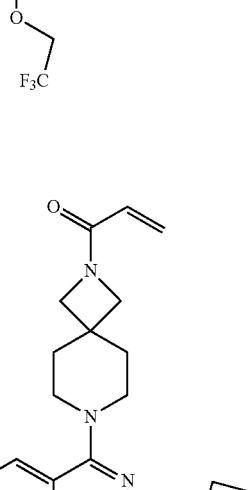 | 728.4 |

TABLE 1-continued

| | Compound structure | [M + H]⁺ |
|---|---|---|
| 95 | 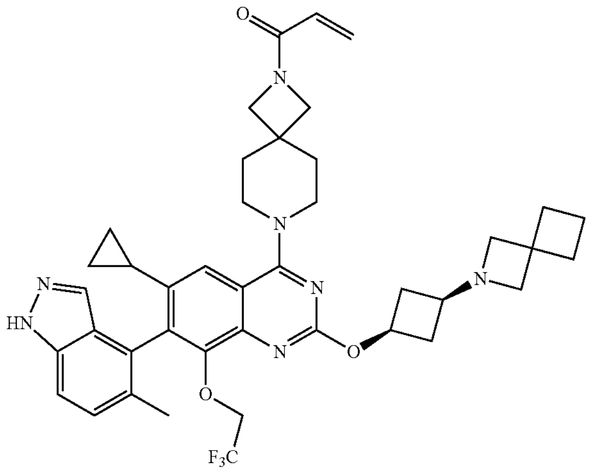 [SMILES: C=CC(=O)N1CC2(CCN(c3nc(O[C@H]4C[C@@H](N5CC6(CCC6)C5)C4)nc4c(OCC(F)(F)F)c(-c5c(C)ccc6[nH]ncc56)c(C5CC5)cc34)CC2)C1] | 742.4 |
| 96 | 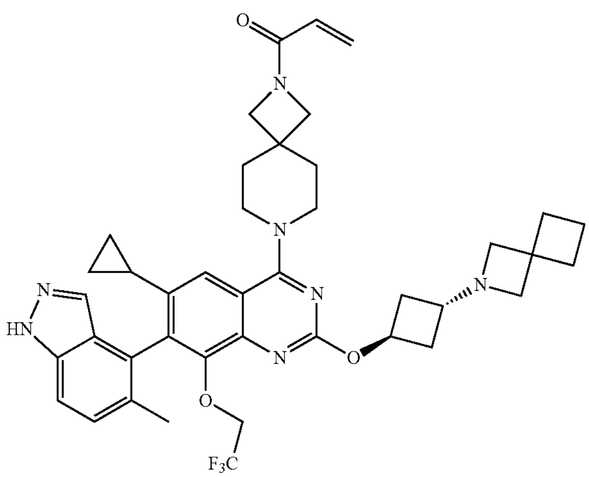 [SMILES: C=CC(=O)N1CC2(CCN(c3nc(O[C@H]4C[C@H](N5CC6(CCC6)C5)C4)nc4c(OCC(F)(F)F)c(-c5c(C)ccc6[nH]ncc56)c(C5CC5)cc34)CC2)C1] | 742.4 |
| 97 | 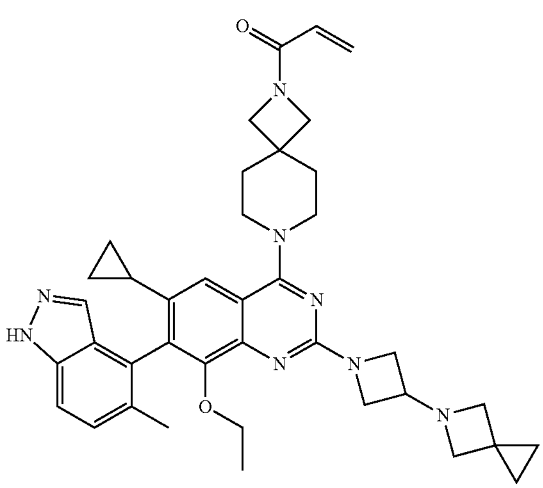 [SMILES: C=CC(=O)N1CC2(CCN(c3nc(N4CC(N5CC6(CC6)C5)C4)nc4c(OCC)c(-c5c(C)ccc6[nH]ncc56)c(C5CC5)cc34)CC2)C1] | 659.4 |

TABLE 1-continued

| | Compound structure | [M + H]+ |
|---|---|---|
| 98 | 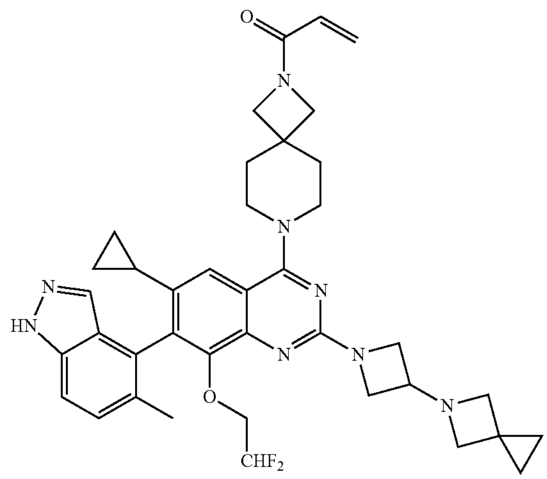 [SMILES: C=CC(=O)N1CC2(CCN(c3nc(N4CC(N5CC6(CC6)C5)C4)nc4c(OCC(F)F)c(-c5c(C)ccc6[nH]ncc56)c(C5CC5)cc34)CC2)C1] | 685.4 |
| 99 | 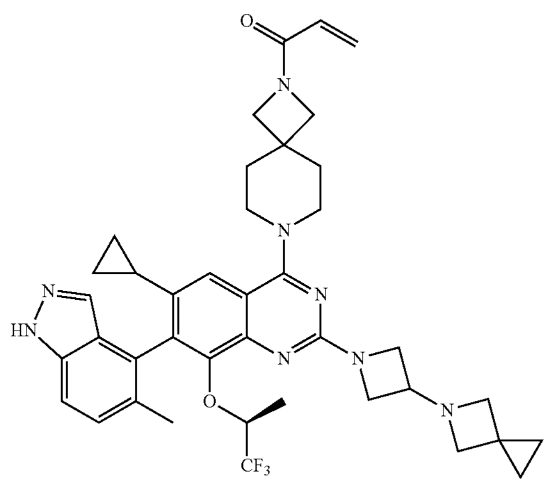 [SMILES: C=CC(=O)N1CC2(CCN(c3nc(N4CC(N5CC6(CC6)C5)C4)nc4c(O[C@@H](C)C(F)(F)F)c(-c5c(C)ccc6[nH]ncc56)c(C5CC5)cc34)CC2)C1] | 727.4 |
| 100 | 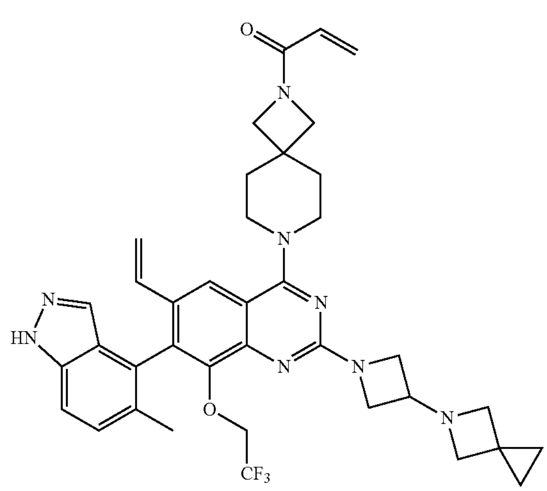 [SMILES: C=CC(=O)N1CC2(CCN(c3nc(N4CC(N5CC6(CC6)C5)C4)nc4c(OCC(F)(F)F)c(-c5c(C)ccc6[nH]ncc56)c(C=C)cc34)CC2)C1] | 699.3 |

TABLE 1-continued
| | Compound structure | [M + H]+ |
|---|---|---|
| 101 | 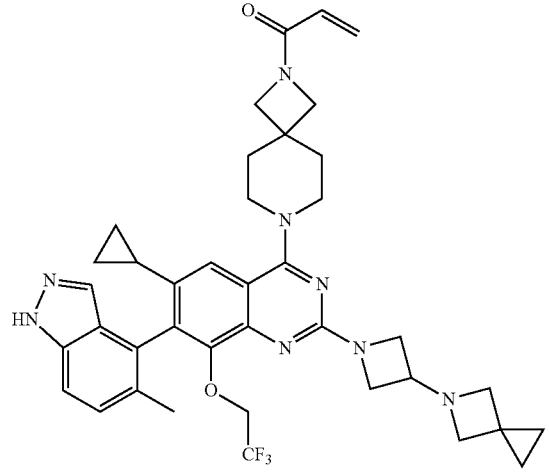 | 685.3 |
| 102 | 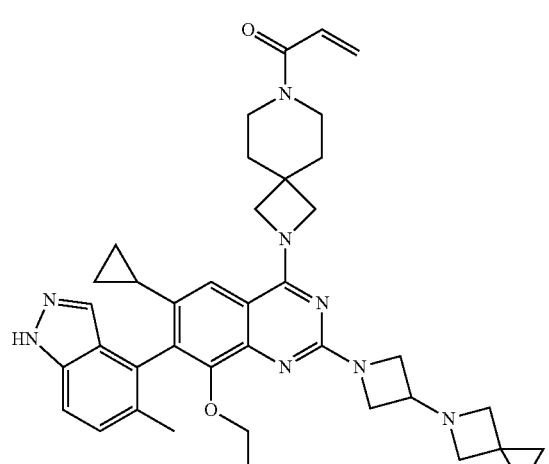 | 713.4 |
| 103 | 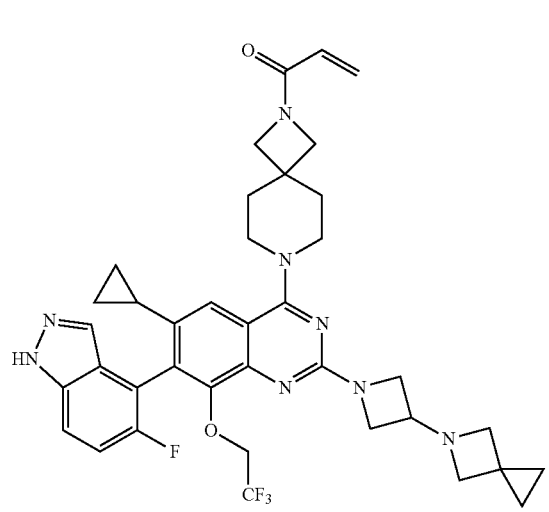 [SMILES: C=CC(=O)N1CC2(CCN(c3nc(N4CC(N5CC6(CC6)C5)C4)nc4c(OCC(F)(F)F)c(-c5c(F)ccc6[nH]ncc56)c(C5CC5)cc34)CC2)C1] | 717.3 |

TABLE 1-continued

| | Compound structure | [M + H]+ |
|---|---|---|
| 104 | 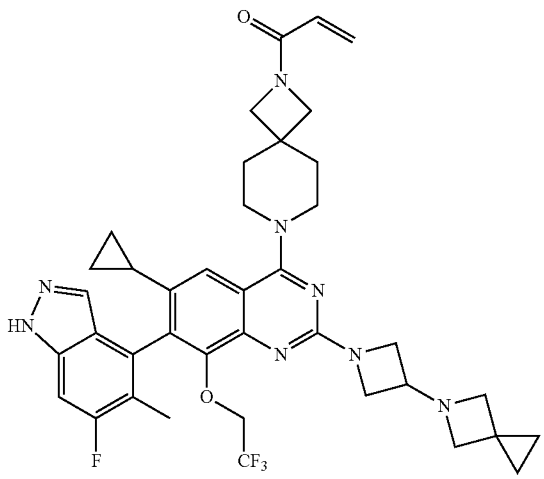 [SMILES: C=CC(=O)N1CC2(CCN(c3nc(N4CC(N5CC6(CC6)C5)C4)nc4c(OCC(F)(F)F)c(-c5c(C)c(F)cc6[nH]ncc56)c(C5CC5)cc34)CC2)C1] | 731.3 |
| 105 | 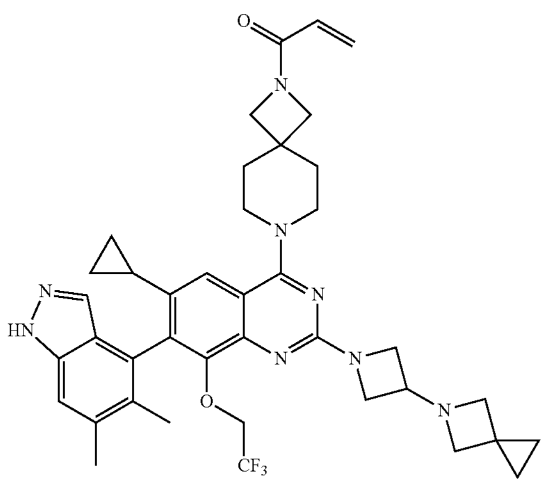 [SMILES: C=CC(=O)N1CC2(CCN(c3nc(N4CC(N5CC6(CC6)C5)C4)nc4c(OCC(F)(F)F)c(-c5c(C)c(C)cc6[nH]ncc56)c(C5CC5)cc34)CC2)C1] | 727.4 |
| 106 | 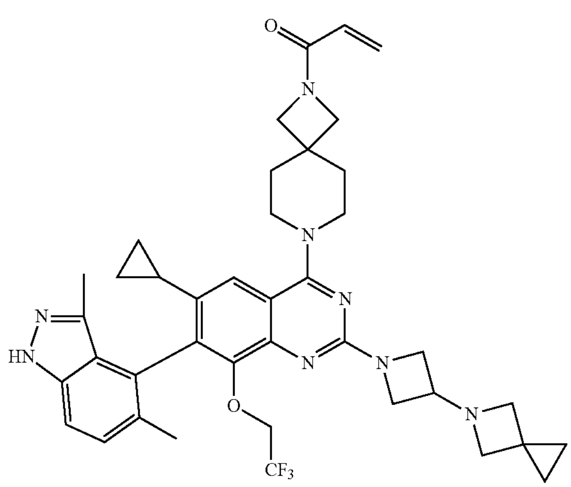 [SMILES: C=CC(=O)N1CC2(CCN(c3nc(N4CC(N5CC6(CC6)C5)C4)nc4c(OCC(F)(F)F)c(-c5c(C)ccc6[nH]nc(C)c56)c(C5CC5)cc34)CC2)C1] | 727.4 |

TABLE 1-continued
| | Compound structure | [M + H]⁺ |
|---|---|---|
| 107 | 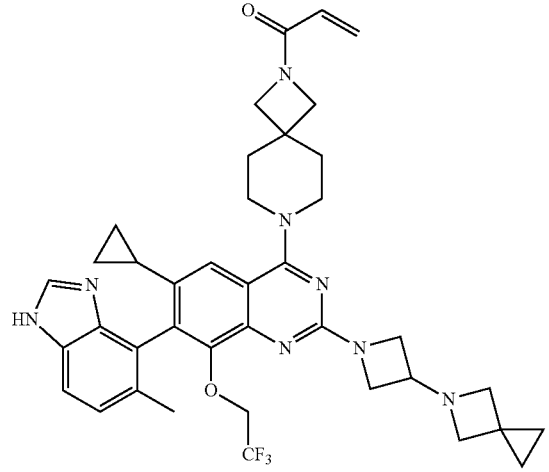 [SMILES: C=CC(=O)N1CC2(CCN(c3nc(N4CC(N5CC6(CC6)C5)C4)nc4c(OCC(F)(F)F)c(-c5c(C)ccc6[nH]cnc56)c(C5CC5)cc34)CC2)C1] | 713.4 |
| 108 | 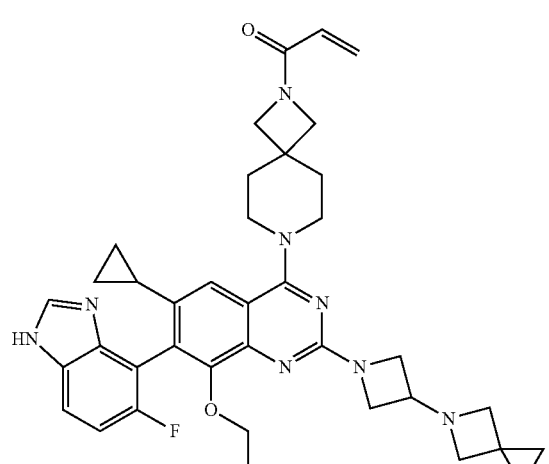 | 717.3 |
| 109 | 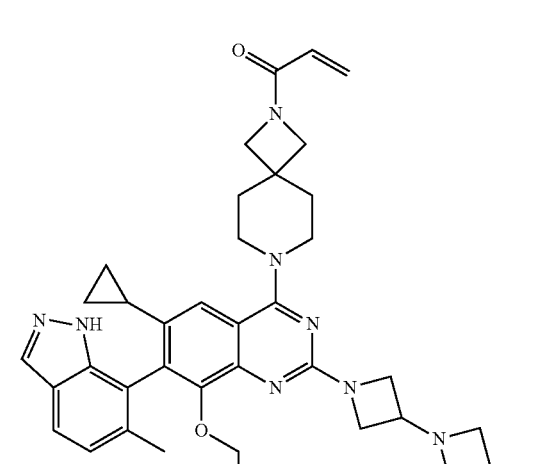 | 713.4 |

TABLE 1-continued

| | Compound structure | [M + H]+ |
|---|---|---|
| 110 | 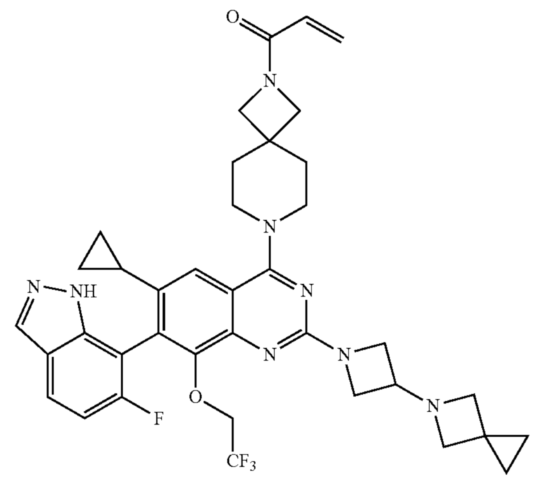 [SMILES: C=CC(=O)N1CC2(CCN(c3nc(N4CC(N5CC6(CC6)C5)C4)nc4c(OCC(F)(F)F)c(-c5c(F)ccc6cn[nH]c56)c(C5CC5)cc34)CC2)C1] | 717.3 |
| 111 | 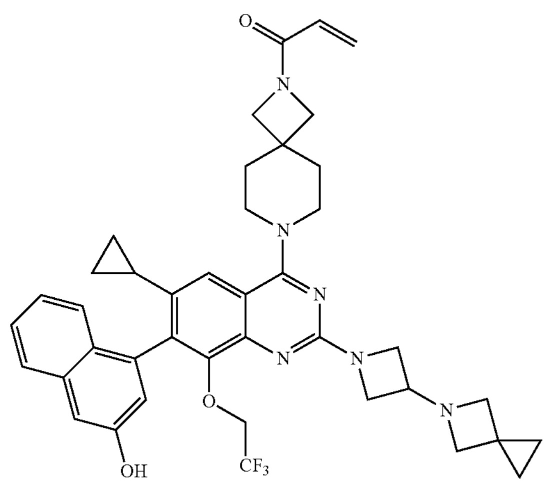 [SMILES: C=CC(=O)N1CC2(CCN(c3nc(N4CC(N5CC6(CC6)C5)C4)nc4c(OCC(F)(F)F)c(-c5cc(O)cc6ccccc56)c(C5CC5)cc34)CC2)C1] | 725.3 |
| 112 | 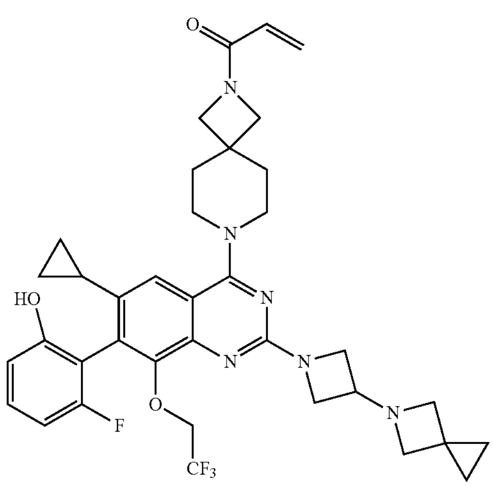 [SMILES: C=CC(=O)N1CC2(CCN(c3nc(N4CC(N5CC6(CC6)C5)C4)nc4c(OCC(F)(F)F)c(-c5c(O)cccc5F)c(C5CC5)cc34)CC2)C1] | 693.3 |

TABLE 1-continued

| Compound structure | [M + H]+ |
|---|---|
| 113 | 695.3 |
| 114 | 715.4 |
| 115 | 727.4 |

TABLE 1-continued
| Compound structure | [M + H]+ |
|---|---|
| 116 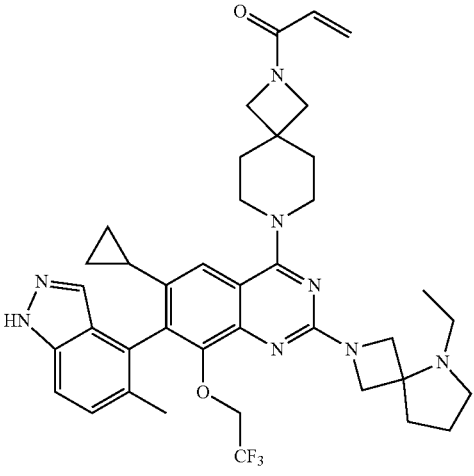 [SMILES: C=CC(=O)N1CC2(CCN(c3nc(N4CC5(CCCN5CC)C4)nc4c(OCC(F)(F)F)c(-c5c(C)ccc6[nH]ncc56)c(C5CC5)cc34)CC2)C1] | 715.4 |
| 117 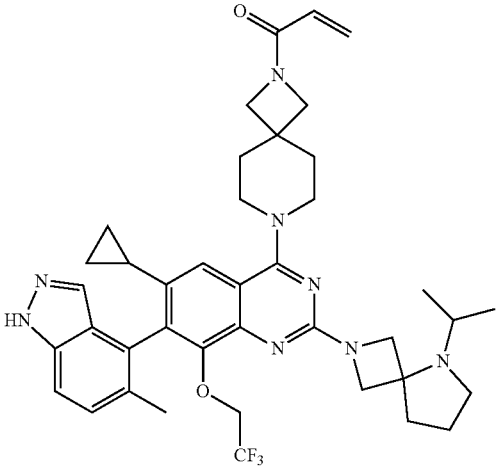 [SMILES: C=CC(=O)N1CC2(CCN(c3nc(N4CC5(CCCN5C(C)C)C4)nc4c(OCC(F)(F)F)c(-c5c(C)ccc6[nH]ncc56)c(C5CC5)cc34)CC2)C1] | 729.4 |
| 118 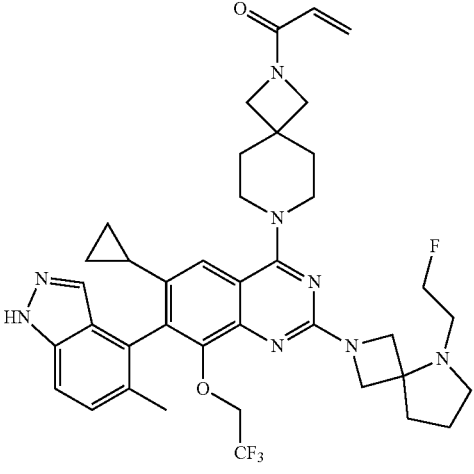 [SMILES: C=CC(=O)N1CC2(CCN(c3nc(N4CC5(CCCN5CCF)C4)nc4c(OCC(F)(F)F)c(-c5c(C)ccc6[nH]ncc56)c(C5CC5)cc34)CC2)C1] | 733.4 |

TABLE 1-continued
| Compound structure | [M + H]⁺ |
|---|---|
| 119 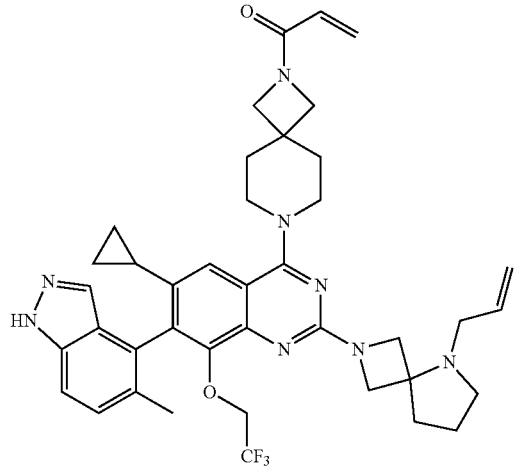 [SMILES: C=CCN1CCCC12CN(c1nc(N3CCC4(CC3)CN(C(=O)C=C)C4)c3cc(C4CC4)c(-c4c(C)ccc5[nH]ncc45)c(OCC(F)(F)F)c3n1)C2] | 727.4 |
| 120 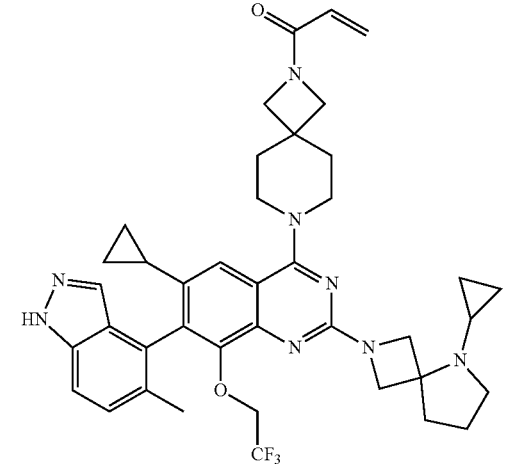 [SMILES: C=CC(=O)N1CC2(CCN(c3nc(N4CC5(CCCN5C5CC5)C4)nc4c(OCC(F)(F)F)c(-c5c(C)ccc6[nH]ncc56)c(C5CC5)cc34)CC2)C1] | 727.4 |
| 121 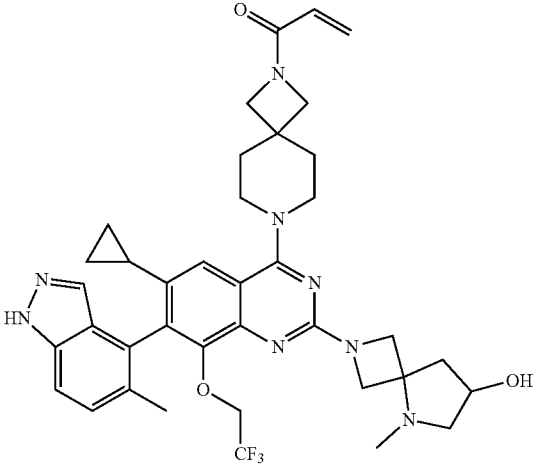 [SMILES: C=CC(=O)N1CC2(CCN(c3nc(N4CC5(CC(O)CN5C)C4)nc4c(OCC(F)(F)F)c(-c5c(C)ccc6[nH]ncc56)c(C5CC5)cc34)CC2)C1] | 717.3 |

TABLE 1-continued
| | Compound structure | [M + H]+ |
|---|---|---|
| 122 | 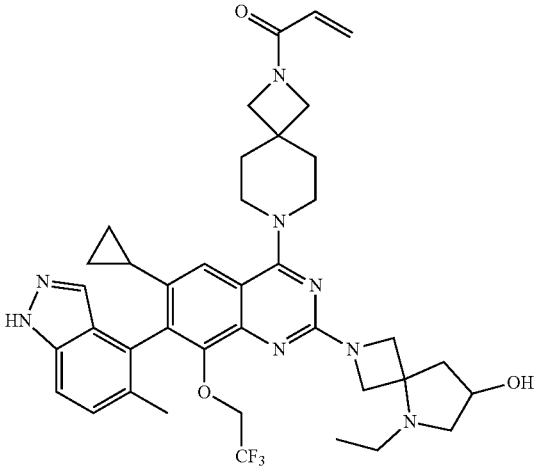 [SMILES: C=CC(=O)N1CC2(CCN(c3nc(N4CC5(CC(O)CN5CC)C4)nc4c(OCC(F)(F)F)c(-c5c(C)ccc6[nH]ncc56)c(C5CC5)cc34)CC2)C1] | 731.4 |
| 123 | 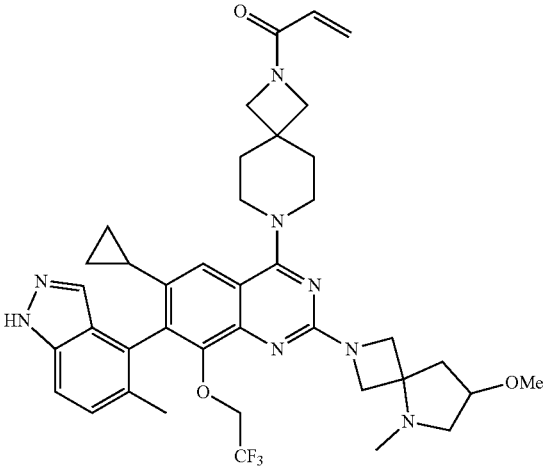 [SMILES: C=CC(=O)N1CC2(CCN(c3nc(N4CC5(CC(OC)CN5C)C4)nc4c(OCC(F)(F)F)c(-c5c(C)ccc6[nH]ncc56)c(C5CC5)cc34)CC2)C1] | 731.4 |
| 124 | 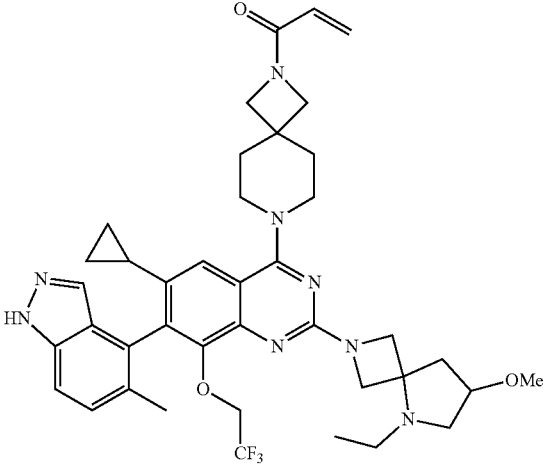 [SMILES: C=CC(=O)N1CC2(CCN(c3nc(N4CC5(CC(OC)CN5CC)C4)nc4c(OCC(F)(F)F)c(-c5c(C)ccc6[nH]ncc56)c(C5CC5)cc34)CC2)C1] | 745.4 |

TABLE 1-continued
| Compound structure | [M + H]+ |
|---|---|
| 125 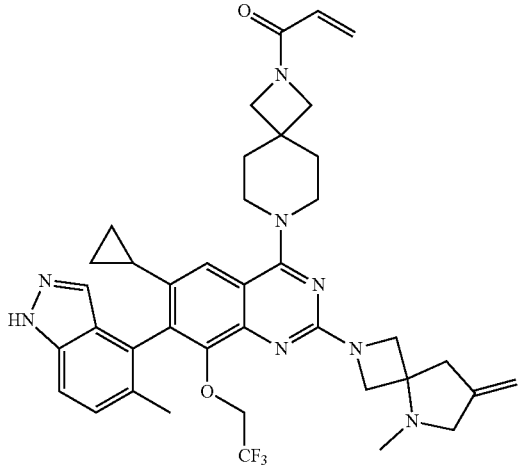 [SMILES: C=CC(=O)N1CC2(CCN(c3nc(N4CC5(CC(=C)CN5C)C4)nc4c(OCC(F)(F)F)c(-c5c(C)ccc6[nH]ncc56)c(C5CC5)cc34)CC2)C1] | 713.4 |
| 126 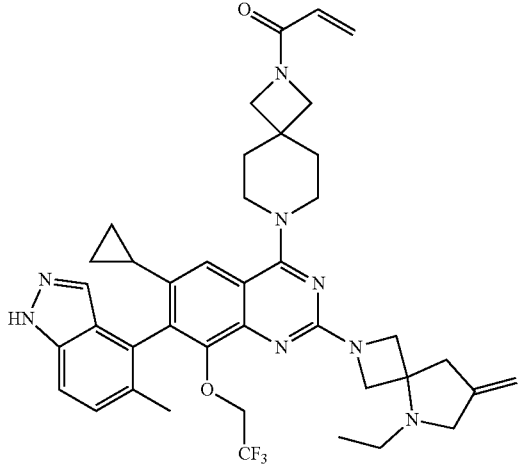 [SMILES: C=CC(=O)N1CC2(CCN(c3nc(N4CC5(CC(=C)CN5CC)C4)nc4c(OCC(F)(F)F)c(-c5c(C)ccc6[nH]ncc56)c(C5CC5)cc34)CC2)C1] | 727.4 |
| 127 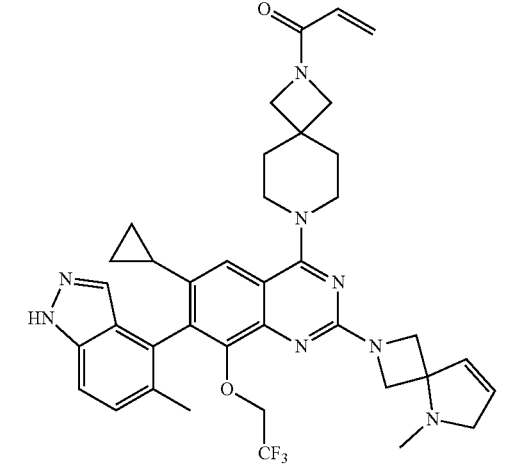 [SMILES: C=CC(=O)N1CC2(CCN(c3nc(N4CC5(C=CCN5C)C4)nc4c(OCC(F)(F)F)c(-c5c(C)ccc6[nH]ncc56)c(C5CC5)cc34)CC2)C1] | 699.3 |

TABLE 1-continued
| Compound structure | [M + H]+ |
|---|---|
| 128 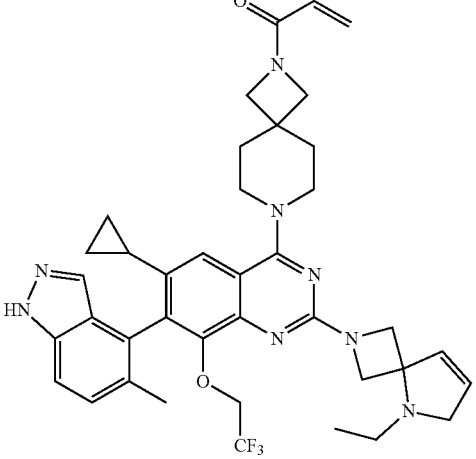 | 713.4 |
| 129 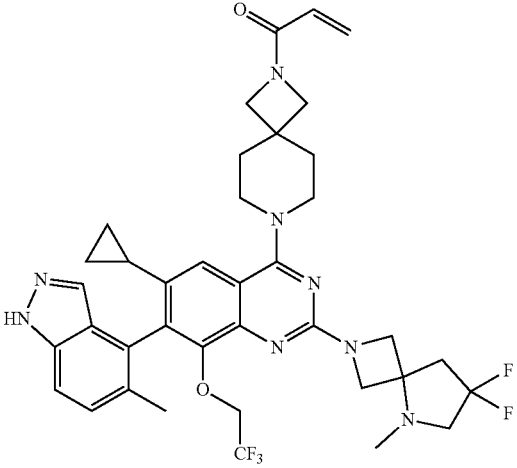 [SMILES: C=CC(=O)N1CC2(CCN(c3nc(N4CC5(C4)CC(F)(F)CN5C)nc4c(OCC(F)(F)F)c(-c5c(C)ccc6[nH]ncc56)c(C5CC5)cc34)CC2)C1] | 737.3 |
| 130 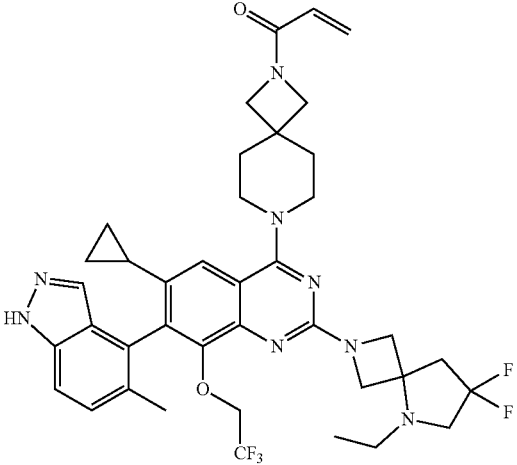 [SMILES: C=CC(=O)N1CC2(CCN(c3nc(N4CC5(C4)CC(F)(F)CN5CC)nc4c(OCC(F)(F)F)c(-c5c(C)ccc6[nH]ncc56)c(C5CC5)cc34)CC2)C1] | 751.3 |

TABLE 1-continued

| Compound structure | [M + H]⁺ |
|---|---|
| 131 | 687.3 |
| 132 | 701.4 |

Example 133: Chiral Resolution of Compound 73

The compounds of the present application may have axial chirality. The compounds with axial chirality can be resolved to obtain two chiral isomers.

The sample was dissolved in ethanol to reach a concentration of 25 mg/mL, and the injection volume was 500 μL. Conditions for preparative chromatography: CHIRALPAK AD-H (20×250 mm, 5 μm) chromatography column; mobile phase: ethanol-n-hexane (40:60); flow rate: 12 mL/min; wavelength of detection: 254 nm. The stepwise eluate was concentrated by rotary evaporation and dried to obtain products 73-a and 73-b:

- a first axially chiral isomer: 73-a; retention time on the chromatographic column: 8.532 min; and
- a second axially chiral isomer: 73-b; retention time on the chromatographic column: 10.126 min.

The compound 67 was chirally resolved by a similar resolution method to obtain their two chiral isomers 67-a and 67-b, and the retention time on the chromatographic column was as follows:

- a first axially chiral isomer: 67-a; retention time on the chromatographic column: 5.413 min; and
- a second axially chiral isomer: 67-b; retention time on the chromatographic column: 7.938 min. Other compounds in the present application can also be chirally resolved using a similar method.

Example 134. pERK and ERK Protein Content Assay in 11358 Cells by Compounds

H358 cells were seeded in a 24-well plate. After one day of growth, a test compound (at a concentration of 1 μM) was added. After 24 h of action of the compound, the cells were lysed, and the cell lysate was transferred to a 96-well ELISA plate. The levels of pERK and ERK in the lysate were measured using an ELISA kit (abcam 176660). The ratio of pERK to ERK was calculated and compared with that of the DMSO group, and the percentage of inhibition of pERK activity by the compound was calculated. The results are shown in Table 2 below.

TABLE 2

Inhibitory activity of the compounds of the present invention against the pERK level in H358 cells

| Compound | Inhibition rate (%) | Compound | Inhibition rate (%) | Compound | Inhibition rate (%) |
|---|---|---|---|---|---|
| 1 | +++ | 2 | +++ | 3 | ++ |
| 4 | +++ | 5 | +++ | 6 | +++ |
| 7 | +++ | 8 | ++ | 9 | +++ |
| 10 | +++ | 11 | +++ | 12 | +++ |
| 13 | +++ | 14 | +++ | 15 | +++ |
| 16 | +++ | 17 | +++ | 18 | +++ |
| 19 | +++ | 20 | ++ | 21 | +++ |
| 22 | +++ | 23 | +++ | 24 | +++ |
| 25 | +++ | 26 | ++ | 27 | ++ |
| 28 | +++ | 29 | +++ | 30 | +++ |
| 31 | +++ | 32 | +++ | 33 | ++ |
| 34 | +++ | 35 | +++ | 36 | ++ |
| 37 | +++ | 38 | +++ | 39 | ++ |
| 40 | ++ | 41 | ++ | 42 | ++ |
| 43 | ++ | 44 | +++ | 45 | +++ |
| 46 | +++ | 47 | +++ | 48 | ++ |
| 49 | +++ | 50 | ++ | 51 | +++ |
| 52 | +++ | 53 | +++ | 54 | +++ |
| 55 | +++ | 56 | +++ | 57 | ++ |
| 58 | +++ | 59 | +++ | 60 | +++ |
| 61 | +++ | 62 | +++ | 63 | +++ |
| 64 | +++ | 65 | ++ | 66 | ++ |
| 67 | +++ | 68 | +++ | 69 | +++ |
| 70 | +++ | 71 | +++ | 72 | +++ |
| 73 | +++ | 74 | +++ | 75 | ++ |
| 76 | +++ | 77 | +++ | 78 | +++ |
| 79 | +++ | 80 | ++ | 81 | +++ |
| 82 | +++ | 83 | ++ | 84 | ++ |
| 85 | +++ | 86 | ++ | 87 | +++ |
| 88 | ++ | 89 | +++ | 90 | ++ |
| 91 | +++ | 92 | ++ | 93 | +++ |
| 94 | ++ | 95 | +++ | 96 | +++ |
| 97 | +++ | 98 | +++ | 99 | +++ |
| 100 | +++ | 101 | +++ | 102 | +++ |
| 103 | +++ | 104 | +++ | 105 | +++ |
| 106 | +++ | 107 | +++ | 108 | +++ |
| 109 | +++ | 110 | +++ | 111 | +++ |
| 112 | +++ | 113 | ++ | 114 | +++ |
| 115 | +++ | 116 | +++ | 117 | +++ |
| 118 | +++ | 119 | +++ | 120 | +++ |
| 121 | +++ | 122 | +++ | 123 | +++ |
| 124 | +++ | 125 | +++ | 126 | +++ |
| 127 | +++ | 128 | +++ | 129 | +++ |
| 130 | +++ | 131 | +++ | 132 | +++ |
| 1-a | +++ | 1-b | +++ | 67-a | +++ |
| 67-b | +++ | 73-a | +++ | 73-b | +++ |
| B | +++ | | | | |

+ indicates an inhibition rate less than or equal to 50%
++ indicates an inhibition rate from 50% to 90%
+++ indicates an inhibition rate greater than 90%.

Example 135. Antiproliferative Activity of Compounds Against H358 Cells

2500 H358 cells were seeded in a 96-well ultra-low attachment plate (corning, 7007). After one day of growth, a serially diluted compound (a maximum concentration of 5 µM, 5-fold dilution, a total of five doses) was added. Three days after the addition of the compound, Cell Titer Glow (Promega, G9681) was added to evaluate pellet growth, and the $IC_{50}$ value was calculated. The results are shown in Table 3 below.

TABLE 3

Antiproliferative activity of the compounds of the present invention against H358 cells

| Compound | $IC_{50}$ | Compound | $IC_{50}$ | Compound | $IC_{50}$ |
|---|---|---|---|---|---|
| 1 | +++ | 2 | +++ | 3 | ++ |
| 4 | +++ | 5 | +++ | 6 | +++ |
| 7 | +++ | 8 | ++ | 9 | +++ |
| 10 | +++ | 11 | +++ | 12 | +++ |
| 13 | +++ | 14 | +++ | 15 | +++ |
| 16 | +++ | 17 | +++ | 18 | +++ |
| 19 | +++ | 20 | ++ | 21 | +++ |
| 22 | +++ | 23 | +++ | 24 | +++ |
| 25 | ++ | 26 | ++ | 27 | ++ |
| 28 | +++ | 29 | +++ | 30 | +++ |
| 31 | +++ | 32 | +++ | 33 | ++ |
| 34 | +++ | 35 | +++ | 36 | ++ |
| 37 | +++ | 38 | ++ | 39 | ++ |
| 40 | + | 41 | ++ | 42 | + |
| 43 | + | 44 | +++ | 45 | +++ |
| 46 | +++ | 47 | +++ | 48 | ++ |
| 49 | +++ | 50 | ++ | 51 | +++ |
| 52 | +++ | 53 | +++ | 54 | +++ |
| 55 | +++ | 56 | +++ | 57 | ++ |
| 58 | +++ | 59 | +++ | 60 | +++ |
| 61 | +++ | 62 | +++ | 63 | +++ |
| 64 | +++ | 65 | ++ | 66 | ++ |
| 67 | +++ | 68 | +++ | 69 | +++ |
| 70 | +++ | 71 | +++ | 72 | +++ |
| 73 | +++ | 74 | +++ | 75 | ++ |
| 76 | +++ | 77 | +++ | 78 | +++ |
| 79 | +++ | 80 | ++ | 81 | +++ |
| 82 | +++ | 83 | ++ | 84 | ++ |
| 85 | +++ | 86 | ++ | 87 | +++ |
| 88 | ++ | 89 | +++ | 90 | ++ |
| 91 | +++ | 92 | + | 93 | +++ |
| 94 | ++ | 95 | +++ | 96 | ++ |
| 97 | +++ | 98 | +++ | 99 | +++ |
| 100 | +++ | 101 | +++ | 102 | +++ |
| 103 | +++ | 104 | +++ | 105 | +++ |
| 106 | +++ | 107 | +++ | 108 | +++ |
| 109 | +++ | 110 | +++ | 111 | ++ |
| 112 | +++ | 113 | ++ | 114 | +++ |
| 115 | +++ | 116 | +++ | 117 | +++ |
| 118 | +++ | 119 | +++ | 120 | +++ |
| 121 | +++ | 122 | +++ | 123 | +++ |
| 124 | +++ | 125 | +++ | 126 | +++ |
| 127 | +++ | 128 | +++ | 129 | +++ |
| 130 | +++ | 131 | +++ | 132 | +++ |
| 1-a | +++ | 1-b | +++ | 67-a | +++ |
| 67-b | +++ | 73-a | +++ | 73-b | +++ |
| B | +++ | | | | |

+ indicates the IC50 of the compound is greater than 1 µM
++ indicates the IC50 of the compound is from 0.3 to 1 µM
+++ indicates the IC50 of the compound is less than 0.3 µM.

As can be seen from the data in Tables 2 and 3, most of the compounds of the present invention have antiproliferative activity against H358 cells less than 0.3 µM, and when $R^4$ is a non-aromatic heterocyclic ring or a spiro ring, the compounds have strong inhibitory activity against the ERK phosphorylation of the RAS pathway, and the compounds have strong inhibitory activity against the proliferation of H358 tumor cells carrying a K-RAS G12C mutation.

Example 136. Evaluation of Antitumor Activity in Mice

Human pancreatic cancer Mia PaCa-2 cells were cultured conventionally in 1640 medium containing 10% fetal bovine serum in a 37° C./5% $CO_2$ incubator. After being subcultured, the cells were collected when they reached the desired amount. $1 \times 10^7$ Mia PaCa-2 cells were injected into the left dorsal side of each nude mouse, and the animals were randomly grouped for administration after tumors grew to 150 mm³. The groups were as follows: 1) solvent control group, 8 mice; 2) compound 6 group, compound 14 group, compound 28 group, compound 44 group, compound 60 group, compound 103 group and control drug B (Example 35 in WO2018/143315), 8 mice in each group. The mice in the solvent control group was intragastrically administered with 0.5% CMC-Na once a day; and the mice in the compound groups were intragastrically administered with 0.5% CMC-Na suspension once a day. On Tuesday and Thursday each week, tumor volumes and body weight of the mice were measured, and the nude mice were sacrificed on day 21 during the treatment period. The test results are shown in Table 4 below.

TABLE 4

Experimental therapeutic effects of compounds on human pancreatic cancer Mia PaCa-2 xenograft tumors in nude mice

| Compound | Dose (mg/kg) | Administration regimen | Anti-tumor effect |
|---|---|---|---|
| 6 | 10 | qd*21 | 35% regression |
| 14 | 10 | qd*21 | 37% regression |
| 28 | 10 | qd*21 | 42% regression |
| 44 | 10 | qd*21 | 23% regression |
| 60 | 10 | qd*21 | 30% regression |
| 103 | 10 | qd*21 | 39% regression |
| B | 10 | qd*21 | 28% regression |

As can be seen from the data in the table above, the compounds of the present invention have strong in vivo antitumor activity, and can cause tumor regression after 21 days of continuous administration at a dosage of 10 mg/kg/day. The compounds 6, 14, 28, 60 and 103 have stronger in vivo activity than the control drug B.

The invention claimed is:

1. A compound of general formula (1) or pharmaceutically acceptable salts thereof:

(1)

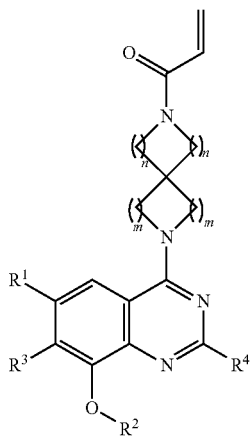

wherein in the general formula (1):
m is an integer of 1 or 2;
n is an integer of 1 or 2;
$R^1$ is H, halogen, C1-C3 alkyl, C2-C4 alkenyl, C2-C4 alkynyl or C3-C6 cycloalkyl;
$R^2$ is C1-C3 alkyl or halogenated C1-C3 alkyl;

$R^3$ is

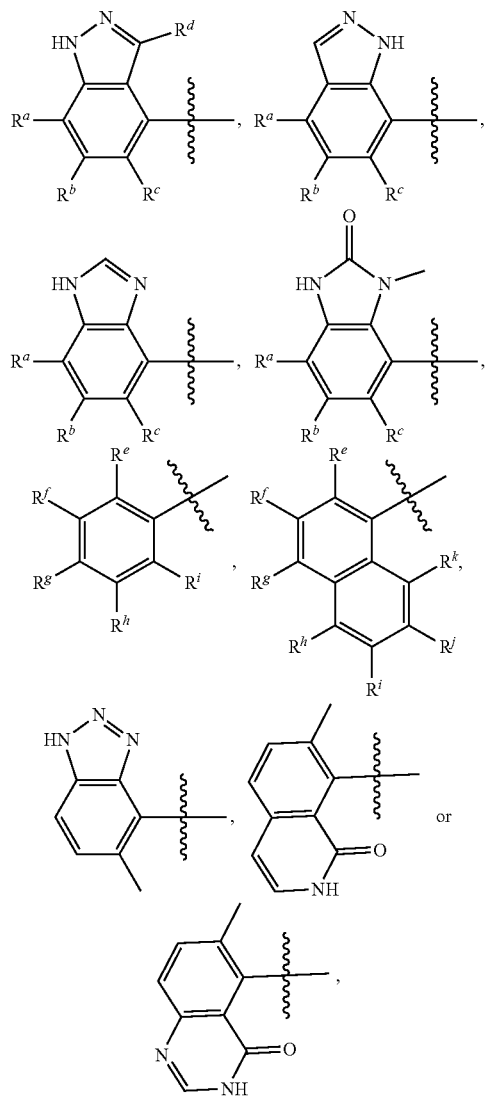

wherein $R^a$ is H or F, $R^b$ is H, F, Cl or Me, $R^c$ is H, F, Cl or Me, $R^d$ is H, F, Cl, $NH_2$, Me or cyclopropyl, and $R^e$, $R^f$, $R^g$, $R^h$, $R^i$, $R^j$ and $R^k$ are independently H, F, Cl, OH, OMe, $NH_2$, $CF_3$, C1-C3 alkyl or C3-C6 cycloalkyl;

$R^4$ is

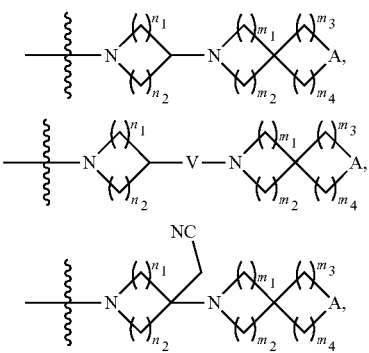

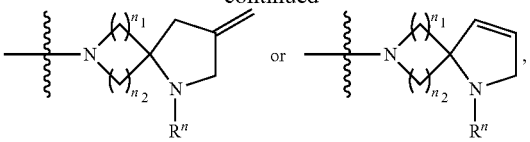

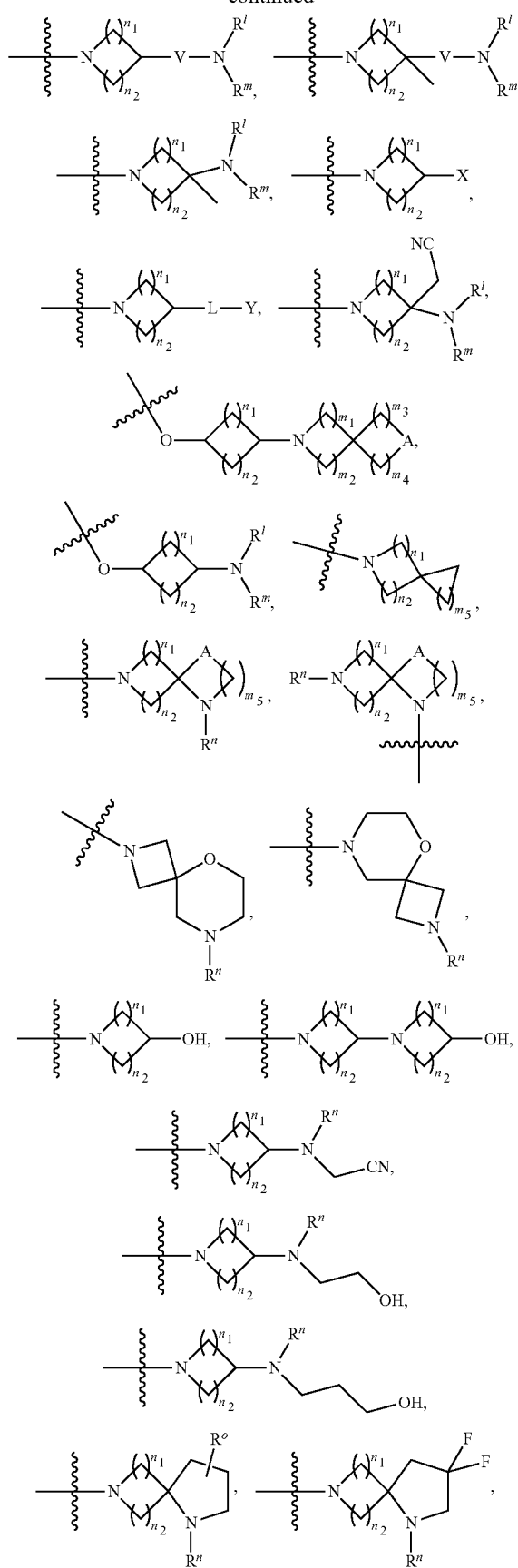

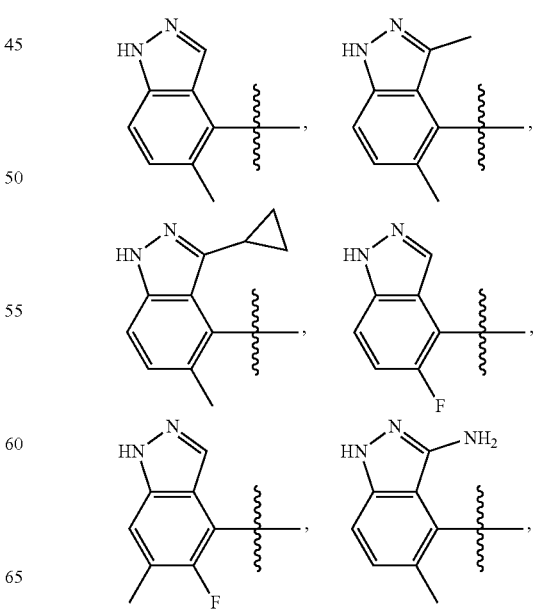

wherein $n_1$ and $n_2$ are independently integers of 1 or 2, $m_1$, $m_2$, $m_3$ and $m_4$ are independently integers of 0, 1, 2, 3 or 4, and $m_5$ is an integer of 1, 2 or 3; A is —$CH_2$—, —O—, —S—, —SO—, —$SO_2$— or —N(C1-C3 alkyl)-, V is —$CH_2$—, —$SO_2$— or —CO—, and L is —O—, —S—, —$SO_2$—, —SO— or —CO—; X is a 5- to 7-membered heteroaryl or a partially saturated 5- to 7-membered heterocycloalkyl; Y is C3-C6 cycloalkyl, heterocycloalkyl, (C3-C6) cycloalkyl-(C1-C3) alkyl- or heterocycloalkyl-(C1-C3) alkyl-; $R^l$ and $R^m$ are independently C1-C3 alkyl, halogenated C1-C3 alkyl, hydroxyl-substituted C1-C3 alkyl, cyano-substituted C1-C3 alkyl, C3-C6 cycloalkyl, (C1-C3) alkoxy-(C2-C3) alkyl-, (halogenated C1-C3) alkoxy-(C2-C3) alkyl-, (C3-C6) cycloalkyl-(C1-C3) alkyl-; or $R^l$ and $R^m$, together with a N atom, form 3- to 8-membered heterocycloalkyl, wherein the 3- to 8-membered heterocycloalkyl can be substituted with 1-3 substituents selected from OH, halogen, cyano, C1-C3 alkyl, C3-C6 cycloalkyl, heterocycloalkyl, (C1-C3) alkoxy and (halogenated C1-C3) alkoxy; $R^n$ is C1-C3 alkyl, C2-C4 alkenyl, C2-C4 alkynyl, C3-C6 cycloalkyl, heterocycloalkyl, halogenated C1-C3 alkyl, hydroxyl-substituted C1-C3 alkyl, cyano-substituted C1-C3 alkyl, (C1-C3) alkoxy-(C2-C3) alkyl-, (halogenated C1-C3) alkoxy-(C2-C3) alkyl-, (C3-C6) cycloalkyl-(C1-C3) alkyl- or heterocycloalkyl-(C1-C3) alkyl-; and $R^o$ is OH, halogen, cyano, C1-C3 alkyl, C1-C3 alkoxy or C3-C6 cycloalkyl.

2. The compound according to claim 1, wherein in the general formula (1), $R^1$ is H, F, Cl, Me, Et, isopropyl, vinyl, ethynyl or cyclopropyl.

3. The compound according to claim 1, wherein in the general formula (1), $R^2$ is $CH_3$, $CH_3CH_2$, $CF_3CH_2$, $CHF_2CH_2$ or $CF_3(CH_3)CH$.

4. The compound according to claim 1, wherein in the general formula (1), $R^3$ is

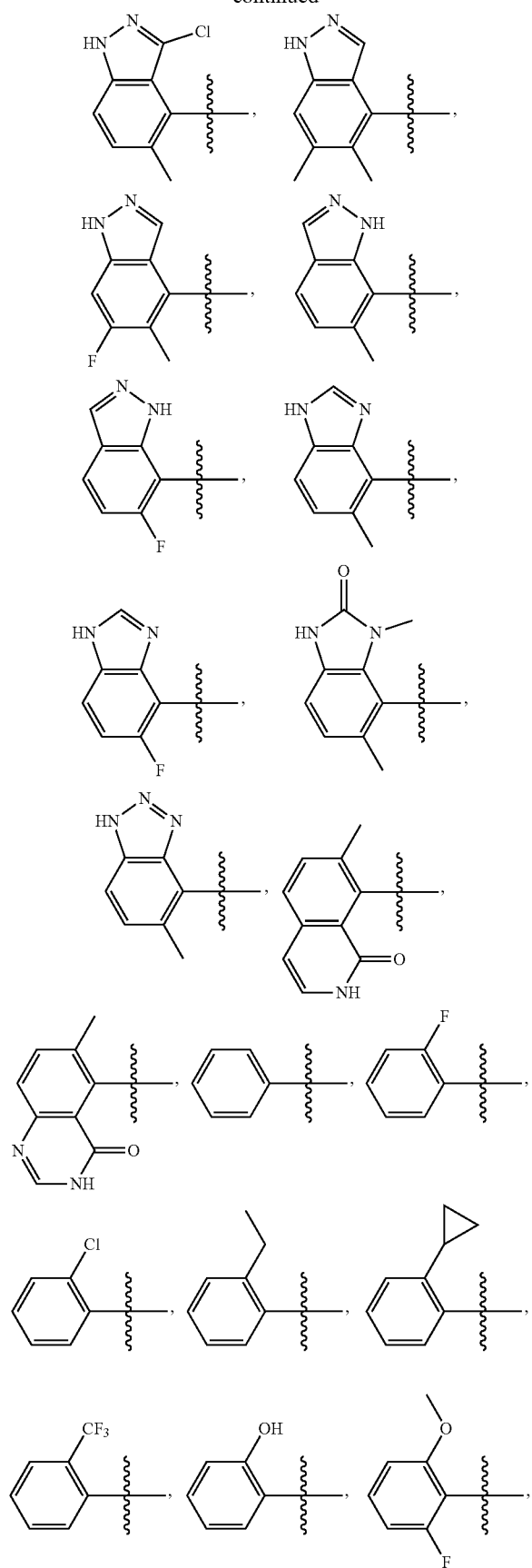
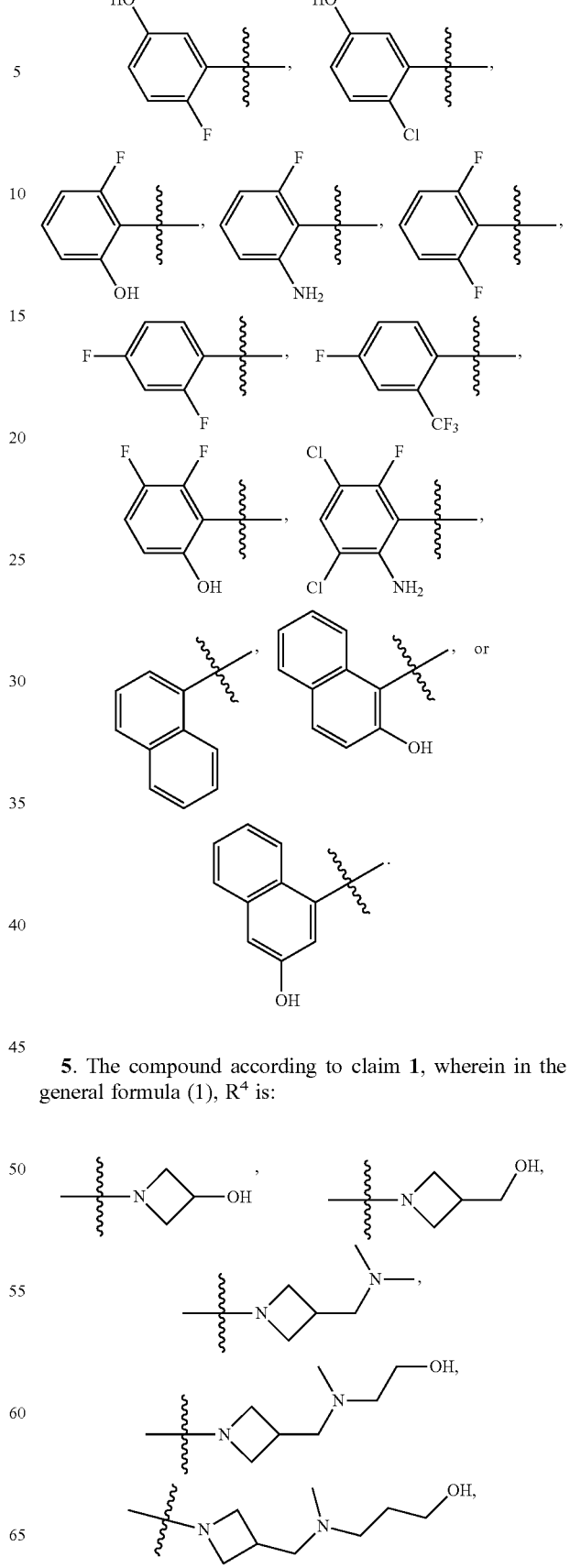
5. The compound according to claim 1, wherein in the general formula (1), $R^4$ is:

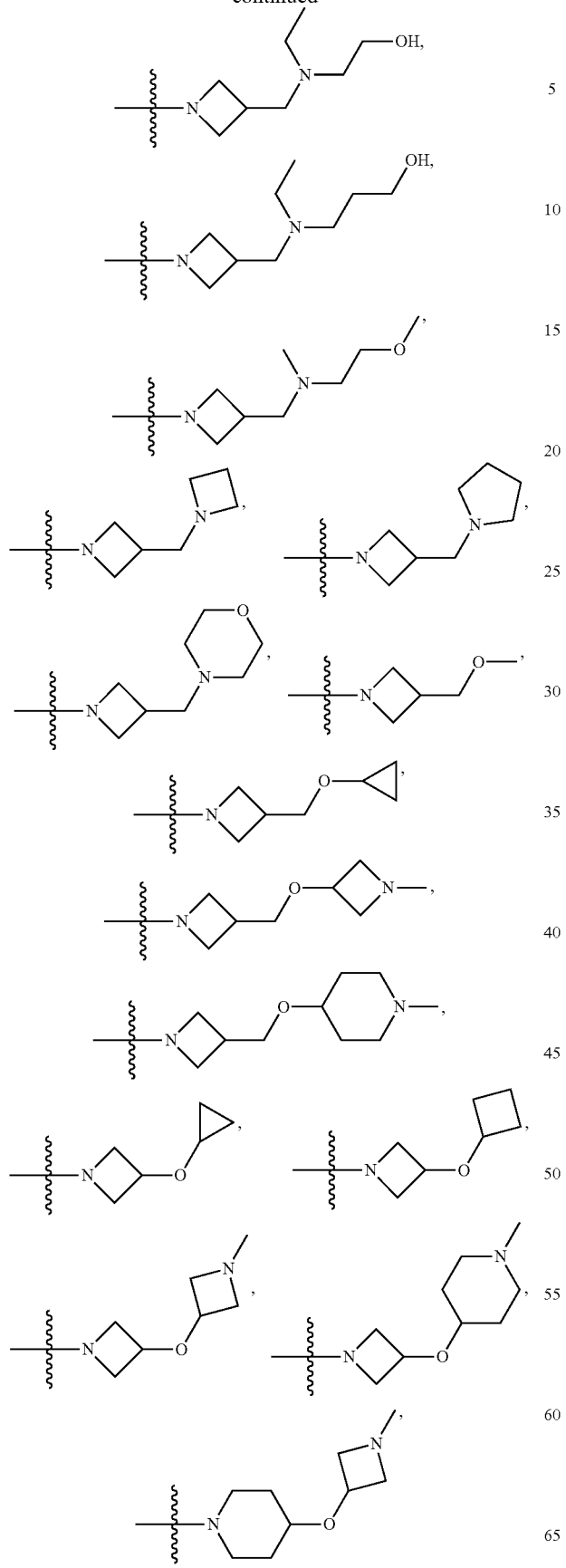
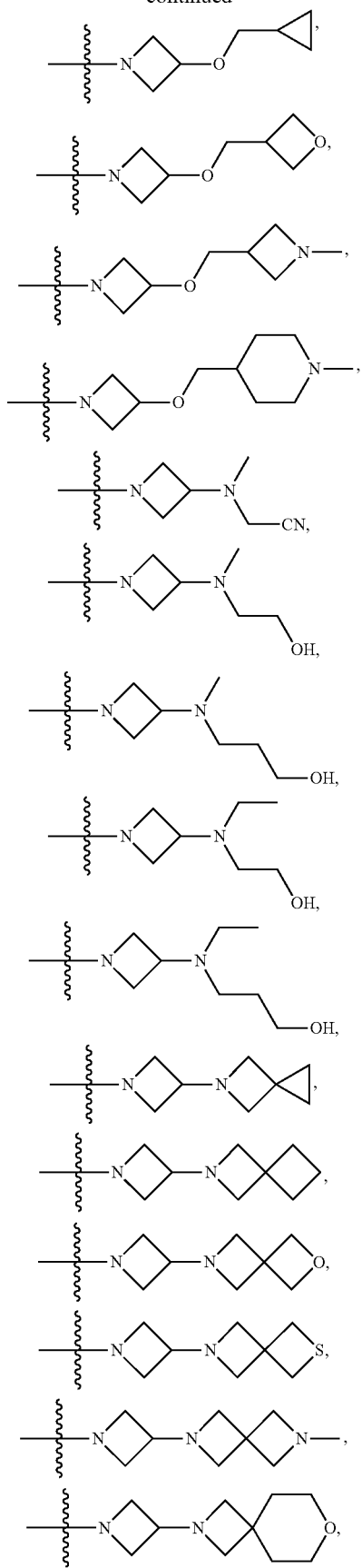

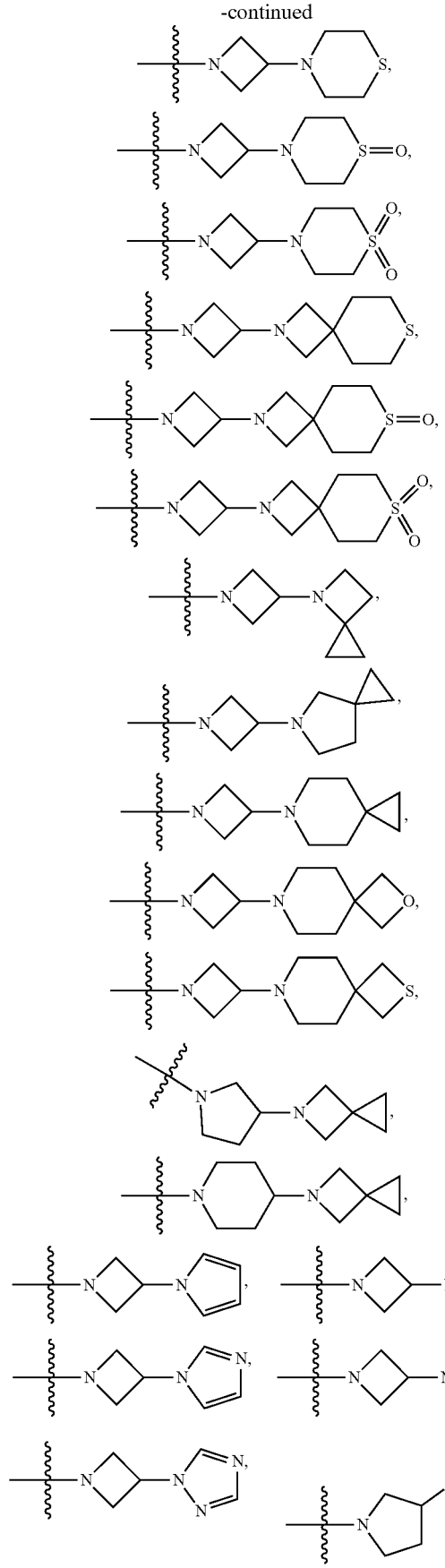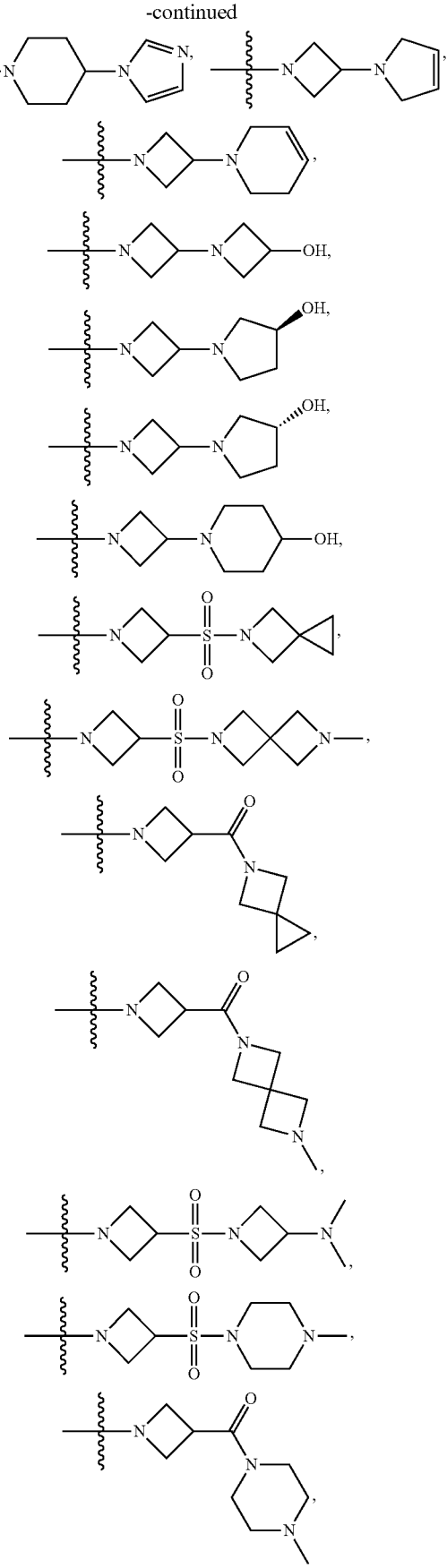

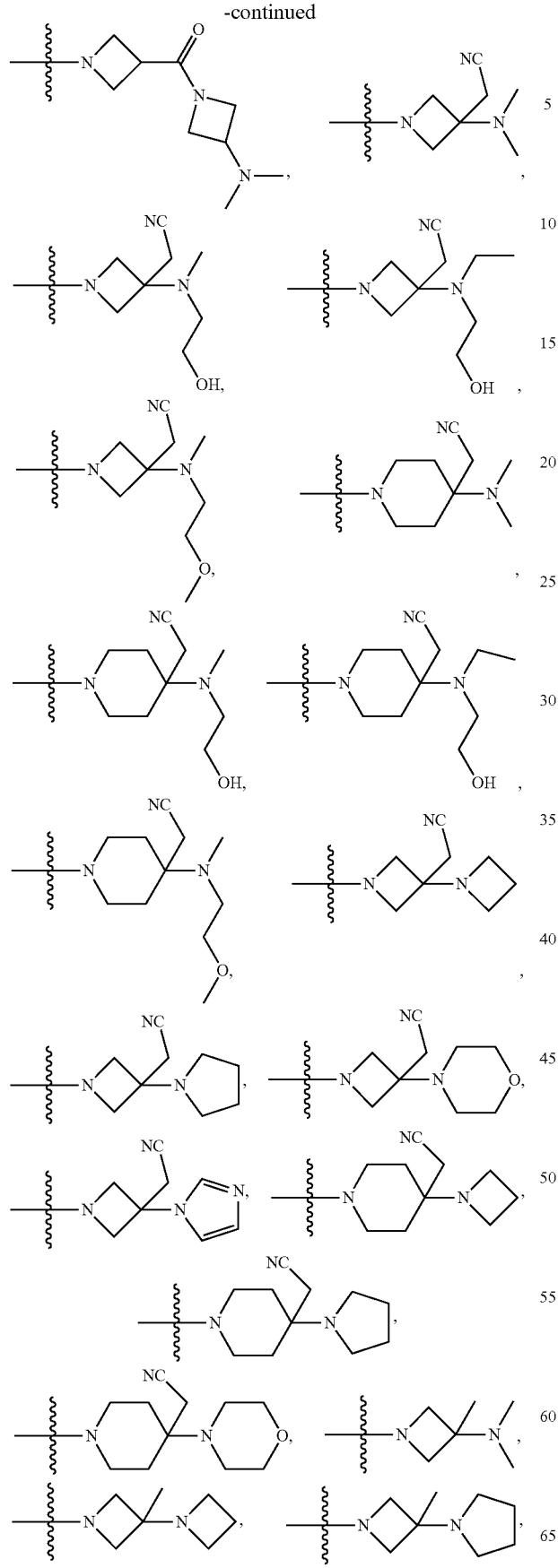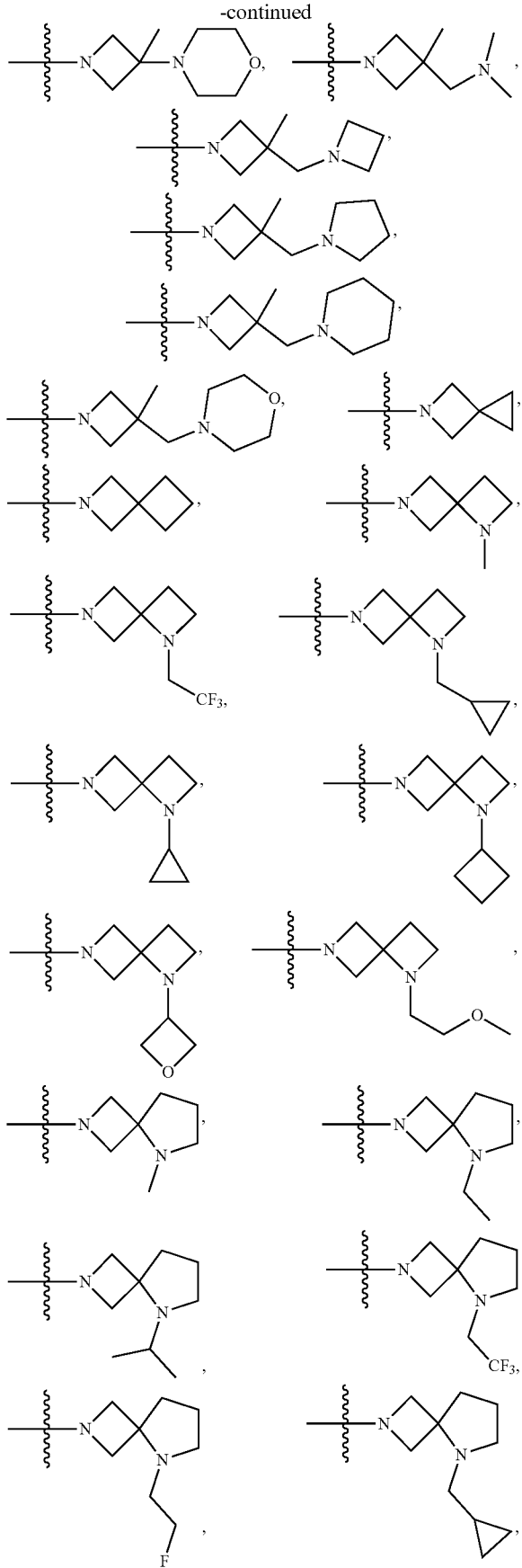

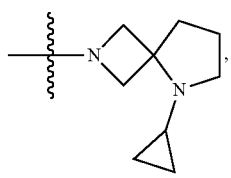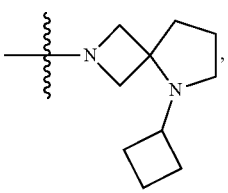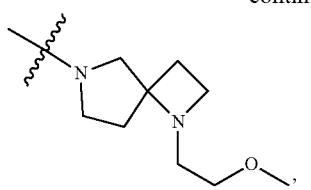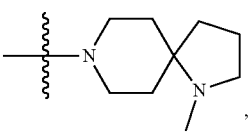
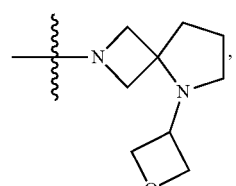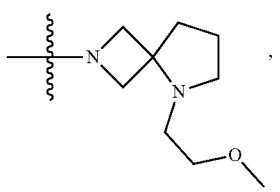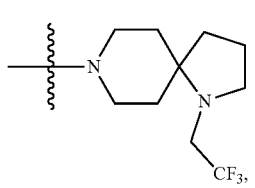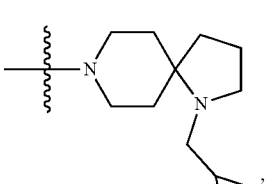
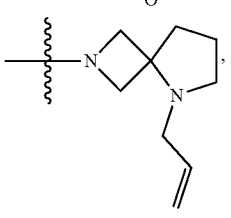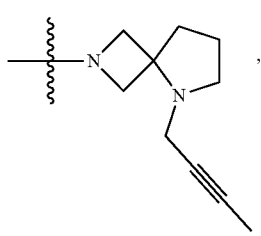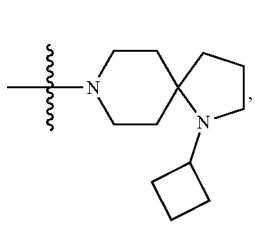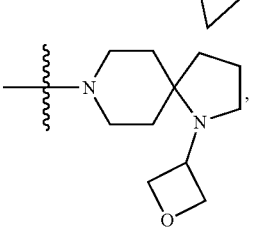
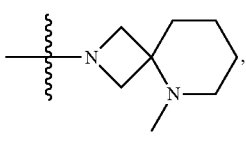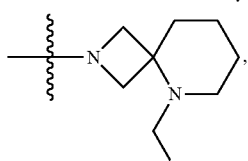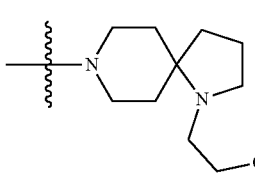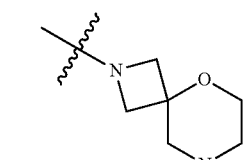
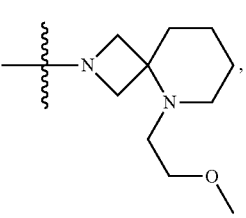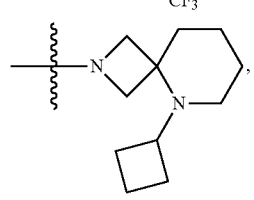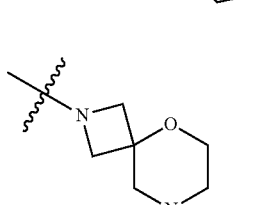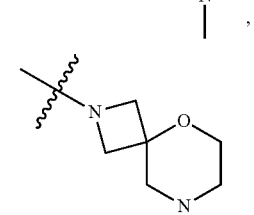
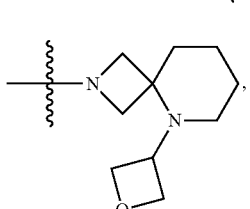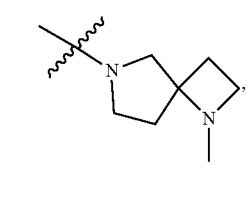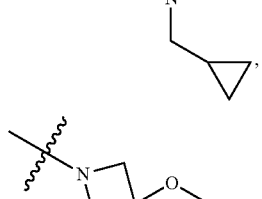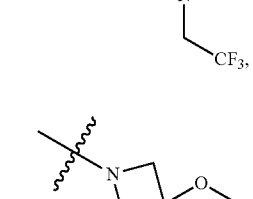
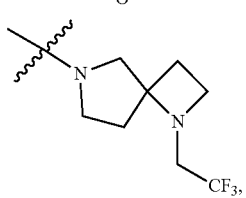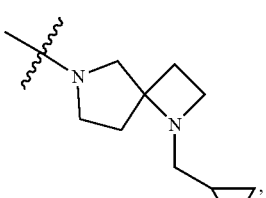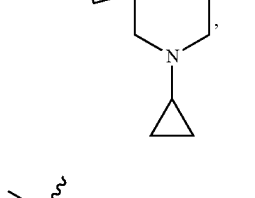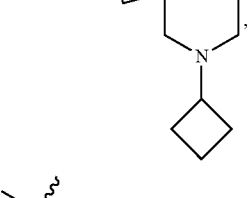
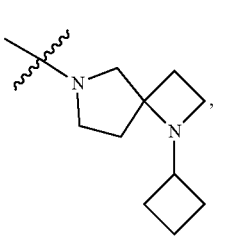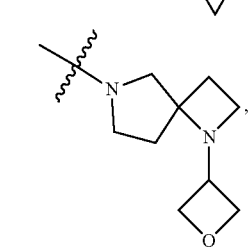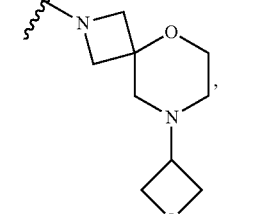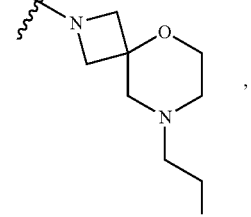

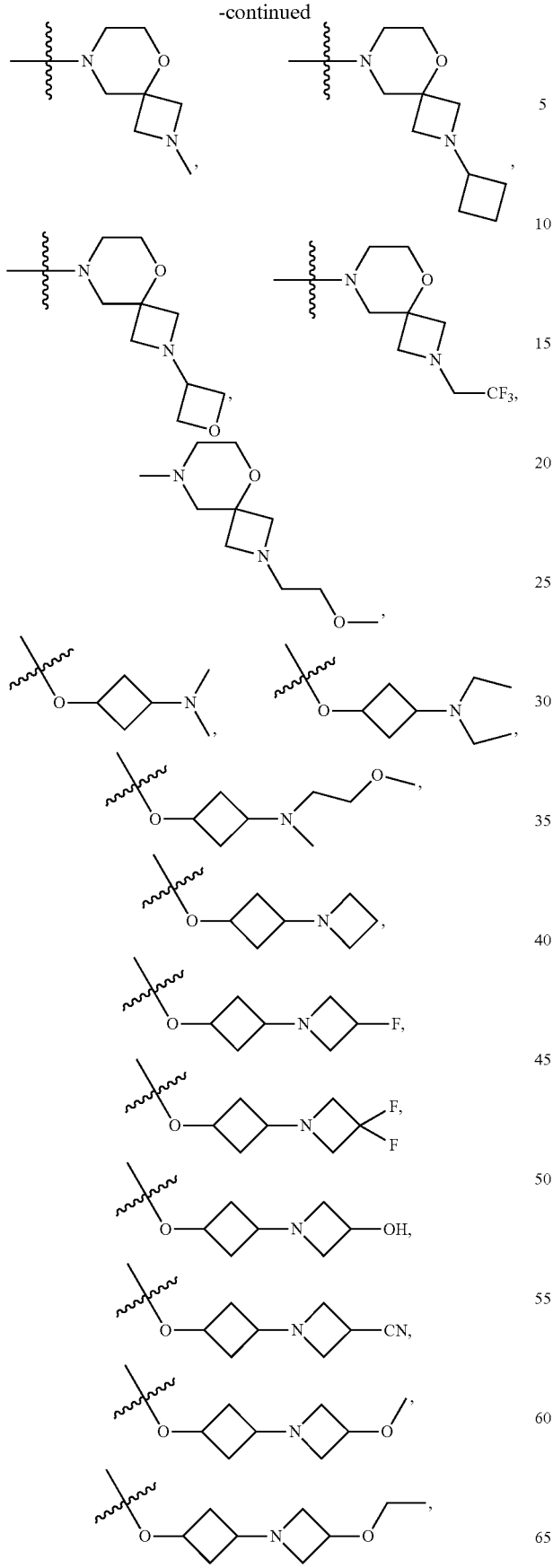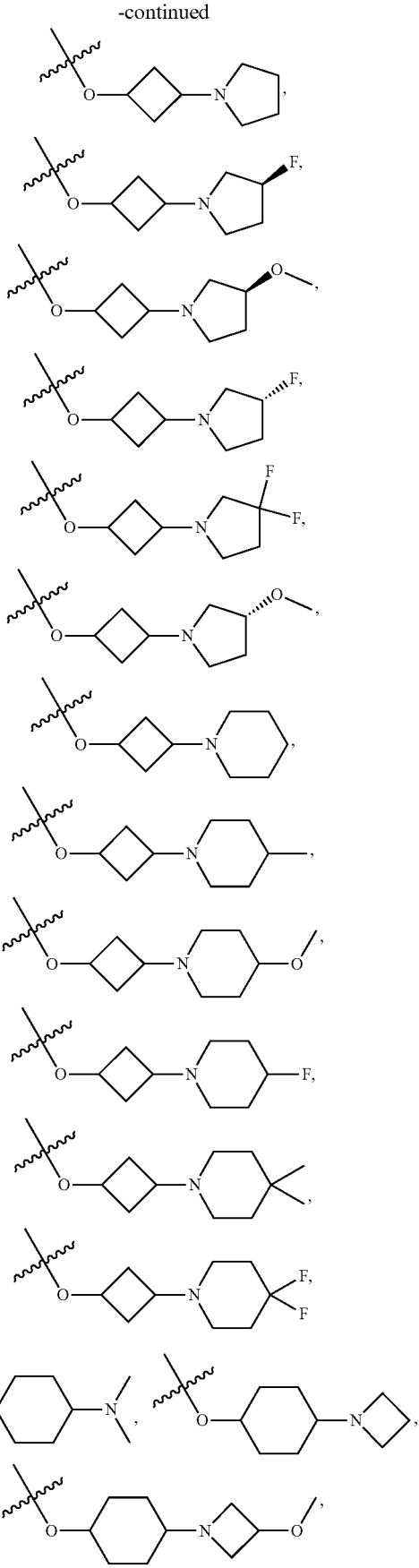

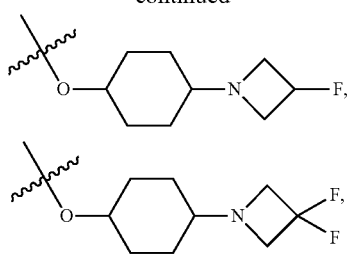
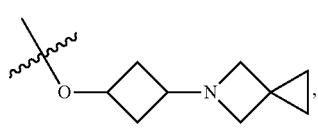
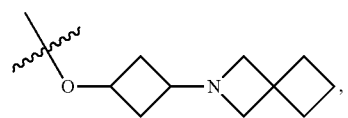
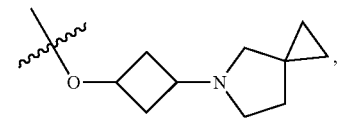
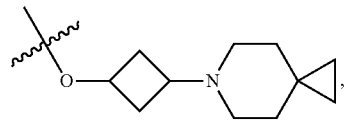
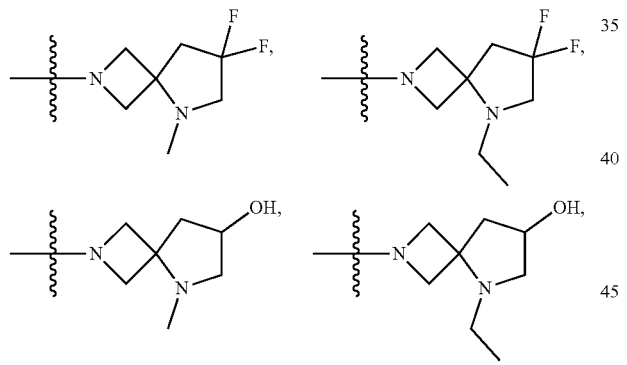
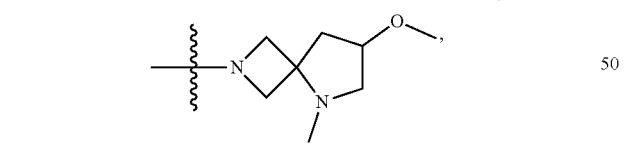
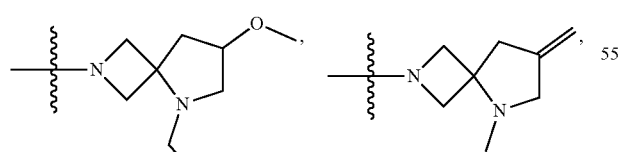
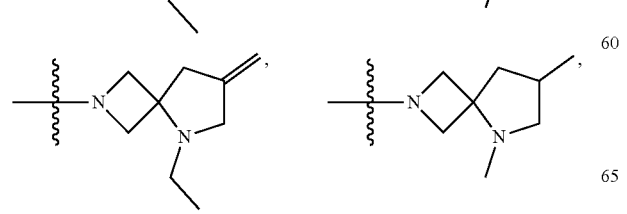
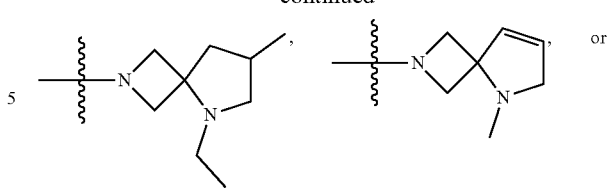
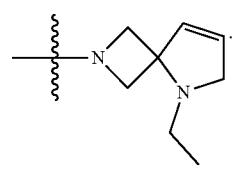
6. The compound according to claim 1 or a pharmaceutically acceptable salt thereof, wherein the compound has one of the following structures:
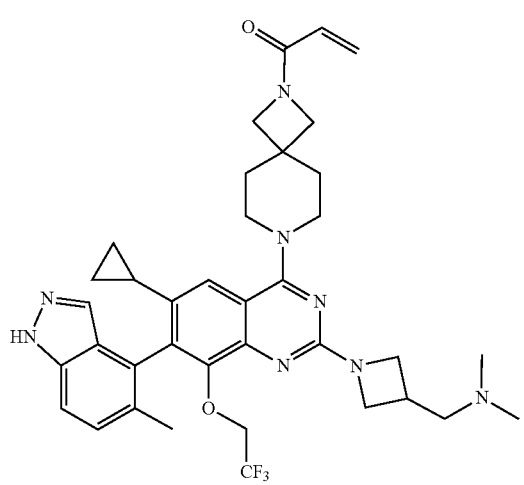

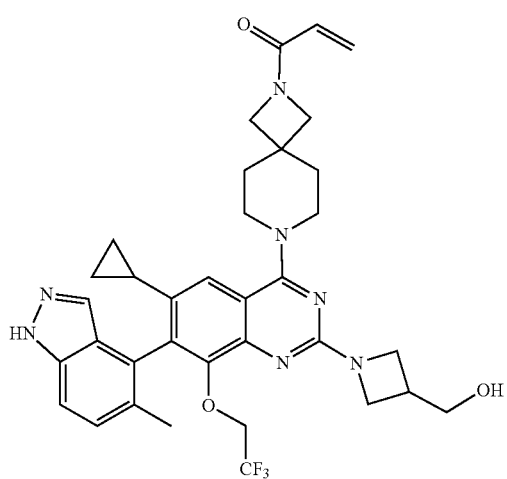
3
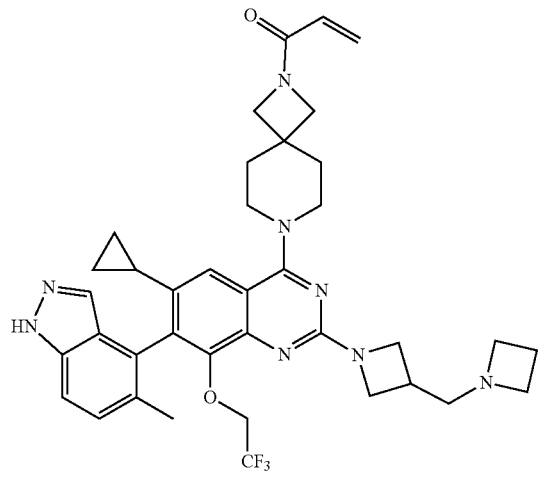
6
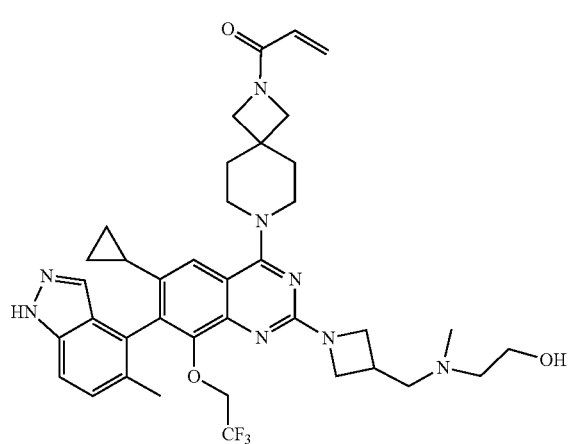
4
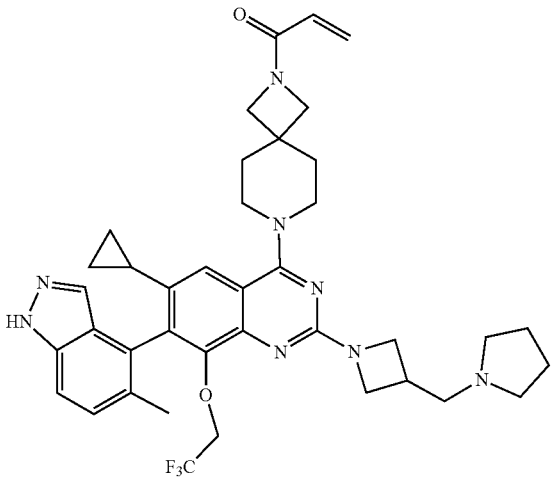
7
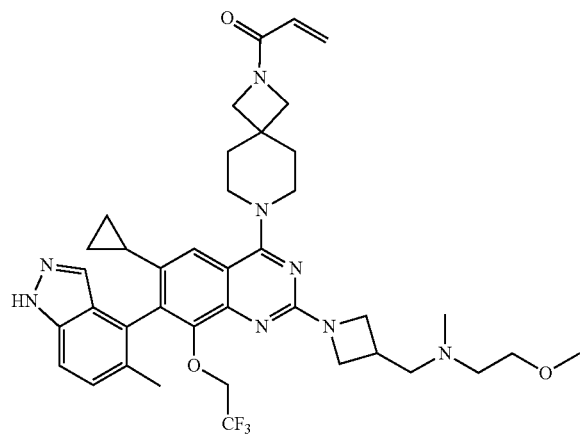
5
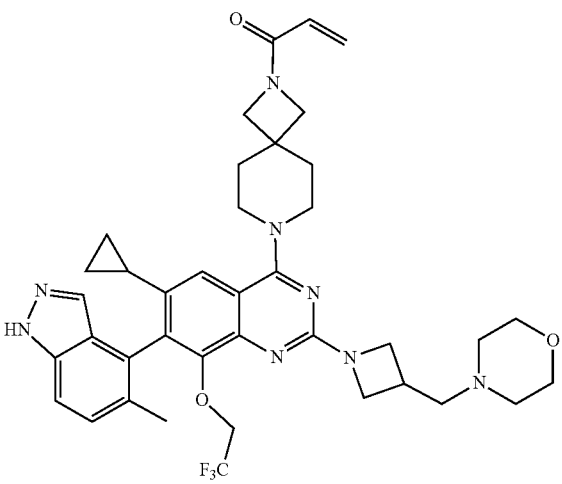
8

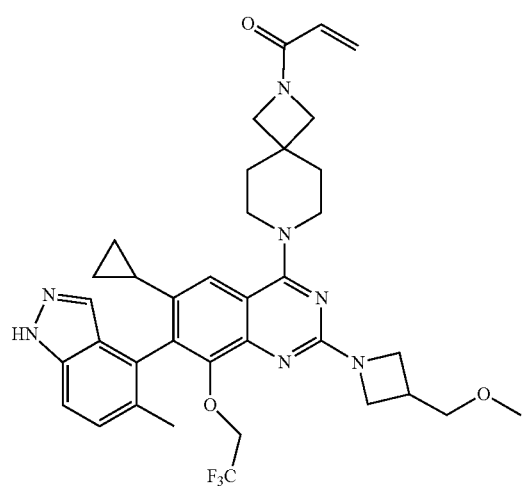
9
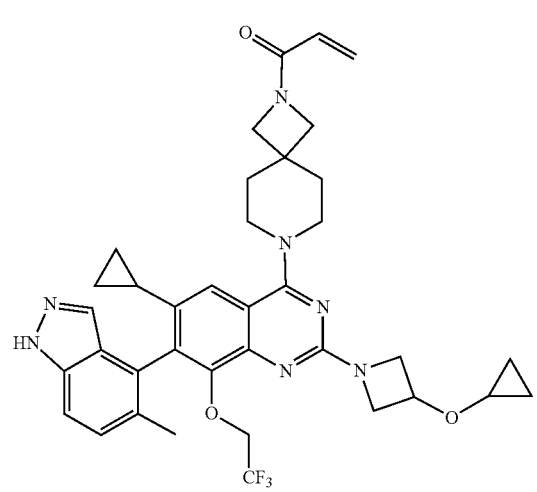
12
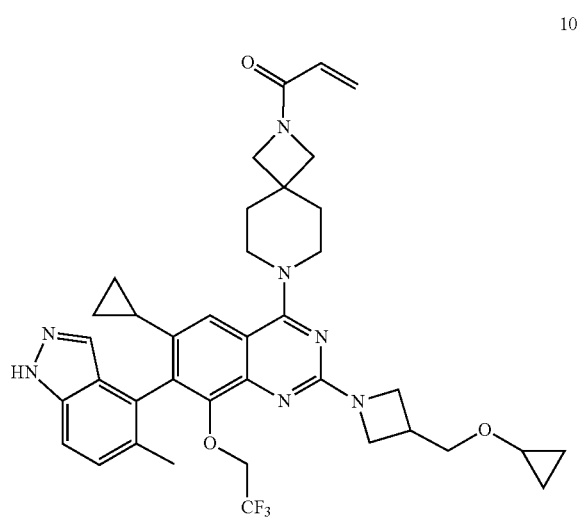
10
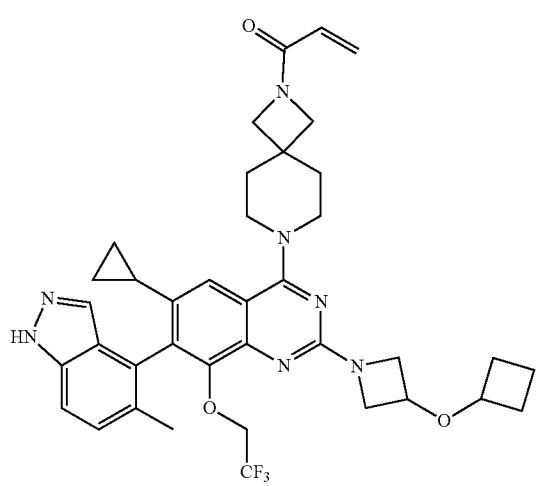
13
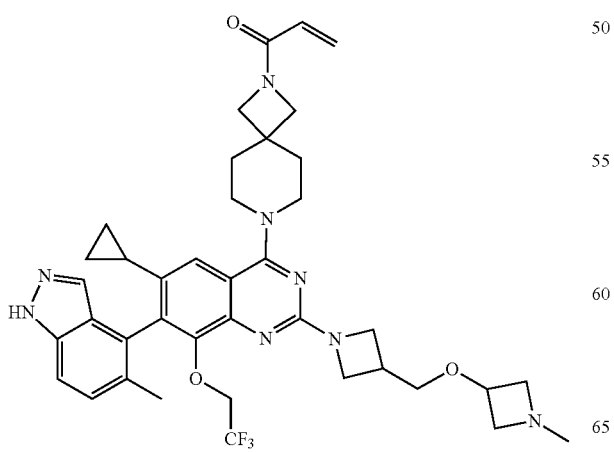
11
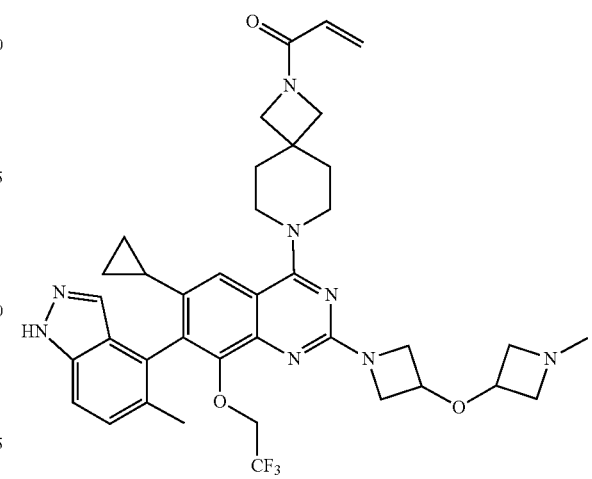
14

15
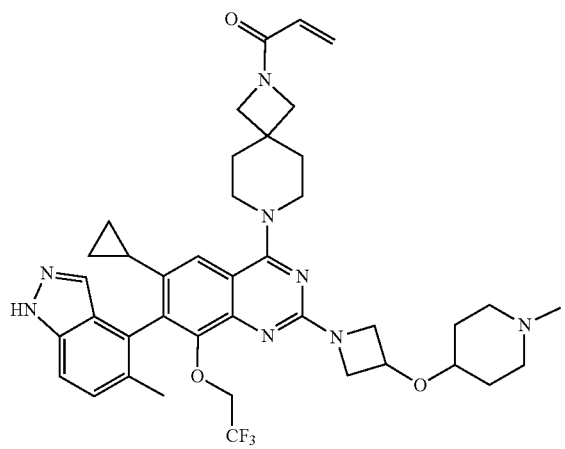
16
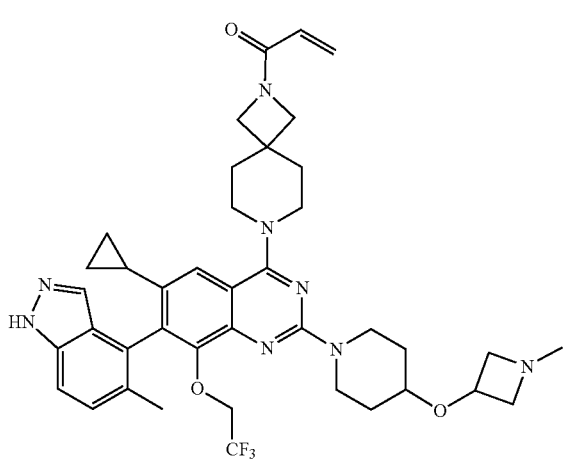
17
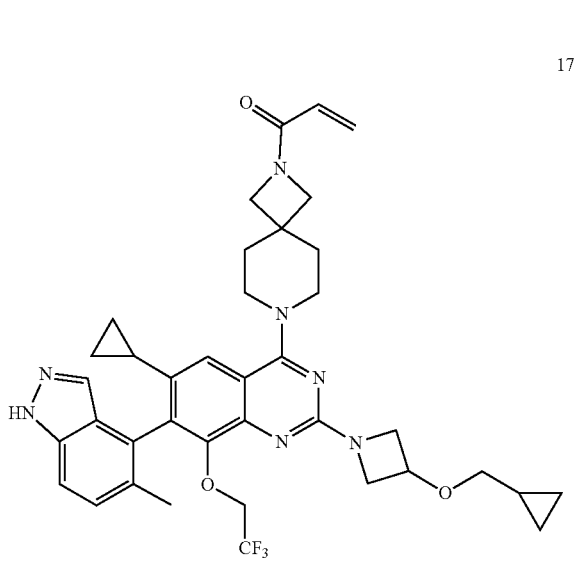
18
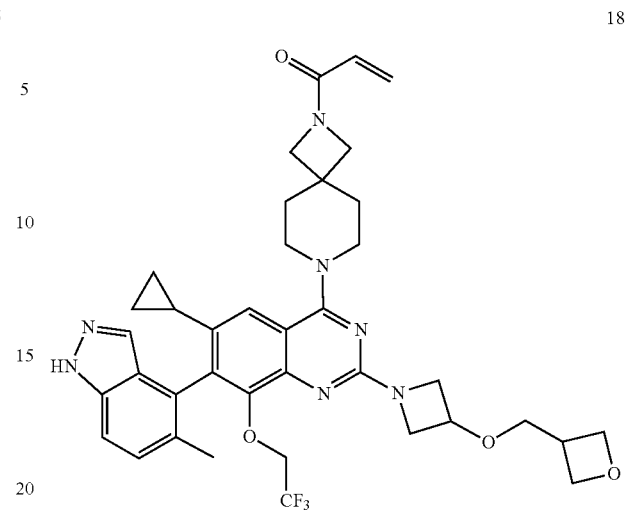
19
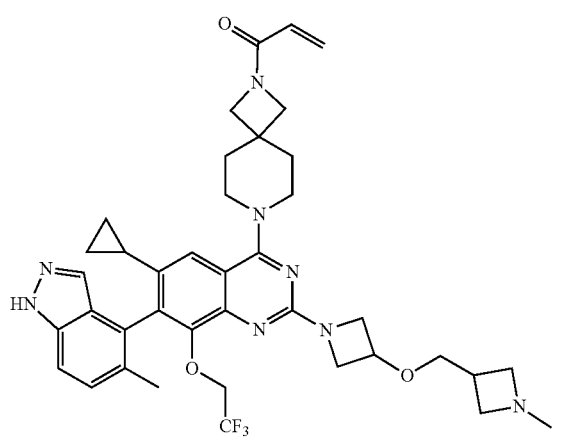
20
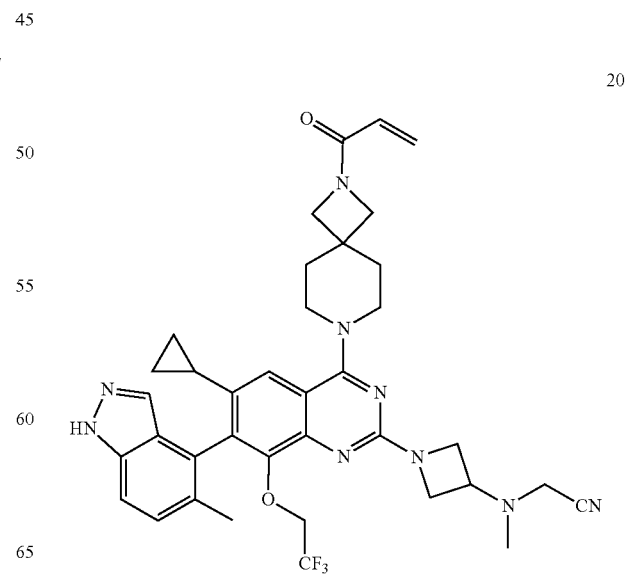

193
-continued

194
-continued

27
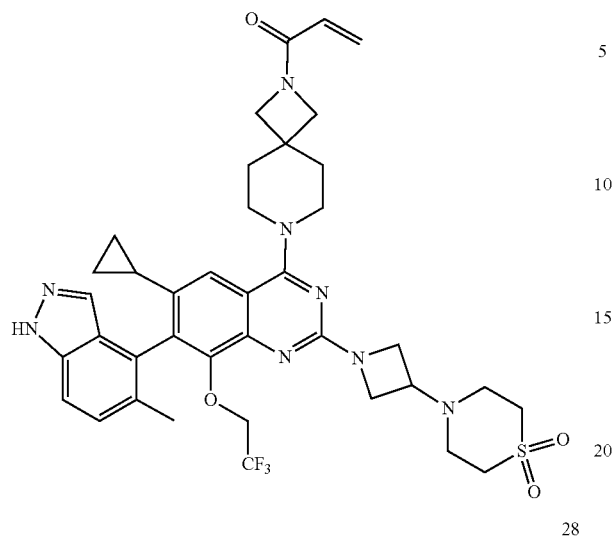
28
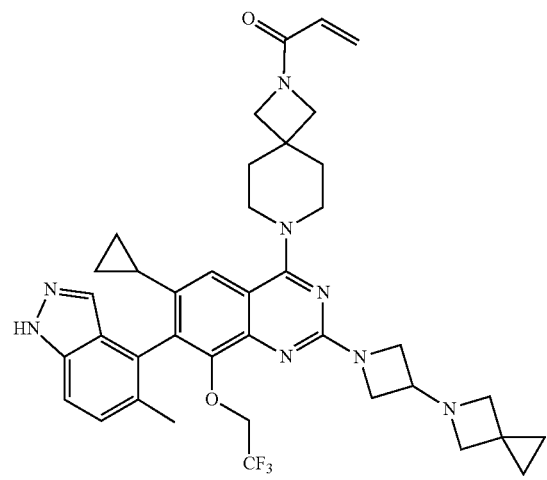
29
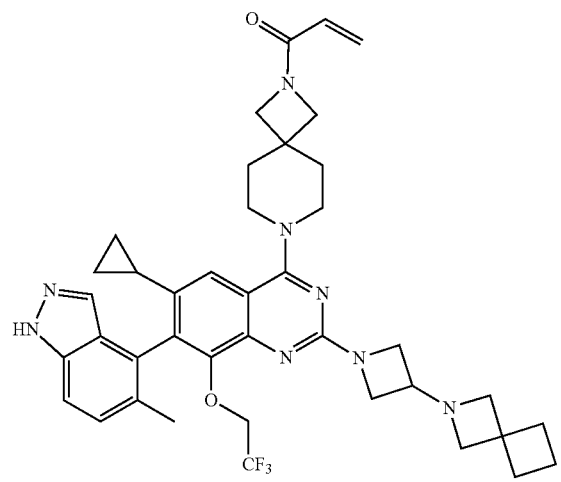
30
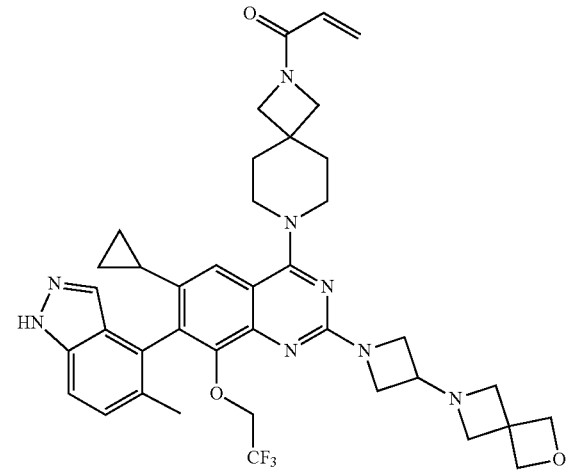
31
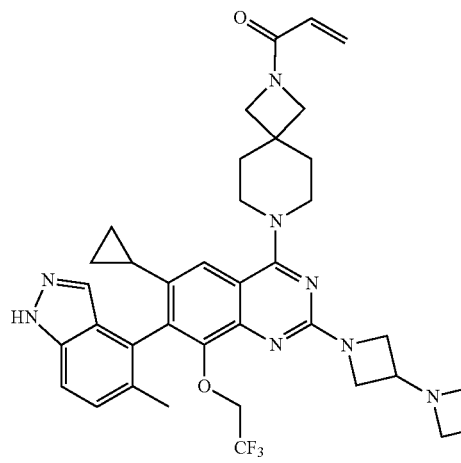
32
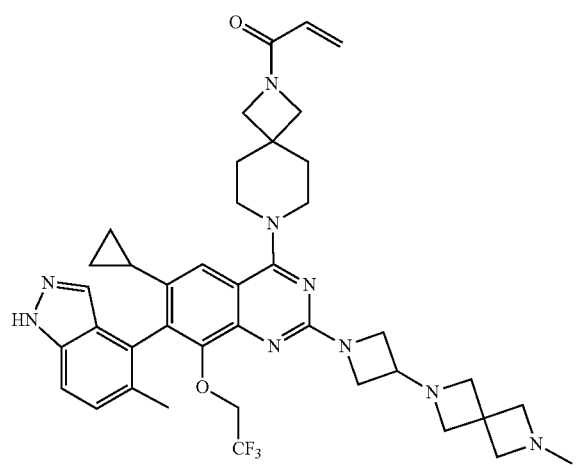

33
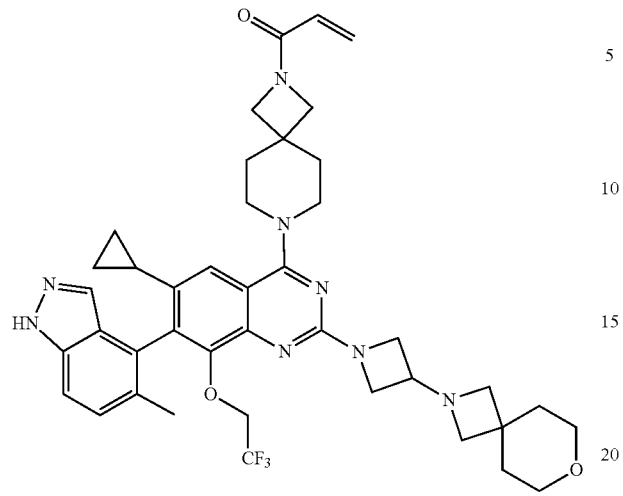
36
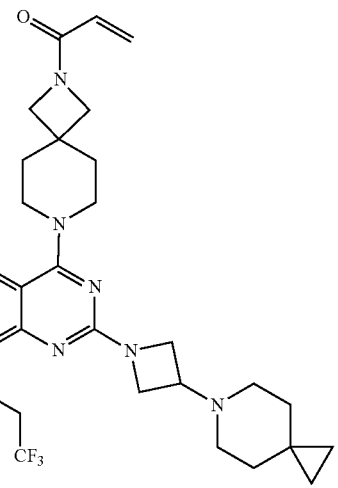
34
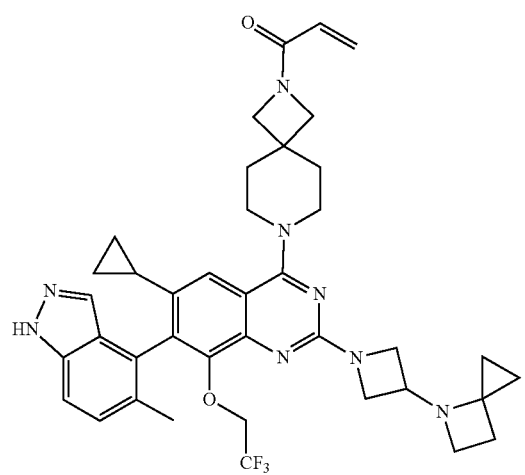
37
35
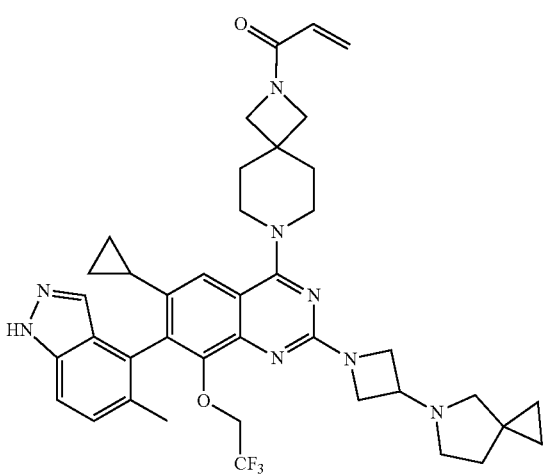
38
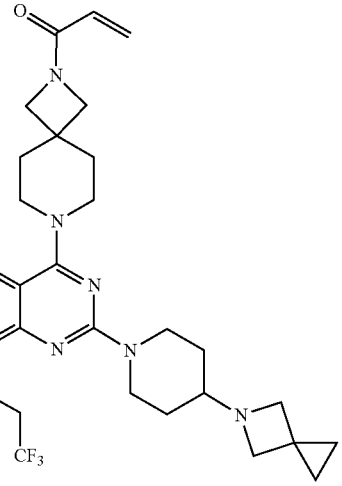

39
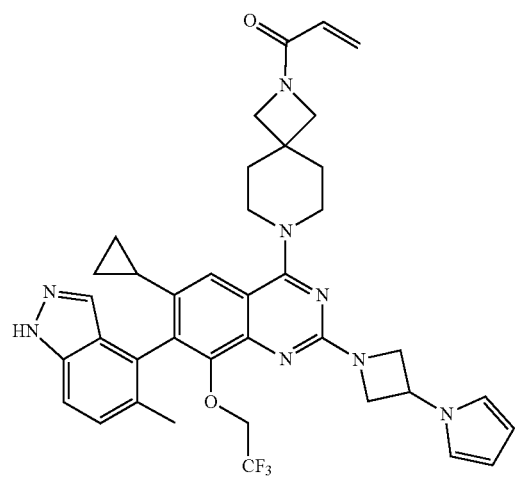
40
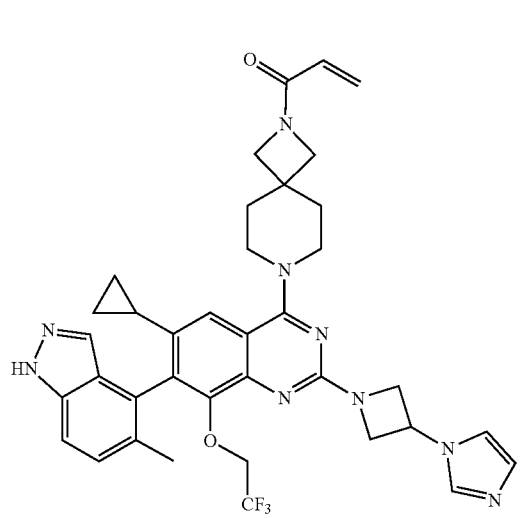
41
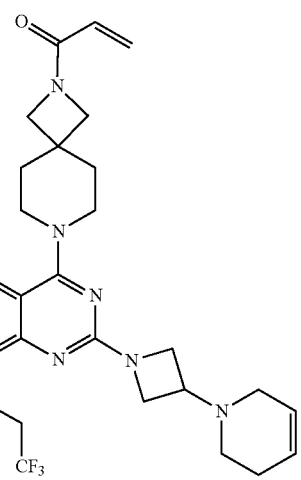
42
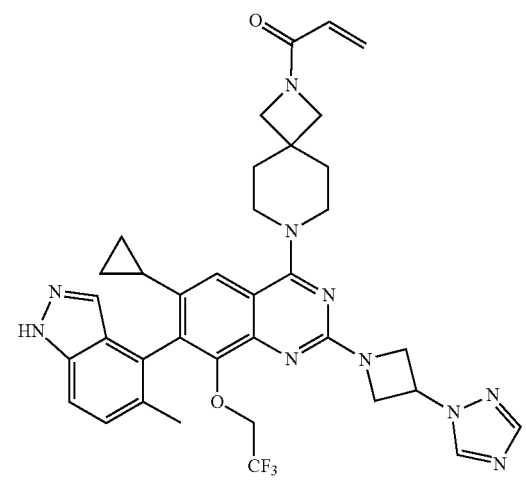
43
44
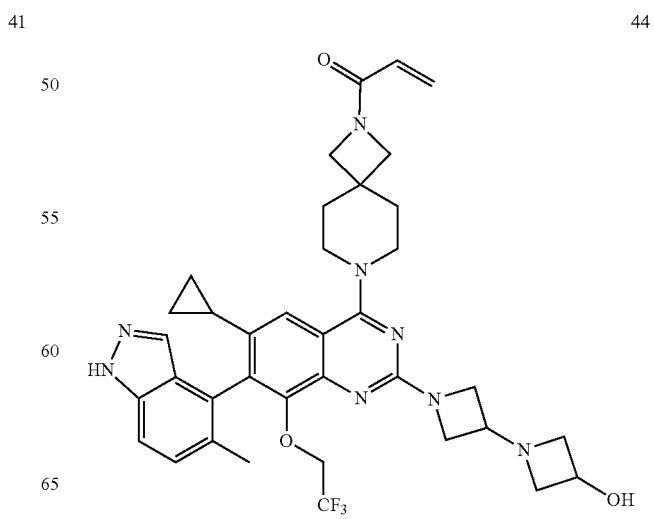

45
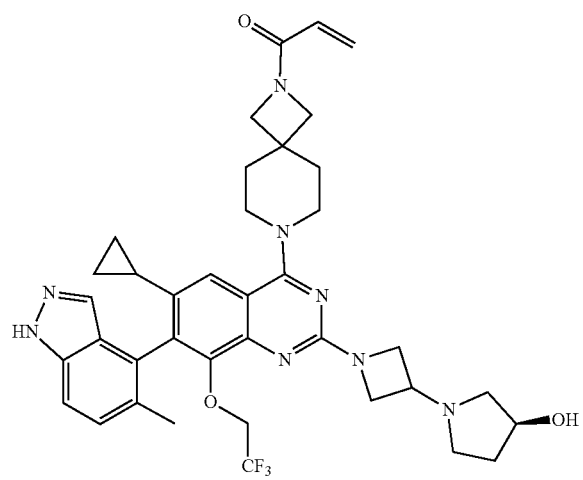
46
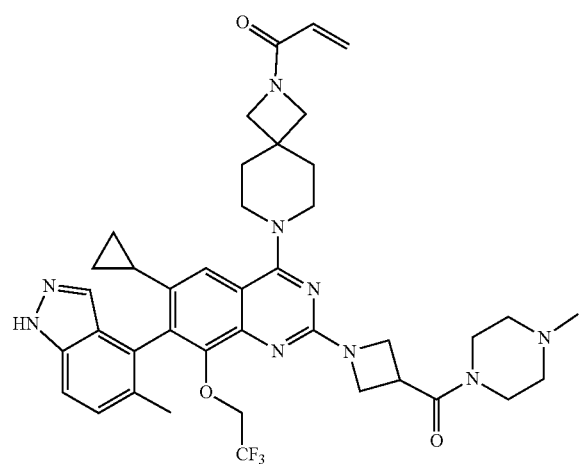
47
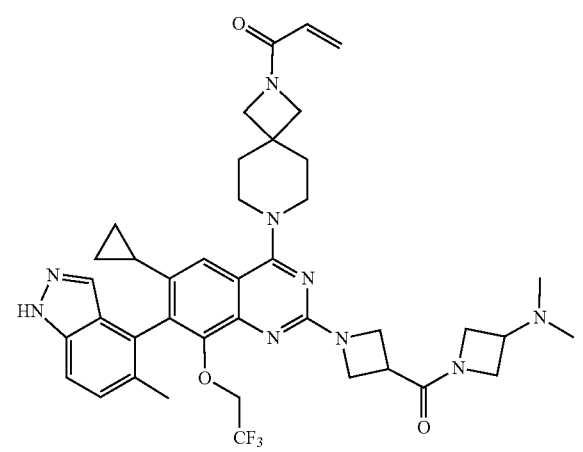
48
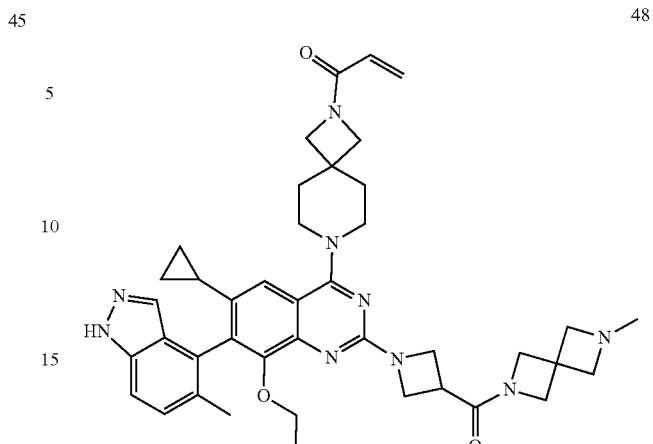
49
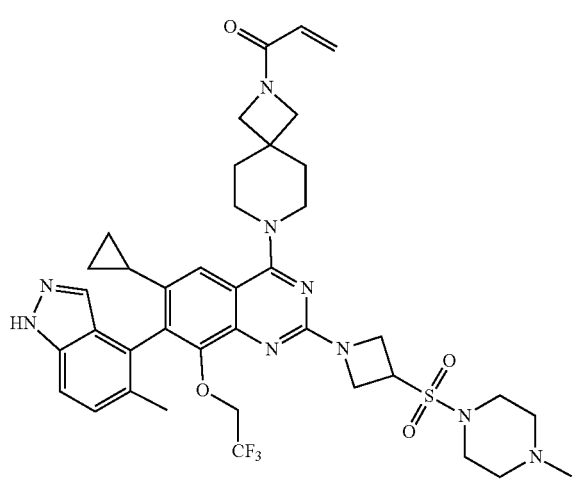
50
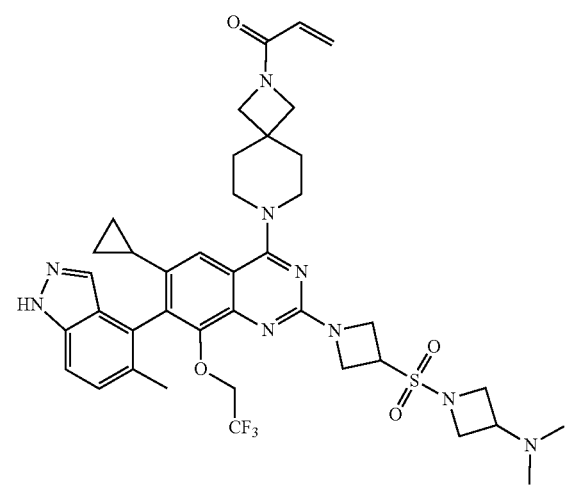

51
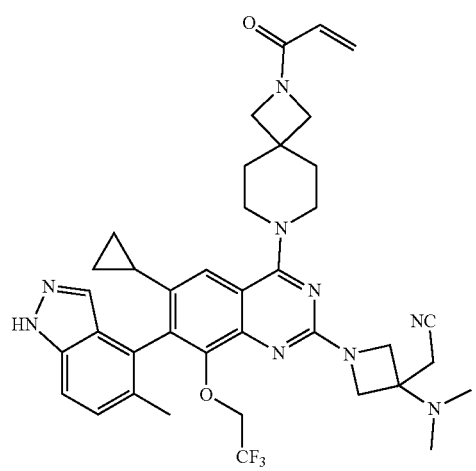
54
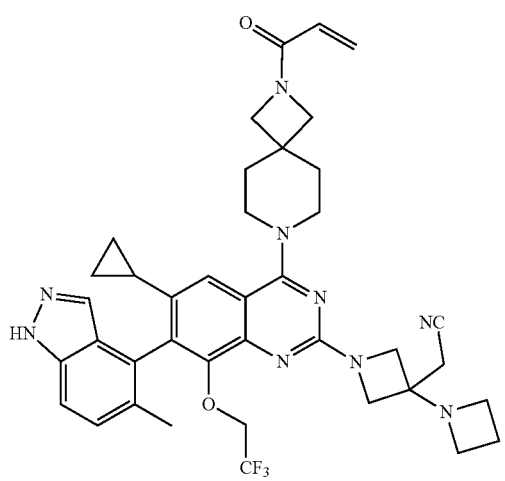
52
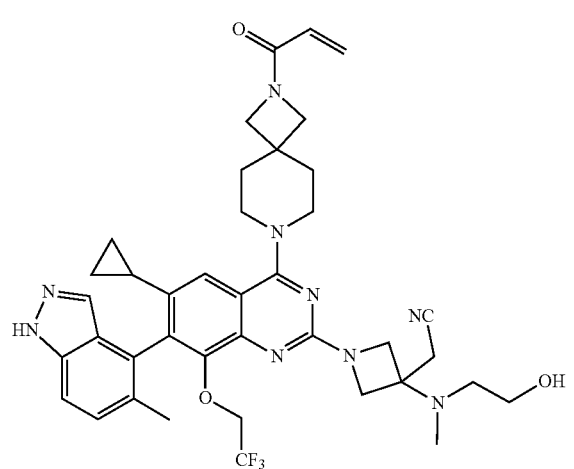
55
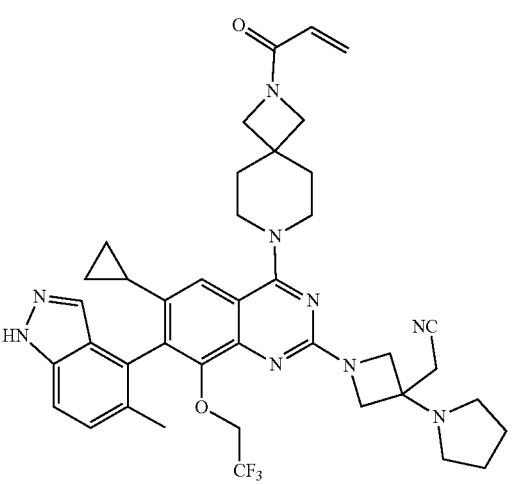
53
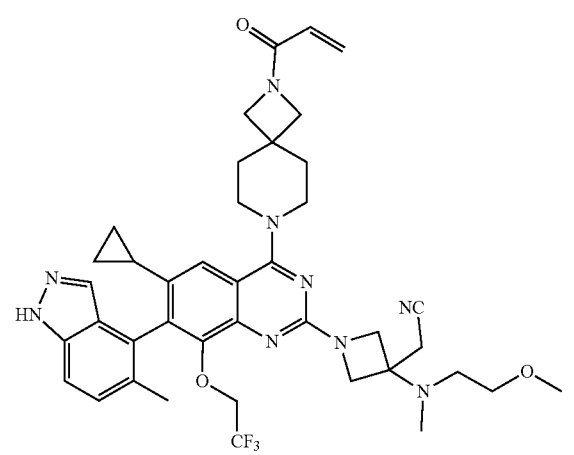
56
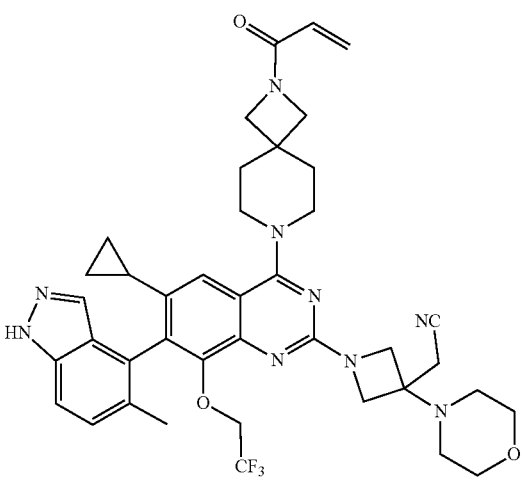

57
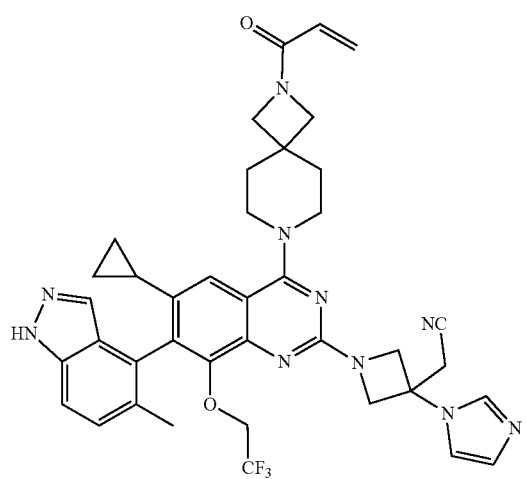
60
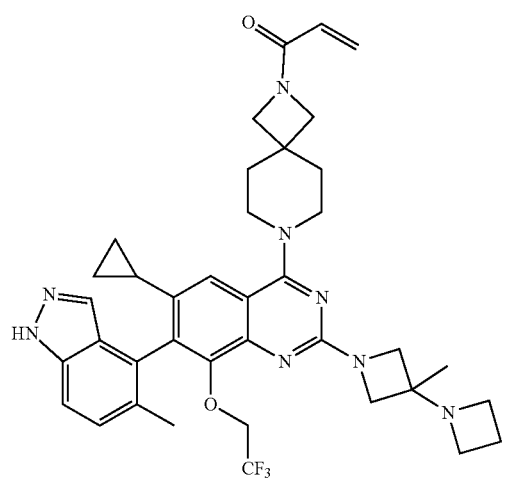
58
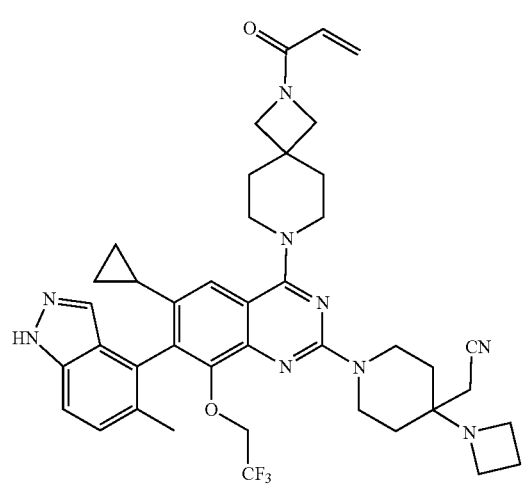
61
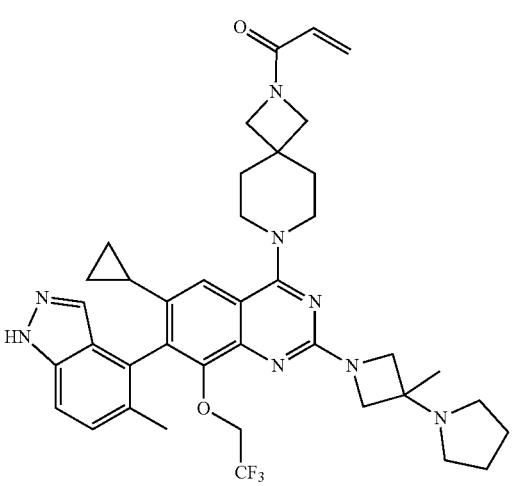
59
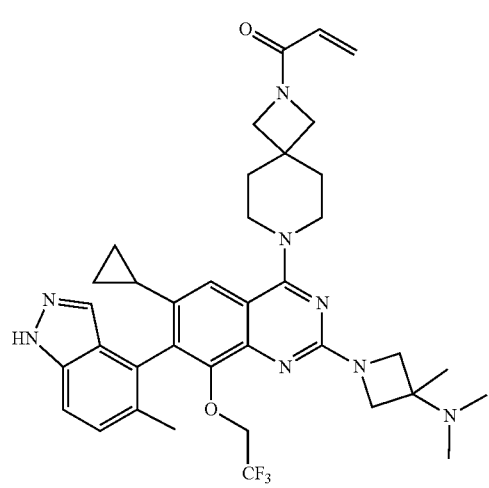
62
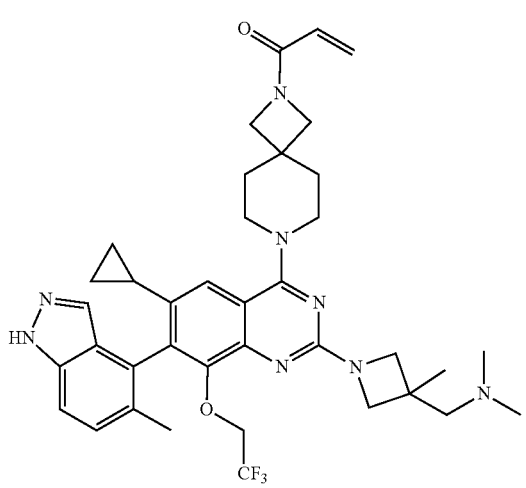

63
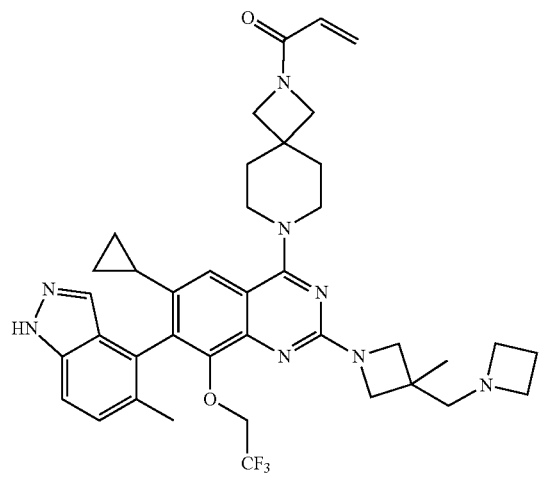
64
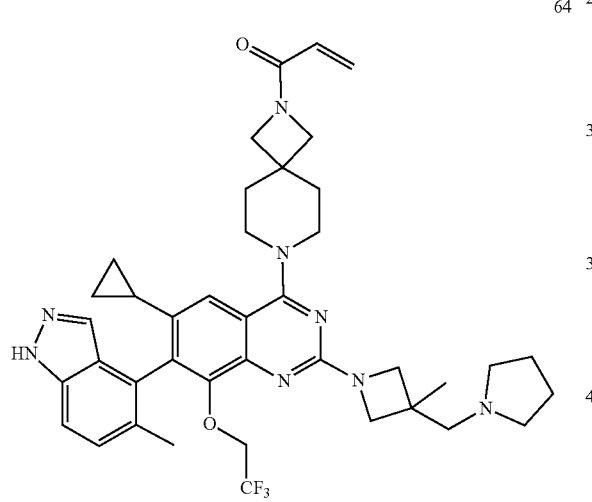
65
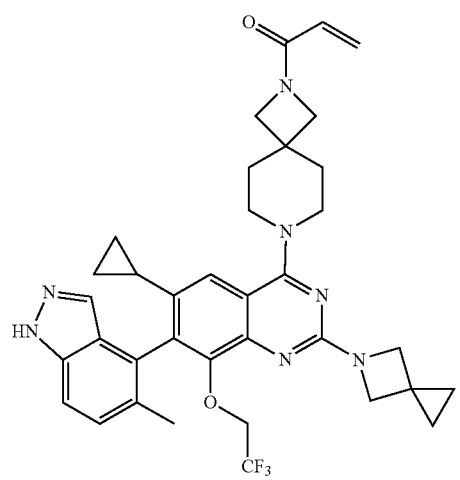
66
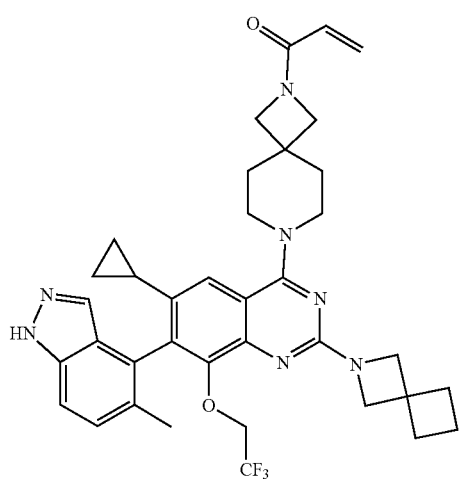
67
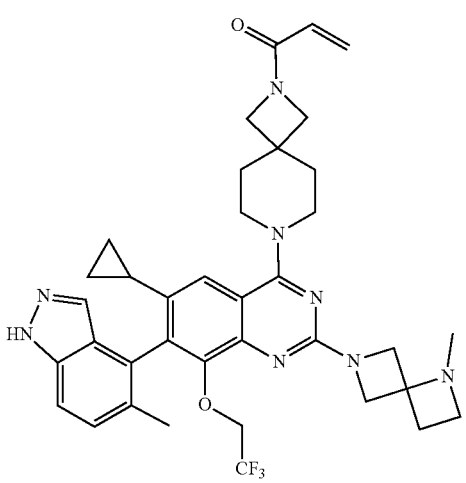
68
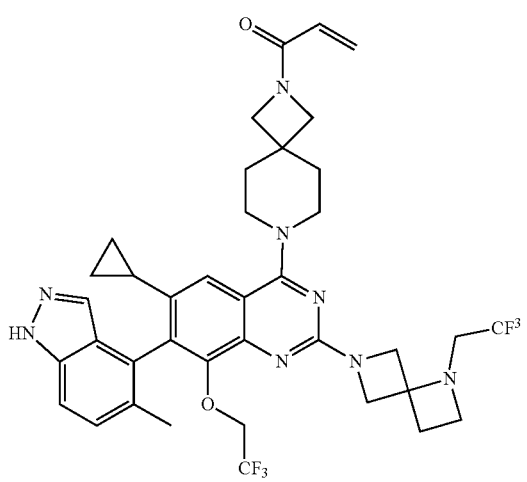

-continued
69
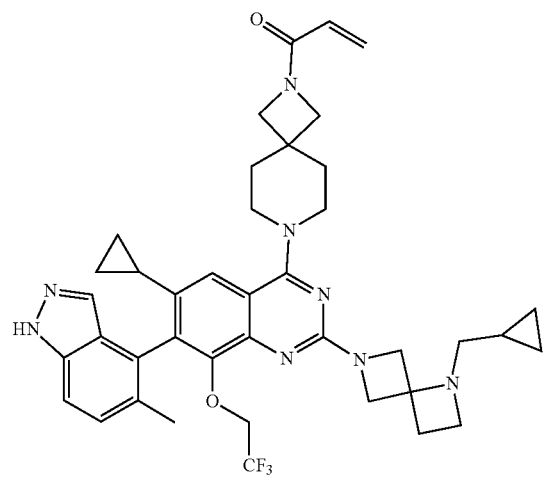
70
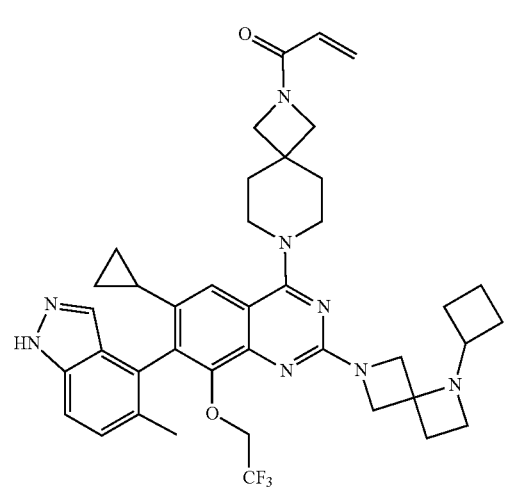
71
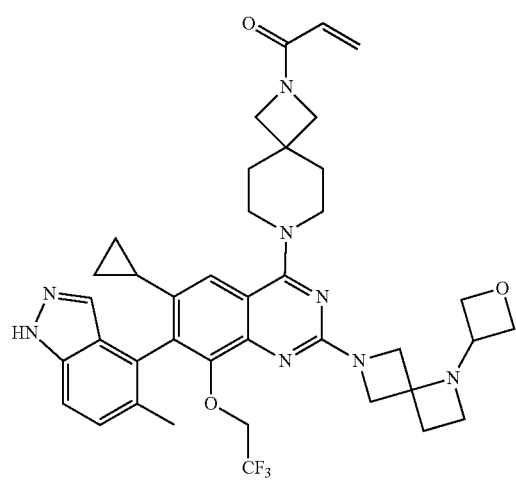
-continued
72
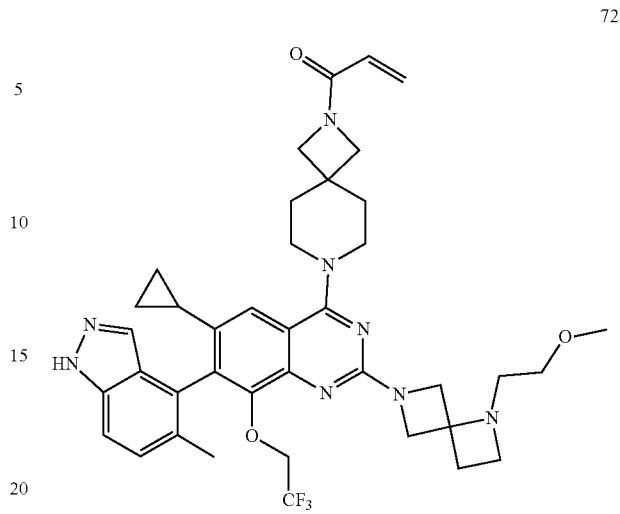
73
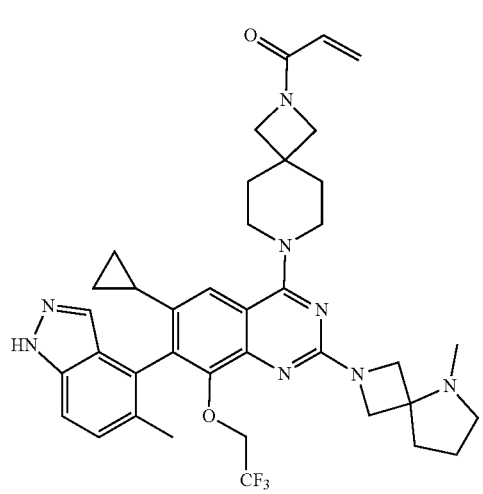
74
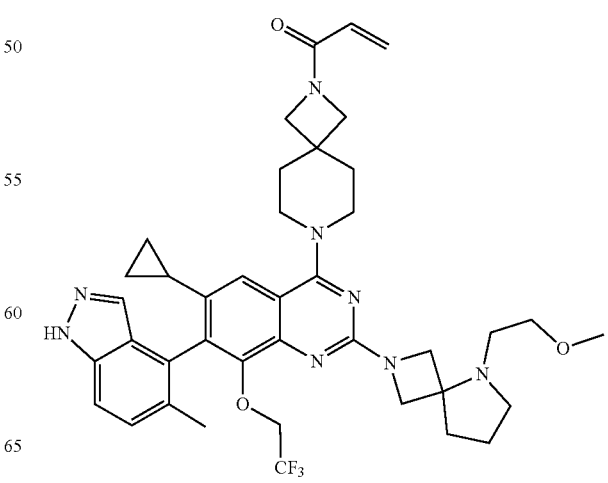

-continued
75
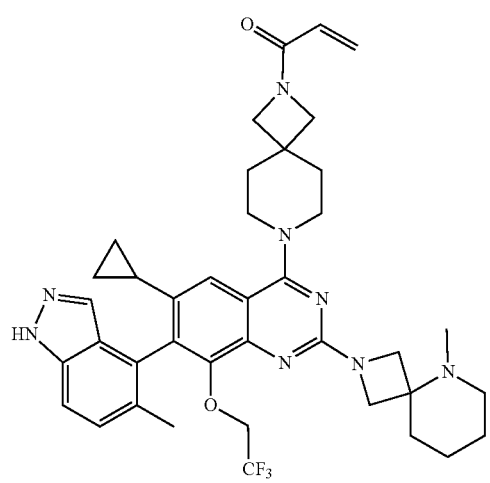
76
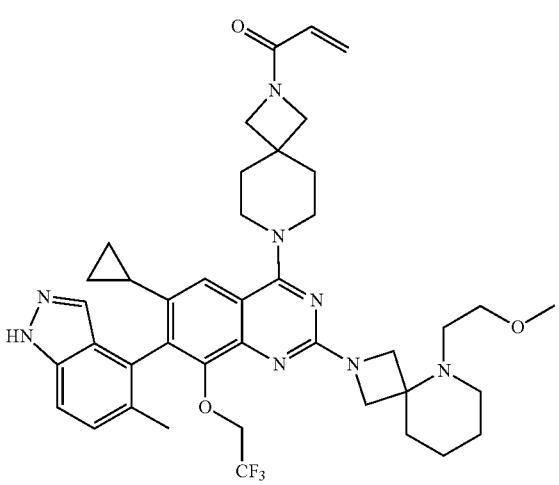
77
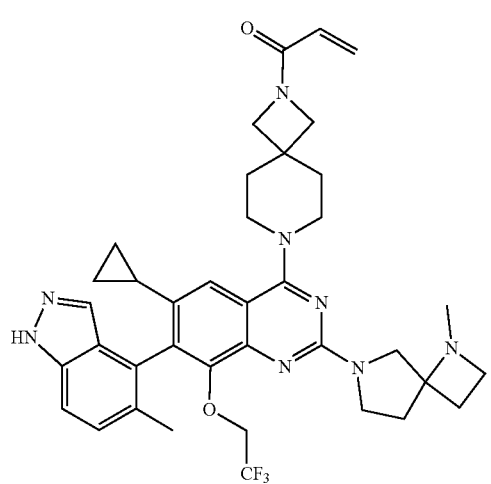
78
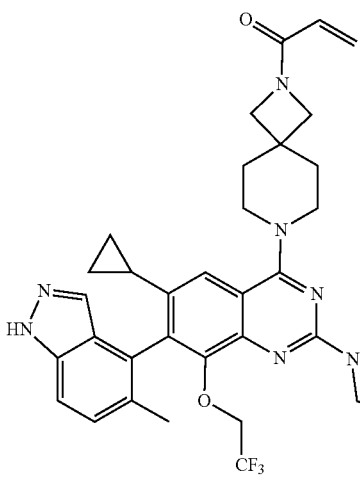
79
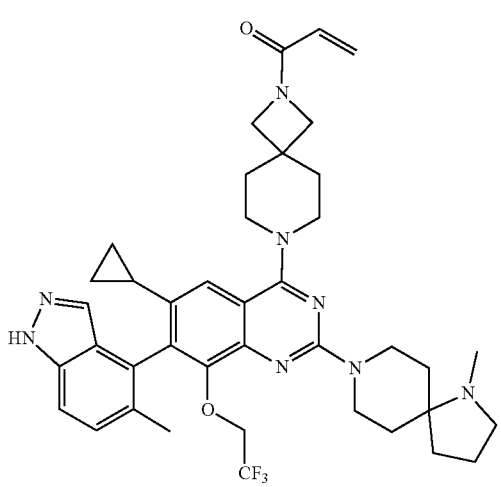
80
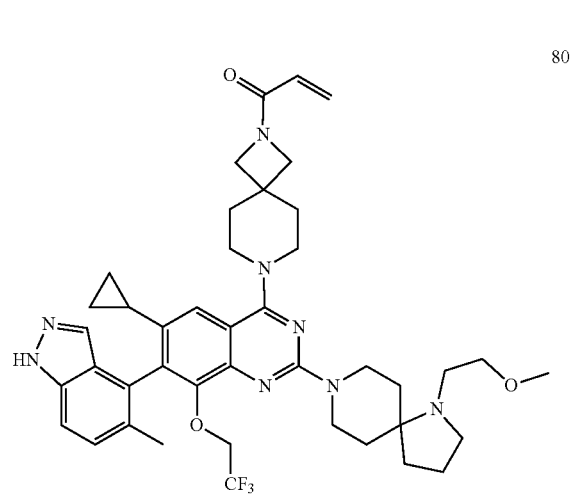

213
-continued
81
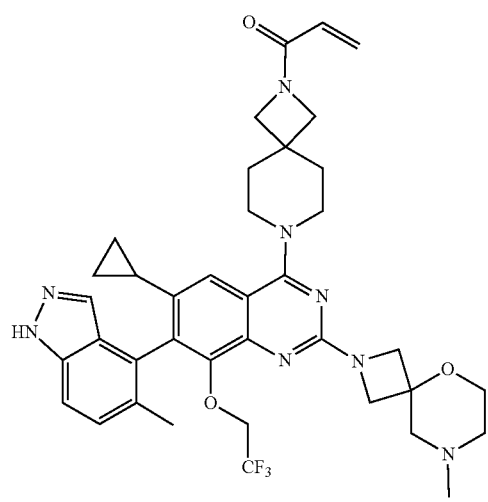
82
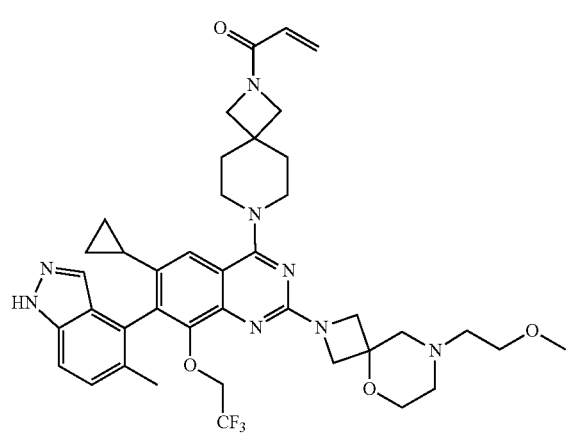
83
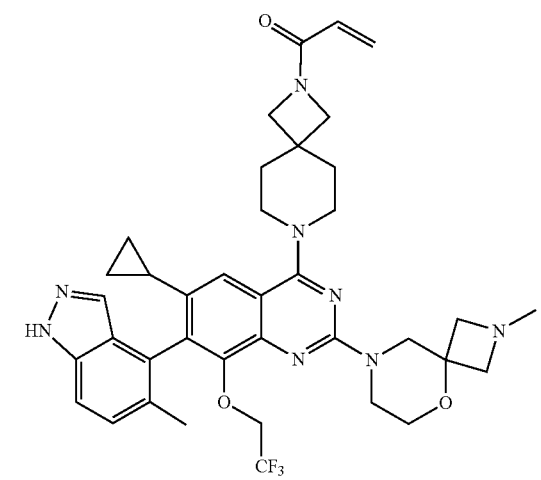
214
-continued
84
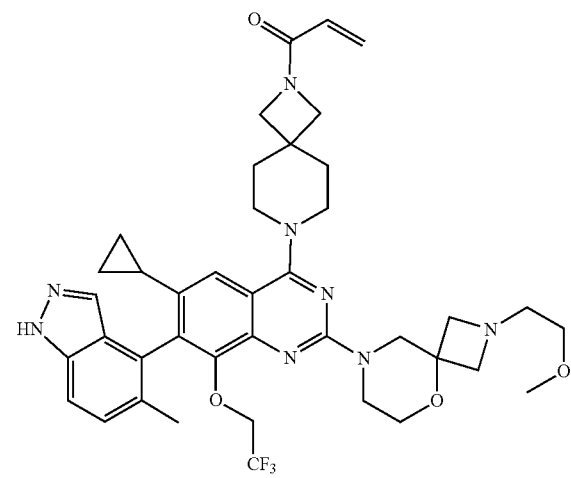
85
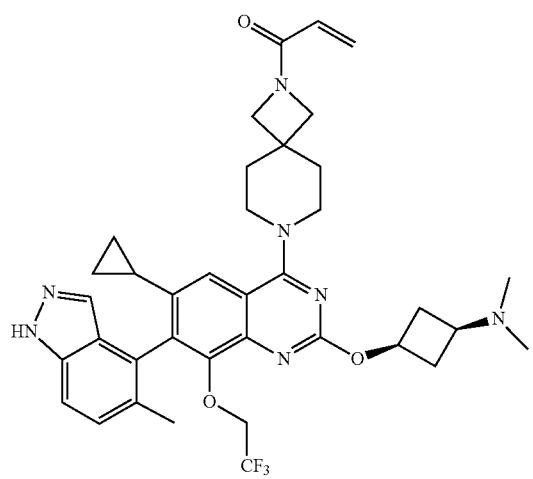
86
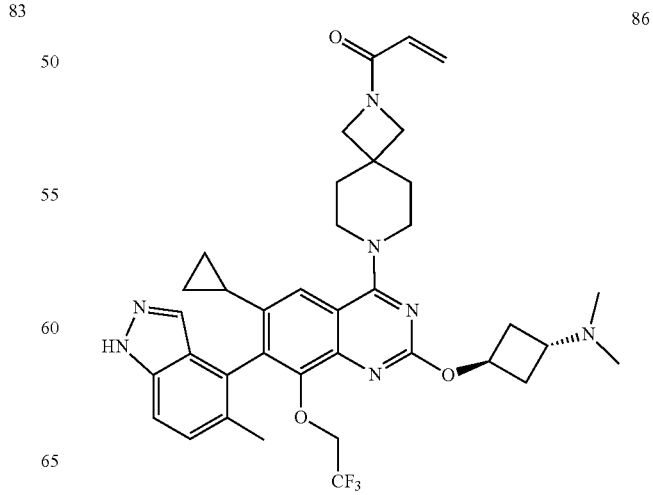

87
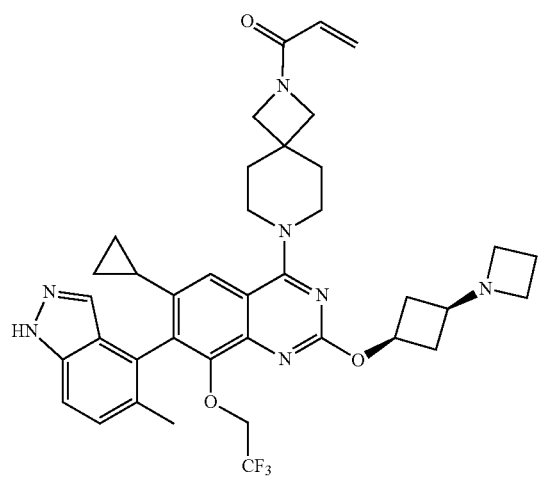
88
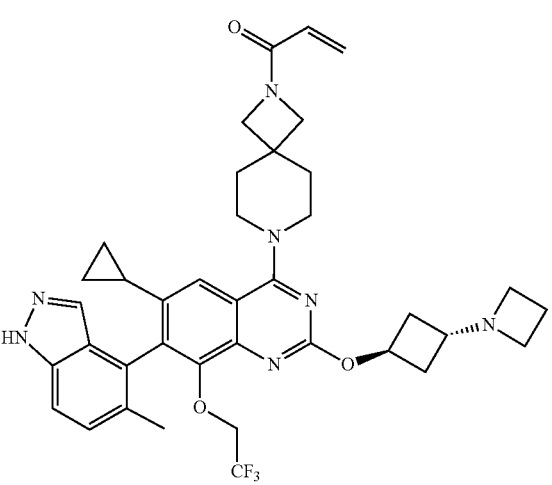
89
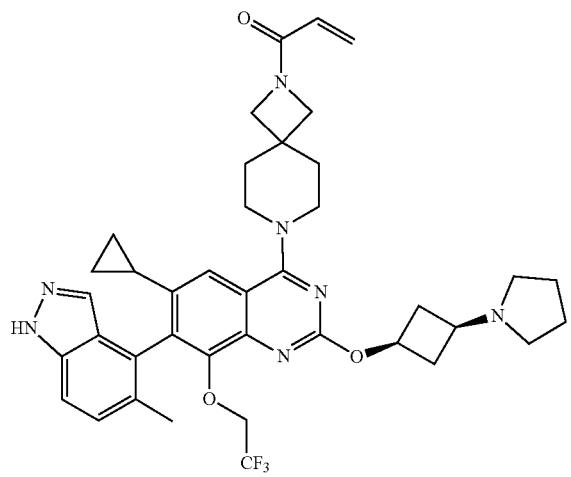
90
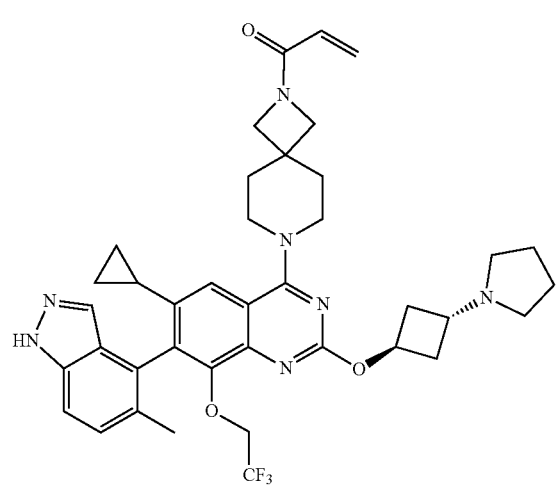
91
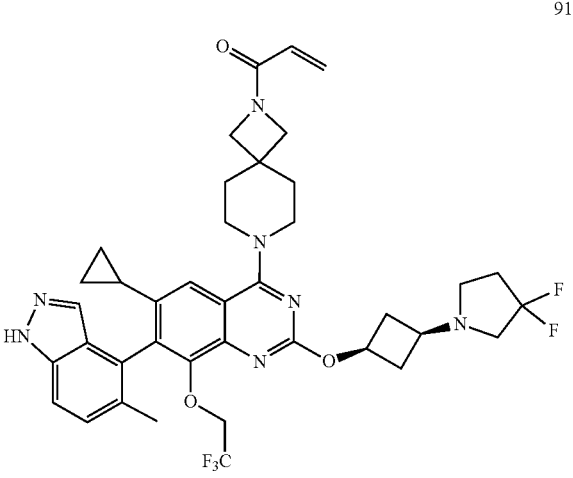
92
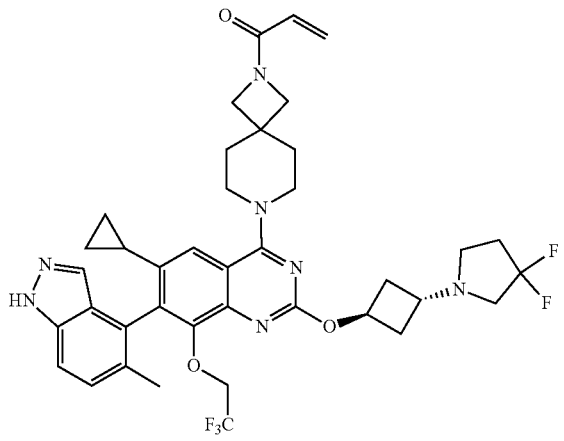

93
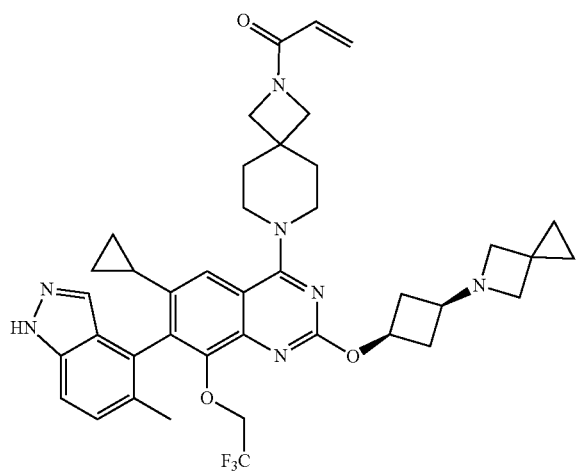
94
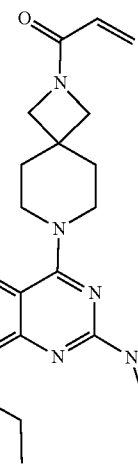
95
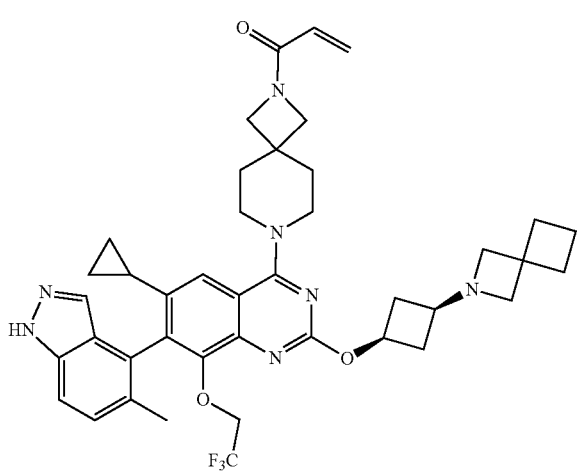
96
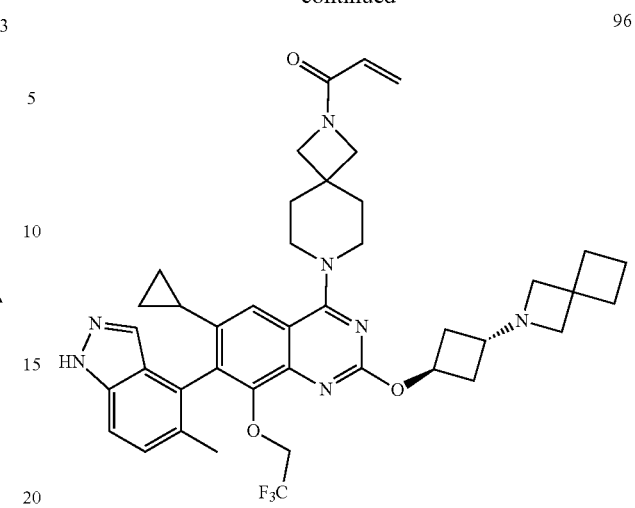
97
98
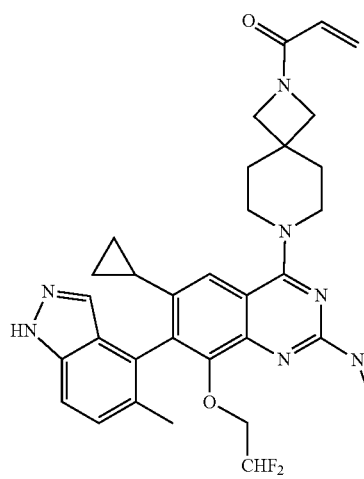

219
99
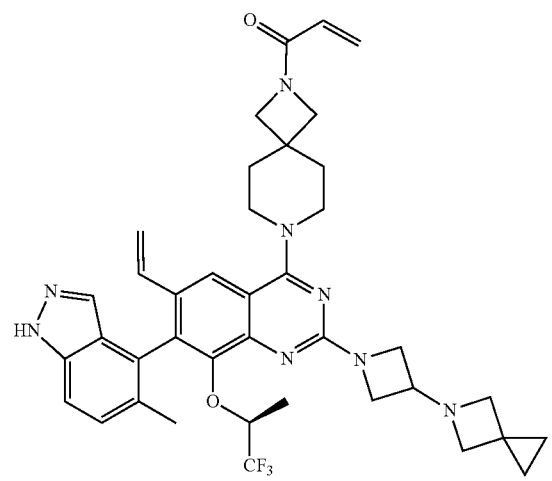
100
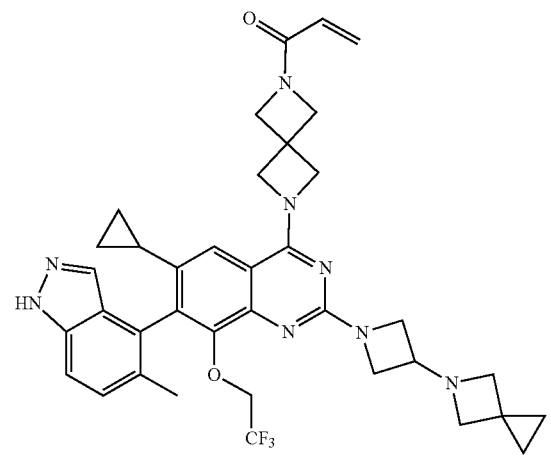
101
102
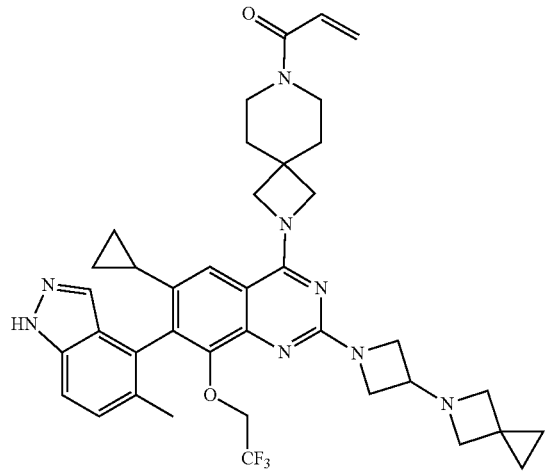
103
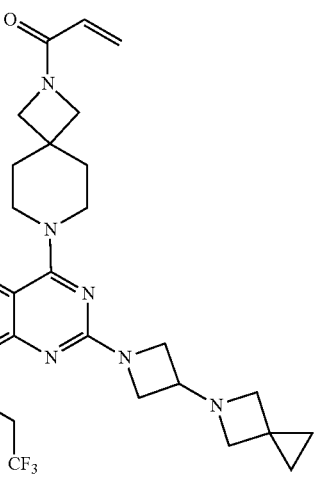
104
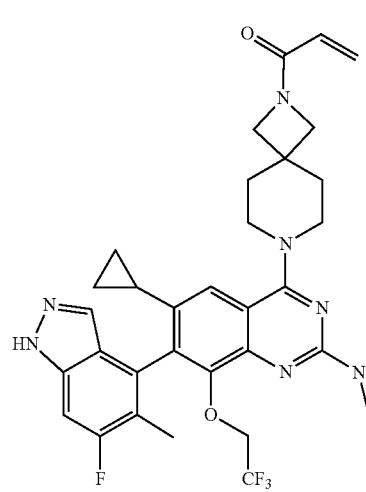

105
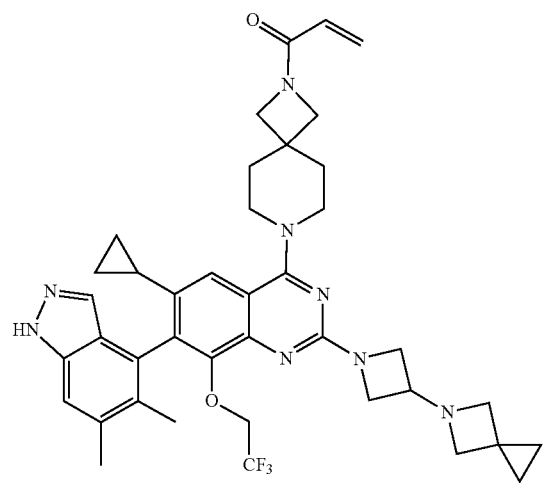
106
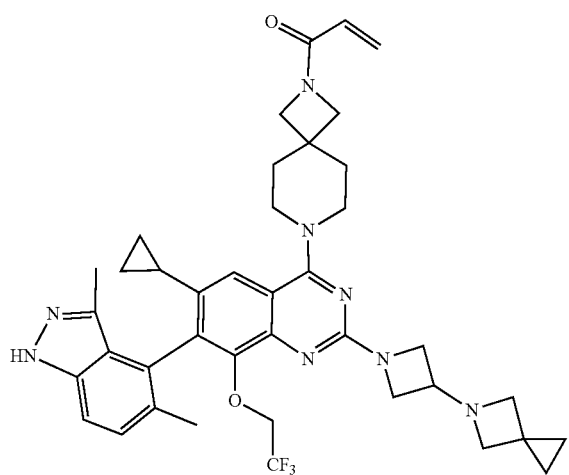
107
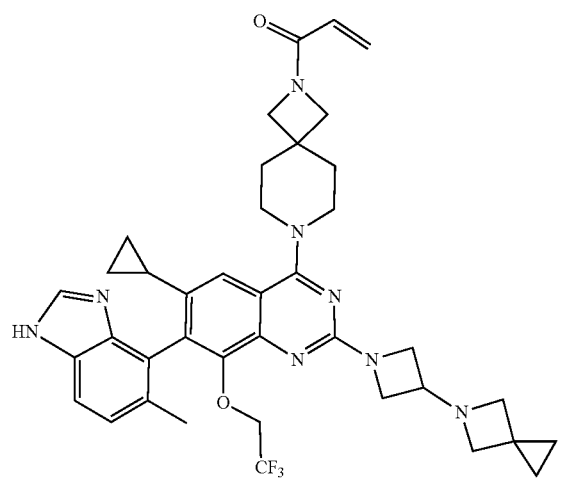
108
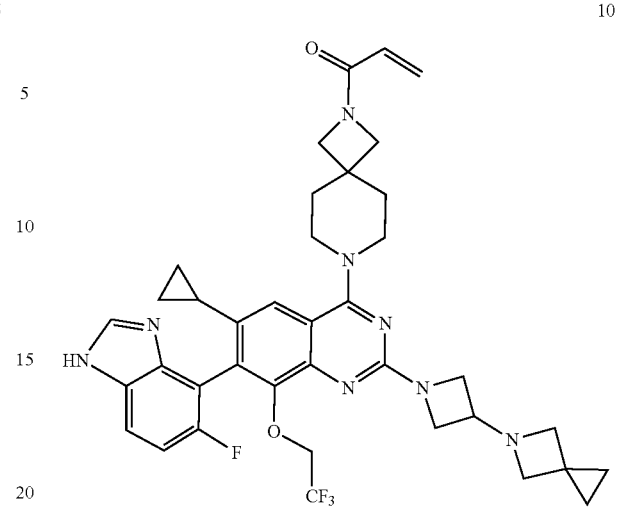
109
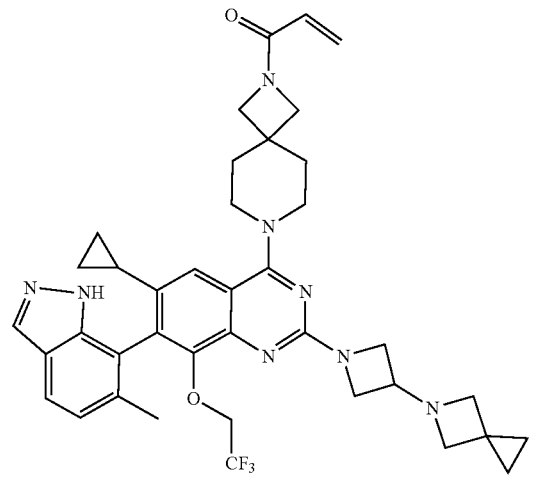
110
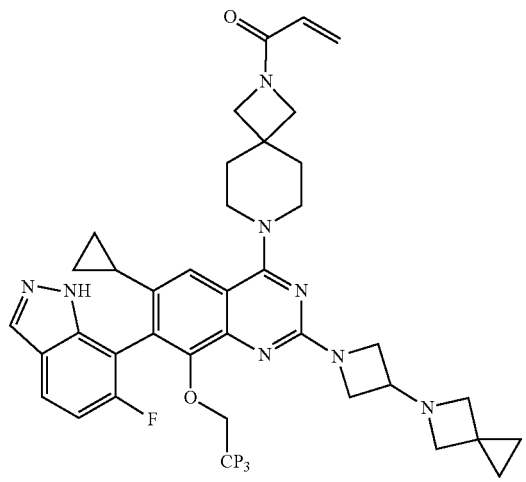

-continued
111
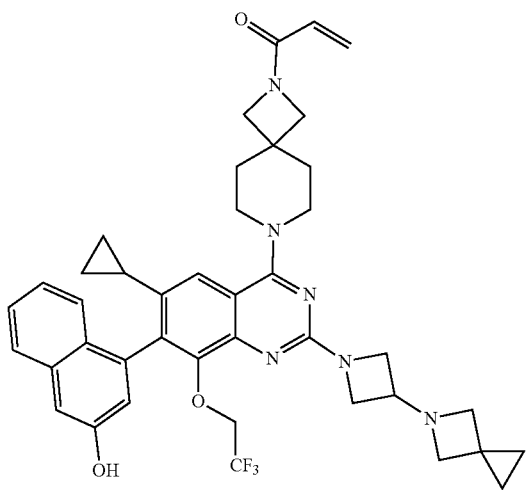
112
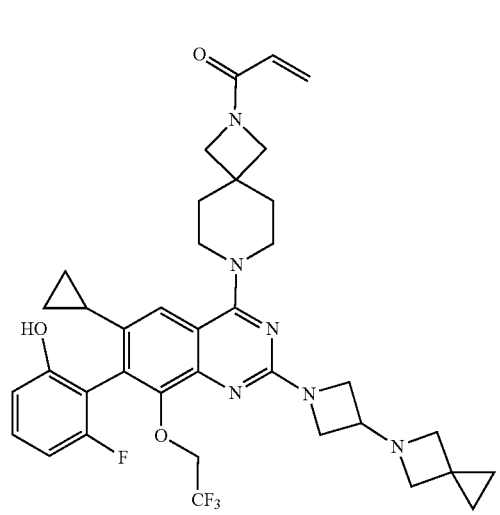
113
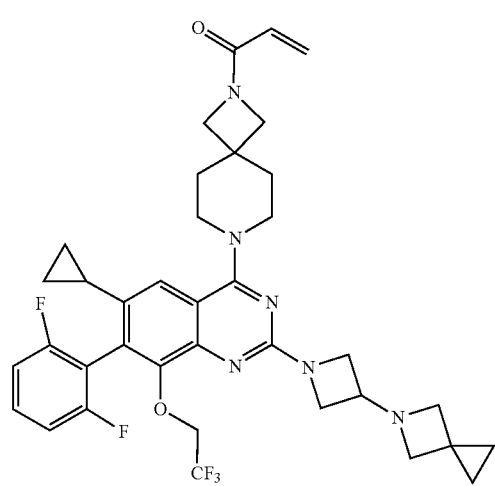
-continued
114
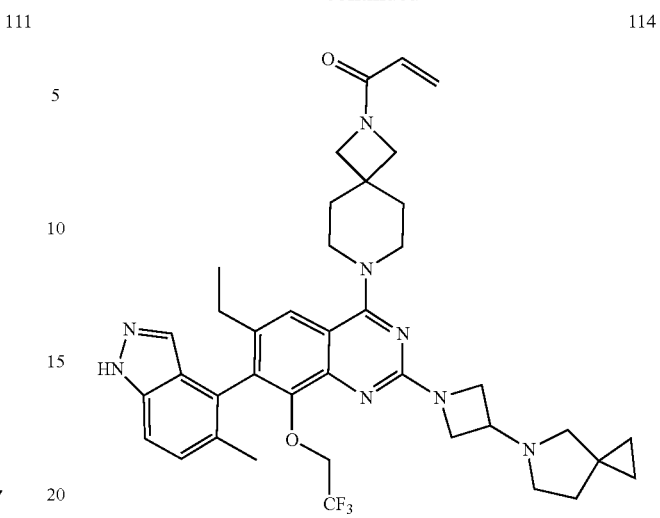
115
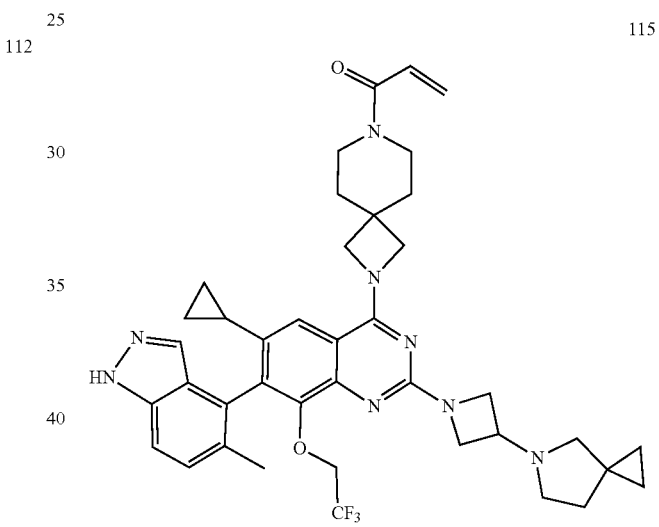
116
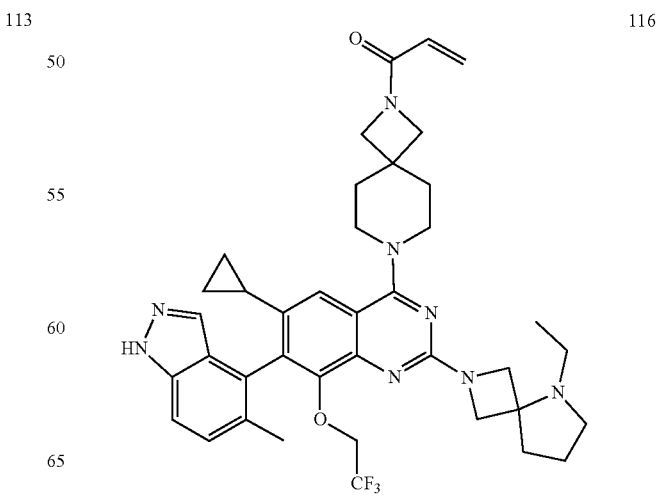

117 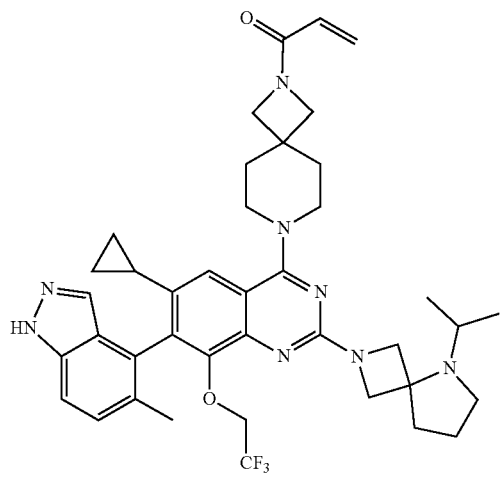
118 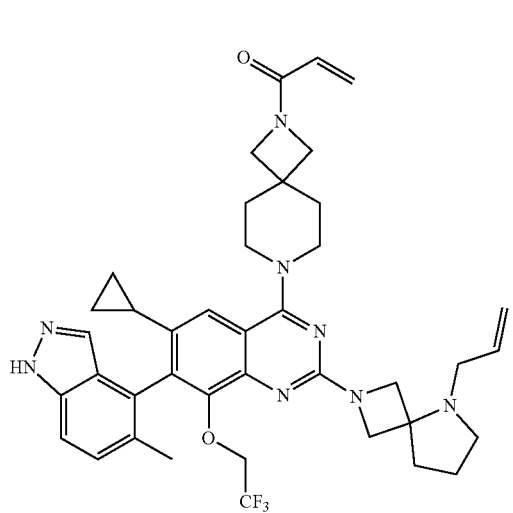
119
120 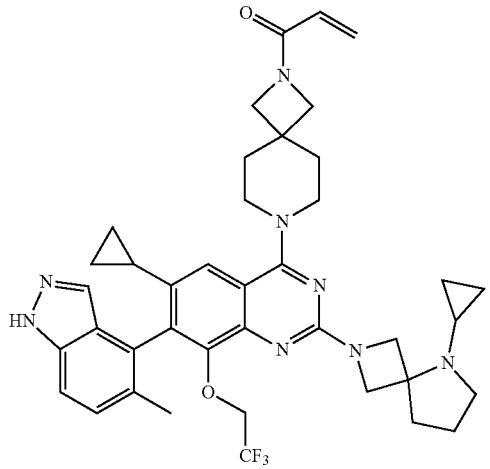
121 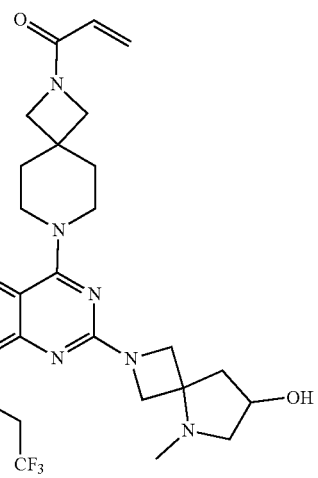
122 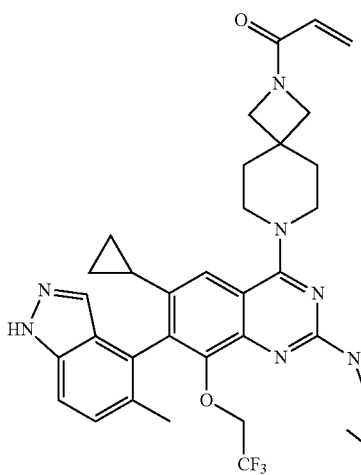

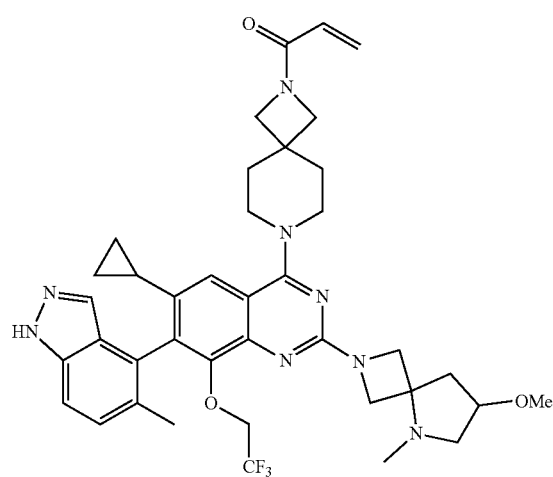
123
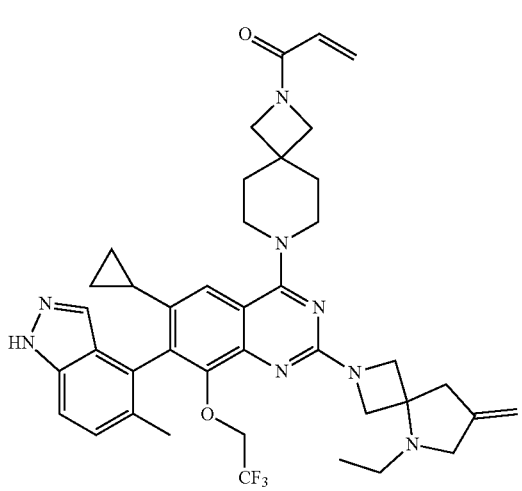
126
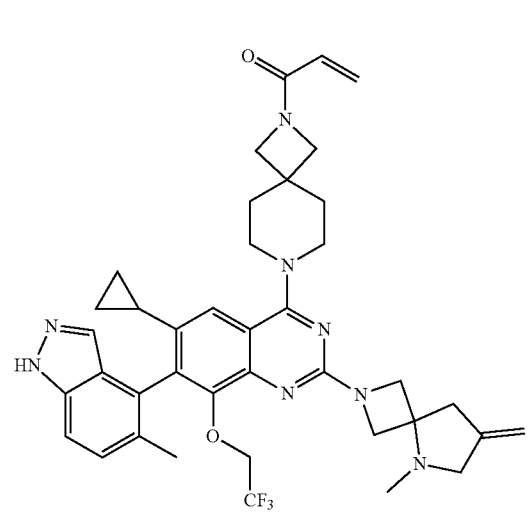
124
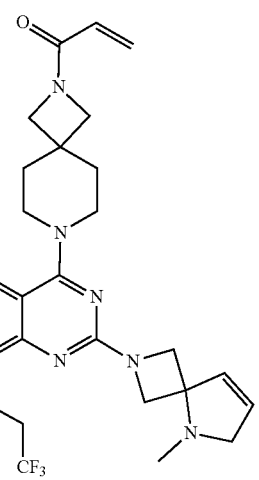
127
125
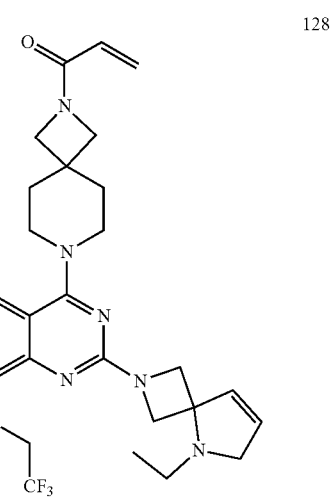
128

129
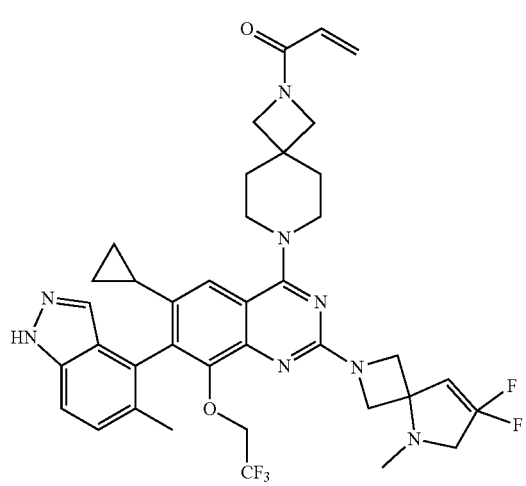
130
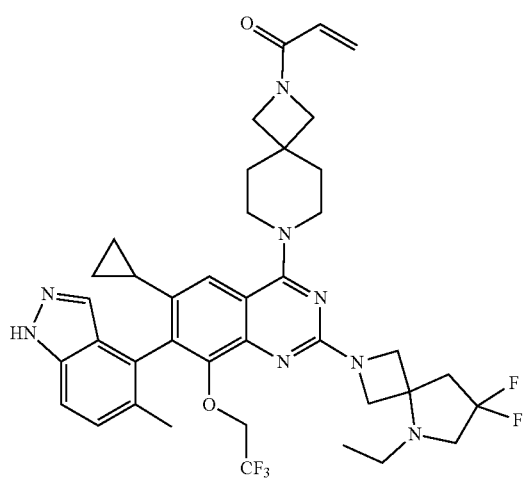
131
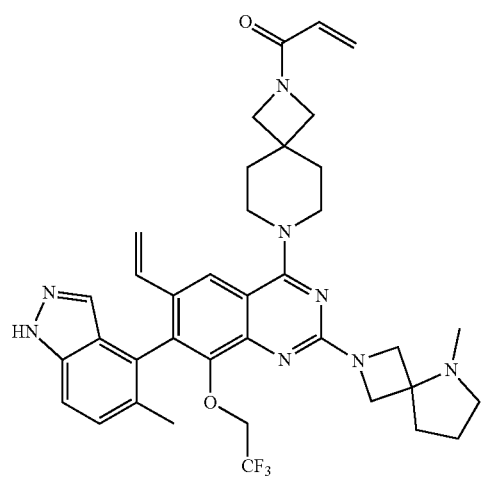 [SMILES: C=CC(=O)N1CC2(CCN(c3nc(N4CC5(CCCN5C)C4)nc4c(OCC(F)(F)F)c(-c5c(C)ccc6[nH]ncc56)c(C=C)cc34)CC2)C1]
or
132
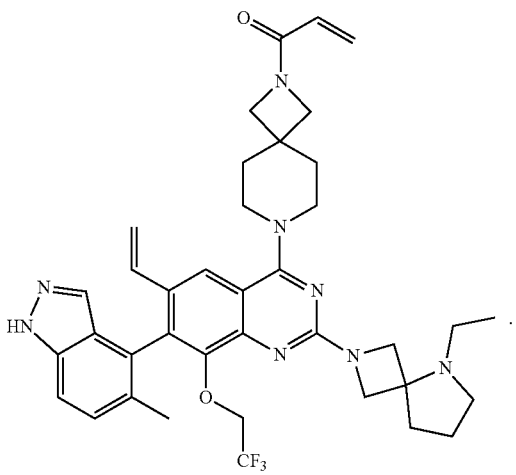
7. A pharmaceutical composition comprising a pharmaceutically acceptable excipient or carrier, and the compound or the pharmaceutically acceptable salts thereof according to claim 1 as active ingredients.
* * * * *